(12) United States Patent
Monda et al.

(10) Patent No.: US 9,447,156 B2
(45) Date of Patent: Sep. 20, 2016

(54) METHODS AND COMPOSITIONS FOR INHIBITING NEDDYLATION OF PROTEINS

(75) Inventors: Julie K. Monda, Memphis, TN (US); Brenda A. Schulman, Memphis, TN (US); Daniel C. Scott, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/118,132

(22) PCT Filed: May 16, 2012

(86) PCT No.: PCT/US2012/038127
§ 371 (c)(1),
(2), (4) Date: Feb. 4, 2014

(87) PCT Pub. No.: WO2012/158789
PCT Pub. Date: Nov. 22, 2012

(65) Prior Publication Data
US 2014/0179593 A1 Jun. 26, 2014

Related U.S. Application Data

(60) Provisional application No. 61/486,972, filed on May 17, 2011.

(51) Int. Cl.
| | |
|---|---|
| G01N 33/53 | (2006.01) |
| C12N 9/99 | (2006.01) |
| C12N 5/00 | (2006.01) |
| C12N 5/02 | (2006.01) |
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| C07K 14/47 | (2006.01) |
| C12N 9/00 | (2006.01) |
| G01N 33/573 | (2006.01) |
| G01N 33/566 | (2006.01) |

(52) U.S. Cl.
CPC ............... *C07K 14/47* (2013.01); *C12N 9/93* (2013.01); *C12Y 603/02019* (2013.01); *G01N 33/566* (2013.01); *G01N 33/573* (2013.01); *A61K 38/00* (2013.01); *C07K 2299/00* (2013.01); *G01N 2333/9015* (2013.01); *G01N 2440/36* (2013.01); *G01N 2500/04* (2013.01)

(58) Field of Classification Search
CPC .. A61K 38/00; C07K 14/47; C07K 2299/00; C12N 9/92; C12Y 603/02019; G01N 2333/9015; G01N 2440/36; G01N 2500/04; G01N 33/566; G01N 33/573
See application file for complete search history.

(56) References Cited

U.S. PATENT DOCUMENTS

| | | |
|---|---|---|
| 7,829,303 B1 | 11/2010 | Benson et al. |
| 2004/0009541 A1 | 1/2004 | Singh et al. |
| 2007/0003520 A1 | 1/2007 | Brown et al. |
| 2007/0110720 A1 | 5/2007 | Brown et al. |
| 2009/0274728 A1 | 11/2009 | Brown et al. |
| 2010/0210035 A1 | 8/2010 | Chau |

FOREIGN PATENT DOCUMENTS

| | | |
|---|---|---|
| EP | 2 182 006 A2 | 5/2010 |
| WO | WO 2006/084281 A1 | 8/2006 |
| WO | WO 2007/092213 A2 | 8/2007 |

OTHER PUBLICATIONS

Barry and Früh, "Viral Modulators of Cullin RING Ubiquitin Ligases: Culling the Host Defense," *Sci STKE*, 2006, vol. 335, pp. 1-6.
Bird, G.H., et al., "Synthesis and Biophysical Characterization of Stabilized α-Helices of BCL-2 Domains," *Methods in Enzymology*, 2008, vol. 446, pp. 369-386.
Broderick, S.R., et al., "SCCRO Promotes Glioma Formation and Malignant Progression in Mice," *Neoplasia*, 2010, vol. 12, No. 6, pp. 476-484.
Duda, D.M., et al., "Structural Insights into NEDD8 Activation of Cullin-RING Ligases: Conformational Control of Conjugation," *Cell*, 2008, vol. 134, No. 6, pp. 995-1006.
Estilo, C.L., et al., "The Role of Novel Oncogenes Squamous Cell Carcinoma-related Oncogene and Phosphatidylinositol 3-Kinase p110 α in Squamous Cell Carcinoma of the Oral Tongue," *Clin. Cancer Res.*, 2003, vol. 9, pp. 2300-2306.
GenBank Accession No. NP_003960, NEDD8-conjugating enzyme Ubc12 [*Homo sapiens*], 2013, 3 pages.
GenBank Accession No. NP_013409, NEDD8-conjugating protein UBC12 [*Saccharomyces cerevisiae* S288c], 2013, 2 pages.
GenBank Accession No. NP_080730, NEDD8-conjugating enzyme UBE2F [*Mus musculus*], 2013, 2 pages.

(Continued)

*Primary Examiner* — Christina Bradley
*Assistant Examiner* — Zachary J Miknis
(74) *Attorney, Agent, or Firm* — Womble Carlyle Sandridge & Rice LLP

(57) ABSTRACT

Provided herein is a novel binding pocket within NEDD8 co-E3 proteins that binds NEDD8 E2 enzymes. Particularly at its M-Terminus. Methods are provided for screening for compounds that bind to the disclosed E2-binding pocket in NEDD8 co-E3 proteins. Compounds that bind to the E2-binding pocket and optionally inhibit the activity of NEDD8 co-E3 proteins and pharmaceutical compositions comprising the same are further provided. The NEDD8 co-E3 inhibitors find use, as agents preventing the NEDDylation of a target protein, in inhibiting cell growth and methods for treating cancers, inflammatory disorders, and pathogenic infections. The preferred inhibitors are peptides corresponding to a M-terminal fragment of Dnc1, e.g. MTLASKLRDD, MLKLRQLQKKKQ, and MIKLF-SLKQQKK, which are substituted at the M-Terminus with an uncharged group (e.g. acyl).

15 Claims, 17 Drawing Sheets

(56) References Cited

OTHER PUBLICATIONS

GenBank Accession No. NP_542409, NEDD8-conjugating enzyme UBE2F isoform 1 [*Homo sapiens*], 2013, 2 pages.
GenBank Accession No. NP_663553, NEDD8-conjugating enzyme Ubc12 isoform 1 [Mus musculus], 2013, 2 pages.
Gong and Yeh, "Identification of the Activating and Conjugating Enzymes of the NEDD8 Conjugation Pathway," *J. Biol. Chem.*, 1999, vol. 274, No. 17, pp. 12036-12042.
Huang, D.T., et al., "A unique E1-E2 interaction required for optimal conjugation of the ubiquitin-like protein NEDD8," *Nature Structural & Molecular Biology*, 2004, vol. 11, No. 10, pp. 927-935.
Huang, D.T., et al., "Ubiquitin-like protein activation," *Oncogene*, 2004, vol. 23, pp. 1958-1971.
Huang, D.T., et al., "Basis for a ubiquitin-like protein thioester switch toggling E1-E2 affinity," *Nature*, 2007, vol. 445, pp. 394-398.
Huang, D.T., et al., "E2-RING Expansion of the NEDD8 Cascade Confers Specificity to Cullin Modification," *Molecular Cell*, 2009, vol. 33, pp. 483-495.
Huang, G., et al., "SCCRO (DCUN1D1) Promotes Nuclear Translocation and Assembly of the Neddylation E3 Complex," *J. Biol. Chem.*, 2011, vol. 286, No. 12, pp. 10297-10304.
Kim, A.Y., et al., "SCCRO (DCUN1D1) is an Essential Component of the E3 Complex for Neddylaytion," *J. Biol. Chem.*, 2008, vol. 283, No. 48, pp. 33211-33220.
Kurz, T., et al., "The conserved protein DCN-1/Dcn1p is required for cullin neddylation in *C. elegans* and *S. cerevisiae*," *Nature*, 2005, vol. 435, pp. 1257-1261.
Kurz, T., et al., "Dcn1 Functions as a Scaffold-Type E3 Ligase for Cullin Neddylation," *Molecular Cell*, 2008, vol. 29, No. 1, pp. 23-35.
Lammer, D., et al., "Modification of yeast Cdc53p by the ubiquitin-related protein Rub1p affects function of the $SCF^{Cdc4}$ complex," *Genes & Development*, 1998, vol. 12, pp. 914-926.
Liakopoulos, D., et al., "A novel protein modification pathway related to the ubiquitin system," *EMBO J.*, 1998, vol. 17, No. 8, pp. 2208-2214.
Long, Y-Q., et al., "α-Helix Stabilized Peptides via an all Hydrocarbon-staple Conferring an Improved Inhibitory Activity against 3'-Processing of HIV-1 Integrase," *Proceedings of the 4th International Peptide Symposium in conjunction with the 7th Australian Peptide Conference and the 2nd Asia-Pacific International Peptide Symposium*, 2007, pp. 1-2.
O-Charoenrat, P., et al., "SCCRO (*DCUN1D1*) Induces Extracellular Matrix Invasion by Activating Matrix Metalloproteinase 2," *Clin. Cancer Res.*, 2008, vol. 14, No. 21, pp. 6780-6789.
Osaka, F., et al., "A new NEDD8-ligating system for cullin-4A," *Genes & Development*, 1998, vol. 12, pp. 2263-2268.
Podust, V.N., et al., "A Nedd8 conjugation pathway is essential for proteolytic targeting of $p27^{KiP1}$ by ubiquitination," *Proc. Natl. Aca. Sci. USA*, 2000, vol. 97, No. 9, pp. 4579-4584.
Polevoda and Sherman, "NatC $N^\alpha$-terminal Acetyltransferase of Yeast Contains Three Subunits, Mak3p, Mak10p, and Mak31p," *J. Biol. Chem.*, 2001, vol. 276, No. 23, pp. 20154-20159.
Polevoda and Sherman, "N-terminal Acetyltransferases and Sequence Requirements for N-terminal Acetylation of Eukaryotic Proteins," *J. Mol. Biol.*, 2003, vol. 325, No. 4, pp. 595-622.
Read, M.A., et al., "Nedd8 Modification of Cul-1 Activates $SCF^{\beta TrCP}$-Dependent Ubiquitination of IκBα," *Molecular and Cell Biology*, 2000, vol. 20, No. 7, pp. 2326-2333.
Ribert and Cossart, "Pathogen-Mediated Posttranslational Modifications: A Re-emerging Field," *Cell*, 2010, vol. 143, pp. 694-702.
Sarkaria, I., et al., "SCCRO Expression Correlates With Invasive Progression in Bronchioloalveolar Carcinoma," *Ann. Thorac. Surg.*, 2004, vol. 78, pp. 1734-1741.
Sarkaria, I., et al., "Squamous Cell Carcinoma Related Oncogene/DCUN1D1 is Highly Conserved and Activated by Amplification in Squamous Cell Carcinomas," *Cancer Res.*, 2006, vol. 66, No. 19, pp. 9437-9444.
Schafmeister, C.E., et al., "An All-Hydrocarbon Cross-Linking System for Enhancing the Helicity and Metabolic Stability of Peptides," *J. Am. Chem. Soc.*, 2000, vol. 122, pp. 5891-5892.
Scott, D.C., et al., "A Dual E3 Mechanism for Rub1 Ligation to Cdc53," *Molecular Cell*, 2010, vol. 39, No. 5, pp. 784-796.
Scott, D.C., et al., "N-Terminal Acetylation Acts as an Avidity Enhancer Within an Interconnected Multiprotein Complex," *Science*, 2011, vol. 334, No. 6056, pp. 674-678.
Scott, D.C., et al., "A Dual E3 Mechanism for Rub1 Ligation to Cdc53," Cold Spring Harbor Laboratory Meeting on the Ubiquitin Family, May 17-21, 2011, p. 3.
Soucy, T.A., et al., "An inhibitor of NEDD8-activating enzyme as a new approach to treat cancer," *Nature*, 2009, vol. 458, pp. 732-736.
Structural Bioinformatics Research Collaboratory for Structural Bioinformatics Protein Data Bank Accession No. 3TDI, "Yeast Cul1WHB-DCN1P Acetylated UBC12N Complex," 2011.
Structural Bioinformatics Research Collaboratory for Structural Bioinformatics Protein Data Bank Accession No. 3TDU, "N-Terminal Acetylation Acts as an Avidity Enhancer Within an Interconnected Multiprotein Complex Structure of a Human Cul1 WHB-DCN1P-Acetylated UBC12N Complex," 2011.
Structural Bioinformatics Research Collaboratory for Structural Bioinformatics Protein Data Bank Accession No. 3TDZ, "N-Terminal Acetylation Acts as an Avidity Enhancer Within an Interconnected Multiprotein Complex Structure of a Human Cul1WHB-DCN1P-Stapled Acetylated UBC12N Complex," 2011.
Talbot, S.G., et al., "Squamous Cell Carcinoma Related Oncogene Regulates Angiogenesis through Vascular Endothelial Growth Factor-A," *Annals of Surgical Oncology*, 2004, vol. 11, No. 5, pp. 530-534.
Zheng, N., et al., "Structure of the Cul1-Rbx1-Skp1-$Fbox^{Skp2}$ SCF ubiquitin ligase complex," *Nature*, 2002, vol. 416, No. 6882, pp. 703-709.
Tanaka, T., et al., "Inhibition of NEDD8-conjugation pathway by novel molecules: Potential approaches to anticancer therapy," *Molecular Oncology*, 2012, vol. 6, No. 3, pp. 267-275.
Yang, X., et al., "Structural Basis for the Function of DCN-1 in Protein Neddylation," *J. Biol. Chem.*, 2007, vol. 282, No. 34, pp. 24490-24494.

METHODS AND COMPOSITIONS FOR INHIBITING NEDDYLATION OF PROTEINS

CROSS-REFERENCE TO RELATED APPLICATIONS

This application is the U.S. National Stage of International Application No. PCT/US2012/038127, filed May 16, 2012, which claims the benefit of U.S. Provisional Patent Application No. 61/486,972, filed May 17, 2011, both of which are hereby incorporated by reference in their entirety.

FEDERALLY SPONSORED RESEARCH OR DEVELOPMENT

This invention was made with United States Government support under grant number R01GM069530 awarded by the National Institutes of Health. The United States Government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named amended439490SEQLIST.TXT, created on Feb. 1, 2014, and having a size of 246 kilobytes and is filed with the Preliminary Amendment filed on Feb. 4, 2014. The sequence listing contained in this ASCII formatted document is part of the specification and is herein incorporated by reference in its entirety.

FIELD OF THE INVENTION

The present invention relates to the inhibition of covalent modifications of proteins through conjugation with other proteins; particularly, neuronal precursor cell expressed developmentally downregulated protein 8 (NEDD8).

BACKGROUND OF THE INVENTION

Post-translational covalent modifications of proteins through conjugation with other proteins is an important biological mechanism for regulating protein metabolism and biological activity. The most well understood post-translational modifier is ubiquitin, an 8.5 kDa protein, that is covalently attached to lysines in a target protein. Polyubiquitination of a protein targets the protein for degradation.

Ubiquitin is conjugated to its target proteins through an enzymatic cascade involving a specific E1 activating enzyme, Uba1 or Uba6, a conjugating enzyme from the family of E2s, and a ubiquitin ligase that is typically from either the RING or HECT classes of E3s (Huang et al. (2004) *Oncogene* 23:1958-71). Target specificity is controlled by the particular combination of E2 and E3 proteins. For example, the multi-protein ubiquitin E3 ligase Skp, cullin, F-box containing complexes (SCFs) ubiquitinate targets involved in cell-cycle progression, transcription, metabolism, and inflammation, such as the cyclin-dependent kinase (CDK) inhibitor p27$^{Kip1}$ and NFκB inhibitor. IkappaB (IκB).

Other proteins that are structurally similar to ubiquitin and are referred to as ubiquitin-like proteins (UBLs) have been identified that covalently modify cellular targets using their own pathways that are parallel to that of ubiquitin. Examples of UBLs include small ubiquitin-like modifier (SUMO) and neuronal precursor cell expressed developmentally downregulated protein 8 (NEDD8). Similar to ubiquitin, UBLs are covalently attached to a lysine on a target protein via an isopeptide linkage with a C-terminal glycine of the UBL, a process that is mediated via an E1 activating enzyme, E2 conjugating enzyme, and an E3 ligase.

The covalent modification of a target protein with the UBL NEDD8 is referred to herein as neddylation. The neddylation of cullin proteins, the best understood targets of NEDD8, is necessary for SCF-mediated ubiquitination and subsequent degradation of SCF target proteins (Podust et al. (2000) *Proc Natl Acad Sci USA* 97:4579-4584; Read et al. (2000) *Mol Cell Biol* 20:2326-2333). SCFs form a subset of cullin-containing ubiquitin E3s. Members of the large family of cullin-containing E3s are called cullin-RING E3s, and contain CUL1, CUL2, Cul3, CUL4A, CUL5, CUL7, or Parc, which are regulated by covalent ligation of NEDD8. Not surprisingly, the NEDD8 pathway enzymes play an essential role in cell proliferation in organisms ranging from fission yeast to mammals (Osaka et al. (2000) *EMBO J.* 19:3475-3484; Tateishi et al. (2001) *J Cell Biol* 155:571-579). Given the importance of NEDD8 conjugation in cell growth and inflammation, further characterization of NEDD8 pathway enzymes and the domains with which they use to interact with one another is needed in order to develop therapeutics that target the neddylation pathway for the treatment of disorders such as cancer and inflammatory diseases.

BRIEF SUMMARY OF THE INVENTION

A novel binding pocket within NEDD8 co-E3 proteins that binds NEDD8 E2 enzymes is provided. Methods are provided for screening for compounds that bind to the disclosed E2-binding pocket in NEDD8 co-E3 proteins, including computational methods and binding assays. In some embodiments, compounds that bind to the pocket inhibit the activity of NEDD8 co-E3 proteins and the subsequent neddylation of protein targets. Compounds (e.g., peptides and small molecules) that bind to the E2-binding pocket and optionally inhibit the activity of NEDD8 co-E3 proteins and pharmaceutical compositions comprising the same are provided. In some embodiments, the inhibitory peptides are amino-terminally acetylated. Methods for inhibiting NEDD8 co-E3 activity and inhibiting cell growth with the NEDD8 co-E3 inhibitors are provided, as well as methods for treating cancer, inflammatory disorders, or pathogenic infections by administering the disclosed NEDD8 co-E3 inhibitors to a subject in need thereof.

These and other aspects of the invention are disclosed in more detail in the description of the invention given below.

BRIEF DESCRIPTION OF THE FIGURES

FIG. 9A presents phosphoimager data of pulse-chase assays monitoring the transfer of NEDD8 from 40 nM Ubc12$^{AcMet}$~NEDD8 to 125 nM Cul1$^{CTD}$-Rbx1 in the absence or presence of 125 nM DCUN1D1$^P$ and the indicated amounts of the peptide inhibitor Acetyl-yUbc12$^{1-12}$ (6:10 Staple).

FIG. 9B provides quantification of FIG. 9A. The amount of Cul1$^{CTD}$~NEDD8 formed at each time point was quantified and normalized with the amount of Cul1$^{CTD}$~NEDD8 formed at two minutes in the presence of DCUN1D1$^P$ and absence of inhibitor set to one.

DETAILED DESCRIPTION OF THE INVENTION

Figure 1A:
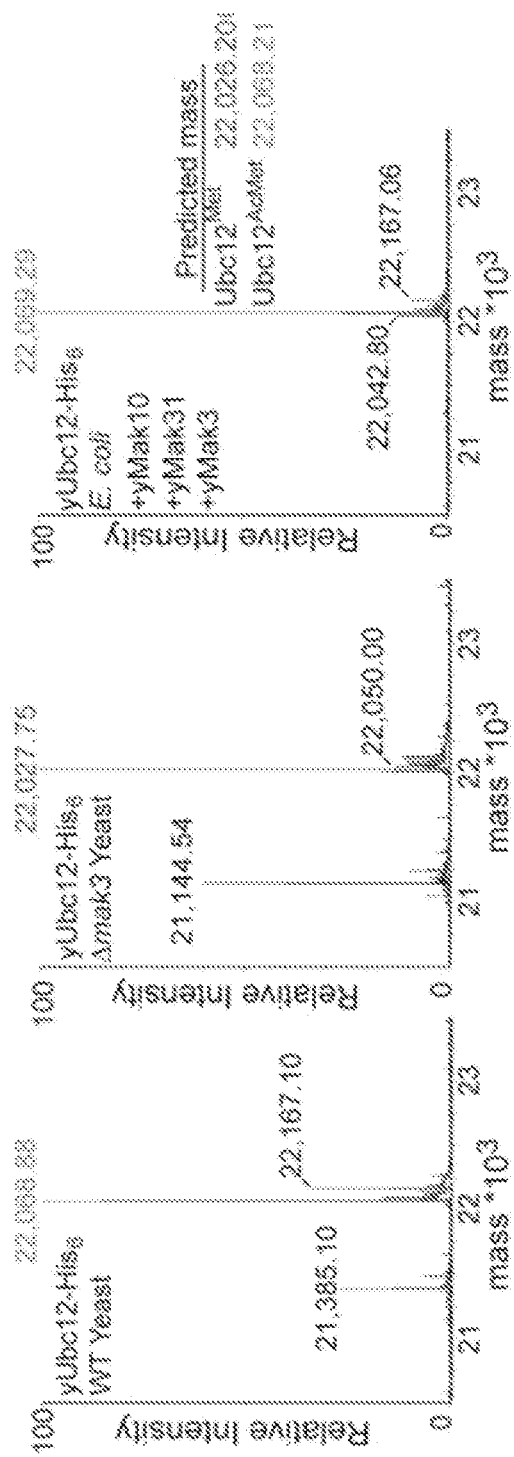
FIG. 1A provides MaxEnt liquid chromatography-time of flight (LC-TOF) spectra of *S. cerevisiae* yUbc12-His6 purified from WT yeast (left), Δmak3 yeast (middle), or from coexpression with yeast NatC subunits in *E. coli* (right).

A novel binding pocket in NEDD8 co-E3 proteins that interacts with the amino-terminal (N-terminal) extension of N-terminally acetylated NEDD8 E2 conjugating enzymes is provided. The disclosed E2-binding pocket of NEDD8 co-E3 proteins finds use in methods for identifying inhibitors of the neddylation cascade. Compounds (e.g., peptides, small molecules) that bind to the disclosed binding pocket and inhibit co-E3 activity are provided herein. These co-E3 inhibitors find use in treating diseases such as cancer, inflammatory disorders, and pathogenic infections.

As used herein, the terms "NEDD8" and "neuronal precursor cell expressed developmentally downregulated protein 8" refer to a member of the family of ubiquitin-like proteins (UBLs) that is covalently attached to target proteins. The human, mouse, and rat NEDD8 sequences are each 81 amino acids in length and are about 6 kDa. The terms "NEDD8" and "neuronal precursor cell expressed developmentally down-regulated protein 8" also refer to the *Saccharomyces cerevisiae* Rub1 protein. Nucleotide and amino acid sequences of NEDD8 proteins are known in the art. Non-limiting examples of NEDD8 sequences include *Homo sapiens* NEDD8, the nucleotide and amino acid sequences of which are set forth in GenBank Acc. Nos. NM_006156 and NP_006147, respectively (and in SEQ ID NOs: 50 and 51, respectively); *Mus musculus* NEDD8, the nucleotide and amino acid sequences of which are set forth in GenBank Acc. Nos. NM_008683 and NP_032709, respectively (and in SEQ ID NOs: 52 and 53, respectively) (Kamitani et al. (1997) *J Biol Chem* 272:28557-28562; Kumar et al. (1992) *Biochem Biophys Res Comm* 185:1155-1161, each of which are herein incorporated by reference in its entirety); and *Saccharomyces cerevisiae* Rub1, the nucleotide and amino acid sequences of which are set forth in GenBank Acc. Nos. Y16890 and CAA76516, respectively (and in SEQ ID NOs: 72 and 73, respectively).

NEDD8 is conjugated to its protein targets through a series of enzymatic reactions similar to other E1-E2-E3 ubiquitin-like (UBL) conjugation cascades. First, NEDD8 is activated in an ATP-dependent manner by an E1 enzyme, NEDD8 activating enzyme (NAE), which is a heterodimer of NAE1 and UBA3 subunits.

As used herein, the terms "NAE," "NEDD8 activating enzyme," "NEDD8 E 1 activating enzyme," and "NEDD8 E1 enzyme" refer to a protein capable of catalyzing the transfer of NEDD8's C terminus to the catalytic cysteine of NEDD8 E2, forming a thiolester-linked E2-NEDD8 intermediate (Gong and Yeh (1999) *J Biol Chem* 274:12036-12042; and Liakopoulos et al. (1998) *EMBO J* 17:2208-2214; Osaka et al. (1998) *Genes Dev* 12:2263-2268, each of which are herein incorporated by reference in its entirety).

The only described NEDD8 E1 enzyme is a heterodimer of NAE1 (also referred to as APPBP1; amyloid beta precursor protein binding protein 1; and NEDD8-activating enzyme E1 regulatory subunit) and UBA3 (also referred to as NEDD8-activating enzyme E1 catalytic subunit or UBEC1) subunits. Nucleotide and amino acid sequences of NAE1 proteins are known in the art. Non-limiting examples of NAE1 sequences include *Homo sapiens* NAE1, the nucleotide and amino acid sequences of which are set forth in GenBank Acc. Nos. NM_001018159 and NP_001018169, respectively (and in SEQ ID NOs: 54 and 55, respectively); and *Mus musculus* NAE1, the nucleotide and amino acid sequences of which are set forth in GenBank Acc, Nos. NM_144931 and NP_659180, respectively (and in SEQ ID NOs: 56 and 57, respectively). In some embodiments of the presently disclosed invention, the NAE1 has the sequence set forth in SEQ ID NO: 55 or 57, or a biologically active fragment or variant thereof that is capable of interacting with UBA3.

Nucleotide and amino acid sequences of UBA3 proteins are also known in the art. Non-limiting examples of UBA3 sequences include *Homo sapiens* UBA3, the nucleotide and amino acid sequences of which are set forth in GenBank Acc. Nos. NM_003968 and NP_003959, respectively (and in SEQ ID NOs: 58 and 59, respectively); and *Mus musculus* UBA3, the nucleotide and amino acid sequences of which are set forth in GenBank Acc. Nos. NM_011666 and NP_035796, respectively (and in SEQ ID NOs: 60 and 61, respectively). The rat, *Xenopus tropicalis*, zebrafish (*Danio rerio*), *Schizosaccharomyces pombe*, and *Saccharomyces cerevisiae* UBA3 amino acid sequences are set forth in SEQ ID NOs: 74, 75, 76, 77, and 78, respectively. In some embodiments of the presently disclosed invention, the NEDD8 UBA3 protein has the sequence set forth in SEQ ID NO: 59, 61, 74, 75, 76, 77, or 78, or a biologically active variant thereof that is capable of interacting with NAE1 and catalyzing a reaction culminating in the generation of a thiolester-linked E2-NEDD8 intermediate.

Figure 4:
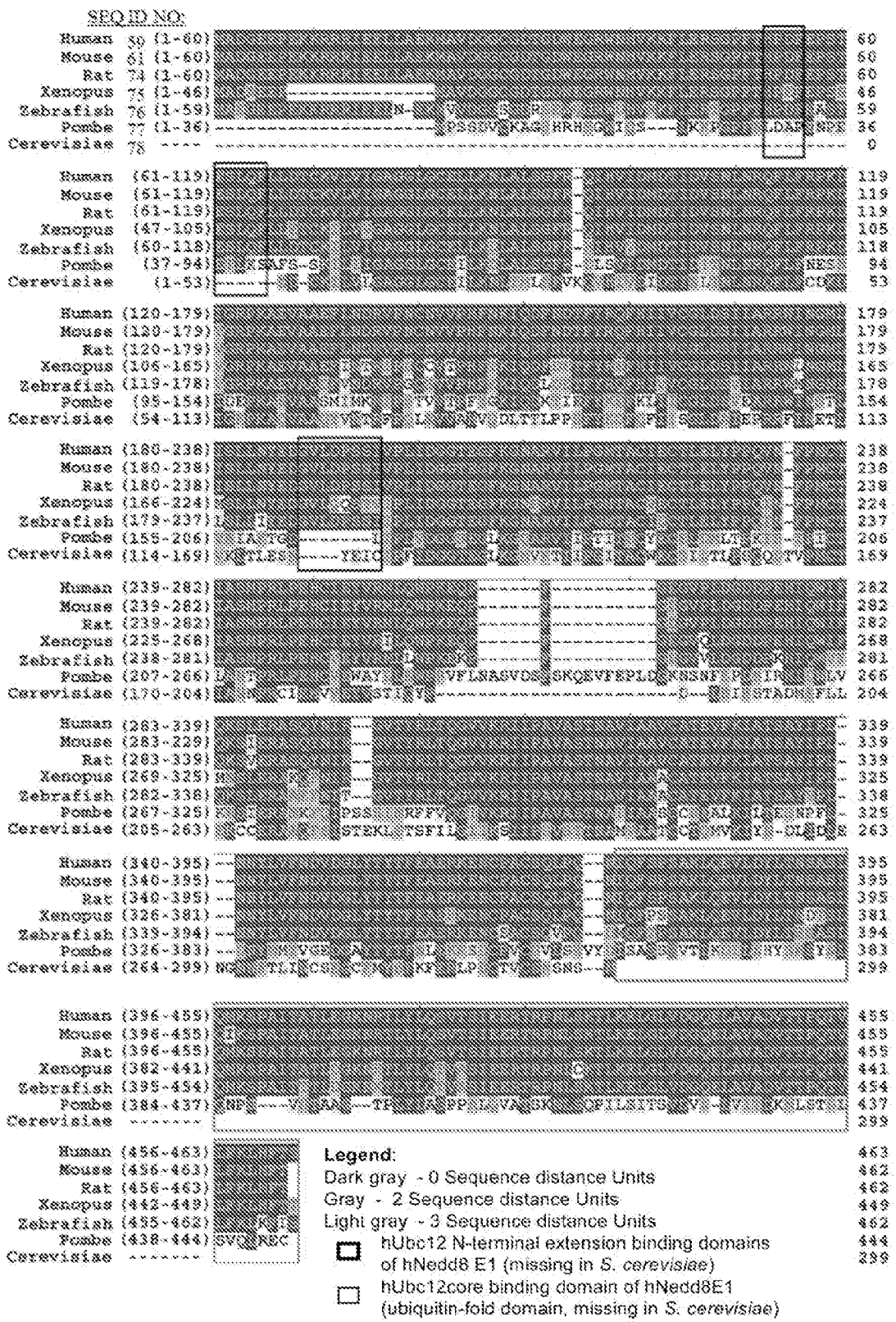
FIG. 4 provides a sequence alignment of Uba3, the Ubc12-binding subunit of NEDD8's E1 enzyme. The ClustalW sequence alignment was generated in MegAlign of Uba3, the Ubc12-binding subunit of NEDD8's heterodimeric E1 enzyme, from human (SEQ ID NO: 59), mouse (SEQ ID NO: 61), rat (SEQ ID NO: 74, *Xenopus tropicalis* (SEQ ID NO: 75), zebrafish (SEQ ID NO: 76), *S. pombe* (SEQ ID NO: 77), and *S. cerevisiae* (SEQ ID NO: 78). Boxes indicate Ubc12-interacting regions identified in crystal structures of human Uba3 complexes with Ubc12 (Huang et al. (2004) *Nat Struct Mol Biol* 11(10):927-935; Huang et al. (2007) *Nature* 445(7126):394-398), which are notably absent from *S. cerevisiae* Uba3p. Black boxes encircling the alignment indicate regions of hUba3 interacting with hUbc12's N-terminal extension. Gray boxes encircling the alignment correspond to Uba3's ubiquitin-fold domain, known to bind the catalytic domain of Ubc12.

Crystal structures of human Uba3 complexes with the NEDD8 E2 enzyme Ubc12 have been solved (Huang et al. (2004) *Nat Struct Mol Biol* 11(10):927-935; Huang et al. (2007) *Nature* 445(7126):394-398), which aided in identifying the Ubc12-interacting regions of NEDD8 E1 enzymes. FIG. 4 provides an alignment of UBA3 proteins from various organisms, highlighting the regions of human Uba3 that interact with human Ubc12's N-terminal extension and Uba3's ubiquitin-fold domain, which binds the catalytic domain of Ubc12.

NEDD8 E2 enzymes play central roles in the E1-E2-E3 NEDD8 conjugation cascade. As used herein, the terms "NEDD8 conjugating enzyme," and "NEDD8 E2 enzyme" refer to a protein capable of transiently binding a NEDD8 E 1 enzyme for generation of a thiolester-linked E2~UBL intermediate (~ denotes covalent complex; -denotes noncovalent complex) and interacting with a NEDD8 E3 ligase as an E2~UBL intermediate. The two known NEDD8 conjugating enzymes are UBC12, which is also known as UBE2M, and UBE2F. Nucleotide and amino acid sequences of UBC12 proteins are known in the art. Non-limiting examples of UBC12 sequences include *Homo sapiens* UBC12 (also known as UBE2M), the nucleotide and amino acid sequences of which are set forth in GenBank Acc. Nos. NM_003969 and NP_003960, respectively (and in SEQ ID NOs: 1 and 2, respectively); *Mus musculus* UBC12, the nucleotide and amino acid sequences of which are set forth in GenBank Acc. Nos. NM_145578 and NP_663553, respectively (and in SEQ ID NOs: 62 and 63, respectively); and *Saccharomyces cerevisiae* UBC12, the nucleotide and amino acid seqeunces of which are set forth in GenBank Acc. Nos. NM_001182194 and NP_013409, respectively (and in SEQ ID NOs: 5 and 6, respectively).

Nucleotide and amino acid sequences of UBE2F proteins are known in the art. Non-limiting examples of UBE2F sequences include *Homo sapiens* UBE2F, the nucleotide and amino acid sequences of which are set forth in GenBank Acc. Nos. NM_080678 and NP_542409, respectively (and in SEQ ID NOs: 3 and 4, respectively); and *Mus musculus* UBE2F, the nucleotide and amino acid sequences of which are set forth in GenBank Acc. Nos, NM_026454 and NP_080730, respectively (and in SEQ ID NOs: 64 and 65, respectively). In some embodiments of the presently disclosed invention, the NEDD8 E2 enzyme has the sequence set forth in SEQ ID NO: 2, 4, 6, 63, or 65, or a biologically active fragment or variant thereof capable of transiently binding a NEDD8 E1 enzyme for generation of a thiolester-linked E2~UBL, intermediate and interacting with a NEDD8 E3 ligase as an E2~UBL intermediate.

NEDD8 E2 enzymes have an about 20 to about 29-residue N-terminal extension upstream of its about 150-residue conserved E2 core domain, which contains the E2 catalytic cysteine. Ubc12's N-terminal sequence is conserved across species, but is not found in other E2 enzymes and is therefore, unique to the NEDD8 pathway. NEDD8 E2 enzymes interact with both NEDD8 E1 and co-E3 proteins via its unique N-terminal extension. As disclosed herein, acetylation of the amino terminus of the N-terminal extension of NEDD8 E2 enzymes enhances binding of yeast Ubc12 to NEDD8 co-E3 proteins and is necessary for binding of mammalian NEDD8 E2 enzymes to co-E3 proteins, but does not affect binding of NEDD8 E2 enzymes to NEDD8 E1 proteins.

Unlike other ubiquitin like proteins known to date, NEDD8 transfer from NEDD8 E2 enzymes to target proteins involves a "dual E3" mechanism (Scott et al. (2010) *Mol Cell* 39(5):784-796): a RING E3 ligase, Rbx1, is essential for target protein neddylation; an auxiliary co-E3, Dcn1, contains a "potentiating neddylation" domain (Dcn1$^P$) thought to bind different regions of Ubc12 and target proteins from Rbx1 (Kim et al. (2008) *J Biol Chem* 283(48):33211-33220; Scott et al. (2010) *Mol Cell* 39(5): 784-796; Kurz et al. (2005) *Nature* 435(7046):1257-1261; and Huang et al. (2011) *J Biol Chem*, each of which is herein incorporated by reference in its entirety).

As used herein, the terms "NEDD8 E3 ligase" and "NEDD8 E3 enzyme" refer to RING domain NEDD8 E3 ligases capable of interacting with an E2~NEDD8 intermediate and catalyzing the transfer of NEDD8 from the E2 NEDD8 intermediate to an E3-associated target's lysine, producing an isopeptide-bonded target~NEDD8 complex; or HECT domain NEDD8 E3 ligases capable of forming an E3~NEDD8 thiolester intermediate and catalyzing the subsequent transfer of NEDD8 onto a target's lysine. The only known NEDD8 E3 ligase is a RING domain E3 ligase. Nucleotide and amino acid sequences of NEDD8 E3 ligases are known in the art. Non-limiting examples of NEDD8 E3 ligase sequences include *Homo sapiens* Rbx1, the nucleotide and amino acid sequences of which are set forth in GenBank Acc. Nos. NM_014248 and NP_055063, respectively (and in SEQ ID NOs: 66 and 67, respectively); *Mus musculus* Rbx1, the nucleotide and amino acid sequences of which are set forth in GenBank Acc. Nos. NM_019712 and NP_062686, respectively (and in SEQ ID NOs: 68 and 69, respectively); and *Saccharomyces cerevisiae* Hrt1, the amino acid sequence of which is set forth in SEQ ID NO: 86. In some embodiments of the presently disclosed invention, the NEDD8 E3 ligase has the sequence set forth in SEQ ID NO: 67, 69, or 86, or a biologically active fragment or variant thereof that is capable of interacting with an E2~NEDD8 intermediate and catalyzing the transfer of NEDD8 onto a target's lysine.

The amino terminus of Hrt1 recruits Cdc53 (yeast cullin ortholog) and the carboxy terminus of Hrt1 comprises the RING domain that activates Ubc12~Rub1 (Rub1 is a NEDD8 ortholog).

As used herein, the terms "NEDD8 co-E3" and "NEDD8 co-E3 protein" refer to a protein capable of interacting with an E2~NEDD8 intermediate and catalyzing the transfer of NEDD8 from the E2~NEDD8 intermediate to an E3-associated target's lysine, wherein the protein does not comprise a RING or HECT domain. A structural model of the Dcn1-Cdc53-Hrt1-Ubc12 complex has been prepared and it suggests that Dcn1 restricts the otherwise flexible RING-Ubc12~Rub1 into a catalytically competent orientation, bringing Ubc12's active site toward Cdc53 (Scott et al. (2010) *Mol Cell* 39:784-796, which is herein incorporated by reference in its entirety). Thus, the term "co-E3 activity" refers to the ability to interact with an E2~NEDD8 intermediate and catalyze the transfer of NEDD8 from the E2~NEDD8 intermediate to an E3-associated target's lysine in the absence of a RING or HECT domain; to enhance the activity of a RING or HECT domain NEDD8 E3 ligase; or to reduce nonspecific E2 NEDD8 discharge, which refers to the transfer of NEDD8 from an E2 catalytic cysteine to a nucleophile, such as a primary amine. Thus, in some embodiments, a NEDD8 co-E3 increases the catalytic rate ($k_{cat}$) of the NEDD8 E3 ligase reaction. In particular embodiments, the $k_{cat}$ of a NEDD8 E3 ligase reaction is increased by about 2-fold, 3-fold, 4-fold, 5-fold, 10-fold, 15-fold, 20-fold, 25-fold, 30-fold, 35-fold, 40-fold, 50-fold, 100-fold, or greater by a NEDD8 co-E3 ligase.

Nucleotide and amino acid sequences of NEDD8 co-E3 proteins are known in the art. Non-limiting examples of NEDD8 co-E3 sequences include *Saccharomyces cerevisiae* Dcn1, the nucleotide and amino acid sequences of which are set forth in GenBank Acc. Nos. NM_001182015 and NP_013229, respectively (and in SEQ ID NOs: 47 and 48, respectively); *Homo sapiens* DCUN1D1 (which is also referred to herein as squamous cell carcinoma-related oncogene or SCCRO or Dcn1), the nucleotide and amino acid sequences of which are set forth in GenBank Acc. Nos. NM_020640 and NP_065691, respectively (and in SEQ ID NOs: 32 and 33, respectively); *Mus musculus* DCUN1D1 (also referred to herein as Dcn1), the nucleotide and amino acid sequences of which are set forth in GenBank Acc. Nos. NM_001205361 and NP_001192290, respectively (and in SEQ ID NOs: 70 and 71, respectively); *Homo sapiens* DCUN1D2 (also referred to herein as Dcn2), the nucleotide and amino acid sequences of which are set forth in GenBank Acc. Nos. NM_001014283 and NP_001014305, respectively (and in SEQ ID NOs: 35 and 36, respectively); *Homo sapiens* DCUN1D3 (also referred to herein as Dcn3), the nucleotide and amino acid sequences of which are set forth in GenBank Acc. Nos. NM_173475.2 and NP_775746.1, respectively (and in SEQ ID NOs: 38 and 39, respectively); *Homo sapiens* DCUN1D4 (also referred to herein as Dcn4), the nucleotide and amino acid sequences of which are set forth in GenBank Acc. Nos. NM_001040402 and NP_001035492, respectively (and in SEQ ID NOs: 41 and 42, respectively); and *Homo sapiens* DCUN1D5 (also referred to herein as Dcn5), the nucleotide and amino acid sequences of which are set forth in GenBank Acc. Nos. NM_032299.3 and NP_115675, respectively (and in SEQ ID NOs: 44 and 45, respectively). In some embodiments of the presently disclosed invention, the NEDD8 co-E3 protein has the sequence set forth in SEQ ID NO: 33, 36, 39, 42, 45, 48, or 71, or a biologically active fragment or variant thereof having co-E3 activity.

Dcn1 and other known NEDD8 co-E3 ligases comprise an amino-terminal ubiquitin associated (UBA) domain (residues 57-69 of yeast Dcn1, the sequence of which is set forth in SEQ ID NO: 48), followed by a disordered linker and a carboxy-terminal "potentiating neddylation" (PONY) domain. The PONY domain of co-E3 ligases, such as Dcn1, is sufficient for binding a NEDD8 E2 (Ubc12) and Cdc53/cullin proteins and for enhancing Cdc53~Rub1 levels (Kurz et al. (2008) *Mol Cell* 29:23-35). The PONY domain of *Homo sapiens* DCUN1D1, DCUN1D2, DCUN1D3, DCUN1D4, DCUN1D5, and *Saccharomyces cerevisiae* Dcn1 is set forth in SEQ ID NOs: 34, 37, 40, 43, 46, and 49, respectively. An alignment of the potentiating neddylation domain from *S. cerevisiae* Dcn1, and human Dcn1, Dcn2, Dcn3, Dcn4, and Dcn5 is provided in FIG. 6, which highlights those residues that form contacts with acetylated *S. cerevisiae* Ubc12$^{1-24}$ or acetylated human Ubc12$^{1-15}$ or with cullin. A further description of the interactions between NEDD8 E2 and co-E3 ligases is provided elsewhere herein.

The most well-characterized neddylated proteins are cullin proteins. As used herein, the term "cullin" refers to a protein belonging to a family of hydrophobic proteins that serve as scaffolds for ubiquitin ligases, such as the Skp, cullin, F-box containing (SCF) ubiquitin ligase. There are 7 known cullin proteins, cullin 1 (also referred to herein as CUL1), cullin 2 (also referred to herein as CUL2), cullin 3 (also referred to herein as CUL3), cullin 4A (also referred to herein as CUL4A), cullin 4B (also referred to herein as CUL4B), cullin 5 (also referred to herein as CUL5), and cullin 7 (also referred to herein as CUL7). The amino acid sequences of human CUL1, CUL2, CUL3, CUL4A, CUL4B, CUL5, and CUL7 are set forth herein as SEQ ID NOs: 79, 80, 81, 82, 83, 84, and 85, respectively. The term "cullin" also refers to the *S. cerevisiae* Cdc53 ortholog. The yeast Cdc53 protein has a C-terminal domain comprised of several subdomains: a four-helix bundle (4HB) that connects to the N-terminal domain, an α/β-subdomain that binds Rbx1's N-terminal strand, and a C-terminal winged-helix subdomain (WHB) that contains the Rub1 acceptor Lys760. Cdc53's N-terminal region binds Skp1-F box protein complexes, which recruit substrates for ubiquitination and the Cdc53's C-terminal region binds the RING protein Hrt1 (Kamura et al. (1999) *Science* 284:657-661; Ohta et al. (1999) *Mol Cell* 3:535-541; Seol et al. (1999) *Genes Dev* 13:1614-1626; Skowyra et al. (1999) *Science* 284:662-665; Tan et al. (1999) *Mol Cell* 3:527-533; each of which are herein incorporated by reference in its entirety). The WHB subdomain of cullin proteins are important for Dcn1 binding (Kurz et al. (2008) *Mol Cell* 29:23-35).

The presently disclosed invention involves biologically active fragments and variants of the various NEDD8 E1, E2, E3, or co-E3 proteins, or of peptides that bind to the E2-binding pocket of co-E3 proteins and optionally inhibit its activity. As used herein "biologically active" fragments or variants of a polypeptide or a nucleotide sequence encoding the same that is useful in the methods of the invention retains substantially the same function as the respective native sequence. For example, a biologically active fragment or variant of a NEDD8 E2 enzyme is one that retains the ability to transiently bind a NEDD8 E1 enzyme for generation of a thiolester-linked E2-UBL intermediate and interact with a NEDD8 E3 ligase as an E2-UBL intermediate. Such nucleotide sequence fragments can comprise at least about 10, at least about 15, at least about 20, at least about 50, at least about 60, at least about 80, at least about 100, at least about 150, at least about 200, at least about 300, at least about 400, at least about 500, at least about 600, at least about 700, at least about 800, at least about 900, at least about 1,000, at least about 1,500, at least about 2,000, at least about 2,500, at least about 3,000, at least about 3,500, at least about 4,000, at least about 4,500, at least about 5,000 contiguous nucleotides or up to the entire contiguous nucleotides of the nucleotide sequence of interest. Biologically active polypeptide fragments can comprise at least about 5, at least about 10, at least about 15, at least about 20, at least about 50, at least about 60, at least about 80, at least about 100, at least about 150, at least about 200, at least about 300, at least about 400, at least about 500, at least about 600, at least about 700, at least about 800, at least about 900, at least about 1,000 contiguous amino acid residues or up to the entire contiguous amino acid residues of the polypeptide. Methods for obtaining such fragments are known in the art and are described in further detail elsewhere herein.

By "variant" is intended substantially similar sequences. Thus, for nucleotide sequences or amino acid sequences, variants include sequences that are functionally equivalent to the nucleotide sequence of interest. Variant nucleotide sequences also include synthetically derived nucleotide sequences that have been generated, for example, by site directed mutagenesis but which still retain the function of the native sequence. Generally, nucleotide sequence variants or amino acid sequence variants of the invention will have at least 40%, at least about 50%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to its respective native nucleotide or amino acid sequence. As discussed elsewhere herein, variants of the nucleotide sequences can encode amino acid sequences that differ conservatively because of the degeneracy of the genetic code. Methods of determining sequence identity are also discussed elsewhere herein.

With respect to the amino acid sequences for the various full length polypeptides, variants include those polypeptides that are derived from the native polypeptides by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Such variants may result from, for example, genetic polymorphism or from human manipulation. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (2d ed., Cold Spring Harbor Laboratory Press, Plainview, N.Y.); U.S. Pat. No. 4,873,192; and the references cited therein; herein incorporated by reference. Guidance as to appropriate amino acid substitutions that may not affect biological activity of the various vector polypeptide may be found in the model of Dayhoff et al. (1978) *Atlas of Polypeptide Sequence and Structure* (Natl. Biomed. Res. Found., Washington, D.C.), herein incorporated by reference. Conservative substitutions, such as exchanging one amino acid with another having similar properties, may be preferred. The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

By "sequence identity" is intended the same nucleotides or amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. The contiguous segment used for comparison to the reference nucleotide sequence or reference amino acid sequence will comprise at least 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are well known in the art.

The determination of percent identity between two sequences can be accomplished using a mathematical algorithm. For example, percent identity of an amino acid sequence can be determined using the Smith-Waterman homology search algorithm using an affine 6 gap search with a gap open penalty of 12 and a gap extension penalty of 2, BLOSUM matrix 62. Alternatively, percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic Version G. The Smith-Waterman homology search algorithm is taught in Smith and Waterman (1981) *Adv. Appl. Math* 2:482-489, herein incorporated by reference. Alternatively, the alignment program GCG Gap (Wisconsin Genetic Computing Group, Suite Version 10.1) using the default parameters may be used. The GCG Gap program applies the Needleman and Wunch algorithm and for the alignment of nucleotide sequences with an open gap penalty of 3 and an extend gap penalty of 1 may be used. Another preferred, non-limiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 2/5:403. BLAST nucleotide searches can be performed with the NBLAST program, score=100, wordlength 12, to obtain nucleotide sequences having sufficient sequence identity. BLAST protein searches can be performed with the XBLAST program, score=50, wordlength=3, to obtain amino acid sequences having sufficient sequence identity. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See www.ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Provided herein (see Examples I and Table 24) and in Scott et al. (2011) *Science* 334:674-678 and supporting online material, which can be found at www.sciencemag.org/content/suppl/2011/09/21/science.1209307.DC1.html (Scott et al. and its supporting online material is herein incorporated by reference in its entirety), is a description of the production and analysis of crystals of four NEDD8 E2/co-E3 complexes: (1) the PONY domain of *S. cerevisiae* Dcn1 and N-terminally acetylated *S. cerevisiae* Ubc12$^{1-24}$; (2) human Cul1$^{WHB}$, the PONY domain of hDcn1 (Dcn1$^P$), and N-terminally acetylated human Ubc12$^{1-15}$; (3) human Cul1$^{WHB}$, human Dcn1$^P$, and N-terminally acetylated human Ubc12$^{1-12}$ comprising a hydrophobic staple between residues 5 and 9; and (4) the PONY domain of human DCUN1D3 and N-terminally acetylated human Ube2f$^{1-25}$. The solved structures of (1) the PONY domain of *S. cerevisiae* Dcn1 and N-terminally acetylated *S. cerevisiae* Ubc12$^{1-24}$; (2) human Cul1$^{WHB}$, the PONY domain of hDcn1 (Dcn1$^P$), and N-terminally acetylated human Ubc12$^{1-15}$; and (3) human Cul1$^{WHB}$, human Dcn1$^P$, and N-terminally acetylated human Ubc12$^{1-12}$ comprising a hydrophobic staple between residues 5 and 9 have been deposited in the Structural Bioinformatics Research Collaboratory for Structural Bioinformatics Protein Data Bank as accession numbers 3TDI, 3TDU, and 3TDZ, respectively, and each of which are herein incorporated by reference in its entirety.

As used herein, the terms "molecular structure" refer to the arrangement of atoms within a particular object (e.g., polypeptide). A three-dimensional molecular structure of a polypeptide is a representation of the tertiary or quaternary structure of the polypeptide.

As used herein, the term "atomic coordinates" refers to mathematical coordinates (represented as "X," "Y" and "Z" values) that describe the positions of atoms in a crystal of a polypeptide with respect to a chosen crystallographic origin. As used herein, the term "crystallographic origin" refers to a reference point in the crystal unit cell with respect to the crystallographic symmetry operation. These atomic coordinates can be used to generate a three-dimensional representation of the molecular structure of the polypeptide. When referring to an E2-binding pocket having a particular set of atomic coordinates of a particular table provided herein, this refers to both the atom itself as well as its "X", "Y", and "Z" values.

Analysis of the four solved three-dimensional molecular structures led to the identification of a novel NEDD8 E2-binding pocket within NEDD8 co-E3 proteins. As used herein, an "E2-binding pocket" or "NEDD8 E2-binding pocket" of a NEDD8 co-E3 protein is comprised of the atoms of the NEDD8 co-E3 protein that interact with a NEDD8 E2 protein, and in some embodiments, additional atoms of the amino acids comprising the interacting atoms. Those atoms of the NEDD8 co-E3 protein that interact with a NEDD8 E2 protein are those atoms that form a bond (e.g., hydrogen bond, van der Waals interactions), with an atom of a NEDD8 E2 protein.

In some embodiments, the E2-binding pocket of a NEDD8 co-E3 protein comprises the atoms of Table 1, which are found in amino acid residues Ile90, Leu93, Val94, Ile97, Leu104, Glu105, Asp106, Leu107, Thr109, Leu110, Ala113, Leu121, Glu122, Leu173, Ile174, Leu175, Asp176, Gln189, Tyr190, and Leu193 of *S. cerevisiae* Dcn1 (SEQ ID NO: 48), or a structural variant thereof. In particular embodiments, the E2-binding pocket of a NEDD8 co-E3 protein comprises at least one of the following amino acid residues: an isoleucine corresponding to position 90 of SEQ ID NO: 48, a leucine corresponding to position 93 of SEQ ID NO: 48, a valine corresponding to position 94 of SEQ ID NO: 48, an isoleucine corresponding to position 97 of SEQ ID NO: 48, a leucine corresponding to position 104 of SEQ ID NO: 48, a glutamic acid corresponding to position 105 of SEQ ID NO: 48, an aspartic acid corresponding to position 106 of SEQ ID NO: 48, a leucine corresponding to position 107 of SEQ ID NO: 48, a threonine corresponding to position 109 of SEQ ID NO: 48, a leucine corresponding to position 110 of SEQ ID NO: 48, an alanine corresponding to position 113 of SEQ ID NO: 48, a leucine corresponding to position 121 of SEQ ID NO: 48, a glutamic acid corresponding to position 122 of SEQ ID NO: 48, a leucine corresponding to position 173 of SEQ ID NO: 48, an isoleucine corresponding to position 174 of SEQ ID NO: 48, a leucine corresponding to position 175 of SEQ ID NO: 48, an aspartic acid corresponding to position 176 of SEQ ID NO: 48, a glutamine corresponding to position 189 of SEQ ID NO: 48, a tyrosine corresponding to position 190 of SEQ ID NO: 48, and a leucine corresponding to position 193 of SEQ ID NO: 48.

As used herein, an amino acid residue of a NEDD8 co-E3 protein at the position corresponding to a particular amino acid residue of SEQ ID NO: 33, 36, 39, 42, 45, or 48 refers to the amino acid residue within the NEDD8 co-E3 protein that appears opposite the amino acid residue at a particular position in SEQ ID NO: 33, 36, 39, 42, 45, or 48 when the NEDD8 co-E3 protein sequence is aligned with SEQ ID NO: 33, 36, 39, 42, 45, or 48 for maximum homology using an alignment program, such as one known in the art (e.g., the GAP program in the GCG software package, using either a BLOSUM62 matrix or a PAM250 matrix).

In some of these embodiments, the E2-binding pocket comprises the atomic coordinates of Table 2 or 3, or a structural variant thereof. In particular embodiments, the co-E3 protein has the amino acid sequence set forth in SEQ ID NO: 48.

In certain embodiments, the E2-binding pocket of a NEDD8 co-E3 protein comprises the atoms of Table 1 and Table 4. The atoms in Table 4 are found in amino acid residues Asn84, Asp89, Asp91, Gly101, Tyr102, Asn103, and Glu186 of SEQ ID NO: 48. Thus, in some embodiments, the E2-binding pocket of a NEDD8 co-E3 protein comprises at least one of the following amino acid residues: an isoleucine corresponding to position 90 of SEQ ID NO: 48, a leucine corresponding to position 93 of SEQ ID NO: 48, a valine corresponding to position 94 of SEQ ID NO: 48, an isoleucine corresponding to position 97 of SEQ ID NO: 48, a leucine corresponding to position 104 of SEQ ID NO: 48, a glutamic acid corresponding to position 105 of SEQ ID NO: 48, an aspartic acid corresponding to position 106 of SEQ ID NO: 48, a leucine corresponding to position 107 of SEQ ID NO: 48, a threonine corresponding to position 109 of SEQ ID NO: 48, a leucine corresponding to position 110 of SEQ ID NO: 48, an alanine corresponding to position 113 of SEQ ID NO: 48, a leucine corresponding to position 121 of SEQ ID NO: 48, a glutamic acid corresponding to position 122 of SEQ ID NO: 48, a leucine corresponding to position 173 of SEQ ID NO: 48, an isoleucine corresponding to position 174 of SEQ ID NO: 48, a leucine corresponding to position 175 of SEQ ID NO: 48, an aspartic acid corresponding to position 176 of SEQ ID NO: 48, a glutamine corresponding to position 189 of SEQ ID NO: 48, a tyrosine corresponding to position 190 of SEQ ID NO: 48, a leucine corresponding to position 193 of SEQ ID NO: 48, an asparagine corresponding to position 84 of SEQ ID NO: 48; an aspartic acid corresponding to position 89 of SEQ ID NO: 48, an aspartic acid corresponding to position 91 of SEQ ID NO: 48, a glycine corresponding to position 101 of SEQ ID NO: 48, a tyrosine corresponding to position 102 of SEQ ID NO: 48, an asparagine corresponding to position 103 of SEQ ID NO: 48, and a glutamic acid corresponding to position 186 of SEQ ID NO: 48.

In some of these embodiments, the E2-binding pocket comprises the atomic coordinates of Table 2 and 5 or a structural variant thereof. In other embodiments, the E2-binding pocket comprises the atomic coordinates of Table 3 and 6, or a structural variant thereof.

TABLE 1

Minimal contacts between *S. cerevisiae* Dcn1 and *S. cerevisiae* Ubc12 with yUbc12 Chain C interactions with yDcn1$^P$ Chain A and yUbc12 Chain D interactions with yDcn1$^P$ Chain B shown.

| yUbc12 Atom | | | yDcn1 Atom | | Distance (Å) |
|---|---|---|---|---|---|
| Acetyl-Met | 1C | O | Leu | 104A | CB | 4.01 |
| | | | Leu | 104A | O | 4.1 |
| | | | Leu | 104A | CD2 | 4.17 |
| Acetyl-Met | 1C | C | Leu | 104A | O | 3.82 |
| | | | Tyr | 190A | OH | 4.08 |
| Acetyl-Met | 1C | CA | Leu | 104A | O | 3.58 |
| | | | Tyr | 190A | OH | 4.44 |
| | | | Thr | 109A | OG1 | 4.21 |
| Acetyl-Met | 1C | N | Leu | 104A | C | 3.94 |
| | | | Leu | 104A | O | 2.73 |
| | | | Thr | 109A | OG1 | 3.31 |
| | | | Thr | 109A | CB | 4.46 |
| Acetyl-Met | 1C | CT1 | Tyr | 190A | CE1 | 3.9 |
| | | | Leu | 104A | O | 3.61 |
| | | | Tyr | 190A | OH | 4.34 |
| | | | Thr | 109A | OG1 | 3.44 |
| | | | Leu | 110A | CD2 | 4.36 |
| | | | Leu | 110A | CG | 4.16 |
| Acetyl-Met | 1C | OT | Tyr | 190A | CD1 | 4.33 |
| | | | Tyr | 190A | CE1 | 3.29 |
| | | | Tyr | 190A | CZ | 3.96 |
| | | | Tyr | 190A | OH | 3.71 |
| | | | Thr | 109A | OG1 | 4.26 |
| | | | Leu | 110A | CD2 | 3.57 |
| | | | Leu | 110A | CG | 3.72 |
| | | | Leu | 110A | CD1 | 4.26 |
| Acetyl-Met | 1C | CT2 | Tyr | 190A | CE1 | 4.3 |
| | | | Leu | 107A | CD2 | 3.9 |
| | | | Leu | 104A | O | 3.55 |
| | | | Glu | 105A | C | 4.32 |
| | | | Glu | 105A | O | 4.27 |
| | | | Asp | 106A | C | 4.13 |
| | | | Asp | 106A | O | 3.63 |
| | | | Leu | 107A | N | 4.37 |
| | | | Leu | 107A | CA | 4.1 |
| | | | Thr | 109A | OG1 | 3.29 |
| | | | Leu | 110A | CG | 4.07 |
| | | | Leu | 110A | CD1 | 4.36 |
| Acetyl-Met | 1C | CB | Leu | 104A | CB | 4.45 |
| | | | Leu | 104A | O | 3.65 |
| | | | Thr | 109A | OG1 | 3.9 |
| | | | Thr | 109A | CB | 4.38 |
| Acetyl-Met | 1C | CG | Leu | 104A | O | 4.32 |
| | | | Thr | 109A | OG1 | 3.11 |
| | | | Ile | 97A | CD1 | 4.01 |
| | | | Thr | 109A | CB | 3.36 |
| | | | Thr | 109A | CG2 | 4.25 |
| | | | Thr | 109A | C | 4.41 |
| | | | Thr | 109A | O | 4.36 |
| Acetyl-Met | 1C | SD | Leu | 121A | CD1 | 3.76 |
| | | | Thr | 109A | OG1 | 4.44 |
| | | | Leu | 121A | CG | 4.44 |
| | | | Leu | 121A | CD2 | 3.83 |
| | | | Thr | 109A | O | 4.39 |
| Acetyl-Met | 1C | CE | Leu | 121A | CD1 | 4.02 |
| | | | Thr | 109A | OG1 | 4.42 |
| | | | Leu | 110A | CD2 | 3.5 |
| | | | Leu | 173A | CD1 | 3.68 |
| | | | Leu | 110A | N | 4.36 |
| | | | Leu | 110A | CA | 4.16 |
| | | | Leu | 110A | CG | 4.29 |
| | | | Leu | 121A | CD2 | 4.07 |
| | | | Thr | 109A | C | 4.27 |
| | | | Ala | 113A | CB | 3.74 |
| | | | Thr | 109A | O | 3.9 |

TABLE 1-continued

Minimal contacts between *S. cerevisiae* Dcn1 and *S. cerevisiae* Ubc12 with yUbc12 Chain C interactions with yDcn1$^P$ Chain A and yUbc12 Chain D interactions with yDcn1$^P$ Chain B shown.

| yUbc12 Atom | | | yDcn1 Atom | | Distance (Å) |
|---|---|---|---|---|---|
| Leu | 2C | N | Tyr | 190A CE1 | 4.48 |
| | | | Tyr | 190A CZ | 4.15 |
| | | | Leu | 104A O | 4.35 |
| | | | Tyr | 190A OH | 3.13 |
| Leu | 2C | CA | Tyr | 190A OH | 3.59 |
| Leu | 2C | CB | Gln | 189A NE2 | 4.2 |
| | | | Tyr | 190A CE1 | 4.43 |
| | | | Tyr | 190A CZ | 3.85 |
| | | | Tyr | 190A CE2 | 4.43 |
| | | | Tyr | 190A OH | 3.31 |
| Leu | 2C | CG | Gln | 189A NE2 | 4.49 |
| | | | Tyr | 190A CE1 | 3.97 |
| | | | Tyr | 190A CZ | 3.87 |
| | | | Leu | 193A CD1 | 4.27 |
| | | | Tyr | 190A OH | 3.75 |
| Leu | 2C | CD1 | Gln | 189A CB | 4.19 |
| | | | Gln | 189A NE2 | 3.5 |
| | | | Tyr | 190A CE1 | 4.16 |
| | | | Tyr | 190A CZ | 4.07 |
| | | | Tyr | 190A CE2 | 4.35 |
| | | | Leu | 193A CD1 | 3.87 |
| | | | Tyr | 190A OH | 4.38 |
| Leu | 2C | CD2 | Leu | 193A CD1 | 4.35 |
| | | | Leu | 104A O | 4.32 |
| | | | Glu | 105A N | 4.5 |
| | | | Glu | 105A CA | 3.87 |
| | | | Glu | 105A CB | 3.94 |
| | | | Glu | 105A CG | 3.74 |
| Leu | 2C | C | Tyr | 190A OH | 3.89 |
| Lys | 3C | N | Tyr | 190A OH | 3.59 |
| Lys | 3C | CB | Leu | 121A CD1 | 4.45 |
| | | | Tyr | 190A OH | 4.29 |
| Lys | 3C | CD | Ile | 174A CA | 4.25 |
| | | | Ile | 174A C | 4.32 |
| | | | Ile | 174A O | 3.82 |
| | | | Leu | 173A O | 3.41 |
| | | | Leu | 173A C | 4.44 |
| Lys | 3C | CE | Ile | 174A C | 4.41 |
| | | | Ile | 174A O | 3.77 |
| | | | Glu | 122A OE2 | 3.24 |
| | | | Leu | 175A O | 4.18 |
| | | | Asp | 176A OD1 | 3.87 |
| | | | Leu | 173A O | 3.62 |
| | | | Glu | 122A CD | 4.13 |
| Lys | 3C | NZ | Asp | 176A N | 4.04 |
| | | | Asp | 176A CB | 4.24 |
| | | | Asp | 176A CG | 3.45 |
| | | | Asp | 176A OD2 | 4.25 |
| | | | Ile | 174A C | 4.41 |
| | | | Ile | 174A O | 3.45 |
| | | | Glu | 122A OE2 | 3.71 |
| | | | Leu | 175A C | 4.28 |
| | | | Leu | 175A O | 4.15 |
| | | | Asp | 176A CA | 3.81 |
| | | | Asp | 176A OD1 | 2.45 |
| Leu | 4C | CB | Val | 94A CG2 | 4.49 |
| | | | Leu | 104A CD2 | 4.41 |
| Leu | 4C | CG | Val | 94A CG2 | 4.16 |
| Leu | 4C | CD1 | Leu | 121A CD1 | 3.91 |
| | | | Ile | 90A CG2 | 3.86 |
| | | | Leu | 121A CB | 4.03 |
| | | | Leu | 121A CG | 4.3 |
| | | | Leu | 93A CD2 | 4.49 |
| | | | Leu | 121A CD2 | 4.38 |
| Leu | 4C | CD2 | Val | 94A CG2 | 4.26 |
| | | | Leu | 93A CD2 | 4.31 |
| | | | Ile | 97A CD1 | 4.05 |
| | | | Leu | 93A CG | 4.35 |
| Acetyl-Met | 1D | O | Leu | 104B CD2 | 4.46 |
| | | | Tyr | 190B OH | 4.22 |
| | | | Leu | 104B O | 4.38 |
| | | | Leu | 104B CB | 3.84 |
| | | | Leu | 104B CG | 4.35 |
| | | | Leu | 104B CD1 | 4.14 |
| Acetyl-Met | 1D | C | Tyr | 190B OH | 3.32 |
| | | | Leu | 104B C | 4.47 |
| | | | Leu | 104B O | 3.71 |
| | | | Leu | 104B CB | 4.09 |
| | | | Tyr | 190B CZ | 4.45 |
| Acetyl-Met | 1D | CA | Tyr | 190B OH | 3.45 |
| | | | Leu | 104B O | 3.61 |
| | | | Thr | 109B OG1 | 4.13 |
| Acetyl-Met | 1D | N | Tyr | 190B OH | 3.67 |
| | | | Leu | 104B C | 4.01 |
| | | | Leu | 104B O | 2.84 |
| | | | Thr | 109B OG1 | 3.38 |
| | | | Tyr | 190B CZ | 4.37 |
| | | | Tyr | 190B CE1 | 4.31 |
| Acetyl-Met | 1D | CT1 | Leu | 110B CG | 3.8 |
| | | | Leu | 110B CD1 | 4.17 |
| | | | Leu | 110B CD2 | 4.41 |
| | | | Tyr | 190B OH | 3.58 |
| | | | Leu | 104B O | 3.81 |
| | | | Thr | 109B OG1 | 3.55 |
| | | | Tyr | 190B CZ | 3.97 |
| | | | Tyr | 190B CE1 | 3.52 |
| Acetyl-Met | 1D | OT | Leu | 110B CB | 4.48 |
| | | | Leu | 110B CG | 3.18 |
| | | | Leu | 110B CD1 | 3.64 |
| | | | Leu | 110B CD2 | 3.44 |
| | | | Tyr | 190B OH | 3.24 |
| | | | Thr | 109B OG1 | 4.24 |
| | | | Tyr | 190B CZ | 3.66 |
| | | | Tyr | 190B CD1 | 4.35 |
| | | | Tyr | 190B CE1 | 3.17 |
| Acetyl-Met | 1D | CT2 | Leu | 110B CG | 3.84 |
| | | | Leu | 110B CD1 | 3.84 |
| | | | Leu | 107B CA | 3.96 |
| | | | Leu | 104B O | 3.81 |
| | | | Thr | 109B OG1 | 3.62 |
| | | | Asp | 106B C | 4.18 |
| | | | Asp | 106B O | 3.68 |
| | | | Leu | 107B N | 4.31 |
| | | | Leu | 107B CD2 | 3.95 |
| | | | Tyr | 190B CE1 | 3.87 |
| | | | Leu | 193B CD1 | 4.19 |
| Acetyl-Met | 1D | CB | Thr | 109B CB | 4.21 |
| | | | Leu | 104B CD2 | 4.23 |
| | | | Leu | 104B C | 4.45 |
| | | | Leu | 104B O | 3.72 |
| | | | Thr | 109B OG1 | 3.58 |
| | | | Leu | 104B CA | 4.28 |
| | | | Leu | 104B CB | 4.19 |
| Acetyl-Met | 1D | CG | Thr | 109B C | 4.33 |
| | | | Thr | 109B O | 4.2 |
| | | | Ile | 97B CD1 | 3.98 |
| | | | Thr | 109B CB | 3.55 |
| | | | Thr | 109B OG1 | 3.19 |
| Acetyl-Met | 1D | SD | Leu | 121B CD2 | 4.09 |
| | | | Leu | 121B CD1 | 3.91 |
| Acetyl-Met | 1D | CE | Ala | 113B CB | 3.73 |
| | | | Thr | 109B C | 4.42 |
| | | | Thr | 109B O | 3.96 |
| | | | Leu | 121B CD2 | 4.21 |
| | | | Leu | 173B CD1 | 3.7 |
| | | | Leu | 110B CA | 4.26 |
| | | | Leu | 110B CG | 4.24 |
| | | | Leu | 110B CD2 | 3.58 |
| | | | Leu | 121B CD1 | 4.35 |

TABLE 1-continued

Minimal contacts between *S. cerevisiae* Dcn1 and *S. cerevisiae* Ubc12 with yUbc12 Chain C interactions with yDcn1$^P$ Chain A and yUbc12 Chain D interactions with yDcn1$^P$ Chain B shown.

| yUbc12 Atom | | | yDcn1 Atom | | | Distance (Å) |
|---|---|---|---|---|---|---|
| Leu | 2D | N | Tyr | 190B | OH | 2.85 |
| | | | Leu | 104B | O | 3.88 |
| | | | Tyr | 190B | CZ | 3.74 |
| | | | Tyr | 190B | CE2 | 4.34 |
| Leu | 2D | CA | Tyr | 190B | OH | 3.65 |
| | | | Tyr | 190B | CZ | 4.37 |
| Leu | 2D | CB | Tyr | 190B | OH | 3.86 |
| | | | Tyr | 190B | CZ | 4.08 |
| | | | Tyr | 190B | CE2 | 3.87 |
| Leu | 2D | CG | Tyr | 190B | OH | 4.39 |
| | | | Tyr | 190B | CZ | 4.31 |
| | | | Tyr | 190B | CE2 | 4.21 |
| | | | Leu | 193B | CD1 | 4.05 |
| Leu | 2D | CD1 | Tyr | 190B | CE2 | 4.27 |
| | | | Tyr | 190B | CD2 | 4.41 |
| | | | Gln | 189B | O | 4.16 |
| | | | Leu | 193B | CD1 | 3.98 |
| | | | Gln | 189B | CB | 4.05 |
| | | | Gln | 189B | C | 4.36 |
| Leu | 2D | CD2 | Leu | 104B | C | 4.33 |
| | | | Leu | 104B | O | 4.17 |
| | | | Glu | 105B | CA | 4 |
| | | | Glu | 105B | N | 4.22 |
| | | | Glu | 105B | CB | 4.46 |
| | | | Glu | 105B | CG | 3.87 |
| | | | Leu | 193B | CD1 | 4.37 |
| Leu | 2D | C | Tyr | 190B | OH | 3.82 |
| Lys | 3D | N | Tyr | 190B | OH | 3.01 |
| | | | Tyr | 190B | CZ | 3.98 |
| | | | Tyr | 190B | CE2 | 4.04 |
| Lys | 3D | CA | Tyr | 190B | OH | 3.92 |
| Lys | 3D | CB | Leu | 121B | CD1 | 4.22 |
| | | | Tyr | 190B | OH | 3.63 |
| Lys | 3D | CG | Leu | 173B | O | 4.25 |
| | | | Leu | 121B | CD1 | 4 |
| Lys | 3D | CD | Leu | 173B | O | 4.3 |
| | | | Ile | 174B | C | 4.29 |
| | | | Ile | 174B | CA | 4.31 |
| | | | Ile | 174B | O | 3.58 |
| | | | Asp | 176B | OD1 | 4 |
| Lys | 3D | CE | Leu | 173B | O | 4.42 |
| | | | Glu | 122B | OE2 | 4.11 |
| | | | Ile | 174B | C | 4.47 |
| | | | Ile | 174B | O | 3.64 |
| | | | Asp | 176B | CG | 4.26 |
| | | | Asp | 176B | OD1 | 3.08 |
| Lys | 3D | NZ | Leu | 173B | O | 3.4 |
| | | | Leu | 175B | O | 3.56 |
| | | | Glu | 122B | CD | 3.93 |
| | | | Glu | 122B | OE2 | 2.93 |
| | | | Ile | 174B | C | 4.15 |
| | | | Leu | 175B | C | 4.08 |
| | | | Ile | 174B | O | 3.64 |
| | | | Asp | 176B | N | 4.29 |
| | | | Asp | 176B | CA | 4.18 |
| | | | Asp | 176B | OD1 | 3.72 |
| Leu | 4D | N | Leu | 121B | CD1 | 4.4 |
| Leu | 4D | CG | Ile | 90B | CG2 | 4.02 |
| | | | Ile | 90B | O | 4.47 |
| | | | Val | 94B | CG2 | 3.81 |
| Leu | 4D | CD1 | Ile | 90B | CG1 | 4.29 |
| | | | Leu | 121B | CB | 4.16 |
| | | | Leu | 93B | CD2 | 4.43 |
| | | | Leu | 121B | CD2 | 4.33 |
| | | | Ile | 90B | CB | 4.4 |
| | | | Ile | 90B | CG2 | 3.7 |
| | | | Leu | 121B | CG | 4.39 |
| | | | Leu | 121B | CD1 | 4.07 |
| Leu | 4D | CD2 | Leu | 93B | CB | 4.15 |
| | | | Leu | 93B | CG | 3.79 |
| | | | Leu | 93B | CD2 | 3.77 |
| | | | Ile | 97B | CD1 | 4.02 |
| | | | Val | 94B | N | 4.34 |
| | | | Val | 94B | CG2 | 3.86 |
| Leu | 4D | O | Ile | 90B | CG2 | 3.87 |

TABLE 2

Atomic coordinates of amino acid residues of yDcn1 Chain B essential for binding yUbc12.

| | Atom No. | Atom Name | | | | X | Y | Z | Occupancy | B-factor |
|---|---|---|---|---|---|---|---|---|---|---|
| ATOM | 187 | N | ILE | B | 90 | −17.000 | −3.153 | −25.375 | 1.00 | 26.78 |
| ATOM | 188 | CA | ILE | B | 90 | −15.892 | −2.790 | −24.488 | 1.00 | 27.28 |
| ATOM | 189 | CB | ILE | B | 90 | −14.690 | −2.236 | −25.299 | 1.00 | 27.75 |
| ATOM | 190 | CG1 | ILE | B | 90 | −14.046 | −3.360 | −26.125 | 1.00 | 28.57 |
| ATOM | 191 | CD1 | ILE | B | 90 | −13.276 | −2.873 | −27.351 | 1.00 | 31.07 |
| ATOM | 192 | CG2 | ILE | B | 90 | −13.656 | −1.614 | −24.375 | 1.00 | 28.76 |
| ATOM | 193 | C | ILE | B | 90 | −16.331 | −1.797 | −23.407 | 1.00 | 27.14 |
| ATOM | 194 | O | ILE | B | 90 | −15.941 | −1.928 | −22.242 | 1.00 | 27.17 |
| ATOM | 209 | N | LEU | B | 93 | −18.305 | −3.687 | −20.756 | 1.00 | 23.07 |
| ATOM | 210 | CA | LEU | B | 93 | −17.487 | −4.475 | −19.843 | 1.00 | 22.86 |
| ATOM | 211 | CB | LEU | B | 93 | −16.484 | −5.377 | −20.591 | 1.00 | 22.77 |
| ATOM | 212 | CG | LEU | B | 93 | −15.645 | −6.359 | −19.739 | 1.00 | 23.37 |
| ATOM | 213 | CD1 | LEU | B | 93 | −16.488 | −7.155 | −18.740 | 1.00 | 23.06 |
| ATOM | 214 | CD2 | LEU | B | 93 | −14.825 | −7.312 | −20.618 | 1.00 | 23.28 |
| ATOM | 215 | C | LEU | B | 93 | −16.802 | −3.612 | −18.784 | 1.00 | 22.47 |
| ATOM | 216 | O | LEU | B | 93 | −16.760 | −3.987 | −17.614 | 1.00 | 22.13 |
| ATOM | 217 | N | VAL | B | 94 | −16.280 | −2.461 | −19.207 | 1.00 | 22.50 |
| ATOM | 218 | CA | VAL | B | 94 | −15.661 | −1.472 | −18.311 | 1.00 | 22.44 |
| ATOM | 219 | CB | VAL | B | 94 | −15.067 | −0.282 | −19.111 | 1.00 | 22.56 |
| ATOM | 220 | CG1 | VAL | B | 94 | −14.565 | 0.820 | −18.189 | 1.00 | 21.37 |
| ATOM | 221 | CG2 | VAL | B | 94 | −13.932 | −0.771 | −20.001 | 1.00 | 23.01 |

TABLE 2-continued

Atomic coordinates of amino acid residues of yDcn1 Chain B essential for binding yUbc12.

| | Atom No. | Atom Name | | | X | Y | Z | Occupancy | B-factor |
|---|---|---|---|---|---|---|---|---|---|
| ATOM | 222 | C | VAL | B | 94 | −16.636 | −0.969 | −17.241 | 1.00 | 22.81 |
| ATOM | 223 | O | VAL | B | 94 | −16.310 | −0.957 | −16.049 | 1.00 | 22.30 |
| ATOM | 244 | N | ILE | B | 97 | −17.365 | −3.889 | −14.797 | 1.00 | 23.81 |
| ATOM | 245 | CA | ILE | B | 97 | −16.271 | −4.009 | −13.840 | 1.00 | 24.10 |
| ATOM | 246 | CB | ILE | B | 97 | −14.901 | −3.980 | −14.553 | 1.00 | 23.81 |
| ATOM | 247 | CG1 | ILE | B | 97 | −14.670 | −5.292 | −15.301 | 1.00 | 21.97 |
| ATOM | 248 | CD1 | ILE | B | 97 | −13.777 | −5.147 | −16.491 | 1.00 | 19.97 |
| ATOM | 249 | CG2 | ILE | B | 97 | −13.760 | −3.721 | −13.556 | 1.00 | 23.53 |
| ATOM | 250 | C | ILE | B | 97 | −16.347 | −2.919 | −12.769 | 1.00 | 24.99 |
| ATOM | 251 | O | ILE | B | 97 | −16.207 | −3.208 | −11.577 | 1.00 | 24.71 |
| ATOM | 302 | N | LEU | B | 104 | −9.556 | −1.736 | −13.282 | 1.00 | 30.61 |
| ATOM | 303 | CA | LEU | B | 104 | −9.073 | −2.533 | −14.405 | 1.00 | 30.52 |
| ATOM | 304 | CB | LEU | B | 104 | −8.981 | −1.689 | −15.675 | 1.00 | 30.40 |
| ATOM | 305 | CG | LEU | B | 104 | −10.217 | −0.909 | −16.135 | 1.00 | 30.20 |
| ATOM | 306 | CD1 | LEU | B | 104 | −9.854 | −0.018 | −17.301 | 1.00 | 28.88 |
| ATOM | 307 | CD2 | LEU | B | 104 | −11.395 | −1.826 | −16.495 | 1.00 | 30.08 |
| ATOM | 308 | C | LEU | B | 104 | −7.719 | −3.189 | −14.112 | 1.00 | 30.86 |
| ATOM | 309 | O | LEU | B | 104 | −7.334 | −4.139 | −14.789 | 1.00 | 31.23 |
| ATOM | 310 | N | GLU | B | 105 | −7.008 | −2.677 | −13.107 | 1.00 | 30.82 |
| ATOM | 311 | CA | GLU | B | 105 | −5.735 | −3.255 | −12.660 | 1.00 | 30.75 |
| ATOM | 312 | CB | GLU | B | 105 | −4.947 | −2.250 | −11.801 | 1.00 | 31.01 |
| ATOM | 313 | CG | GLU | B | 105 | −4.454 | −1.002 | −12.547 | 1.00 | 34.35 |
| ATOM | 314 | CD | GLU | B | 105 | −5.495 | 0.131 | −12.635 | 1.00 | 38.44 |
| ATOM | 315 | OE1 | GLU | B | 105 | −6.630 | −0.025 | −12.121 | 1.00 | 39.33 |
| ATOM | 316 | OE2 | GLU | B | 105 | −5.166 | 1.192 | −13.223 | 1.00 | 39.74 |
| ATOM | 317 | C | GLU | B | 105 | −5.939 | −4.552 | −11.871 | 1.00 | 29.84 |
| ATOM | 318 | O | GLU | B | 105 | −4.991 | −5.313 | −11.687 | 1.00 | 29.75 |
| ATOM | 319 | N | ASP | B | 106 | −7.164 | −4.787 | −11.393 | 1.00 | 28.79 |
| ATOM | 320 | CA | ASP | B | 106 | −7.466 | −5.960 | −10.575 | 1.00 | 27.99 |
| ATOM | 321 | CB | ASP | B | 106 | −8.806 | −5.800 | −9.845 | 1.00 | 28.43 |
| ATOM | 322 | CG | ASP | B | 106 | −8.778 | −4.721 | −8.757 | 1.00 | 30.42 |
| ATOM | 323 | OD1 | ASP | B | 106 | −7.717 | −4.520 | −8.116 | 1.00 | 32.67 |
| ATOM | 324 | OD2 | ASP | B | 106 | −9.836 | −4.082 | −8.527 | 1.00 | 31.35 |
| ATOM | 325 | C | ASP | B | 106 | −7.492 | −7.233 | −11.420 | 1.00 | 27.00 |
| ATOM | 326 | O | ASP | B | 106 | −8.260 | −7.336 | −12.384 | 1.00 | 26.52 |
| ATOM | 327 | N | LEU | B | 107 | −6.651 | −8.199 | −11.051 | 1.00 | 25.92 |
| ATOM | 328 | CA | LEU | B | 107 | −6.592 | −9.494 | −11.756 | 1.00 | 25.10 |
| ATOM | 329 | CB | LEU | B | 107 | −5.474 | −10.388 | −11.204 | 1.00 | 25.01 |
| ATOM | 330 | CG | LEU | B | 107 | −4.012 | −10.030 | −11.483 | 1.00 | 25.41 |
| ATOM | 331 | CD1 | LEU | B | 107 | −3.132 | −11.160 | −11.002 | 1.00 | 26.14 |
| ATOM | 332 | CD2 | LEU | B | 107 | −3.759 | −9.781 | −12.962 | 1.00 | 25.10 |
| ATOM | 333 | C | LEU | B | 107 | −7.926 | −10.248 | −11.743 | 1.00 | 24.17 |
| ATOM | 334 | O | LEU | B | 107 | −8.231 | −10.968 | −12.688 | 1.00 | 23.94 |
| ATOM | 340 | N | THR | B | 109 | −10.630 | −9.254 | −12.532 | 1.00 | 20.74 |
| ATOM | 341 | CA | THR | B | 109 | −11.358 | −8.910 | −13.749 | 1.00 | 20.00 |
| ATOM | 342 | CB | THR | B | 109 | −11.009 | −7.506 | −14.241 | 1.00 | 20.13 |
| ATOM | 343 | OG1 | THR | B | 109 | −9.607 | −7.447 | −14.529 | 1.00 | 21.02 |
| ATOM | 344 | CG2 | THR | B | 109 | −11.372 | −6.445 | −13.185 | 1.00 | 19.14 |
| ATOM | 345 | C | THR | B | 109 | −11.098 | −9.920 | −14.870 | 1.00 | 19.91 |
| ATOM | 346 | O | THR | B | 109 | −11.932 | −10.086 | −15.768 | 1.00 | 19.52 |
| ATOM | 347 | N | LEU | B | 110 | −9.940 | −10.587 | −14.809 | 1.00 | 19.41 |
| ATOM | 348 | CA | LEU | B | 110 | −9.612 | −11.680 | −15.716 | 1.00 | 18.82 |
| ATOM | 349 | CB | LEU | B | 110 | −8.118 | −11.996 | −15.665 | 1.00 | 18.81 |
| ATOM | 350 | CG | LEU | B | 110 | −7.233 | −11.177 | −16.602 | 1.00 | 19.63 |
| ATOM | 351 | CD1 | LEU | B | 110 | −5.757 | −11.366 | −16.250 | 1.00 | 18.67 |
| ATOM | 352 | CD2 | LEU | B | 110 | −7.519 | −11.548 | −18.066 | 1.00 | 18.09 |
| ATOM | 353 | C | LEU | B | 110 | −10.410 | −12.941 | −15.406 | 1.00 | 18.59 |
| ATOM | 354 | O | LEU | B | 110 | −10.817 | −13.646 | −16.324 | 1.00 | 17.95 |
| ATOM | 369 | N | ALA | B | 113 | −13.765 | −12.239 | −16.984 | 1.00 | 18.55 |
| ATOM | 370 | CA | ALA | B | 113 | −13.760 | −12.421 | −18.436 | 1.00 | 18.75 |
| ATOM | 371 | CB | ALA | B | 113 | −12.557 | −11.717 | −19.068 | 1.00 | 18.05 |
| ATOM | 372 | C | ALA | B | 113 | −13.772 | −13.909 | −18.784 | 1.00 | 19.11 |
| ATOM | 373 | O | ALA | B | 113 | −14.497 | −14.348 | −19.687 | 1.00 | 18.94 |
| ATOM | 434 | N | LEU | B | 121 | −11.230 | −9.617 | −26.513 | 1.00 | 30.79 |
| ATOM | 435 | CA | LEU | B | 121 | −11.866 | −8.449 | −25.908 | 1.00 | 31.55 |
| ATOM | 436 | CB | LEU | B | 121 | −10.860 | −7.659 | −25.075 | 1.00 | 31.43 |
| ATOM | 437 | CG | LEU | B | 121 | −10.332 | −8.355 | −23.817 | 1.00 | 31.12 |
| ATOM | 438 | CD1 | LEU | B | 121 | −9.213 | −7.527 | −23.191 | 1.00 | 30.04 |
| ATOM | 439 | CD2 | LEU | B | 121 | −11.457 | −8.632 | −22.807 | 1.00 | 30.44 |
| ATOM | 440 | C | LEU | B | 121 | −12.509 | −7.548 | −26.950 | 1.00 | 32.31 |
| ATOM | 441 | O | LEU | B | 121 | −13.418 | −6.783 | −26.638 | 1.00 | 32.69 |
| ATOM | 442 | N | GLU | B | 122 | −12.036 | −7.659 | −28.188 | 1.00 | 33.07 |
| ATOM | 443 | CA | GLU | B | 122 | −12.507 | −6.842 | −29.293 | 1.00 | 33.86 |
| ATOM | 444 | CB | GLU | B | 122 | −11.527 | −6.931 | −30.474 | 1.00 | 34.09 |

TABLE 2-continued

Atomic coordinates of amino acid residues of yDcn1 Chain B essential for binding yUbc12.

| | Atom No. | Atom Name | | | X | Y | Z | Occupancy | B-factor |
|---|---|---|---|---|---|---|---|---|---|
| ATOM | 445 | CG | GLU | B | 122 | −10.065 | −6.525 | −30.148 | 1.00 | 35.66 |
| ATOM | 446 | CD | GLU | B | 122 | −9.214 | −7.651 | −29.515 | 1.00 | 37.96 |
| ATOM | 447 | OE1 | GLU | B | 122 | −9.750 | −8.745 | −29.236 | 1.00 | 38.95 |
| ATOM | 448 | OE2 | GLU | B | 122 | −7.993 | −7.440 | −29.300 | 1.00 | 38.39 |
| ATOM | 449 | C | GLU | B | 122 | −13.922 | −7.244 | −29.727 | 1.00 | 34.10 |
| ATOM | 450 | O | GLU | B | 122 | −14.689 | −6.403 | −30.199 | 1.00 | 34.37 |
| ATOM | 874 | N | LEU | B | 173 | −5.876 | −13.081 | −24.295 | 1.00 | 27.16 |
| ATOM | 875 | CA | LEU | B | 173 | −6.626 | −11.828 | −24.339 | 1.00 | 27.91 |
| ATOM | 876 | CB | LEU | B | 173 | −7.349 | −11.582 | −23.011 | 1.00 | 27.86 |
| ATOM | 877 | CG | LEU | B | 173 | −8.606 | −12.381 | −22.684 | 1.00 | 26.53 |
| ATOM | 878 | CD1 | LEU | B | 173 | −9.208 | −11.801 | −21.423 | 1.00 | 23.89 |
| ATOM | 879 | CD2 | LEU | B | 173 | −9.605 | −12.329 | −23.848 | 1.00 | 25.91 |
| ATOM | 880 | C | LEU | B | 173 | −5.762 | −10.612 | −24.635 | 1.00 | 28.87 |
| ATOM | 881 | O | LEU | B | 173 | −6.252 | −9.630 | −25.203 | 1.00 | 29.01 |
| ATOM | 882 | N | ILE | B | 174 | −4.494 | −10.655 | −24.222 | 1.00 | 29.78 |
| ATOM | 883 | CA | ILE | B | 174 | −3.571 | −9.545 | −24.473 | 1.00 | 30.66 |
| ATOM | 884 | CB | ILE | B | 174 | −2.274 | −9.654 | −23.640 | 1.00 | 30.37 |
| ATOM | 885 | CG1 | ILE | B | 174 | −2.571 | −9.533 | −22.145 | 1.00 | 30.97 |
| ATOM | 886 | CD1 | ILE | B | 174 | −1.443 | −10.039 | −21.251 | 1.00 | 31.49 |
| ATOM | 887 | CG2 | ILE | B | 174 | −1.287 | −8.569 | −24.026 | 1.00 | 30.73 |
| ATOM | 888 | C | ILE | B | 174 | −3.230 | −9.489 | −25.958 | 1.00 | 31.61 |
| ATOM | 889 | O | ILE | B | 174 | −2.929 | −8.415 | −26.494 | 1.00 | 31.77 |
| ATOM | 890 | N | LEU | B | 175 | −3.279 | −10.649 | −26.616 | 1.00 | 32.57 |
| ATOM | 891 | CA | LEU | B | 175 | −3.011 | −10.740 | −28.046 | 1.00 | 33.68 |
| ATOM | 892 | CB | LEU | B | 175 | −3.232 | −12.164 | −28.553 | 1.00 | 33.40 |
| ATOM | 893 | CG | LEU | B | 175 | −2.038 | −13.108 | −28.646 | 1.00 | 33.23 |
| ATOM | 894 | CD1 | LEU | B | 175 | −2.475 | −14.462 | −29.171 | 1.00 | 32.15 |
| ATOM | 895 | CD2 | LEU | B | 175 | −0.973 | −12.517 | −29.552 | 1.00 | 33.47 |
| ATOM | 896 | C | LEU | B | 175 | −3.915 | −9.793 | −28.806 | 1.00 | 34.64 |
| ATOM | 897 | O | LEU | B | 175 | −5.136 | −9.836 | −28.634 | 1.00 | 35.03 |
| ATOM | 898 | N | ASP | B | 176 | −3.314 | −8.918 | −29.614 | 1.00 | 35.77 |
| ATOM | 899 | CA | ASP | B | 176 | −4.084 | −8.053 | −30.510 | 1.00 | 36.75 |
| ATOM | 900 | CB | ASP | B | 176 | −3.204 | −6.954 | −31.120 | 1.00 | 37.22 |
| ATOM | 901 | CG | ASP | B | 176 | −2.718 | −5.939 | −30.098 | 1.00 | 38.70 |
| ATOM | 902 | OD1 | ASP | B | 176 | −3.105 | −6.022 | −28.908 | 1.00 | 41.31 |
| ATOM | 903 | OD2 | ASP | B | 176 | −1.935 | −5.044 | −30.492 | 1.00 | 40.73 |
| ATOM | 904 | C | ASP | B | 176 | −4.670 | −8.929 | −31.614 | 1.00 | 36.97 |
| ATOM | 905 | O | ASP | B | 176 | −4.183 | −10.046 | −31.831 | 1.00 | 37.27 |
| ATOM | 1001 | N | GLN | B | 189 | 3.796 | −4.772 | −18.447 | 1.00 | 20.32 |
| ATOM | 1002 | CA | GLN | B | 189 | 2.672 | −4.221 | −17.680 | 1.00 | 21.04 |
| ATOM | 1003 | CB | GLN | B | 189 | 1.788 | −3.313 | −18.553 | 1.00 | 21.59 |
| ATOM | 1004 | CG | GLN | B | 189 | 2.471 | −2.017 | −19.012 | 1.00 | 24.86 |
| ATOM | 1005 | CD | GLN | B | 189 | 1.627 | −1.176 | −19.980 | 1.00 | 30.95 |
| ATOM | 1006 | OE1 | GLN | B | 189 | 0.584 | −1.617 | −20.484 | 1.00 | 32.81 |
| ATOM | 1007 | NE2 | GLN | B | 189 | 2.091 | 0.057 | −20.240 | 1.00 | 34.12 |
| ATOM | 1008 | C | GLN | B | 189 | 1.828 | −5.307 | −17.005 | 1.00 | 20.86 |
| ATOM | 1009 | O | GLN | B | 189 | 1.480 | −5.169 | −15.829 | 1.00 | 20.70 |
| ATOM | 1010 | N | TYR | B | 190 | 1.512 | −6.387 | −17.725 | 1.00 | 20.44 |
| ATOM | 1011 | CA | TYR | B | 190 | 0.788 | −7.510 | −17.097 | 1.00 | 20.64 |
| ATOM | 1012 | CB | TYR | B | 190 | 0.072 | −8.398 | −18.121 | 1.00 | 20.85 |
| ATOM | 1013 | CG | TYR | B | 190 | −1.295 | −7.875 | −18.511 | 1.00 | 22.90 |
| ATOM | 1014 | CD1 | TYR | B | 190 | −2.454 | −8.460 | −18.007 | 1.00 | 24.80 |
| ATOM | 1015 | CE1 | TYR | B | 190 | −3.720 | −7.982 | −18.364 | 1.00 | 25.31 |
| ATOM | 1016 | CZ | TYR | B | 190 | −3.825 | −6.906 | −19.230 | 1.00 | 25.68 |
| ATOM | 1017 | OH | TYR | B | 190 | −5.069 | −6.425 | −19.583 | 1.00 | 25.69 |
| ATOM | 1018 | CE2 | TYR | B | 190 | −2.681 | −6.306 | −19.742 | 1.00 | 25.12 |
| ATOM | 1019 | CD2 | TYR | B | 190 | −1.430 | −6.789 | −19.384 | 1.00 | 23.39 |
| ATOM | 1020 | C | TYR | B | 190 | 1.634 | −8.354 | −16.138 | 1.00 | 20.10 |
| ATOM | 1021 | O | TYR | B | 190 | 1.133 | −8.764 | −15.094 | 1.00 | 19.57 |
| ATOM | 1045 | N | LEU | B | 193 | 1.535 | −6.975 | −12.748 | 1.00 | 20.07 |
| ATOM | 1046 | CA | LEU | B | 193 | 0.316 | −7.313 | −12.019 | 1.00 | 20.06 |
| ATOM | 1047 | CB | LEU | B | 193 | −0.922 | −7.167 | −12.909 | 1.00 | 20.10 |
| ATOM | 1048 | CG | LEU | B | 193 | −1.217 | −5.770 | −13.476 | 1.00 | 20.30 |
| ATOM | 1049 | CD1 | LEU | B | 193 | −2.506 | −5.798 | −14.258 | 1.00 | 19.96 |
| ATOM | 1050 | CD2 | LEU | B | 193 | −1.263 | −4.673 | −12.390 | 1.00 | 20.81 |
| ATOM | 1051 | C | LEU | B | 193 | 0.395 | −8.711 | −11.423 | 1.00 | 20.19 |
| ATOM | 1052 | O | LEU | B | 193 | 0.190 | −8.887 | −10.221 | 1.00 | 20.50 |

TABLE 3

Atomic coordinates of amino acid residues of yDcn1 Chain A essential for binding yUbc12.

| | Atom No. | Atom Name | | | X | Y | Z | Occu-pancy | B-factor |
|---|---|---|---|---|---|---|---|---|---|
| ATOM | 1906 | N | ILE | A | 90 | −2.222 | −45.427 | −20.314 | 1.00 | 21.48 |
| ATOM | 1907 | CA | ILE | A | 90 | −3.339 | −45.857 | −19.489 | 1.00 | 22.02 |
| ATOM | 1908 | CB | ILE | A | 90 | −4.434 | −46.463 | −20.379 | 1.00 | 22.47 |
| ATOM | 1909 | CG1 | ILE | A | 90 | −5.253 | −45.340 | −21.002 | 1.00 | 23.62 |
| ATOM | 1910 | CD1 | ILE | A | 90 | −6.077 | −44.572 | −19.976 | 1.00 | 26.80 |
| ATOM | 1911 | CG2 | ILE | A | 90 | −5.389 | −47.303 | −19.578 | 1.00 | 23.20 |
| ATOM | 1912 | C | ILE | A | 90 | −2.935 | −46.825 | −18.384 | 1.00 | 21.85 |
| ATOM | 1913 | O | ILE | A | 90 | −3.369 | −46.679 | −17.243 | 1.00 | 21.90 |
| ATOM | 1928 | N | LEU | A | 93 | −1.200 | −44.808 | −15.777 | 1.00 | 19.63 |
| ATOM | 1929 | CA | LEU | A | 93 | −2.179 | −44.094 | −14.947 | 1.00 | 19.61 |
| ATOM | 1930 | CB | LEU | A | 93 | −3.210 | −43.349 | −15.811 | 1.00 | 19.52 |
| ATOM | 1931 | CG | LEU | A | 93 | −4.211 | −42.444 | −15.074 | 1.00 | 18.80 |
| ATOM | 1932 | CD1 | LEU | A | 93 | −3.517 | −41.460 | −14.123 | 1.00 | 16.51 |
| ATOM | 1933 | CD2 | LEU | A | 93 | −5.095 | −41.703 | −16.067 | 1.00 | 18.64 |
| ATOM | 1934 | C | LEU | A | 93 | −2.874 | −45.028 | −13.952 | 1.00 | 19.66 |
| ATOM | 1935 | O | LEU | A | 93 | −2.998 | −44.694 | −12.775 | 1.00 | 19.34 |
| ATOM | 1936 | N | VAL | A | 94 | −3.316 | −46.191 | −14.436 | 1.00 | 20.02 |
| ATOM | 1937 | CA | VAL | A | 94 | −3.895 | −47.231 | −13.576 | 1.00 | 20.55 |
| ATOM | 1938 | CB | VAL | A | 94 | −4.275 | −48.515 | −14.381 | 1.00 | 20.23 |
| ATOM | 1939 | CG1 | VAL | A | 94 | −4.684 | −49.648 | −13.453 | 1.00 | 19.91 |
| ATOM | 1940 | CG2 | VAL | A | 94 | −5.409 | −48.223 | −15.353 | 1.00 | 20.95 |
| ATOM | 1941 | C | VAL | A | 94 | −2.968 | −47.587 | −12.408 | 1.00 | 21.13 |
| ATOM | 1942 | O | VAL | A | 94 | −3.399 | −47.571 | −11.247 | 1.00 | 21.68 |
| ATOM | 1963 | N | ILE | A | 97 | −2.551 | −44.631 | −9.955 | 1.00 | 19.78 |
| ATOM | 1964 | CA | ILE | A | 97 | −3.723 | −44.543 | −9.089 | 1.00 | 20.30 |
| ATOM | 1965 | CB | ILE | A | 97 | −5.053 | −44.675 | −9.910 | 1.00 | 20.09 |
| ATOM | 1966 | CG1 | ILE | A | 97 | −5.296 | −43.410 | −10.745 | 1.00 | 19.51 |
| ATOM | 1967 | CD1 | ILE | A | 97 | −6.192 | −43.624 | −11.960 | 1.00 | 19.12 |
| ATOM | 1968 | CG2 | ILE | A | 97 | −6.261 | −44.945 | −8.997 | 1.00 | 20.08 |
| ATOM | 1969 | C | ILE | A | 97 | −3.635 | −45.556 | −7.938 | 1.00 | 21.00 |
| ATOM | 1970 | O | ILE | A | 97 | −3.840 | −45.204 | −6.761 | 1.00 | 20.37 |
| ATOM | 2021 | N | LEU | A | 104 | −10.173 | −47.353 | −8.911 | 1.00 | 29.83 |
| ATOM | 2022 | CA | LEU | A | 104 | −10.542 | −46.612 | −10.123 | 1.00 | 30.31 |
| ATOM | 2023 | CB | LEU | A | 104 | −10.528 | −47.522 | −11.352 | 1.00 | 30.63 |
| ATOM | 2024 | CG | LEU | A | 104 | −9.261 | −48.272 | −11.763 | 1.00 | 31.62 |
| ATOM | 2025 | CD1 | LEU | A | 104 | −8.933 | −49.439 | −10.812 | 1.00 | 33.32 |
| ATOM | 2026 | CD2 | LEU | A | 104 | −9.442 | −48.785 | −13.180 | 1.00 | 32.12 |
| ATOM | 2027 | C | LEU | A | 104 | −11.905 | −45.940 | −10.024 | 1.00 | 30.38 |
| ATOM | 2028 | O | LEU | A | 104 | −12.200 | −45.008 | −10.772 | 1.00 | 30.61 |
| ATOM | 2029 | N | GLU | A | 105 | −12.724 | −46.408 | −9.089 | 1.00 | 30.37 |
| ATOM | 2030 | CA | GLU | A | 105 | −14.089 | −45.925 | −8.944 | 1.00 | 30.32 |
| ATOM | 2031 | CB | GLU | A | 105 | −15.027 | −47.060 | −8.505 | 1.00 | 30.79 |
| ATOM | 2032 | CG | GLU | A | 105 | −14.852 | −48.382 | −9.278 | 1.00 | 34.03 |
| ATOM | 2033 | CD | GLU | A | 105 | −13.910 | −49.374 | −8.588 | 1.00 | 37.92 |
| ATOM | 2034 | OE1 | GLU | A | 105 | −13.067 | −48.946 | −7.770 | 1.00 | 40.04 |
| ATOM | 2035 | OE2 | GLU | A | 105 | −14.018 | −50.591 | −8.863 | 1.00 | 39.49 |
| ATOM | 2036 | C | GLU | A | 105 | −14.181 | −44.755 | −7.969 | 1.00 | 29.38 |
| ATOM | 2037 | O | GLU | A | 105 | −15.248 | −44.154 | −7.827 | 1.00 | 29.38 |
| ATOM | 2038 | N | ASP | A | 106 | −13.076 | −44.453 | −7.286 | 1.00 | 28.35 |
| ATOM | 2039 | CA | ASP | A | 106 | −13.009 | −43.299 | −6.390 | 1.00 | 27.37 |
| ATOM | 2040 | CB | ASP | A | 106 | −11.772 | −43.351 | −5.483 | 1.00 | 27.73 |
| ATOM | 2041 | CG | ASP | A | 106 | −11.780 | −44.528 | −4.520 | 1.00 | 28.81 |
| ATOM | 2042 | OD1 | ASP | A | 106 | −12.877 | −44.964 | −4.089 | 1.00 | 31.71 |
| ATOM | 2043 | OD2 | ASP | A | 106 | −10.674 | −45.011 | −4.184 | 1.00 | 28.03 |
| ATOM | 2044 | C | ASP | A | 106 | −12.944 | −42.039 | −7.238 | 1.00 | 26.37 |
| ATOM | 2045 | O | ASP | A | 106 | −12.138 | −41.952 | −8.177 | 1.00 | 26.21 |
| ATOM | 2046 | N | LEU | A | 107 | −13.788 | −41.067 | −6.903 | 1.00 | 25.02 |
| ATOM | 2047 | CA | LEU | A | 107 | −13.857 | −39.806 | −7.646 | 1.00 | 24.02 |
| ATOM | 2048 | CB | LEU | A | 107 | −15.111 | −39.011 | −7.251 | 1.00 | 24.13 |
| ATOM | 2049 | CG | LEU | A | 107 | −16.464 | −39.654 | −7.601 | 1.00 | 24.37 |
| ATOM | 2050 | CD1 | LEU | A | 107 | −17.625 | −38.816 | −7.098 | 1.00 | 24.63 |
| ATOM | 2051 | CD2 | LEU | A | 107 | −16.630 | −39.928 | −9.101 | 1.00 | 24.56 |
| ATOM | 2052 | C | LEU | A | 107 | −12.589 | −38.955 | −7.544 | 1.00 | 23.14 |
| ATOM | 2053 | O | LEU | A | 107 | −12.312 | −38.151 | −8.430 | 1.00 | 23.15 |
| ATOM | 2059 | N | THR | A | 109 | −9.811 | −39.869 | −8.275 | 1.00 | 20.00 |
| ATOM | 2060 | CA | THR | A | 109 | −9.090 | −40.122 | −9.527 | 1.00 | 19.48 |
| ATOM | 2061 | CB | THR | A | 109 | −9.400 | −41.516 | −10.126 | 1.00 | 19.37 |
| ATOM | 2062 | OG1 | THR | A | 109 | −10.783 | −41.600 | −10.504 | 1.00 | 19.30 |
| ATOM | 2063 | CG2 | THR | A | 109 | −9.065 | −42.606 | −9.129 | 1.00 | 20.66 |
| ATOM | 2064 | C | THR | A | 109 | −9.367 | −39.047 | −10.576 | 1.00 | 18.77 |
| ATOM | 2065 | O | THR | A | 109 | −8.517 | −38.779 | −11.418 | 1.00 | 18.55 |
| ATOM | 2066 | N | LEU | A | 110 | −10.557 | −38.449 | −10.525 | 1.00 | 18.32 |
| ATOM | 2067 | CA | LEU | A | 110 | −10.897 | −37.323 | −11.405 | 1.00 | 18.09 |
| ATOM | 2068 | CB | LEU | A | 110 | −12.408 | −37.051 | −11.408 | 1.00 | 18.21 |

TABLE 3-continued

Atomic coordinates of amino acid residues of
yDcn1 Chain A essential for binding yUbc12.

| | Atom No. | Atom Name | | | X | Y | Z | Occupancy | B-factor |
|---|---|---|---|---|---|---|---|---|---|
| ATOM | 2069 | CG | LEU | A | 110 | −13.322 | −38.008 | −12.173 | 1.00 | 19.07 |
| ATOM | 2070 | CD1 | LEU | A | 110 | −14.784 | −37.727 | −11.833 | 1.00 | 19.91 |
| ATOM | 2071 | CD2 | LEU | A | 110 | −13.098 | −37.862 | −13.661 | 1.00 | 20.22 |
| ATOM | 2072 | C | LEU | A | 110 | −10.154 | −36.050 | −11.012 | 1.00 | 17.74 |
| ATOM | 2073 | O | LEU | A | 110 | −9.798 | −35.262 | −11.877 | 1.00 | 17.47 |
| ATOM | 2088 | N | ALA | A | 113 | −6.659 | −36.664 | −12.409 | 1.00 | 16.15 |
| ATOM | 2089 | CA | ALA | A | 113 | −6.724 | −36.421 | −13.847 | 1.00 | 16.33 |
| ATOM | 2090 | CB | ALA | A | 113 | −7.934 | −37.130 | −14.448 | 1.00 | 15.86 |
| ATOM | 2091 | C | ALA | A | 113 | −6.769 | −34.929 | −14.143 | 1.00 | 16.46 |
| ATOM | 2092 | O | ALA | A | 113 | −6.073 | −34.432 | −15.042 | 1.00 | 16.39 |
| ATOM | 2153 | N | LEU | A | 121 | −8.648 | −39.338 | −21.818 | 1.00 | 26.23 |
| ATOM | 2154 | CA | LEU | A | 121 | −7.960 | −40.441 | −21.168 | 1.00 | 26.53 |
| ATOM | 2155 | CB | LEU | A | 121 | −8.935 | −41.261 | −20.341 | 1.00 | 26.04 |
| ATOM | 2156 | CG | LEU | A | 121 | −9.410 | −40.537 | −19.073 | 1.00 | 25.47 |
| ATOM | 2157 | CD1 | LEU | A | 121 | −10.506 | −41.328 | −18.368 | 1.00 | 23.26 |
| ATOM | 2158 | CD2 | LEU | A | 121 | −8.260 | −40.242 | −18.117 | 1.00 | 22.91 |
| ATOM | 2159 | C | LEU | A | 121 | −7.210 | −41.300 | −22.176 | 1.00 | 27.40 |
| ATOM | 2160 | O | LEU | A | 121 | −6.244 | −41.976 | −21.832 | 1.00 | 27.21 |
| ATOM | 2161 | N | GLU | A | 122 | −7.652 | −41.223 | −23.429 | 1.00 | 28.34 |
| ATOM | 2162 | CA | GLU | A | 122 | −7.059 | −41.940 | −24.547 | 1.00 | 29.67 |
| ATOM | 2163 | CB | GLU | A | 122 | −7.893 | −41.694 | −25.815 | 1.00 | 30.04 |
| ATOM | 2164 | CG | GLU | A | 122 | −9.327 | −42.285 | −25.788 | 1.00 | 32.62 |
| ATOM | 2165 | CD | GLU | A | 122 | −10.340 | −41.459 | −24.962 | 1.00 | 36.03 |
| ATOM | 2166 | OE1 | GLU | A | 122 | −9.945 | −40.458 | −24.326 | 1.00 | 37.15 |
| ATOM | 2167 | OE2 | GLU | A | 122 | −11.546 | −41.817 | −24.951 | 1.00 | 37.17 |
| ATOM | 2168 | C | GLU | A | 122 | −5.604 | −41.538 | −24.807 | 1.00 | 29.90 |
| ATOM | 2169 | O | GLU | A | 122 | −4.828 | −42.329 | −25.341 | 1.00 | 29.76 |
| ATOM | 2593 | N | LEU | A | 173 | −14.257 | −36.100 | −20.020 | 1.00 | 27.24 |
| ATOM | 2594 | CA | LEU | A | 173 | −13.462 | −37.319 | −20.047 | 1.00 | 28.20 |
| ATOM | 2595 | CB | LEU | A | 173 | −12.752 | −37.534 | −18.702 | 1.00 | 27.88 |
| ATOM | 2596 | CG | LEU | A | 173 | −11.564 | −36.653 | −18.295 | 1.00 | 26.35 |
| ATOM | 2597 | CD1 | LEU | A | 173 | −10.879 | −37.249 | −17.070 | 1.00 | 24.58 |
| ATOM | 2598 | CD2 | LEU | A | 173 | −10.565 | −36.496 | −19.415 | 1.00 | 23.46 |
| ATOM | 2599 | C | LEU | A | 173 | −14.284 | −38.561 | −20.404 | 1.00 | 29.58 |
| ATOM | 2600 | O | LEU | A | 173 | −13.745 | −39.509 | −20.986 | 1.00 | 30.13 |
| ATOM | 2601 | N | ILE | A | 174 | −15.566 | −38.577 | −20.028 | 1.00 | 30.42 |
| ATOM | 2602 | CA | ILE | A | 174 | −16.469 | −39.669 | −20.419 | 1.00 | 31.46 |
| ATOM | 2603 | CB | ILE | A | 174 | −17.863 | −39.576 | −19.712 | 1.00 | 31.45 |
| ATOM | 2604 | CG1 | ILE | A | 174 | −17.714 | −39.524 | −18.182 | 1.00 | 32.09 |
| ATOM | 2605 | CD1 | ILE | A | 174 | −18.987 | −39.100 | −17.425 | 1.00 | 31.01 |
| ATOM | 2606 | CG2 | ILE | A | 174 | −18.727 | −40.771 | −20.069 | 1.00 | 31.27 |
| ATOM | 2607 | C | ILE | A | 174 | −16.639 | −39.721 | −21.958 | 1.00 | 32.27 |
| ATOM | 2608 | O | ILE | A | 174 | −16.727 | −40.805 | −22.548 | 1.00 | 32.29 |
| ATOM | 2609 | N | LEU | A | 175 | −16.662 | −38.548 | −22.595 | 1.00 | 33.10 |
| ATOM | 2610 | CA | LEU | A | 175 | −16.824 | −36.438 | −24.046 | 1.00 | 33.94 |
| ATOM | 2611 | CB | LEU | A | 175 | −16.591 | −37.000 | −24.504 | 1.00 | 33.73 |
| ATOM | 2612 | CG | LEU | A | 175 | −17.754 | −36.016 | −24.433 | 1.00 | 32.38 |
| ATOM | 2613 | CD1 | LEU | A | 175 | −17.305 | −34.695 | −25.015 | 1.00 | 31.73 |
| ATOM | 2614 | CD2 | LEU | A | 175 | −18.961 | −36.553 | −25.170 | 1.00 | 30.45 |
| ATOM | 2615 | C | LEU | A | 175 | −15.899 | −39.346 | −24.836 | 1.00 | 35.08 |
| ATOM | 2616 | O | LEU | A | 175 | −14.676 | −39.224 | −24.732 | 1.00 | 35.38 |
| ATOM | 2617 | N | ASP | A | 176 | −16.491 | −40.256 | −25.612 | 1.00 | 36.30 |
| ATOM | 2618 | CA | ASP | A | 176 | −15.745 | −41.072 | −26.566 | 1.00 | 37.58 |
| ATOM | 2619 | CB | ASP | A | 176 | −16.638 | −42.160 | −27.185 | 1.00 | 37.78 |
| ATOM | 2620 | CG | ASP | A | 176 | −16.713 | −43.424 | −26.336 | 1.00 | 38.93 |
| ATOM | 2621 | OD1 | ASP | A | 176 | −15.702 | −43.778 | −25.687 | 1.00 | 40.88 |
| ATOM | 2622 | OD2 | ASP | A | 176 | −17.783 | −44.073 | −26.324 | 1.00 | 39.22 |
| ATOM | 2623 | C | ASP | A | 176 | −15.208 | −40.161 | −27.664 | 1.00 | 38.32 |
| ATOM | 2624 | O | ASP | A | 176 | −15.816 | −39.123 | −27.955 | 1.00 | 38.43 |
| ATOM | 2720 | N | GLN | A | 189 | −24.108 | −44.371 | −14.531 | 1.00 | 23.07 |
| ATOM | 2721 | CA | GLN | A | 189 | −22.967 | −44.901 | −13.784 | 1.00 | 23.84 |
| ATOM | 2722 | CB | GLN | A | 189 | −21.967 | −45.602 | −14.716 | 1.00 | 24.30 |
| ATOM | 2723 | CG | GLN | A | 189 | −22.352 | −47.016 | −15.106 | 1.00 | 26.75 |
| ATOM | 2724 | CD | GLN | A | 189 | −21.292 | −47.707 | −15.960 | 1.00 | 31.60 |
| ATOM | 2725 | OE1 | GLN | A | 189 | −21.601 | −48.637 | −16.715 | 1.00 | 34.94 |
| ATOM | 2726 | NE2 | GLN | A | 189 | −20.037 | −47.268 | −15.842 | 1.00 | 32.62 |
| ATOM | 2727 | C | GLN | A | 189 | −22.245 | −43.822 | −12.980 | 1.00 | 23.49 |
| ATOM | 2728 | O | GLN | A | 189 | −21.936 | −44.017 | −11.802 | 1.00 | 23.77 |
| ATOM | 2729 | N | TYR | A | 190 | −21.980 | −42.684 | −13.609 | 1.00 | 22.91 |
| ATOM | 2730 | CA | TYR | A | 190 | −21.298 | −41.606 | −12.912 | 1.00 | 22.41 |
| ATOM | 2731 | CB | TYR | A | 190 | −20.578 | −40.677 | −13.886 | 1.00 | 22.75 |
| ATOM | 2732 | CG | TYR | A | 190 | −19.344 | −41.317 | −14.475 | 1.00 | 25.31 |
| ATOM | 2733 | CD1 | TYR | A | 190 | −18.109 | −41.216 | −13.839 | 1.00 | 27.94 |
| ATOM | 2734 | CE1 | TYR | A | 190 | −16.965 | −41.818 | −14.389 | 1.00 | 30.54 |

TABLE 3-continued

Atomic coordinates of amino acid residues of yDcn1 Chain A essential for binding yUbc12.

| | Atom No. | Atom Name | | | X | Y | Z | Occupancy | B-factor |
|---|---|---|---|---|---|---|---|---|---|
| ATOM | 2735 | CZ | TYR | A | 190 | −17.072 | −42.532 | −15.580 | 1.00 | 30.87 |
| ATOM | 2736 | OH | TYR | A | 190 | −15.967 | −43.134 | −16.144 | 1.00 | 33.77 |
| ATOM | 2737 | CE2 | TYR | A | 190 | −18.292 | −42.651 | −16.215 | 1.00 | 29.70 |
| ATOM | 2738 | CD2 | TYR | A | 190 | −19.416 | −42.047 | −15.664 | 1.00 | 28.05 |
| ATOM | 2739 | C | TYR | A | 190 | −22.212 | −40.836 | −11.971 | 1.00 | 21.59 |
| ATOM | 2740 | O | TYR | A | 190 | −21.766 | −40.423 | −10.891 | 1.00 | 21.41 |
| ATOM | 2764 | N | LEU | A | 193 | −22.165 | −42.386 | −8.662 | 1.00 | 20.37 |
| ATOM | 2765 | CA | LEU | A | 193 | −20.961 | −42.081 | −7.894 | 1.00 | 20.05 |
| ATOM | 2766 | CB | LEU | A | 193 | −19.711 | −42.257 | −8.753 | 1.00 | 20.28 |
| ATOM | 2767 | CG | LEU | A | 193 | −19.352 | −43.673 | −9.200 | 1.00 | 20.34 |
| ATOM | 2768 | CD1 | LEU | A | 193 | −18.137 | −43.611 | −10.088 | 1.00 | 20.81 |
| ATOM | 2769 | CD2 | LEU | A | 193 | −19.125 | −44.614 | −8.014 | 1.00 | 19.15 |
| ATOM | 2770 | C | LEU | A | 193 | −21.011 | −40.669 | −7.325 | 1.00 | 19.95 |
| ATOM | 2771 | O | LEU | A | 193 | −20.753 | −40.470 | −6.136 | 1.00 | 20.12 |

TABLE 4

Additional contacts that contribute to, but are not essential, for contact between S. cerevisiae Dcn1 and S. cerevisiae Ubc12 with yUbc12 Chain C interactions with yDcn1$^P$ Chain A and yUbc12 Chain D interactions with yDcn1$^P$ Chain B shown.

| yUbc12 Atom | | | yDcn1 Atom | | | Distance (Å) |
|---|---|---|---|---|---|---|
| Arg | 5C | NE | Leu | 104A | CD2 | 4.07 |
| Arg | 5C | CZ | Leu | 104A | CB | 4.43 |
| | | | Glu | 105A | CD | 4.44 |
| | | | Glu | 105A | OE2 | 3.95 |
| | | | Leu | 104A | CD2 | 4.28 |
| Arg | 5C | NH1 | Glu | 105A | CG | 4.02 |
| | | | Glu | 105A | CD | 4.28 |
| | | | Glu | 105A | OE2 | 3.96 |
| Arg | 5C | NH2 | Leu | 104A | CB | 4.21 |
| | | | Glu | 105A | CG | 4.21 |
| | | | Glu | 105A | CD | 3.64 |
| | | | Glu | 105A | OE1 | 4.3 |
| | | | Glu | 105A | OE2 | 3.05 |
| | | | Leu | 104A | CD2 | 4.39 |
| | | | Leu | 104A | CG | 4.46 |
| | | | Leu | 104A | CD1 | 4.13 |
| Leu | 7C | CB | Ile | 90A | CD1 | 4.44 |
| | | | Ile | 90A | CG2 | 4.39 |
| Leu | 7C | CD1 | Leu | 121A | CB | 4.19 |
| Leu | 7C | CD2 | Glu | 122A | OE2 | 4.34 |
| | | | Glu | 122A | CG | 3.85 |
| | | | Glu | 122A | CD | 4.36 |
| Leu | 7C | C | Ile | 90A | CD1 | 3.57 |
| Leu | 7C | O | Ile | 90A | CD1 | 3.4 |
| Gln | 8C | N | Ile | 90A | CD1 | 3.49 |
| Gln | 8C | CA | Ile | 90A | CD1 | 3.4 |
| Gln | 8C | CB | Ile | 90A | CD1 | 4.18 |
| | | | Asp | 91A | OD1 | 4.43 |
| Gln | 8C | CG | Ile | 90A | CD1 | 3.79 |
| | | | Val | 94A | CG2 | 4.28 |
| | | | Asp | 91A | OD1 | 3.49 |
| Gln | 8C | CD | Val | 94A | CG1 | 4.46 |
| | | | Val | 94A | CG2 | 3.58 |
| | | | Asp | 91A | OD1 | 3.87 |
| | | | Val | 94A | CB | 4.37 |
| Gln | 8C | OE1 | Val | 94A | CG1 | 4.46 |
| | | | Val | 94A | CG2 | 3.72 |
| Gln | 8C | NE2 | Val | 94A | CG1 | 3.83 |
| | | | Val | 94A | CG2 | 3.53 |
| | | | Asp | 91A | OD1 | 3.24 |
| | | | Asp | 91A | CG | 4.36 |
| | | | Asp | 91A | CA | 4.34 |
| | | | Val | 94A | CB | 3.84 |

TABLE 4-continued

Additional contacts that contribute to, but are not essential, for contact between S. cerevisiae Dcn1 and S. cerevisiae Ubc12 with yUbc12 Chain C interactions with yDcn1$^P$ Chain A and yUbc12 Chain D interactions with yDcn1$^P$ Chain B shown.

| yUbc12 Atom | | | yDcn1 Atom | | | Distance (Å) |
|---|---|---|---|---|---|---|
| Lys | 11C | CB | Ile | 90A | CD1 | 4.03 |
| Lys | 11C | CD | Ile | 90A | CD1 | 4.14 |
| | | | Asp | 89A | OD2 | 4.33 |
| | | | Asp | 91A | CG | 4.43 |
| | | | Asp | 91A | OD2 | 3.44 |
| Lys | 11C | CE | Asp | 89A | CG | 4.47 |
| | | | Asp | 89A | OD2 | 3.48 |
| | | | Asp | 91A | OD2 | 3.64 |
| Lys | 11C | NZ | Asp | 89A | CG | 4.01 |
| | | | Asp | 89A | OD2 | 2.97 |
| | | | Asp | 91A | CG | 3.92 |
| | | | Asp | 91A | OD2 | 2.7 |
| | | | Asn | 84A | CB | 4.47 |
| Arg | 5D | N | Leu | 104B | CD1 | 4.25 |
| Arg | 5D | CA | Leu | 104B | CD1 | 4.37 |
| Arg | 5D | CB | Leu | 104B | CD1 | 3.71 |
| Arg | 5D | CG | Leu | 104B | CD1 | 4.36 |
| Arg | 5D | NE | Leu | 104B | CD1 | 3.9 |
| Arg | 5D | CZ | Leu | 104B | CB | 4.48 |
| | | | Leu | 104B | CD1 | 3.74 |
| | | | Glu | 105B | OE2 | 4.2 |
| Arg | 5D | NH1 | Leu | 104B | CD1 | 4.31 |
| | | | Glu | 105B | OE2 | 4.16 |
| Arg | 5D | NH2 | Leu | 104B | CB | 3.97 |
| | | | Leu | 104B | CG | 4.04 |
| | | | Leu | 104B | CD1 | 3.67 |
| | | | Glu | 105B | OE2 | 3.4 |
| | | | Glu | 105B | CD | 4 |
| | | | Glu | 105B | OE1 | 4.12 |
| Gln | 6D | CD | Glu | 186B | CD | 4.47 |
| | | | Glu | 186B | OE2 | 3.46 |
| Gln | 6D | OE1 | Glu | 186B | CG | 3.8 |
| | | | Glu | 186B | CD | 3.69 |
| | | | Glu | 186B | OE2 | 2.9 |
| Gln | 6D | NE2 | Asp | 176B | OD1 | 4.18 |
| | | | Glu | 186B | CD | 4.41 |
| | | | Glu | 186B | OE2 | 3.25 |
| Leu | 7D | CB | Ile | 90B | CD1 | 3.77 |
| Leu | 7D | CG | Ile | 90B | CD1 | 4.25 |
| Leu | 7D | CD1 | Leu | 121B | CB | 4.01 |
| | | | Leu | 121B | C | 4.43 |
| | | | Ile | 90B | CD1 | 3.76 |
| | | | Glu | 122B | CG | 4.4 |

TABLE 4-continued

Additional contacts that contribute to, but are not essential, for contact between *S. cerevisiae* Dcn1 and *S. cerevisiae* Ubc12 with yUbc12 Chain C interactions with yDcn1$^P$ Chain A and yUbc12 Chain D interactions with yDcn1$^P$ Chain B shown.

| yUbc12 | Atom | yDcn1 | Atom | | Distance (Å) |
|---|---|---|---|---|---|
| Leu | 7D | CD2 | Glu | 122B | CG | 4.4 |
| Gln | 8D | CG | Ile | 90B | CG2 | 4.17 |
|  |  |  | Asp | 91B | OD1 | 4.03 |
| Gln | 8D | CD | Asp | 91B | OD1 | 4.34 |
|  |  |  | Val | 94B | CG2 | 4.02 |
| Gln | 8D | OE1 | Val | 94B | CG2 | 4.29 |
| Gln | 8D | NE2 | Asp | 91B | OD1 | 3.6 |
|  |  |  | Val | 94B | CB | 4.02 |
|  |  |  | Val | 94B | CG2 | 3.75 |
|  |  |  | Val | 94B | CG1 | 3.87 |

TABLE 5

Atomic coordinates of residues that contribute to, but are not required for, binding of yDcn1 Chain B to yUbc12.

| | Atom No. | Atom Name | | | X | Y | Z | Occupancy | B-factor |
|---|---|---|---|---|---|---|---|---|---|
| ATOM | 136 | N | ASN | B | 84 | −24.546 | −0.988 | −25.260 | 1.00 | 25.93 |
| ATOM | 137 | CA | ASN | B | 84 | −24.488 | 0.253 | −26.016 | 1.00 | 27.03 |
| ATOM | 138 | CB | ASN | B | 84 | −23.072 | 0.833 | −25.998 | 1.00 | 27.10 |
| ATOM | 139 | CG | ASN | B | 84 | −22.586 | 1.127 | −24.609 | 1.00 | 26.68 |
| ATOM | 140 | OD1 | ASN | B | 84 | −23.153 | 1.954 | −23.903 | 1.00 | 27.53 |
| ATOM | 141 | ND2 | ASN | B | 84 | −21.525 | 0.454 | −24.205 | 1.00 | 26.15 |
| ATOM | 142 | C | ASN | B | 84 | −24.887 | −0.019 | −27.445 | 1.00 | 27.74 |
| ATOM | 143 | O | ASN | B | 84 | −24.248 | −0.823 | −28.120 | 1.00 | 27.97 |
| ATOM | 179 | N | ASP | B | 89 | −20.480 | −4.359 | −25.414 | 1.00 | 26.21 |
| ATOM | 180 | CA | ASP | B | 89 | −19.176 | −4.073 | −25.996 | 1.00 | 26.19 |
| ATOM | 181 | CB | ASP | B | 89 | −19.314 | −2.957 | −27.045 | 1.00 | 26.08 |
| ATOM | 182 | CG | ASP | B | 89 | −19.779 | −1.625 | −26.445 | 1.00 | 26.39 |
| ATOM | 183 | OD1 | ASP | B | 89 | −19.976 | −1.535 | −25.210 | 1.00 | 26.46 |
| ATOM | 184 | OD2 | ASP | B | 89 | −19.945 | −0.655 | −27.218 | 1.00 | 27.17 |
| ATOM | 185 | C | ASP | B | 89 | −18.124 | −3.716 | −24.930 | 1.00 | 26.36 |
| ATOM | 186 | O | ASP | B | 89 | −18.336 | −3.935 | −23.735 | 1.00 | 25.92 |
| ATOM | 195 | N | ASP | B | 91 | −17.152 | −0.819 | −23.793 | 1.00 | 26.91 |
| ATOM | 196 | CA | ASP | B | 91 | −17.667 | 0.172 | −22.850 | 1.00 | 26.57 |
| ATOM | 197 | CB | ASP | B | 91 | −18.385 | 1.308 | −23.586 | 1.00 | 27.05 |
| ATOM | 198 | CG | ASP | B | 91 | −17.432 | 2.176 | −24.392 | 1.00 | 29.32 |
| ATOM | 199 | OD1 | ASP | B | 91 | −16.274 | 2.369 | −23.951 | 1.00 | 31.34 |
| ATOM | 200 | OD2 | ASP | B | 91 | −17.840 | 2.667 | −25.469 | 1.00 | 31.93 |
| ATOM | 201 | C | ASP | B | 91 | −18.579 | −0.476 | −21.814 | 1.00 | 25.69 |
| ATOM | 202 | O | ASP | B | 91 | −18.575 | −0.092 | −20.643 | 1.00 | 25.22 |
| ATOM | 278 | N | GLY | B | 101 | −17.275 | −3.210 | −8.645 | 1.00 | 29.34 |
| ATOM | 279 | CA | GLY | B | 101 | −16.450 | −2.623 | −7.591 | 1.00 | 29.68 |
| ATOM | 280 | C | GLY | B | 101 | −14.959 | −2.810 | −7.784 | 1.00 | 29.86 |
| ATOM | 281 | O | GLY | B | 101 | −14.203 | −2.788 | −6.815 | 1.00 | 30.12 |
| ATOM | 282 | N | TYR | B | 102 | −14.530 | −2.981 | −9.033 | 1.00 | 29.95 |
| ATOM | 283 | CA | TYR | B | 102 | −13.125 | −3.256 | −9.329 | 1.00 | 29.83 |
| ATOM | 284 | CB | TYR | B | 102 | −12.976 | −4.620 | −10.014 | 1.00 | 29.64 |
| ATOM | 285 | CG | TYR | B | 102 | −13.264 | −5.790 | −9.097 | 1.00 | 28.75 |
| ATOM | 286 | CD1 | TYR | B | 102 | −12.267 | −6.325 | −8.285 | 1.00 | 27.79 |
| ATOM | 287 | CE1 | TYR | B | 102 | −12.529 | −7.385 | −7.429 | 1.00 | 27.33 |
| ATOM | 288 | CZ | TYR | B | 102 | −13.798 | −7.929 | −7.382 | 1.00 | 28.21 |
| ATOM | 289 | OH | TYR | B | 102 | −14.063 | −8.983 | −6.538 | 1.00 | 28.62 |
| ATOM | 290 | CE2 | TYR | B | 102 | −14.812 | −7.417 | −8.175 | 1.00 | 28.92 |
| ATOM | 291 | CD2 | TYR | B | 102 | −14.539 | −6.349 | −9.029 | 1.00 | 29.04 |
| ATOM | 292 | C | TYR | B | 102 | −12.471 | −2.173 | −10.169 | 1.00 | 30.22 |
| ATOM | 293 | O | TYR | B | 102 | −13.155 | −1.397 | −10.842 | 1.00 | 30.20 |
| ATOM | 294 | N | ASN | B | 103 | −11.141 | −2.110 | −10.079 | 1.00 | 30.62 |
| ATOM | 295 | CA | ASN | B | 103 | −10.307 | −1.343 | −11.000 | 1.00 | 30.76 |
| ATOM | 296 | CB | ASN | B | 103 | −9.066 | −0.790 | −10.286 | 1.00 | 30.89 |
| ATOM | 297 | CG | ASN | B | 103 | −9.406 | 0.188 | −9.160 | 1.00 | 32.03 |
| ATOM | 298 | OD1 | ASN | B | 103 | −10.086 | 1.193 | −9.372 | 1.00 | 34.05 |
| ATOM | 299 | ND2 | ASN | B | 103 | −8.912 | −0.096 | −7.960 | 1.00 | 32.51 |
| ATOM | 300 | C | ASN | B | 103 | −9.874 | −2.289 | −12.114 | 1.00 | 30.71 |
| ATOM | 301 | O | ASN | B | 103 | −9.821 | −3.509 | −11.911 | 1.00 | 30.68 |
| ATOM | 980 | N | GLU | B | 186 | 3.220 | −4.286 | −23.322 | 1.00 | 25.28 |
| ATOM | 981 | CA | GLU | B | 186 | 1.962 | −4.813 | −22.773 | 1.00 | 25.53 |
| ATOM | 982 | CB | GLU | B | 186 | 1.005 | −5.255 | −23.886 | 1.00 | 26.28 |
| ATOM | 983 | CG | GLU | B | 186 | 0.428 | −4.141 | −24.769 | 1.00 | 30.25 |
| ATOM | 984 | CD | GLU | B | 186 | −0.261 | −4.683 | −26.032 | 1.00 | 35.54 |
| ATOM | 985 | OE1 | GLU | B | 186 | −0.215 | −5.914 | −26.273 | 1.00 | 38.14 |
| ATOM | 986 | OE2 | GLU | B | 186 | −0.848 | −3.877 | −26.794 | 1.00 | 38.37 |

TABLE 5-continued

Atomic coordinates of residues that contribute to, but are not required for, binding of yDcn1 Chain B to yUbc12.

| | Atom No. | Atom Name | | | X | Y | Z | Occupancy | B-factor |
|---|---|---|---|---|---|---|---|---|---|
| ATOM | 987 | C | GLU | B | 186 | 2.231 | −5.998 | −21.836 | 1.00 | 24.41 |
| ATOM | 988 | O | GLU | B | 186 | 1.635 | −6.093 | −20.756 | 1.00 | 24.41 |

TABLE 6

Atomic coordinates of residues that contribute to, but are not required for, binding of yDcn1 Chain A to yUbc12.

| | Atom No. | Atom Name | | | X | Y | Z | Occupancy | B-factor |
|---|---|---|---|---|---|---|---|---|---|
| ATOM | 1855 | N | ASN | A | 84 | 5.480 | −47.125 | −19.771 | 1.00 | 24.51 |
| ATOM | 1856 | CA | ASN | A | 84 | 5.351 | −48.370 | −20.509 | 1.00 | 24.71 |
| ATOM | 1857 | CB | ASN | A | 84 | 3.911 | −48.902 | −20.440 | 1.00 | 25.23 |
| ATOM | 1858 | CG | ASN | A | 84 | 3.565 | −49.475 | −19.082 | 1.00 | 26.13 |
| ATOM | 1859 | CD1 | ASN | A | 84 | 4.293 | −50.299 | −18.541 | 1.00 | 30.17 |
| ATOM | 1860 | ND2 | ASN | A | 84 | 2.447 | −49.049 | −18.529 | 1.00 | 27.12 |
| ATOM | 1861 | C | ASN | A | 84 | 5.729 | −48.075 | −21.938 | 1.00 | 24.19 |
| ATOM | 1862 | O | ASN | A | 84 | 5.204 | −47.140 | −22.528 | 1.00 | 24.25 |
| ATOM | 1898 | N | ASP | A | 89 | 1.132 | −44.006 | −20.314 | 1.00 | 21.24 |
| ATOM | 1899 | CA | ASP | A | 89 | −0.152 | −44.370 | −20.921 | 1.00 | 21.52 |
| ATOM | 1900 | CB | ASP | A | 89 | 0.045 | −45.548 | −21.893 | 1.00 | 21.94 |
| ATOM | 1901 | CG | ASP | A | 89 | 0.661 | −46.781 | −21.218 | 1.00 | 23.83 |
| ATOM | 1902 | CD1 | ASP | A | 89 | 0.856 | −46.789 | −19.967 | 1.00 | 27.18 |
| ATOM | 1903 | OD2 | ASP | A | 89 | 0.951 | −47.755 | −21.946 | 1.00 | 27.23 |
| ATOM | 1904 | C | ASP | A | 89 | −1.171 | −44.759 | −19.860 | 1.00 | 21.03 |
| ATOM | 1905 | O | ASP | A | 89 | −0.986 | −44.504 | −18.677 | 1.00 | 20.38 |
| ATOM | 1914 | N | ASP | A | 91 | −2.097 | −47.801 | −18.722 | 1.00 | 22.01 |
| ATOM | 1915 | CA | ASP | A | 91 | −1.539 | −48.709 | −17.724 | 1.00 | 21.76 |
| ATOM | 1916 | CB | ASP | A | 91 | −0.654 | −49.764 | −18.384 | 1.00 | 22.52 |
| ATOM | 1917 | CG | ASP | A | 91 | −1.404 | −50.617 | −19.386 | 1.00 | 23.98 |
| ATOM | 1918 | OD1 | ASP | A | 91 | −2.482 | −51.150 | −19.045 | 1.00 | 25.33 |
| ATOM | 1919 | OD2 | ASP | A | 91 | −0.903 | −50.762 | −20.520 | 1.00 | 26.75 |
| ATOM | 1920 | C | ASP | A | 91 | −0.745 | −47.940 | −16.676 | 1.00 | 21.29 |
| ATOM | 1921 | O | ASP | A | 91 | −0.916 | −48.190 | −15.480 | 1.00 | 21.45 |
| ATOM | 1997 | N | GLY | A | 101 | −2.947 | −45.057 | −3.801 | 1.00 | 22.73 |
| ATOM | 1998 | CA | GLY | A | 101 | −3.770 | −45.643 | −2.749 | 1.00 | 23.50 |
| ATOM | 1999 | C | GLY | A | 101 | −5.257 | −45.694 | −3.055 | 1.00 | 24.28 |
| ATOM | 2000 | O | GLY | A | 101 | −6.068 | −45.834 | −2.140 | 1.00 | 24.21 |
| ATOM | 2001 | N | TYR | A | 102 | −5.616 | −45.604 | −4.334 | 1.00 | 25.12 |
| ATOM | 2002 | CA | TYR | A | 102 | −7.025 | −45.504 | −4.736 | 1.00 | 26.13 |
| ATOM | 2003 | CB | TYR | A | 102 | −7.305 | −44.158 | −5.419 | 1.00 | 25.91 |
| ATOM | 2004 | CG | TYR | A | 102 | −7.145 | −43.006 | −4.469 | 1.00 | 26.01 |
| ATOM | 2005 | CD1 | TYR | A | 102 | −8.209 | −42.587 | −3.663 | 1.00 | 26.06 |
| ATOM | 2006 | CE1 | TYR | A | 102 | −8.056 | −41.536 | −2.767 | 1.00 | 26.07 |
| ATOM | 2007 | CZ | TYR | A | 102 | −6.827 | −40.904 | −2.664 | 1.00 | 25.39 |
| ATOM | 2008 | OH | TYR | A | 102 | −6.657 | −39.872 | −1.780 | 1.00 | 25.43 |
| ATOM | 2009 | CE2 | TYR | A | 102 | −5.758 | −41.306 | −3.446 | 1.00 | 26.78 |
| ATOM | 2010 | CD2 | TYR | A | 102 | −5.919 | −42.351 | −4.346 | 1.00 | 25.73 |
| ATOM | 2011 | C | TYR | A | 102 | −7.529 | −46.640 | −5.612 | 1.00 | 26.90 |
| ATOM | 2012 | O | TYR | A | 102 | −6.748 | −47.385 | −6.199 | 1.00 | 27.17 |
| ATOM | 2013 | N | ASN | A | 103 | −8.852 | −46.760 | −5.649 | 1.00 | 28.08 |
| ATOM | 2014 | CA | ASN | A | 103 | −9.578 | −47.619 | −6.565 | 1.00 | 29.35 |
| ATOM | 2015 | CB | ASN | A | 103 | −10.792 | −48.231 | −5.854 | 1.00 | 29.88 |
| ATOM | 2016 | CG | ASN | A | 103 | −10.399 | −49.134 | −4.687 | 1.00 | 32.31 |
| ATOM | 2017 | OD1 | ASN | A | 103 | −9.440 | −49.903 | −4.782 | 1.00 | 35.88 |
| ATOM | 2018 | ND2 | ASN | A | 103 | −11.140 | −49.045 | −3.585 | 1.00 | 33.38 |
| ATOM | 2019 | C | ASN | A | 103 | −10.045 | −46.753 | −7.729 | 1.00 | 29.59 |
| ATOM | 2020 | O | ASN | A | 103 | −10.294 | −45.555 | −7.552 | 1.00 | 29.55 |
| ATOM | 2699 | N | GLU | A | 186 | −23.763 | −44.689 | −19.329 | 1.00 | 26.90 |
| ATOM | 2700 | CA | GLU | A | 186 | −22.562 | −44.138 | −18.718 | 1.00 | 26.47 |
| ATOM | 2701 | CB | GLU | A | 186 | −21.512 | −43.836 | −19.791 | 1.00 | 26.96 |
| ATOM | 2702 | CG | GLU | A | 186 | −20.845 | −45.096 | −20.328 | 1.00 | 29.85 |
| ATOM | 2703 | CD | GLU | A | 186 | −20.272 | −44.939 | −21.736 | 1.00 | 34.58 |
| ATOM | 2704 | OE1 | GLU | A | 186 | −20.423 | −43.852 | −22.339 | 1.00 | 37.35 |
| ATOM | 2705 | OE2 | GLU | A | 186 | −19.666 | −45.912 | −22.245 | 1.00 | 36.39 |
| ATOM | 2706 | C | GLU | A | 186 | −22.862 | −42.917 | −17.846 | 1.00 | 25.40 |
| ATOM | 2707 | O | GLU | A | 186 | −22.228 | −42.733 | −16.803 | 1.00 | 25.32 |

In other embodiments, the E2-binding pocket of a NEDD8 co-E3 protein comprises the atoms of Table 7, which are found in amino acid residues Ile83, Ile86, Gln87, Pro97, Ala98, Ser99, Val102, Leu103, Ala106, Gln114, Cys115, Phe117, Phe164, Asn167, Met177, Ala180, Tyr181, and Leu184 of human Dcn1 (SEQ ID NO: 33), or a structural variant thereof. In particular embodiments, the E2-binding pocket of a NEDD8 co-E3 protein comprises at least one of the following amino acid residues: an isoleucine corresponding to position 83 of SEQ ID NO: 33, an isoleucine corresponding to position 86 of SEQ ID NO: 33, a glutamine corresponding to position 87 of SEQ ID NO: 33, a proline corresponding to position 97 of SEQ ID NO: 33, an alanine corresponding to position 98 of SEQ ID NO: 33, a serine corresponding to position 99 of SEQ ID NO: 33, a valine corresponding to position 102 of SEQ ID NO: 33, a leucine corresponding to position 103 of SEQ ID NO: 33, an alanine corresponding to position 106 of SEQ ID NO: 33, a glutamine corresponding to position 114 of SEQ ID NO: 33, a cysteine corresponding to position 115 of SEQ ID NO: 33, a phenylalanine corresponding to position 117 of SEQ ID NO: 33, a phenylalanine corresponding to position 164 of SEQ ID NO: 33, an asparagine corresponding to position 167 of SEQ ID NO: 33, a methionine corresponding to position 177 of SEQ ID NO: 33, an alanine corresponding to position 180 of SEQ ID NO: 33, a tyrosine corresponding to position 181 of SEQ ID NO: 33, and a leucine corresponding to position 184 of SEQ ID NO: 33.

In some of these embodiments, the E2-binding pocket comprises the atomic coordinates of Table 8, 9, 10, or 11, or a structural variant thereof. In particular embodiments, the co-E3 protein has the amino acid sequence set forth in SEQ ID NO: 33.

In certain embodiments, the E2-binding pocket of a NEDD8 co-E3 protein comprises the atoms of Tables 7 and 12. The atoms in Table 12 are found in amino acid residues Asp84, Ala94, Leu95, and Asp96 of SEQ ID NO: 33. Thus, in some embodiments, the E2-binding pocket of a NEDD8 co-E3 protein comprises at least one of the following amino acid residues: an isoleucine corresponding to position 83 of SEQ ID NO: 33, an isoleucine corresponding to position 86 of SEQ ID NO: 33, a glutamine corresponding to position 87 of SEQ ID NO: 33, a proline corresponding to position 97 of SEQ ID NO: 33, an alanine corresponding to position 98 of SEQ ID NO: 33, a serine corresponding to position 99 of SEQ ID NO: 33, a valine corresponding to position 102 of SEQ ID NO: 33, a leucine corresponding to position 103 of SEQ ID NO; 33, an alanine corresponding to position 106 of SEQ ID NO: 33, a glutamine corresponding to position 114 of SEQ ID NO: 33, a cysteine corresponding to position 115 of SEQ ID NO: 33, a phenylalanine corresponding to position 117 of SEQ ID NO: 33, a phenylalanine corresponding to position 164 of SEQ ID NO: 33, an asparagine corresponding to position 167 of SEQ ID NO: 33, a methionine corresponding to position 177 of SEQ ID NO: 33, an alanine corresponding to position 180 of SEQ ID NO; 33, a tyrosine corresponding to position 18I of SEQ ID NO: 33, a leucine corresponding to position 184 of SEQ ID NO: 33, an aspartic acid corresponding to position 84 of SEQ ID NO: 33, an alanine corresponding to position 94 of SEQ ID NO: 33, a leucine corresponding to position 95 of SEQ ID NO: 33, and an aspartic acid corresponding to position 96 of SEQ ID NO: 33.

In some of these embodiments, the E2-binding pocket comprises the atomic coordinates of Tables 8 and 13; Tables 9 and 14; Tables 10 and 15; or Tables 11 and 16; or a structural variant thereof.

TABLE 7

Minimal contacts between human Dcn1 and human Ubc12 with hUbc12 Chain E interactions with hDcn1$^P$ Chain B and hUbc12 Chain F interactions with hDcn1$^P$ ChainA shown.

| hUbc12 Atom | | | hDcn1 Atom | | | Distance (Å) |
|---|---|---|---|---|---|---|
| Acetyl-Met | 1E | O | Pro | 97B | O | 4.28 |
| | | | Cys | 115B | SG | 4.31 |
| Acetyl-Met | 1E | C | Gln | 114B | OE1 | 3.79 |
| | | | Tyr | 181B | OH | 4.2 |
| | | | Pro | 97B | O | 4.19 |
| | | | Cys | 115B | SG | 4.24 |
| Acetyl-Met | 1E | CA | Gln | 114B | OE1 | 4.13 |
| | | | Tyr | 181B | OH | 4.11 |
| | | | Pro | 97B | C | 4.46 |
| | | | Pro | 97B | O | 3.62 |
| | | | Cys | 115B | SG | 4.27 |
| Acetyl-Met | 1E | N | Ala | 98B | CA | 3.95 |
| | | | Tyr | 181B | OH | 4.3 |
| | | | Val | 102B | CG1 | 4.46 |
| | | | Pro | 97B | C | 3.72 |
| | | | Pro | 97B | O | 2.7 |
| | | | Ala | 98B | N | 4.26 |
| Acetyl-Met | 1E | CT1 | Phe | 164B | CE2 | 4.29 |
| | | | Tyr | 181B | CE1 | 4.26 |
| | | | Tyr | 181B | CZ | 4.38 |
| | | | Tyr | 181B | OH | 3.64 |
| | | | Pro | 97B | O | 3.59 |
| Acetyl-Met | 1E | OT | Leu | 103B | CD1 | 4.34 |
| | | | Phe | 164B | CE2 | 3.32 |
| | | | Phe | 164B | CD2 | 4.31 |
| | | | Gln | 114B | CB | 4.29 |
| | | | Tyr | 181B | CE1 | 3.45 |
| | | | Tyr | 181B | CZ | 3.44 |
| | | | Tyr | 181B | OH | 2.61 |
| | | | Phe | 164B | CZ | 4.04 |
| Acetyl-Met | 1E | CT2 | Leu | 103B | CD1 | 4.33 |
| | | | Ser | 99B | O | 3.61 |
| | | | Val | 102B | C | 4.33 |
| | | | Leu | 103B | N | 3.67 |
| | | | Leu | 103B | CA | 3.91 |
| | | | Leu | 103B | CB | 3.76 |
| | | | Ala | 98B | CA | 4.24 |
| | | | Ala | 98B | C | 4.2 |
| | | | Ala | 98B | O | 4.47 |
| | | | Leu | 184B | CD2 | 4.07 |
| | | | Val | 102B | CB | 4.36 |
| | | | Val | 102B | CG1 | 4.25 |
| | | | Pro | 97B | O | 3.58 |
| Acetyl-Met | 1E | CB | Pro | 97B | CB | 4.35 |
| | | | Pro | 97B | C | 4.29 |
| | | | Pro | 97B | O | 3.55 |
| | | | Cys | 115B | SG | 3.98 |
| | | | Ile | 86B | CG2 | 4.42 |
| Acetyl-Met | 1E | CG | Val | 102B | CG1 | 3.87 |
| | | | Pro | 97B | C | 4.45 |
| | | | Pro | 97B | O | 3.53 |
| | | | Ile | 86B | CG2 | 3.63 |
| Acetyl-Met | 1E | SD | Phe | 164B | CZ | 3.9 |
| | | | Val | 102B | CG1 | 4.47 |
| | | | Gln | 114B | CA | 4.31 |
| | | | Gln | 114B | C | 4.36 |
| | | | Cys | 115B | N | 3.4 |
| | | | Cys | 115B | CA | 4.02 |
| | | | Ile | 86B | CG2 | 4.1 |
| Acetyl-Met | 1E | CE | Phe | 117B | CZ | 3.7 |
| | | | Ala | 106B | CB | 4.48 |
| | | | Phe | 164B | CZ | 4.24 |
| | | | Val | 102B | CG1 | 3.71 |
| | | | Phe | 117B | CE1 | 4.04 |
| | | | Phe | 117B | CE2 | 4.49 |
| | | | Ile | 86B | CD1 | 4.34 |
| | | | Ile | 86B | CG2 | 4.02 |
| Ile | 2E | N | Gln | 114B | CD | 4.32 |
| | | | Gln | 114B | OE1 | 3.24 |
| | | | Tyr | 181B | CZ | 4.13 |
| | | | Tyr | 181B | OH | 3.28 |
| Ile | 2E | CA | Gln | 114B | OE1 | 3.88 |
| | | | Tyr | 181B | OH | 4.11 |

TABLE 7-continued

Minimal contacts between human Dcn1 and human Ubc12 with hUbc12 Chain E interactions with hDcn1$^P$ Chain B and hUbc12 Chain F interactions with hDcn1$^P$ ChainA shown.

| hUbc12 Atom | | | hDcn1 Atom | | | Distance (Å) |
|---|---|---|---|---|---|---|
| Ile | 2E | CB | Gln | 114B | OE1 | 4.23 |
| | | | Tyr | 181B | CZ | 3.8 |
| | | | Tyr | 181B | OH | 3.75 |
| | | | Tyr | 181B | CE2 | 3.7 |
| | | | Tyr | 181B | CD2 | 4.42 |
| | | | Met | 177B | SD | 4.01 |
| Ile | 2E | CG1 | Tyr | 181B | CG | 4.48 |
| | | | Tyr | 181B | CD1 | 4.32 |
| | | | Tyr | 181B | CE1 | 3.85 |
| | | | Tyr | 181B | CZ | 3.51 |
| | | | Tyr | 181B | OH | 3.76 |
| | | | Tyr | 181B | CE2 | 3.69 |
| | | | Tyr | 181B | CD2 | 4.16 |
| Ile | 2E | CD1 | Ala | 98B | CA | 4.32 |
| | | | Ala | 98B | CB | 3.64 |
| | | | Ala | 98B | O | 4.16 |
| Ile | 2E | CG2 | Ala | 180B | CB | 3.66 |
| | | | Met | 177B | SD | 3.73 |
| Ile | 2E | C | Gln | 114B | OE1 | 3.83 |
| Lys | 3E | N | Gln | 114B | CD | 3.92 |
| | | | Gln | 114B | OE1 | 2.87 |
| | | | Gln | 114B | NE2 | 4.33 |
| | | | Cys | 115B | SG | 4.07 |
| Lys | 3E | CA | Gln | 114B | CD | 4.5 |
| | | | Gln | 114B | OE1 | 3.64 |
| | | | Met | 177B | CE | 4.45 |
| | | | Cys | 115B | SG | 4.16 |
| Lys | 3E | CB | Gln | 114B | CD | 3.78 |
| | | | Gln | 114B | OE1 | 3.3 |
| | | | Gln | 114B | NE2 | 3.92 |
| | | | Met | 177B | CE | 3.86 |
| | | | Cys | 115B | SG | 4.11 |
| Lys | 3E | CG | Met | 177B | CE | 3.63 |
| Lys | 3E | CD | Met | 177B | CE | 3.52 |
| Lys | 3E | NZ | Asn | 167B | OD1 | 4.22 |
| Lys | 3E | C | Cys | 115B | SG | 3.72 |
| Lys | 3E | O | Cys | 115B | SG | 4.34 |
| Leu | 4E | N | Cys | 115B | SG | 3.31 |
| Leu | 4E | CA | Cys | 115B | SG | 3.54 |
| Leu | 4E | CB | Cys | 115B | SG | 3.87 |
| Leu | 4E | CG | Cys | 115B | SG | 4.49 |
| | | | Ile | 83B | O | 4.35 |
| Leu | 4E | CD1 | Cys | 115B | CA | 4.29 |
| | | | Cys | 115B | CB | 3.97 |
| | | | Cys | 115B | SG | 3.82 |
| | | | Ile | 86B | CB | 4.13 |
| | | | Ile | 86B | CG2 | 4.13 |
| | | | Ile | 83B | O | 3.71 |
| | | | Ile | 83B | CG2 | 3.74 |
| | | | Ile | 83B | CA | 3.86 |
| | | | Ile | 83B | CB | 3.73 |
| | | | Ile | 83B | C | 4.24 |
| Leu | 4E | CD2 | Pro | 97B | CB | 3.78 |
| | | | Pro | 97B | CG | 4.09 |
| | | | Ile | 86B | CG2 | 4.22 |
| | | | Ile | 83B | O | 4.37 |
| | | | Gln | 87B | N | 4.12 |
| | | | Gln | 87B | CA | 4.12 |
| | | | Gln | 87B | CB | 4.21 |
| | | | Gln | 87B | OE1 | 3.57 |
| | | | Gln | 87B | CD | 4.31 |
| Acetyl-Met | 1F | O | Pro | 97A | O | 4.39 |
| | | | Cys | 115A | SG | 4.36 |
| Acetyl-Met | 1F | C | Pro | 97A | O | 4.33 |
| | | | Cys | 115A | SG | 4.23 |
| | | | Gln | 114A | OE1 | 3.8 |
| | | | Tyr | 181A | OH | 4.28 |
| Acetyl-Met | 1F | CA | Pro | 97A | C | 4.48 |
| | | | Pro | 97A | O | 3.73 |
| | | | Cys | 115A | SG | 4.23 |
| | | | Gln | 114A | OE1 | 4.14 |
| | | | Tyr | 181A | OH | 4.21 |
| Acetyl-Met | 1F | N | Pro | 97A | C | 3.72 |
| | | | Pro | 97A | O | 2.79 |
| | | | Ala | 98A | N | 4.21 |
| | | | Ala | 98A | CA | 3.88 |
| | | | Tyr | 181A | OH | 4.37 |
| Acetyl-Met | 1F | CT1 | Pro | 97A | O | 3.65 |
| | | | Ala | 98A | CA | 4.5 |
| | | | Tyr | 181A | CE1 | 4.26 |
| | | | Tyr | 181A | CZ | 4.41 |
| | | | Phe | 164A | CE2 | 4.2 |
| | | | Tyr | 181A | OH | 3.69 |
| Acetyl-Met | 1F | OT | Leu | 103A | CD1 | 4.46 |
| | | | Tyr | 181A | CE1 | 3.54 |
| | | | Tyr | 181A | CZ | 3.57 |
| | | | Phe | 164A | CZ | 3.92 |
| | | | Phe | 164A | CE2 | 3.18 |
| | | | Phe | 164A | CD2 | 4.18 |
| | | | Gln | 114A | CB | 4.17 |
| | | | Tyr | 181A | OH | 2.74 |
| Acetyl-Met | 1F | CT2 | Ala | 98A | C | 4.16 |
| | | | Ala | 98A | O | 4.35 |
| | | | Pro | 97A | O | 3.6 |
| | | | Ala | 98A | CA | 4.19 |
| | | | Ser | 99A | O | 3.64 |
| | | | Val | 102A | CB | 4.44 |
| | | | Val | 102A | CG1 | 4.33 |
| | | | Leu | 103A | N | 3.83 |
| | | | Leu | 184A | CD2 | 4.05 |
| | | | Leu | 103A | CA | 4.04 |
| | | | Leu | 103A | CB | 3.81 |
| | | | Leu | 103A | CD1 | 4.45 |
| | | | Tyr | 181A | CE1 | 4.49 |
| Acetyl-Met | 1F | CB | Pro | 97A | C | 4.26 |
| | | | Pro | 97A | O | 3.6 |
| | | | Pro | 97A | CB | 4.31 |
| | | | Cys | 115A | SG | 3.95 |
| | | | Ile | 86A | CG2 | 4.45 |
| Acetyl-Met | 1F | CG | Pro | 97A | C | 4.4 |
| | | | Pro | 97A | O | 3.53 |
| | | | Val | 102A | CG1 | 3.85 |
| | | | Ile | 86A | CG2 | 3.75 |
| Acetyl-Met | 1F | SD | Val | 102A | CG1 | 4.44 |
| | | | Phe | 164A | CZ | 3.86 |
| | | | Ile | 86A | CG2 | 4.17 |
| | | | Cys | 115A | CA | 4 |
| | | | Gln | 114A | CA | 4.31 |
| | | | Gln | 114A | C | 4.35 |
| | | | Cys | 115A | N | 3.38 |
| Acetyl-Met | 1F | CE | Val | 102A | CG1 | 3.7 |
| | | | Phe | 117A | CE1 | 4.13 |
| | | | Phe | 117A | CZ | 3.69 |
| | | | Phe | 117A | CE2 | 4.4 |
| | | | Phe | 164A | CZ | 4.26 |
| | | | Ile | 86A | CD1 | 4.29 |
| | | | Ile | 86A | CG2 | 4.09 |
| Ile | 2F | N | Tyr | 181A | CZ | 4.22 |
| | | | Gln | 114A | CD | 4.28 |
| | | | Gln | 114A | OE1 | 3.26 |
| | | | Tyr | 181A | OH | 3.35 |
| Ile | 2F | CA | Gln | 114A | OE1 | 3.92 |
| | | | Tyr | 181A | OH | 4.16 |
| Ile | 2F | CB | Tyr | 181A | CZ | 3.88 |
| | | | Met | 177A | SD | 4.02 |
| | | | Gln | 114A | OE1 | 4.25 |
| | | | Tyr | 181A | OH | 3.76 |
| | | | Tyr | 181A | CE2 | 3.77 |
| Ile | 2F | CG1 | Tyr | 181A | CG | 4.5 |
| | | | Tyr | 181A | CD1 | 4.36 |
| | | | Tyr | 181A | CE1 | 3.85 |
| | | | Tyr | 181A | CZ | 3.43 |
| | | | Tyr | 181A | CD2 | 4.11 |

TABLE 7-continued

Minimal contacts between human Dcn1 and human Ubc12 with hUbc12 Chain E interactions with hDcn1$^P$ Chain B and hUbc12 Chain F interactions with hDcn1$^P$ ChainA shown.

| hUbc12 Atom | | | hDcn1 Atom | | | Distance (Å) |
|---|---|---|---|---|---|---|
| | | | Ala | 180A | CB | 4.43 |
| | | | Tyr | 181A | OH | 3.65 |
| | | | Tyr | 181A | CE2 | 3.58 |
| Ile | 2F | CD1 | Ala | 98A | CB | 3.66 |
| | | | Ala | 98A | O | 4.19 |
| | | | Ala | 98A | CA | 4.3 |
| Ile | 2F | CG2 | Met | 177A | SD | 3.78 |
| | | | Ala | 180A | CB | 3.75 |
| Ile | 2F | C | Gln | 114A | OE1 | 3.86 |
| Lys | 3F | N | Cys | 115A | SG | 4.11 |
| | | | Gln | 114A | CD | 3.96 |
| | | | Gln | 114A | OE1 | 2.89 |
| | | | Gln | 114A | NE2 | 4.36 |
| Lys | 3F | CA | Cys | 115A | SG | 4.14 |
| | | | Gln | 114A | OE1 | 3.66 |
| Lys | 3F | CB | Cys | 115A | SG | 3.94 |
| | | | Gln | 114A | CD | 3.88 |
| | | | Gln | 114A | OE1 | 3.27 |
| | | | Gln | 114A | NE2 | 4.16 |
| Lys | 3F | CG | Met | 177A | SD | 3.99 |
| | | | Met | 177A | CE | 3.2 |
| | | | Gln | 114A | CD | 3.91 |
| | | | Gln | 114A | OE1 | 3.67 |
| | | | Gln | 114A | NE2 | 3.69 |
| Lys | 3F | CD | Met | 177A | CE | 3.67 |
| | | | Gln | 114A | CD | 4.1 |
| | | | Gln | 114A | OE1 | 4.25 |
| | | | Gln | 114A | NE2 | 3.78 |
| Lys | 3F | NZ | Asn | 167A | OD1 | 3.99 |
| Lys | 3F | C | Cys | 115A | SG | 3.8 |
| Lys | 3F | O | Cys | 115A | SG | 4.5 |
| Leu | 4F | N | Cys | 115A | SG | 3.34 |
| Leu | 4F | CA | Cys | 115A | SG | 3.58 |
| Leu | 4F | CB | Cys | 115A | SG | 3.82 |
| Leu | 4F | CG | Gln | 87A | OE1 | 4.29 |
| Leu | 4F | CD1 | Cys | 115A | SG | 4.09 |
| | | | Ile | 86A | CB | 4.08 |
| | | | Ile | 86A | CG2 | 3.97 |
| | | | Cys | 115A | CB | 4.28 |
| | | | Ile | 83A | C | 4.24 |
| | | | Ile | 83A | O | 3.66 |
| | | | Ile | 83A | CA | 3.96 |
| | | | Ile | 83A | CB | 3.75 |
| | | | Ile | 83A | CG2 | 4.05 |
| Leu | 4F | CD2 | Gln | 87A | CB | 4.26 |
| | | | Gln | 87A | CD | 4.2 |
| | | | Gln | 87A | OE1 | 3.46 |
| | | | Pro | 97A | CB | 3.63 |
| | | | Pro | 97A | CG | 3.88 |
| | | | Gln | 87A | N | 4.16 |
| | | | Gln | 87A | CA | 4.12 |
| | | | Ile | 86A | CG2 | 4.09 |

TABLE 8

Atomic coordinates of amino acid residues of hDcn1 Chain A essential for binding hUbc12 from structure with stapled hUbc12 peptide.

| | Atom No. | Atom Name | | | X | Y | Z | Occu-pancy | B-factor |
|---|---|---|---|---|---|---|---|---|---|
| ATOM | 198 | N | ILE | A | 83 | 13.031 | 40.450 | 4.212 | 1.00 | 11.06 |
| ATOM | 199 | CA | ILE | A | 83 | 12.692 | 41.331 | 5.343 | 1.00 | 11.10 |
| ATOM | 200 | CB | ILE | A | 83 | 12.045 | 40.580 | 6.548 | 1.00 | 11.11 |
| ATOM | 201 | CG1 | ILE | A | 83 | 13.025 | 39.622 | 7.224 | 1.00 | 12.43 |
| ATOM | 202 | CD1 | ILE | A | 83 | 12.509 | 39.060 | 8.572 | 1.00 | 12.78 |
| ATOM | 203 | CG2 | ILE | A | 83 | 10.770 | 39.869 | 6.106 | 1.00 | 11.68 |
| ATOM | 204 | C | ILE | A | 83 | 13.839 | 42.249 | 5.794 | 1.00 | 10.27 |
| ATOM | 205 | O | ILE | A | 83 | 13.610 | 43.411 | 6.117 | 1.00 | 9.79 |
| ATOM | 218 | N | ILE | A | 86 | 14.182 | 44.958 | 3.139 | 1.00 | 9.70 |
| ATOM | 219 | CA | ILE | A | 86 | 13.051 | 45.879 | 3.287 | 1.00 | 10.08 |
| ATOM | 220 | CB | ILE | A | 86 | 11.691 | 45.130 | 3.541 | 1.00 | 10.44 |
| ATOM | 221 | CG1 | ILE | A | 86 | 11.201 | 44.403 | 2.280 | 1.00 | 10.75 |
| ATOM | 222 | CD1 | ILE | A | 86 | 10.930 | 45.295 | 1.085 | 1.00 | 12.22 |
| ATOM | 223 | CG2 | ILE | A | 86 | 10.611 | 46.083 | 4.067 | 1.00 | 10.11 |
| ATOM | 224 | C | ILE | A | 86 | 13.311 | 46.862 | 4.423 | 1.00 | 9.98 |
| ATOM | 225 | O | ILE | A | 86 | 13.098 | 48.064 | 4.264 | 1.00 | 9.90 |
| ATOM | 226 | N | GLN | A | 87 | 13.764 | 46.349 | 5.567 | 1.00 | 10.21 |
| ATOM | 227 | CA | GLN | A | 87 | 14.082 | 47.199 | 6.708 | 1.00 | 10.45 |
| ATOM | 228 | CB | GLN | A | 87 | 14.505 | 46.369 | 7.922 | 1.00 | 10.47 |
| ATOM | 229 | CG | GLN | A | 87 | 14.872 | 47.217 | 9.154 | 1.00 | 10.24 |
| ATOM | 230 | CD | GLN | A | 87 | 13.657 | 47.835 | 9.835 | 0.67 | 9.76 |
| ATOM | 231 | OE1 | GLN | A | 87 | 12.747 | 47.136 | 10.263 | 1.00 | 11.23 |
| ATOM | 232 | NE2 | GLN | A | 87 | 13.650 | 49.151 | 9.947 | 1.00 | 9.80 |
| ATOM | 233 | C | GLN | A | 87 | 15.190 | 48.197 | 6.361 | 1.00 | 10.65 |
| ATOM | 234 | O | GLN | A | 87 | 15.079 | 49.379 | 6.676 | 1.00 | 10.43 |
| ATOM | 306 | N | PRO | A | 97 | 8.934 | 51.727 | 8.623 | 1.00 | 12.49 |
| ATOM | 307 | CA | PRO | A | 97 | 8.458 | 50.775 | 7.613 | 1.00 | 12.43 |
| ATOM | 308 | CB | PRO | A | 97 | 9.098 | 49.454 | 8.041 | 1.00 | 12.32 |
| ATOM | 309 | CG | PRO | A | 97 | 10.354 | 49.872 | 8.779 | 1.00 | 11.89 |
| ATOM | 310 | CD | PRO | A | 97 | 9.949 | 51.127 | 9.513 | 1.00 | 12.41 |
| ATOM | 311 | C | PRO | A | 97 | 6.935 | 50.663 | 7.572 | 1.00 | 12.50 |
| ATOM | 312 | O | PRO | A | 97 | 6.386 | 50.382 | 6.524 | 1.00 | 12.36 |
| ATOM | 313 | N | ALA | A | 98 | 6.279 | 50.895 | 8.710 | 1.00 | 12.89 |

TABLE 8-continued

Atomic coordinates of amino acid residues of hDcn1 Chain A essential for binding hUbc12 from structure with stapled hUbc12 peptide.

| | Atom No. | Atom Name | | | X | Y | Z | Occupancy | B-factor |
|---|---|---|---|---|---|---|---|---|---|
| ATOM | 314 | CA | ALA | A 98 | 4.831 | 50.836 | 8.815 | 1.00 | 13.39 |
| ATOM | 315 | CB | ALA | A 98 | 4.426 | 50.451 | 10.252 | 1.00 | 13.37 |
| ATOM | 316 | C | ALA | A 98 | 4.138 | 52.141 | 8.396 | 1.00 | 13.61 |
| ATOM | 317 | O | ALA | A 98 | 2.931 | 52.264 | 8.554 | 1.00 | 14.04 |
| ATOM | 318 | N | SER | A 99 | 4.889 | 53.105 | 7.864 | 1.00 | 13.57 |
| ATOM | 319 | CA | SER | A 99 | 4.318 | 54.420 | 7.534 | 1.00 | 13.68 |
| ATOM | 320 | CB | SER | A 99 | 5.396 | 55.509 | 7.572 | 1.00 | 13.92 |
| ATOM | 321 | OG | SER | A 99 | 6.281 | 55.392 | 6.464 | 1.00 | 14.94 |
| ATOM | 322 | C | SER | A 99 | 3.577 | 54.467 | 6.189 | 1.00 | 13.30 |
| ATOM | 323 | O | SER | A 99 | 3.791 | 53.623 | 5.310 | 1.00 | 13.12 |
| ATOM | 338 | N | VAL | A 102 | 5.854 | 54.647 | 2.979 | 1.00 | 9.89 |
| ATOM | 339 | CA | VAL | A 102 | 6.354 | 53.352 | 2.502 | 1.00 | 9.86 |
| ATOM | 340 | CB | VAL | A 102 | 6.884 | 52.478 | 3.682 | 1.00 | 10.15 |
| ATOM | 341 | CG1 | VAL | A 102 | 7.180 | 51.047 | 3.233 | 1.00 | 9.36 |
| ATOM | 342 | CG2 | VAL | A 102 | 8.139 | 53.106 | 4.290 | 1.00 | 8.80 |
| ATOM | 343 | C | VAL | A 102 | 5.284 | 52.604 | 1.692 | 1.00 | 9.91 |
| ATOM | 344 | O | VAL | A 102 | 5.589 | 51.953 | 0.692 | 1.00 | 10.20 |
| ATOM | 345 | N | LEU | A 103 | 4.031 | 52.702 | 2.123 | 1.00 | 9.82 |
| ATOM | 346 | CA | LEU | A 103 | 2.926 | 52.077 | 1.388 | 1.00 | 9.65 |
| ATOM | 347 | CB | LEU | A 103 | 1.623 | 52.189 | 2.187 | 1.00 | 9.74 |
| ATOM | 348 | CG | LEU | A 103 | 0.366 | 51.488 | 1.645 | 1.00 | 9.65 |
| ATOM | 349 | CD1 | LEU | A 103 | 0.615 | 50.022 | 1.289 | 1.00 | 9.76 |
| ATOM | 350 | CD2 | LEU | A 103 | −0.762 | 51.606 | 2.661 | 1.00 | 8.19 |
| ATOM | 351 | C | LEU | A 103 | 2.767 | 52.696 | −0.006 | 1.00 | 9.65 |
| ATOM | 352 | O | LEU | A 103 | 2.483 | 51.993 | −0.990 | 1.00 | 9.39 |
| ATOM | 369 | N | ALA | A 106 | 5.491 | 51.324 | −2.295 | 1.00 | 11.19 |
| ATOM | 370 | CA | ALA | A 106 | 5.107 | 49.981 | −2.730 | 1.00 | 11.36 |
| ATOM | 371 | CB | ALA | A 106 | 4.610 | 49.160 | −1.550 | 1.00 | 11.21 |
| ATOM | 372 | C | ALA | A 106 | 4.047 | 50.032 | −3.832 | 1.00 | 11.22 |
| ATOM | 373 | O | ALA | A 106 | 4.085 | 49.236 | −4.769 | 1.00 | 11.65 |
| ATOM | 436 | N | GLN | A 114 | 3.331 | 42.667 | 0.750 | 1.00 | 11.54 |
| ATOM | 437 | CA | GLN | A 114 | 4.091 | 43.403 | 1.767 | 1.00 | 11.10 |
| ATOM | 438 | CB | GLN | A 114 | 3.200 | 43.832 | 2.955 | 1.00 | 10.82 |
| ATOM | 439 | CG | GLN | A 114 | 2.418 | 42.702 | 3.641 | 1.00 | 9.56 |
| ATOM | 440 | CD | GLN | A 114 | 1.970 | 43.064 | 5.062 | 1.00 | 9.99 |
| ATOM | 441 | OE1 | GLN | A 114 | 0.868 | 42.701 | 5.494 | 1.00 | 10.07 |
| ATOM | 442 | NE2 | GLN | A 114 | 2.818 | 43.780 | 5.787 | 1.00 | 5.79 |
| ATOM | 443 | C | GLN | A 114 | 5.289 | 42.596 | 2.254 | 1.00 | 10.86 |
| ATOM | 444 | O | GLN | A 114 | 5.268 | 41.370 | 2.216 | 1.00 | 10.95 |
| ATOM | 445 | N | CYS | A 115 | 6.324 | 43.312 | 2.689 | 1.00 | 11.28 |
| ATOM | 446 | CA | CYS | A 115 | 7.530 | 42.756 | 3.322 | 1.00 | 11.28 |
| ATOM | 447 | CB | CYS | A 115 | 7.177 | 41.891 | 4.536 | 1.00 | 11.40 |
| ATOM | 448 | SG | CYS | A 115 | 6.269 | 42.812 | 5.794 | 1.00 | 11.83 |
| ATOM | 449 | C | CYS | A 115 | 8.493 | 42.025 | 2.382 | 1.00 | 11.75 |
| ATOM | 450 | O | CYS | A 115 | 9.382 | 41.294 | 2.836 | 1.00 | 11.65 |
| ATOM | 460 | N | PHE | A 117 | 10.183 | 42.611 | −2.011 | 1.00 | 11.84 |
| ATOM | 461 | CA | PHE | A 117 | 10.100 | 43.012 | −3.413 | 1.00 | 11.80 |
| ATOM | 462 | CB | PHE | A 117 | 10.823 | 44.337 | −3.678 | 1.00 | 11.71 |
| ATOM | 463 | CG | PHE | A 117 | 10.223 | 45.539 | −3.003 | 1.00 | 11.95 |
| ATOM | 464 | CD1 | PHE | A 117 | 8.855 | 45.793 | −3.052 | 1.00 | 12.60 |
| ATOM | 465 | CE1 | PHE | A 117 | 8.321 | 46.933 | −2.440 | 1.00 | 12.58 |
| ATOM | 466 | CZ | PHE | A 117 | 9.163 | 47.836 | −1.789 | 1.00 | 11.89 |
| ATOM | 467 | CE2 | PHE | A 117 | 10.532 | 47.605 | −1.757 | 1.00 | 12.68 |
| ATOM | 468 | CD2 | PHE | A 117 | 11.057 | 46.465 | −2.368 | 1.00 | 12.57 |
| ATOM | 469 | C | PHE | A 117 | 10.803 | 41.964 | −4.252 | 1.00 | 11.62 |
| ATOM | 470 | O | PHE | A 117 | 11.867 | 41.482 | −3.871 | 1.00 | 11.77 |
| ATOM | 852 | N | PHE | A 164 | −2.039 | 43.997 | −1.681 | 1.00 | 11.20 |
| ATOM | 853 | CA | PHE | A 164 | −0.671 | 44.121 | −1.150 | 1.00 | 11.38 |
| ATOM | 854 | CB | PHE | A 164 | −0.271 | 45.597 | −1.193 | 1.00 | 11.09 |
| ATOM | 855 | CG | PHE | A 164 | 1.083 | 45.896 | −0.624 | 1.00 | 11.82 |
| ATOM | 856 | CD1 | PHE | A 164 | 2.238 | 45.586 | −1.333 | 1.00 | 10.42 |
| ATOM | 857 | CE1 | PHE | A 164 | 3.504 | 45.881 | −0.801 | 1.00 | 11.27 |
| ATOM | 858 | CZ | PHE | A 164 | 3.611 | 46.506 | 0.436 | 1.00 | 10.73 |
| ATOM | 859 | CE2 | PHE | A 164 | 2.466 | 46.842 | 1.144 | 1.00 | 11.29 |
| ATOM | 860 | CD2 | PHE | A 164 | 1.203 | 46.535 | 0.612 | 1.00 | 10.92 |
| ATOM | 861 | C | PHE | A 164 | −0.571 | 43.567 | 0.276 | 1.00 | 11.74 |
| ATOM | 862 | O | PHE | A 164 | 0.378 | 42.852 | 0.617 | 1.00 | 11.82 |
| ATOM | 877 | N | ASN | A 167 | −2.074 | 37.844 | 2.624 | 1.00 | 18.39 |
| ATOM | 878 | CA | ASN | A 167 | −1.150 | 36.746 | 2.375 | 1.00 | 20.42 |
| ATOM | 879 | CB | ASN | A 167 | −1.347 | 35.618 | 3.392 | 1.00 | 20.66 |
| ATOM | 880 | CG | ASN | A 167 | −1.107 | 36.073 | 4.821 | 1.00 | 22.22 |
| ATOM | 881 | OD1 | ASN | A 167 | −1.802 | 35.643 | 5.744 | 1.00 | 24.64 |
| ATOM | 882 | ND2 | ASN | A 167 | −0.119 | 36.949 | 5.013 | 1.00 | 24.02 |
| ATOM | 883 | C | ASN | A 167 | −1.308 | 36.220 | 0.961 | 1.00 | 21.22 |

TABLE 8-continued

Atomic coordinates of amino acid residues of hDcn1 Chain A essential for binding hUbc12 from structure with stapled hUbc12 peptide.

| | Atom No. | Atom Name | | | X | Y | Z | Occupancy | B-factor |
|---|---|---|---|---|---|---|---|---|---|
| ATOM | 884 | O | ASN | A | 167 | -2.432 | 36.089 | 0.479 | 1.00 | 21.40 |
| ATOM | 951 | N | MET | A | 177 | -4.843 | 42.866 | 10.516 | 1.00 | 10.02 |
| ATOM | 952 | CA | MET | A | 177 | -4.125 | 43.512 | 9.425 | 1.00 | 10.50 |
| ATOM | 953 | CB | MET | A | 177 | -3.652 | 42.449 | 8.431 | 1.00 | 10.73 |
| ATOM | 954 | CG | MET | A | 177 | -2.496 | 42.886 | 7.552 | 1.00 | 13.40 |
| ATOM | 955 | SD | MET | A | 177 | -0.990 | 43.167 | 8.501 | 1.00 | 15.69 |
| ATOM | 956 | CE | MET | A | 177 | -0.624 | 41.511 | 9.064 | 1.00 | 15.67 |
| ATOM | 957 | C | MET | A | 177 | -5.002 | 44.547 | 8.705 | 1.00 | 10.32 |
| ATOM | 958 | O | MET | A | 177 | -4.536 | 45.635 | 8.370 | 1.00 | 10.56 |
| ATOM | 972 | N | ALA | A | 180 | -5.365 | 47.632 | 10.862 | 1.00 | 9.44 |
| ATOM | 973 | CA | ALA | A | 180 | -4.089 | 48.350 | 10.775 | 1.00 | 9.83 |
| ATOM | 974 | CB | ALA | A | 180 | -2.915 | 47.382 | 10.914 | 1.00 | 9.97 |
| ATOM | 975 | C | ALA | A | 180 | -3.960 | 49.171 | 9.486 | 1.00 | 9.72 |
| ATOM | 976 | O | ALA | A | 180 | -3.606 | 50.344 | 9.539 | 1.00 | 9.95 |
| ATOM | 977 | N | TYR | A | 181 | -4.275 | 48.574 | 8.341 | 1.00 | 9.95 |
| ATOM | 978 | CA | TYR | A | 181 | -4.206 | 49.302 | 7.069 | 1.00 | 10.52 |
| ATOM | 979 | CB | TYR | A | 181 | -4.174 | 48.352 | 5.862 | 1.00 | 10.51 |
| ATOM | 980 | CG | TYR | A | 181 | -2.795 | 47.759 | 5.628 | 1.00 | 10.25 |
| ATOM | 981 | CD1 | TYR | A | 181 | -1.812 | 48.485 | 4.963 | 1.00 | 11.37 |
| ATOM | 982 | CE1 | TYR | A | 181 | -0.533 | 47.965 | 4.764 | 1.00 | 12.31 |
| ATOM | 983 | CZ | TYR | A | 181 | -0.221 | 46.695 | 5.237 | 1.00 | 12.09 |
| ATOM | 984 | OH | TYR | A | 181 | 1.050 | 46.188 | 5.040 | 1.00 | 10.57 |
| ATOM | 985 | CE2 | TYR | A | 181 | -1.178 | 45.951 | 5.911 | 1.00 | 11.41 |
| ATOM | 986 | CD2 | TYR | A | 181 | -2.456 | 46.490 | 6.103 | 1.00 | 10.74 |
| ATOM | 987 | C | TYR | A | 181 | -5.287 | 50.388 | 6.927 | 1.00 | 10.90 |
| ATOM | 988 | O | TYR | A | 181 | -5.014 | 51.471 | 6.394 | 1.00 | 11.09 |
| ATOM | 1011 | N | LEU | A | 184 | -4.270 | 53.352 | 8.754 | 1.00 | 13.42 |
| ATOM | 1012 | CA | LEU | A | 184 | -3.243 | 54.021 | 7.973 | 1.00 | 14.11 |
| ATOM | 1013 | CB | LEU | A | 184 | -2.224 | 52.997 | 7.460 | 1.00 | 14.21 |
| ATOM | 1014 | CG | LEU | A | 184 | -0.841 | 53.458 | 7.012 | 1.00 | 15.69 |
| ATOM | 1015 | CD1 | LEU | A | 184 | -0.110 | 54.189 | 8.135 | 1.00 | 15.46 |
| ATOM | 1016 | CD2 | LEU | A | 184 | -0.033 | 52.252 | 6.522 | 1.00 | 15.38 |
| ATOM | 1017 | C | LEU | A | 184 | -3.825 | 54.840 | 6.810 | 1.00 | 14.10 |
| ATOM | 1018 | O | LEU | A | 184 | -3.521 | 56.020 | 6.690 | 1.00 | 14.39 |

TABLE 9

Atomic coordinates of amino acid residues of hDcn1 Chain B essential for binding hUbc12 from structure with stapled hUbc12 peptide.

| | Atom No. | Atom Name | | | X | Y | Z | Occupancy | B-factor |
|---|---|---|---|---|---|---|---|---|---|
| ATOM | 2412 | N | ILE | B | 83 | -30.405 | 108.348 | -21.310 | 1.00 | 22.06 |
| ATOM | 2413 | CA | ILE | B | 83 | -29.529 | 107.901 | -22.393 | 1.00 | 21.85 |
| ATOM | 2414 | CB | ILE | B | 83 | -30.307 | 107.192 | -23.536 | 1.00 | 21.90 |
| ATOM | 2415 | CG1 | ILE | B | 83 | -31.335 | 108.117 | -24.185 | 1.00 | 21.89 |
| ATOM | 2416 | CD1 | ILE | B | 83 | -31.892 | 107.564 | -25.477 | 1.00 | 21.91 |
| ATOM | 2417 | CG2 | ILE | B | 83 | -30.979 | 105.921 | -23.005 | 1.00 | 21.93 |
| ATOM | 2418 | C | ILE | B | 83 | -28.560 | 108.983 | -22.902 | 1.00 | 21.52 |
| ATOM | 2419 | O | ILE | B | 83 | -27.395 | 108.687 | -23.175 | 1.00 | 21.21 |
| ATOM | 2432 | N | ILE | B | 86 | -25.810 | 109.354 | -20.278 | 1.00 | 20.01 |
| ATOM | 2433 | CA | ILE | B | 86 | -24.882 | 108.227 | -20.411 | 1.00 | 19.96 |
| ATOM | 2434 | CB | ILE | B | 86 | -25.632 | 106.873 | -20.671 | 1.00 | 20.05 |
| ATOM | 2435 | CG1 | ILE | B | 86 | -26.467 | 106.442 | -19.450 | 1.00 | 20.17 |
| ATOM | 2436 | CD1 | ILE | B | 86 | -25.690 | 106.246 | -18.153 | 1.00 | 19.80 |
| ATOM | 2437 | CG2 | ILE | B | 86 | -24.662 | 105.766 | -21.113 | 1.00 | 19.91 |
| ATOM | 2438 | C | ILE | B | 86 | -23.874 | 108.506 | -21.530 | 1.00 | 19.93 |
| ATOM | 2439 | O | ILE | B | 86 | -22.666 | 108.343 | -21.341 | 1.00 | 19.67 |
| ATOM | 2440 | N | GLN | B | 87 | -24.383 | 108.938 | -22.684 | 1.00 | 20.03 |
| ATOM | 2441 | CA | GLN | B | 87 | -23.539 | 109.293 | -23.826 | 1.00 | 20.34 |
| ATOM | 2442 | CB | GLN | B | 87 | -24.396 | 109.721 | -25.025 | 1.00 | 20.22 |
| ATOM | 2443 | CG | GLN | B | 87 | -23.607 | 110.009 | -26.307 | 1.00 | 20.12 |
| ATOM | 2444 | CD | GLN | B | 87 | -23.008 | 108.758 | -26.930 | 0.99 | 20.10 |
| ATOM | 2445 | OE1 | GLN | B | 87 | -23.728 | 107.857 | -27.361 | 1.00 | 19.31 |
| ATOM | 2446 | NE2 | GLN | B | 87 | -21.681 | 108.704 | -26.989 | 1.00 | 20.30 |
| ATOM | 2447 | C | GLN | B | 87 | -22.549 | 110.392 | -23.452 | 1.00 | 20.46 |
| ATOM | 2448 | O | GLN | B | 87 | -21.352 | 110.280 | -23.726 | 1.00 | 20.60 |
| ATOM | 2520 | N | PRO | B | 97 | -19.269 | 103.969 | -25.674 | 1.00 | 22.67 |
| ATOM | 2521 | CA | PRO | B | 97 | -20.254 | 103.509 | -24.684 | 1.00 | 22.62 |
| ATOM | 2522 | CB | PRO | B | 97 | -21.551 | 104.178 | -25.141 | 1.00 | 22.57 |

TABLE 9-continued

Atomic coordinates of amino acid residues of hDcn1 Chain B essential for binding hUbc12 from structure with stapled hUbc12 peptide.

| | Atom No. | Atom Name | | | X | Y | Z | Occupancy | B-factor |
|---|---|---|---|---|---|---|---|---|---|
| ATOM | 2523 | CG | PRO | B | 97 | −21.104 | 105.391 | −25.892 | 1.00 | 22.66 |
| ATOM | 2524 | CD | PRO | B | 97 | −19.839 | 104.980 | −26.585 | 1.00 | 22.59 |
| ATOM | 2525 | C | PRO | B | 97 | −20.426 | 101.988 | −24.639 | 1.00 | 22.66 |
| ATOM | 2526 | O | PRO | B | 97 | −20.804 | 101.448 | −23.598 | 1.00 | 22.58 |
| ATOM | 2527 | N | ALA | B | 98 | −20.139 | 101.312 | −25.752 | 1.00 | 22.54 |
| ATOM | 2528 | CA | ALA | B | 98 | −20.255 | 99.858 | −25.834 | 1.00 | 22.70 |
| ATOM | 2529 | CB | ALA | B | 98 | −20.715 | 99.437 | −27.234 | 1.00 | 22.63 |
| ATOM | 2530 | C | ALA | B | 98 | −18.962 | 99.130 | −25.453 | 1.00 | 22.71 |
| ATOM | 2531 | O | ALA | B | 98 | −18.874 | 97.912 | −25.585 | 1.00 | 23.00 |
| ATOM | 2532 | N | SER | B | 99 | −17.966 | 99.872 | −24.974 | 1.00 | 22.72 |
| ATOM | 2533 | CA | SER | B | 99 | −16.659 | 99.291 | −24.670 | 1.00 | 22.62 |
| ATOM | 2534 | CB | SER | B | 99 | −15.563 | 100.356 | −24.749 | 1.00 | 22.71 |
| ATOM | 2535 | OG | SER | B | 99 | −15.605 | 101.204 | −23.615 | 1.00 | 23.45 |
| ATOM | 2536 | C | SER | B | 99 | −16.627 | 98.606 | −23.306 | 1.00 | 22.39 |
| ATOM | 2537 | O | SER | B | 99 | −17.471 | 98.871 | −22.443 | 1.00 | 22.27 |
| ATOM | 2552 | N | VAL | B | 102 | −16.397 | 100.871 | −20.002 | 1.00 | 20.71 |
| ATOM | 2553 | CA | VAL | B | 102 | −17.675 | 101.406 | −19.530 | 1.00 | 20.51 |
| ATOM | 2554 | CB | VAL | B | 102 | −18.519 | 101.986 | −20.699 | 1.00 | 20.67 |
| ATOM | 2555 | CG1 | VAL | B | 102 | −19.911 | 102.406 | −20.225 | 1.00 | 20.65 |
| ATOM | 2556 | CG2 | VAL | B | 102 | −17.805 | 103.177 | −21.332 | 1.00 | 20.43 |
| ATOM | 2557 | C | VAL | B | 102 | −18.460 | 100.357 | −18.727 | 1.00 | 20.40 |
| ATOM | 2558 | O | VAL | B | 102 | −19.110 | 100.693 | −17.735 | 1.00 | 20.38 |
| ATOM | 2559 | N | LEU | B | 103 | −18.334 | 99.094 | −19.147 | 1.00 | 20.15 |
| ATOM | 2560 | CA | LEU | B | 103 | −18.999 | 97.991 | −18.399 | 1.00 | 20.02 |
| ATOM | 2561 | CB | LEU | B | 103 | −18.941 | 96.682 | −19.200 | 1.00 | 19.79 |
| ATOM | 2562 | CG | LEU | B | 103 | −19.610 | 95.427 | −18.617 | 1.00 | 20.45 |
| ATOM | 2563 | CD1 | LEU | B | 103 | −21.060 | 95.686 | −18.213 | 1.00 | 20.61 |
| ATOM | 2564 | CD2 | LEU | B | 103 | −19.524 | 94.245 | −19.594 | 1.00 | 20.05 |
| ATOM | 2565 | C | LEU | B | 103 | −18.351 | 97.814 | −17.017 | 1.00 | 19.81 |
| ATOM | 2566 | O | LEU | B | 103 | −19.041 | 97.559 | −16.027 | 1.00 | 19.65 |
| ATOM | 2583 | N | ALA | B | 106 | −19.655 | 100.587 | −14.795 | 1.00 | 20.13 |
| ATOM | 2584 | CA | ALA | B | 106 | −21.017 | 100.219 | −14.405 | 1.00 | 20.18 |
| ATOM | 2585 | CB | ALA | B | 106 | −21.765 | 99.659 | −15.593 | 1.00 | 20.03 |
| ATOM | 2586 | C | ALA | B | 106 | −21.007 | 99.215 | −13.249 | 1.00 | 20.37 |
| ATOM | 2587 | O | ALA | B | 106 | −21.790 | 99.331 | −12.297 | 1.00 | 20.20 |
| ATOM | 2650 | N | GLN | B | 114 | −28.388 | 98.507 | −17.786 | 1.00 | 19.92 |
| ATOM | 2651 | CA | GLN | B | 114 | −27.641 | 99.225 | −18.818 | 1.00 | 20.09 |
| ATOM | 2652 | CB | GLN | B | 114 | −27.253 | 98.283 | −19.977 | 1.00 | 19.77 |
| ATOM | 2653 | CG | GLN | B | 114 | −28.425 | 97.614 | −20.687 | 1.00 | 18.83 |
| ATOM | 2654 | CD | GLN | B | 114 | −28.066 | 97.115 | −22.078 | 1.00 | 18.37 |
| ATOM | 2655 | OE1 | GLN | B | 114 | −27.419 | 97.821 | −22.857 | 1.00 | 18.08 |
| ATOM | 2656 | NE2 | GLN | B | 114 | −28.501 | 95.900 | −22.402 | 1.00 | 16.31 |
| ATOM | 2657 | C | GLN | B | 114 | −28.403 | 100.440 | −19.347 | 1.00 | 20.26 |
| ATOM | 2658 | O | GLN | B | 114 | −29.638 | 100.462 | −19.325 | 1.00 | 20.37 |
| ATOM | 2659 | N | CYS | B | 115 | −27.645 | 101.440 | −19.803 | 1.00 | 20.71 |
| ATOM | 2660 | CA | CYS | B | 115 | −28.163 | 102.672 | −20.438 | 1.00 | 20.94 |
| ATOM | 2661 | CB | CYS | B | 115 | −29.037 | 102.341 | −21.650 | 1.00 | 21.06 |
| ATOM | 2662 | SG | CYS | B | 115 | −28.203 | 101.301 | −22.847 | 1.00 | 21.61 |
| ATOM | 2663 | C | CYS | B | 115 | −28.878 | 103.664 | −19.512 | 1.00 | 21.23 |
| ATOM | 2664 | O | CYS | B | 115 | −29.614 | 104.542 | −19.982 | 1.00 | 21.16 |
| ATOM | 2674 | N | PHE | B | 117 | −28.223 | 105.377 | −15.127 | 1.00 | 21.67 |
| ATOM | 2675 | CA | PHE | B | 117 | −27.839 | 105.322 | −13.715 | 1.00 | 21.68 |
| ATOM | 2676 | CB | PHE | B | 117 | −26.477 | 105.984 | −13.463 | 1.00 | 21.63 |
| ATOM | 2677 | CG | PHE | B | 117 | −25.319 | 105.324 | −14.166 | 1.00 | 22.09 |
| ATOM | 2678 | CD1 | PHE | B | 117 | −25.134 | 103.944 | −14.111 | 1.00 | 21.98 |
| ATOM | 2679 | CE1 | PHE | B | 117 | −24.050 | 103.347 | −14.754 | 1.00 | 22.16 |
| ATOM | 2680 | CZ | PHE | B | 117 | −23.127 | 104.133 | −15.437 | 1.00 | 21.74 |
| ATOM | 2681 | CE2 | PHE | B | 117 | −23.291 | 105.507 | −15.483 | 1.00 | 21.59 |
| ATOM | 2682 | CD2 | PHE | B | 117 | −24.380 | 106.097 | −14.842 | 1.00 | 21.55 |
| ATOM | 2683 | C | PHE | B | 117 | −28.880 | 106.059 | −12.886 | 1.00 | 21.55 |
| ATOM | 2684 | O | PHE | B | 117 | −29.336 | 107.137 | −13.271 | 1.00 | 21.64 |
| ATOM | 3066 | N | PHE | B | 164 | −27.140 | 93.194 | −15.243 | 1.00 | 19.87 |
| ATOM | 3067 | CA | PHE | B | 164 | −26.985 | 94.525 | −15.822 | 1.00 | 20.00 |
| ATOM | 3068 | CB | PHE | B | 164 | −25.500 | 94.894 | −15.809 | 1.00 | 20.10 |
| ATOM | 3069 | CG | PHE | B | 164 | −25.185 | 96.227 | −16.431 | 1.00 | 20.07 |
| ATOM | 3070 | CD1 | PHE | B | 164 | −25.504 | 97.413 | −15.774 | 1.00 | 20.33 |
| ATOM | 3071 | CE1 | PHE | B | 164 | −25.201 | 98.652 | −16.344 | 1.00 | 19.91 |
| ATOM | 3072 | CZ | PHE | B | 164 | −24.556 | 98.709 | −17.579 | 1.00 | 19.28 |
| ATOM | 3073 | CE2 | PHE | B | 164 | −24.227 | 97.532 | −18.241 | 1.00 | 20.37 |
| ATOM | 3074 | CD2 | PHE | B | 164 | −24.542 | 96.295 | −17.662 | 1.00 | 20.04 |
| ATOM | 3075 | C | PHE | B | 164 | −27.543 | 94.604 | −17.252 | 1.00 | 20.03 |
| ATOM | 3076 | O | PHE | B | 164 | −28.208 | 95.577 | −17.616 | 1.00 | 19.88 |
| ATOM | 3091 | N | ASN | B | 167 | −33.402 | 93.223 | −19.278 | 1.00 | 23.56 |
| ATOM | 3092 | CA | ASN | B | 167 | −34.452 | 94.170 | −18.910 | 1.00 | 25.06 |

TABLE 9-continued

Atomic coordinates of amino acid residues of hDcn1 Chain B essential for binding hUbc12 from structure with stapled hUbc12 peptide.

|   | Atom No. | Atom Name | | | X | Y | Z | Occupancy | B-factor |
|---|---|---|---|---|---|---|---|---|---|
| ATOM | 3093 | CB | ASN | B | 167 | −35.630 | 94.094 | −19.885 | 1.00 | 25.40 |
| ATOM | 3094 | CG | ASN | B | 167 | −35.207 | 94.269 | −21.327 | 1.00 | 26.53 |
| ATOM | 3095 | OD1 | ASN | B | 167 | −35.598 | 93.486 | −22.193 | 1.00 | 28.48 |
| ATOM | 3096 | ND2 | ASN | B | 167 | −34.401 | 95.293 | −21.595 | 1.00 | 27.88 |
| ATOM | 3097 | C | ASN | B | 167 | −34.945 | 93.921 | −17.488 | 1.00 | 25.57 |
| ATOM | 3098 | O | ASN | B | 167 | −35.087 | 92.765 | −17.079 | 1.00 | 25.68 |
| ATOM | 3165 | N | MET | B | 177 | −28.572 | 90.183 | −27.289 | 1.00 | 17.20 |
| ATOM | 3166 | CA | MET | B | 177 | −27.921 | 90.921 | −26.216 | 1.00 | 17.43 |
| ATOM | 3167 | CB | MET | B | 177 | −28.969 | 91.422 | −25.212 | 1.00 | 17.67 |
| ATOM | 3168 | CG | MET | B | 177 | −28.531 | 92.623 | −24.387 | 1.00 | 19.15 |
| ATOM | 3169 | SD | MET | B | 111 | −28.144 | 94.055 | −25.410 | 1.00 | 21.43 |
| ATOM | 3170 | CE | MET | B | 177 | −29.768 | 94.544 | −25.987 | 1.00 | 22.65 |
| ATOM | 3171 | C | MET | B | 177 | −26.868 | 90.049 | −25.528 | 1.00 | 17.09 |
| ATOM | 3172 | O | MET | B | 177 | −25.758 | 90.510 | −25.258 | 1.00 | 16.99 |
| ATOM | 3186 | N | ALA | B | 180 | −23.753 | 89.661 | −27.733 | 1.00 | 17.12 |
| ATOM | 3187 | CA | ALA | B | 180 | −22.999 | 90.911 | −27.738 | 1.00 | 17.35 |
| ATOM | 3188 | CB | ALA | B | 180 | −23.929 | 92.104 | −27.945 | 1.00 | 17.41 |
| ATOM | 3189 | C | ALA | B | 180 | −22.183 | 91.081 | −26.458 | 1.00 | 17.51 |
| ATOM | 3190 | O | ALA | B | 180 | −21.041 | 91.537 | −26.509 | 1.00 | 17.37 |
| ATOM | 3191 | N | TYR | B | 181 | −22.763 | 90.710 | −25.317 | 1.00 | 17.76 |
| ATOM | 3192 | CA | TYR | B | 181 | −22.041 | 90.799 | −24.045 | 1.00 | 18.12 |
| ATOM | 3193 | CB | TYR | B | 181 | −22.995 | 90.874 | −22.845 | 1.00 | 18.11 |
| ATOM | 3194 | CG | TYR | B | 181 | −23.543 | 92.269 | −22.622 | 1.00 | 18.19 |
| ATOM | 3195 | CD1 | TYR | B | 181 | −22.789 | 93.238 | −21.952 | 1.00 | 18.71 |
| ATOM | 3196 | CE1 | TYR | B | 181 | −23.283 | 94.531 | −21.749 | 1.00 | 19.16 |
| ATOM | 3197 | CZ | TYR | B | 181 | −24.544 | 94.866 | −22.224 | 1.00 | 19.33 |
| ATOM | 3198 | OH | TYR | B | 181 | −25.035 | 96.146 | −22.033 | 1.00 | 19.73 |
| ATOM | 3199 | CE2 | TYR | B | 181 | −25.309 | 93.921 | −22.900 | 1.00 | 18.60 |
| ATOM | 3200 | CD2 | TYR | B | 181 | −24.805 | 92.629 | −23.094 | 1.00 | 18.30 |
| ATOM | 3201 | C | TYR | B | 181 | −20.989 | 89.707 | −23.872 | 1.00 | 18.34 |
| ATOM | 3202 | O | TYR | B | 181 | −19.907 | 89.973 | −23.352 | 1.00 | 18.28 |
| ATOM | 3225 | N | LEU | B | 184 | −18.023 | 90.608 | −25.720 | 1.00 | 21.89 |
| ATOM | 3226 | CA | LEU | B | 184 | −17.324 | 91.670 | −25.010 | 1.00 | 22.22 |
| ATOM | 3227 | CB | LEU | B | 184 | −18.328 | 92.723 | −24.521 | 1.00 | 22.27 |
| ATOM | 3228 | CG | LEU | B | 184 | −17.831 | 94.108 | −24.104 | 1.00 | 22.26 |
| ATOM | 3229 | CD1 | LEU | B | 184 | −17.213 | 94.861 | −25.272 | 1.00 | 21.91 |
| ATOM | 3230 | CD2 | LEU | B | 184 | −18.972 | 94.913 | −23.499 | 1.00 | 22.24 |
| ATOM | 3231 | C | LEU | B | 184 | −16.515 | 91.123 | −23.836 | 1.00 | 22.40 |
| ATOM | 3232 | O | LEU | B | 184 | −15.325 | 91.410 | −23.714 | 1.00 | 22.83 |

TABLE 10

Atomic coordinates of amino acid residues of hDcn1 Chain A essential for binding hUbc12.

|   | Atom No. | Atom Name | | | X | Y | Z | Occupancy | B-factor |
|---|---|---|---|---|---|---|---|---|---|
| ATOM | 196 | N | ILE | A | 83 | 36.977 | −14.686 | −20.772 | 1.00 | 12.90 |
| ATOM | 197 | CA | ILE | A | 83 | 36.506 | −15.088 | −22.103 | 1.00 | 13.86 |
| ATOM | 198 | CB | ILE | A | 83 | 37.408 | −14.550 | −23.249 | 1.00 | 14.02 |
| ATOM | 199 | CG1 | ILE | A | 83 | 38.829 | −15.121 | −23.160 | 1.00 | 14.11 |
| ATOM | 200 | CD1 | ILE | A | 83 | 39.710 | −14.759 | −24.349 | 1.00 | 15.19 |
| ATOM | 201 | CG2 | ILE | A | 83 | 37.426 | −13.022 | −23.244 | 1.00 | 14.59 |
| ATOM | 202 | C | ILE | A | 83 | 36.282 | −16.597 | −22.244 | 1.00 | 14.48 |
| ATOM | 203 | O | ILE | A | 83 | 35.350 | −17.023 | −22.926 | 1.00 | 14.64 |
| ATOM | 216 | N | ILE | A | 86 | 33.068 | −17.241 | −20.441 | 1.00 | 9.57 |
| ATOM | 217 | CA | ILE | A | 86 | 31.948 | −16.711 | −21.229 | 1.00 | 9.17 |
| ATOM | 218 | CB | ILE | A | 86 | 32.238 | −15.296 | −21.827 | 1.00 | 8.85 |
| ATOM | 219 | CG1 | ILE | A | 86 | 32.344 | −14.228 | −20.724 | 1.00 | 9.45 |
| ATOM | 220 | CD1 | ILE | A | 86 | 31.063 | −13.939 | −19.963 | 1.00 | 10.17 |
| ATOM | 221 | CG2 | ILE | A | 86 | 31.154 | −14.890 | −22.848 | 1.00 | 9.18 |
| ATOM | 222 | C | ILE | A | 86 | 31.582 | −17.703 | −22.335 | 1.00 | 9.55 |
| ATOM | 223 | O | ILE | A | 86 | 30.403 | −17.993 | −22.547 | 1.00 | 9.03 |
| ATOM | 224 | N | GLN | A | 87 | 32.591 | −18.224 | −23.028 | 1.00 | 10.48 |
| ATOM | 225 | CA | GLN | A | 87 | 32.377 | −19.248 | −24.049 | 1.00 | 11.22 |
| ATOM | 226 | CB | GLN | A | 87 | 33.700 | −19.650 | −24.710 | 1.00 | 11.32 |
| ATOM | 227 | CG | GLN | A | 87 | 33.546 | −20.663 | −25.841 | 1.00 | 12.84 |
| ATOM | 228 | CD | GLN | A | 87 | 32.742 | −20.115 | −27.008 | 0.67 | 13.76 |
| ATOM | 229 | OE1 | GLN | A | 87 | 33.143 | −19.144 | −27.646 | 1.00 | 16.05 |
| ATOM | 230 | NE2 | GLN | A | 87 | 31.601 | −20.736 | −27.291 | 1.00 | 15.09 |

TABLE 10-continued

Atomic coordinates of amino acid residues of hDcn1 Chain A essential for binding hUbc12.

|      | Atom No. | Atom Name |     |   |    | X      | Y       | Z       | Occupancy | B-factor |
|------|----------|-----------|-----|---|----|--------|---------|---------|-----------|----------|
| ATOM | 231      | C         | GLN | A | 87 | 31.679 | −20.479 | −23.467 | 1.00      | 11.20    |
| ATOM | 232      | O         | GLN | A | 87 | 30.738 | −21.002 | −24.066 | 1.00      | 11.47    |
| ATOM | 304      | H         | PRO | A | 97 | 27.365 | −17.205 | −28.903 | 1.00      | 9.39     |
| ATOM | 305      | CA        | PRO | A | 97 | 27.770 | −16.104 | −28.025 | 1.00      | 9.60     |
| ATOM | 306      | CB        | PRO | A | 97 | 29.295 | −16.200 | −28.024 | 1.00      | 9.57     |
| ATOM | 307      | CG        | PRO | A | 97 | 29.575 | −17.639 | −28.292 | 1.00      | 9.43     |
| ATOM | 308      | CD        | PRO | A | 97 | 28.486 | −18.109 | −29.214 | 1.00      | 9.60     |
| ATOM | 309      | C         | PRO | A | 97 | 27.322 | −14.723 | −28.507 | 1.00      | 9.56     |
| ATOM | 310      | O         | PRO | A | 97 | 27.104 | −13.836 | −27.683 | 1.00      | 9.53     |
| ATOM | 311      | N         | ALA | A | 98 | 27.156 | −14.566 | −29.820 | 1.00      | 10.14    |
| ATOM | 312      | CA        | ALA | A | 98 | 26.780 | −13.293 | −30.431 | 1.00      | 10.80    |
| ATOM | 313      | CB        | ALA | A | 98 | 27.526 | −13.116 | −31.758 | 1.00      | 10.99    |
| ATOM | 314      | C         | ALA | A | 98 | 25.270 | −13.144 | −30.640 | 1.00      | 11.25    |
| ATOM | 315      | O         | ALA | A | 98 | 24.818 | −12.229 | −31.340 | 1.00      | 12.29    |
| ATOM | 316      | N         | SER | A | 99 | 24.490 | −14.032 | −30.029 | 1.00      | 11.27    |
| ATOM | 317      | CA        | SER | A | 99 | 23.039 | −14.011 | −30.210 | 1.00      | 11.21    |
| ATOM | 318      | CB        | SER | A | 99 | 22.439 | −15.384 | −29.919 | 1.00      | 11.58    |
| ATOM | 319      | OG        | SER | A | 99 | 22.566 | −15.712 | −28.553 | 1.00      | 12.43    |
| ATOM | 320      | C         | SER | A | 99 | 22.370 | −12.956 | −29.335 | 1.00      | 10.50    |
| ATOM | 321      | O         | SER | A | 99 | 22.918 | −12.540 | −28.313 | 1.00      | 9.98     |
| ATOM | 336      | N         | VAL | A | 102 | 21.794 | −13.908 | −25.598 | 1.00      | 7.12     |
| ATOM | 337      | CA        | VAL | A | 102 | 22.960 | −13.673 | −24.751 | 1.00      | 6.85     |
| ATOM | 338      | CB        | VAL | A | 102 | 24.260 | −14.153 | −25.433 | 1.00      | 6.88     |
| ATOM | 339      | CG1       | VAL | A | 102 | 25.492 | −13.783 | −24.603 | 1.00      | 7.40     |
| ATOM | 340      | CG2       | VAL | A | 102 | 24.198 | −15.661 | −25.669 | 1.00      | 7.91     |
| ATOM | 341      | C         | VAL | A | 102 | 23.037 | −12.205 | −24.314 | 1.00      | 6.55     |
| ATOM | 342      | O         | VAL | A | 102 | 23.311 | −11.926 | −23.150 | 1.00      | 6.96     |
| ATOM | 343      | N         | LEU | A | 103 | 22.789 | −11.276 | −25.237 | 1.00      | 6.21     |
| ATOM | 344      | CA        | LEU | A | 103 | 22.751 | −9.852  | −24.891 | 1.00      | 6.05     |
| ATOM | 345      | CB        | LEU | A | 103 | 22.576 | −8.990  | −26.146 | 1.00      | 6.39     |
| ATOM | 346      | CG        | LEU | A | 103 | 22.643 | −7.472  | −25.936 | 1.00      | 5.17     |
| ATOM | 347      | CD1       | LEU | A | 103 | 23.967 | −7.059  | −25.301 | 1.00      | 6.27     |
| ATOM | 348      | CD2       | LEU | A | 103 | 22.475 | −6.764  | −27.258 | 1.00      | 6.33     |
| ATOM | 349      | C         | LEU | A | 103 | 21.661 | −9.529  | −23.870 | 1.00      | 6.49     |
| ATOM | 350      | O         | LEU | A | 103 | 21.872 | −8.721  | −22.956 | 1.00      | 6.43     |
| ATOM | 367      | N         | ALA | A | 106 | 22.865 | −10.651 | −20.508 | 1.00      | 7.03     |
| ATOM | 368      | CA        | ALA | A | 106 | 23.841 | −9.666  | −20.041 | 1.00      | 6.99     |
| ATOM | 369      | CB        | ALA | A | 106 | 24.801 | −9.293  | −21.165 | 1.00      | 7.01     |
| ATOM | 370      | C         | ALA | A | 106 | 23.169 | −8.416  | −19.464 | 1.00      | 6.61     |
| ATOM | 371      | O         | ALA | A | 106 | 23.605 | −7.879  | −18.442 | 1.00      | 7.01     |
| ATOM | 446      | N         | GLN | A | 114 | 30.971 | −6.245  | −22.517 | 1.00      | 7.54     |
| ATOM | 447      | CA        | GLN | A | 114 | 30.955 | −7.504  | −23.257 | 1.00      | 8.01     |
| ATOM | 448      | CB        | GLN | A | 114 | 30.775 | −7.256  | −24.758 | 1.00      | 7.85     |
| ATOM | 449      | CG        | GLN | A | 114 | 31.857 | −6.400  | −25.406 | 1.00      | 7.92     |
| ATOM | 450      | CD        | GLN | A | 114 | 31.964 | −6.653  | −26.896 | 1.00      | 8.14     |
| ATOM | 451      | OE1       | GLN | A | 114 | 31.982 | −7.801  | −27.341 | 1.00      | 9.25     |
| ATOM | 452      | NE2       | GLN | A | 114 | 32.060 | −5.580  | −27.674 | 1.00      | 7.38     |
| ATOM | 453      | C         | GLN | A | 114 | 32.186 | −8.380  | −22.996 | 1.00      | 8.45     |
| ATOM | 454      | O         | GLN | A | 114 | 33.298 | −7.883  | −22.747 | 1.00      | 8.88     |
| ATOM | 455      | N         | CYS | A | 115 | 31.949 | −9.691  | −23.029 | 1.00      | 9.24     |
| ATOM | 456      | CA        | CYS | A | 115 | 32.990 | −10.723 | −22.948 | 1.00      | 9.94     |
| ATOM | 457      | CB        | CYS | A | 115 | 34.087 | −10.498 | −23.996 | 1.00      | 10.22    |
| ATOM | 458      | SG        | CYS | A | 115 | 33.482 | −10.519 | −25.689 | 1.00      | 11.14    |
| ATOM | 459      | C         | CYS | A | 115 | 33.596 | −10.896 | −21.559 | 1.00      | 10.57    |
| ATOM | 460      | O         | CYS | A | 115 | 34.726 | −11.387 | −21.417 | 1.00      | 10.06    |
| ATOM | 470      | N         | PHE | A | 117 | 31.900 | −11.315 | −17.158 | 1.00      | 10.88    |
| ATOM | 471      | CA        | PHE | A | 117 | 31.016 | −10.979 | −16.047 | 1.00      | 10.54    |
| ATOM | 472      | CB        | PHE | A | 117 | 29.925 | −12.035 | −15.829 | 1.00      | 10.31    |
| ATOM | 473      | CG        | PHE | A | 117 | 28.955 | −12.191 | −16.974 | 1.00      | 10.63    |
| ATOM | 474      | CD1       | PHE | A | 117 | 28.370 | −11.086 | −17.585 | 1.00      | 10.88    |
| ATOM | 475      | CE1       | PHE | A | 117 | 27.466 | −11.249 | −18.632 | 1.00      | 11.40    |
| ATOM | 476      | CZ        | PHE | A | 117 | 27.122 | −12.526 | −19.065 | 1.00      | 10.91    |
| ATOM | 477      | CE2       | PHE | A | 117 | 27.689 | −13.637 | −18.454 | 1.00      | 11.21    |
| ATOM | 478      | CD2       | PHE | A | 117 | 28.595 | −13.465 | −17.410 | 1.00      | 11.19    |
| ATOM | 479      | C         | PHE | A | 117 | 31.842 | −10.888 | −14.774 | 1.00      | 10.24    |
| ATOM | 480      | O         | PHE | A | 117 | 32.678 | −11.748 | −14.507 | 1.00      | 10.91    |
| ATOM | 868      | N         | PHE | A | 164 | 27.612 | −1.423  | −22.879 | 1.00      | 8.55     |
| ATOM | 869      | CA        | PHE | A | 164 | 28.065 | −2.810  | −22.824 | 1.00      | 8.10     |
| ATOM | 870      | CB        | PHE | A | 164 | 26.836 | −3.708  | −22.983 | 1.00      | 8.03     |
| ATOM | 871      | CG        | PHE | A | 164 | 27.133 | −5.176  | −22.982 | 1.00      | 7.71     |
| ATOM | 872      | CD1       | PHE | A | 164 | 27.444 | −5.836  | −21.798 | 1.00      | 7.58     |
| ATOM | 873      | CE1       | PHE | A | 164 | 27.695 | −7.206  | −21.787 | 1.00      | 8.30     |
| ATOM | 874      | CZ        | PHE | A | 164 | 27.620 | −7.932  | −22.970 | 1.00      | 8.55     |
| ATOM | 875      | CE2       | PHE | A | 164 | 27.296 | −7.287  | −24.158 | 1.00      | 7.42     |

TABLE 10-continued

Atomic coordinates of amino acid residues of hDcn1 Chain A essential for binding hUbc12.

| | Atom No. | Atom Name | | | X | Y | Z | Occupancy | B-factor |
|---|---|---|---|---|---|---|---|---|---|
| ATOM | 876 | CD2 | PHE | A | 164 | 27.062 | −5.912 | −24.161 | 1.00 | 7.45 |
| ATOM | 877 | C | PHE | A | 164 | 29.089 | −3.107 | −23.920 | 1.00 | 8.08 |
| ATOM | 878 | O | PHE | A | 164 | 30.094 | −3.790 | −23.689 | 1.00 | 7.67 |
| ATOM | 893 | N | ASN | A | 167 | 34.518 | 0.021 | −24.949 | 1.00 | 18.51 |
| ATOM | 894 | CA | ASN | A | 167 | 35.584 | −0.198 | −23.981 | 1.00 | 23.93 |
| ATOM | 895 | CB | ASN | A | 167 | 36.945 | 0.137 | −24.598 | 1.00 | 24.56 |
| ATOM | 896 | CG | ASN | A | 167 | 37.254 | −0.702 | −25.827 | 1.00 | 27.69 |
| ATOM | 897 | OD1 | ASN | A | 167 | 37.067 | −1.920 | −25.830 | 1.00 | 30.17 |
| ATOM | 898 | ND2 | ASN | A | 167 | 37.740 | −0.051 | −26.877 | 1.00 | 29.71 |
| ATOM | 899 | C | ASN | A | 167 | 35.354 | 0.648 | −22.732 | 1.00 | 27.76 |
| ATOM | 900 | O | ASN | A | 167 | 34.860 | 1.775 | −22.833 | 1.00 | 27.47 |
| ATOM | 972 | N | MET | A | 177 | 32.057 | −2.089 | −34.346 | 1.00 | 9.67 |
| ATOM | 973 | CA | MET | A | 177 | 31.336 | −2.605 | −33.182 | 1.00 | 8.98 |
| ATOM | 974 | CB | MET | A | 177 | 32.086 | −2.279 | −31.885 | 1.00 | 9.19 |
| ATOM | 975 | CG | MET | A | 177 | 31.772 | −3.243 | −30.739 | 1.00 | 10.77 |
| ATOM | 976 | SD | MET | A | 177 | 32.121 | −4.976 | −31.150 | 1.00 | 13.17 |
| ATOM | 977 | CE | MET | A | 177 | 33.883 | −4.902 | −31.440 | 1.00 | 14.81 |
| ATOM | 978 | C | MET | A | 177 | 29.899 | −2.081 | −33.121 | 1.00 | 8.33 |
| ATOM | 979 | O | MET | A | 177 | 28.973 | −2.845 | −32.850 | 1.00 | 7.85 |
| ATOM | 993 | N | ALA | A | 180 | 27.819 | −3.852 | −35.736 | 1.00 | 7.21 |
| ATOM | 994 | CA | ALA | A | 180 | 27.550 | −5.215 | −35.276 | 1.00 | 7.23 |
| ATOM | 995 | CB | ALA | A | 180 | 28.814 | −5.842 | −34.679 | 1.00 | 7.51 |
| ATOM | 996 | C | ALA | A | 180 | 26.383 | −5.261 | −34.281 | 1.00 | 7.58 |
| ATOM | 997 | O | ALA | A | 180 | 25.485 | −6.095 | −34.406 | 1.00 | 7.82 |
| ATOM | 998 | N | TYR | A | 181 | 26.379 | −4.344 | −33.316 | 1.00 | 7.11 |
| ATOM | 999 | CA | TYR | A | 181 | 25.315 | −4.309 | −32.316 | 1.00 | 6.57 |
| ATOM | 1000 | CB | TYR | A | 181 | 25.759 | −3.593 | −31.036 | 1.00 | 7.02 |
| ATOM | 1001 | CG | TYR | A | 181 | 26.605 | −4.491 | −30.160 | 1.00 | 6.87 |
| ATOM | 1002 | CD1 | TYR | A | 181 | 26.007 | −5.394 | −29.275 | 1.00 | 7.10 |
| ATOM | 1003 | CE1 | TYR | A | 181 | 26.771 | −6.228 | −28.481 | 1.00 | 7.04 |
| ATOM | 1004 | CZ | TYR | A | 181 | 28.149 | −6.176 | −28.558 | 1.00 | 7.84 |
| ATOM | 1005 | OH | TYR | A | 181 | 28.901 | −7.006 | −27.768 | 1.00 | 9.69 |
| ATOM | 1006 | CE2 | TYR | A | 181 | 28.775 | −5.298 | −29.426 | 1.00 | 7.94 |
| ATOM | 1007 | CD2 | TYR | A | 181 | 27.998 | −4.463 | −30.227 | 1.00 | 7.63 |
| ATOM | 1008 | C | TYR | A | 181 | 24.009 | −3.755 | −32.876 | 1.00 | 6.27 |
| ATOM | 1009 | O | TYR | A | 181 | 22.947 | −4.239 | −32.515 | 1.00 | 6.90 |
| ATOM | 1032 | N | LEU | A | 184 | 22.293 | −6.498 | −34.554 | 1.00 | 8.61 |
| ATOM | 1033 | CA | LEU | A | 184 | 21.717 | −7.379 | −33.544 | 1.00 | 9.06 |
| ATOM | 1034 | CB | LEU | A | 184 | 22.740 | −7.634 | −32.429 | 1.00 | 9.47 |
| ATOM | 1035 | CG | LEU | A | 184 | 22.475 | −8.763 | −31.427 | 1.00 | 10.45 |
| ATOM | 1036 | CD1 | LEU | A | 184 | 22.222 | −10.090 | −32.134 | 1.00 | 11.79 |
| ATOM | 1037 | CD2 | LEU | A | 184 | 23.652 | −8.883 | −30.468 | 1.00 | 11.28 |
| ATOM | 1038 | C | LEU | A | 184 | 20.400 | −6.841 | −32.966 | 1.00 | 9.44 |
| ATOM | 1039 | O | LEU | A | 184 | 19.392 | −7.552 | −32.958 | 1.00 | 10.68 |

TABLE 11

Atomic coordinates of amino acid residues of hDcn1 Chain B essential for binding hUbc12.

| | Atom No. | Atom Name | | | X | Y | Z | Occupancy | B-factor |
|---|---|---|---|---|---|---|---|---|---|
| ATOM | 1819 | N | ILE | B | 83 | 29.948 | 2.614 | 6.205 | 1.00 | 14.95 |
| ATOM | 1820 | CA | ILE | B | 83 | 28.894 | 3.066 | 7.119 | 1.00 | 15.72 |
| ATOM | 1821 | CB | ILE | B | 83 | 29.070 | 2.516 | 8.566 | 1.00 | 15.81 |
| ATOM | 1822 | CG1 | ILE | B | 83 | 30.448 | 2.860 | 9.141 | 1.00 | 16.94 |
| ATOM | 1823 | CD1 | ILE | B | 83 | 30.633 | 2.394 | 10.579 | 1.00 | 18.68 |
| ATOM | 1824 | CG2 | ILE | B | 83 | 28.840 | 1.009 | 8.592 | 1.00 | 16.52 |
| ATOM | 1825 | C | ILE | B | 83 | 28.672 | 4.583 | 7.111 | 1.00 | 15.83 |
| ATOM | 1826 | O | ILE | B | 83 | 27.533 | 5.044 | 7.233 | 1.00 | 15.95 |
| ATOM | 1839 | N | ILE | B | 86 | 26.874 | 5.426 | 3.809 | 1.00 | 13.37 |
| ATOM | 1840 | CA | ILE | B | 86 | 25.480 | 4.984 | 3.892 | 1.00 | 12.69 |
| ATOM | 1841 | CB | ILE | B | 86 | 25.337 | 3.542 | 4.485 | 1.00 | 12.54 |
| ATOM | 1842 | CG1 | ILE | B | 86 | 26.021 | 2.496 | 3.586 | 1.00 | 12.43 |
| ATOM | 1843 | CD1 | ILE | B | 86 | 25.317 | 2.196 | 2.257 | 1.00 | 12.53 |
| ATOM | 1844 | CG2 | ILE | B | 86 | 23.859 | 3.187 | 4.725 | 1.00 | 12.96 |
| ATOM | 1845 | C | ILE | B | 86 | 24.654 | 5.989 | 4.703 | 1.00 | 12.56 |
| ATOM | 1846 | O | ILE | B | 86 | 23.542 | 6.341 | 4.310 | 1.00 | 12.49 |
| ATOM | 1847 | N | GLN | B | 87 | 25.207 | 6.449 | 5.822 | 1.00 | 12.84 |
| ATOM | 1848 | CA | GLN | B | 87 | 24.552 | 7.470 | 6.634 | 1.00 | 13.49 |

TABLE 11-continued

Atomic coordinates of amino acid residues of hDcn1 Chain B essential for binding hUbc12.

| | Atom No. | Atom Name | | | X | Y | Z | Occupancy | B-factor |
|---|---|---|---|---|---|---|---|---|---|
| ATOM | 1849 | CB | GLN | B | 87 | 25.390 | 7.787 | 7.878 | 1.00 | 13.64 |
| ATOM | 1850 | CG | GLN | B | 87 | 24.756 | 8.801 | 8.836 | 1.00 | 15.44 |
| ATOM | 1851 | CD | GLN | B | 87 | 23.413 | 8.346 | 9.383 | 1.00 | 16.30 |
| ATOM | 1852 | OE1 | GLN | B | 87 | 23.328 | 7.357 | 10.113 | 1.00 | 18.29 |
| ATOM | 1853 | NE2 | GLN | B | 87 | 22.358 | 9.073 | 9.039 | 0.84 | 17.18 |
| ATOM | 1854 | C | GLN | B | 87 | 24.278 | 8.739 | 5.815 | 1.00 | 13.78 |
| ATOM | 1855 | O | GLN | B | 87 | 23.177 | 9.286 | 5.867 | 0.88 | 13.69 |
| ATOM | 1927 | N | PRO | B | 97 | 17.781 | 5.711 | 8.137 | 1.00 | 11.79 |
| ATOM | 1928 | CA | PRO | B | 97 | 18.531 | 4.583 | 7.573 | 1.00 | 11.68 |
| ATOM | 1929 | CB | PRO | B | 97 | 19.873 | 4.646 | 8.310 | 1.00 | 11.76 |
| ATOM | 1930 | CG | PRO | B | 97 | 20.002 | 6.061 | 8.735 | 1.00 | 11.97 |
| ATOM | 1931 | CD | PRO | B | 97 | 18.605 | 6.494 | 9.074 | 1.00 | 11.71 |
| ATOM | 1932 | C | PRO | B | 97 | 17.869 | 3.225 | 7.797 | 1.00 | 12.06 |
| ATOM | 1933 | O | PRO | B | 97 | 18.101 | 2.309 | 7.017 | 1.00 | 12.24 |
| ATOM | 1934 | N | ALA | B | 98 | 17.049 | 3.113 | 8.841 | 1.00 | 12.54 |
| ATOM | 1935 | CA | ALA | B | 98 | 16.374 | 1.860 | 9.181 | 1.00 | 12.70 |
| ATOM | 1936 | CB | ALA | B | 98 | 16.361 | 1.668 | 10.698 | 1.00 | 12.91 |
| ATOM | 1937 | C | ALA | B | 98 | 14.952 | 1.766 | 8.609 | 1.00 | 13.00 |
| ATOM | 1938 | O | ALA | B | 98 | 14.168 | 0.906 | 9.021 | 1.00 | 13.88 |
| ATOM | 1939 | N | SER | B | 99 | 14.622 | 2.641 | 7.663 | 1.00 | 13.24 |
| ATOM | 1940 | CA | SER | B | 99 | 13.279 | 2.672 | 7.082 | 1.00 | 13.23 |
| ATOM | 1941 | CB | SER | B | 99 | 12.953 | 4.062 | 6.531 | 1.00 | 13.54 |
| ATOM | 1942 | OG | SER | B | 99 | 13.704 | 4.337 | 5.363 | 1.00 | 14.52 |
| ATOM | 1943 | C | SER | B | 99 | 13.092 | 1.629 | 5.986 | 1.00 | 12.89 |
| ATOM | 1944 | O | SER | B | 99 | 14.056 | 1.196 | 5.349 | 1.00 | 12.57 |
| ATOM | 1959 | H | VAL | B | 102 | 14.549 | 2.518 | 2.526 | 1.00 | 9.33 |
| ATOM | 1960 | CA | VAL | B | 102 | 15.975 | 2.245 | 2.364 | 1.00 | 9.28 |
| ATOM | 1961 | CB | VAL | B | 102 | 16.792 | 2.715 | 3.583 | 1.00 | 9.50 |
| ATOM | 1962 | CG1 | VAL | B | 102 | 18.242 | 2.256 | 3.483 | 1.00 | 9.82 |
| ATOM | 1963 | CG2 | VAL | B | 102 | 16.730 | 4.243 | 3.694 | 1.00 | 9.83 |
| ATOM | 1964 | C | VAL | B | 102 | 16.217 | 0.765 | 2.040 | 1.00 | 8.85 |
| ATOM | 1965 | O | VAL | B | 102 | 17.042 | 0.444 | 1.186 | 1.00 | 9.10 |
| ATOM | 1966 | N | LEU | B | 103 | 15.477 | −0.126 | 2.694 | 1.00 | 8.30 |
| ATOM | 1967 | CA | LEU | B | 103 | 15.550 | −1.554 | 2.369 | 1.00 | 7.93 |
| ATOM | 1968 | CB | LEU | B | 103 | 14.711 | −2.380 | 3.350 | 1.00 | 8.08 |
| ATOM | 1969 | CG | LEU | B | 103 | 14.821 | −3.899 | 3.221 | 1.00 | 7.79 |
| ATOM | 1970 | CD1 | LEU | B | 103 | 16.257 | −4.353 | 3.403 | 1.00 | 8.56 |
| ATOM | 1971 | CD2 | LEU | B | 103 | 13.939 | −4.569 | 4.243 | 1.00 | 9.12 |
| ATOM | 1972 | C | LEU | B | 103 | 15.123 | −1.847 | 0.925 | 1.00 | 7.70 |
| ATOM | 1973 | O | LEU | B | 103 | 15.727 | −2.687 | 0.246 | 1.00 | 7.60 |
| ATOM | 1990 | N | ALA | B | 106 | 17.929 | −0.799 | −1.331 | 1.00 | 7.92 |
| ATOM | 1991 | CA | ALA | B | 106 | 18.975 | −1.823 | −1.244 | 1.00 | 7.82 |
| ATOM | 1992 | CB | ALA | B | 106 | 19.211 | −2.221 | 0.201 | 1.00 | 7.95 |
| ATOM | 1993 | C | ALA | B | 106 | 18.642 | −3.054 | −2.099 | 1.00 | 7.83 |
| ATOM | 1994 | O | ALA | B | 106 | 19.513 | −3.619 | −2.767 | 1.00 | 7.89 |
| ATOM | 2063 | N | GLN | B | 114 | 23.763 | −5.496 | 4.444 | 1.00 | 10.08 |
| ATOM | 2064 | CA | GLN | B | 114 | 23.384 | −4.238 | 5.078 | 1.00 | 9.77 |
| ATOM | 2065 | CB | GLN | B | 114 | 22.454 | −4.492 | 6.267 | 1.00 | 9.56 |
| ATOM | 2066 | CG | GLN | B | 114 | 23.081 | −5.287 | 7.408 | 1.00 | 9.34 |
| ATOM | 2067 | CD | GLN | B | 114 | 22.379 | −5.053 | 8.719 | 1.00 | 8.85 |
| ATOM | 2068 | OE1 | GLN | B | 114 | 22.105 | −3.910 | 9.098 | 1.00 | 9.42 |
| ATOM | 2069 | NE2 | GLN | B | 114 | 22.098 | −6.135 | 9.437 | 1.00 | 8.52 |
| ATOM | 2070 | C | GLN | B | 114 | 24.592 | −3.416 | 5.528 | 1.00 | 10.01 |
| ATOM | 2071 | O | GLN | B | 114 | 25.608 | −3.968 | 5.960 | 1.00 | 10.08 |
| ATOM | 2072 | N | CYS | B | 115 | 24.450 | −2.095 | 5.401 | 1.00 | 10.57 |
| ATOM | 2073 | CA | CYS | B | 115 | 25.405 | −1.099 | 5.915 | 1.00 | 11.33 |
| ATOM | 2074 | CB | CYS | B | 115 | 25.797 | −1.391 | 7.369 | 1.00 | 11.41 |
| ATOM | 2075 | SG | CYS | B | 115 | 24.404 | −1.367 | 8.516 | 1.00 | 13.01 |
| ATOM | 2076 | C | CYS | B | 115 | 26.639 | −0.897 | 5.037 | 1.00 | 11.90 |
| ATOM | 2077 | O | CYS | B | 115 | 27.651 | −0.352 | 5.488 | 1.00 | 12.13 |
| ATOM | 2087 | N | PHE | B | 117 | 27.457 | −0.565 | 0.404 | 1.00 | 12.62 |
| ATOM | 2088 | CA | PHE | B | 117 | 27.233 | −0.894 | −0.999 | 1.00 | 12.39 |
| ATOM | 2089 | CB | PHE | B | 117 | 26.485 | 0.223 | −1.740 | 1.00 | 12.42 |
| ATOM | 2090 | CG | PHE | B | 117 | 25.068 | 0.452 | −1.285 | 1.00 | 12.77 |
| ATOM | 2091 | CD1 | PHE | B | 117 | 24.193 | −0.609 | −1.057 | 1.00 | 12.77 |
| ATOM | 2092 | CE1 | PHE | B | 117 | 22.874 | −0.370 | −0.656 | 1.00 | 12.83 |
| ATOM | 2093 | CZ | PHE | B | 117 | 22.423 | 0.936 | −0.498 | 1.00 | 12.86 |
| ATOM | 2094 | CE2 | PHE | B | 117 | 23.280 | 1.999 | −0.743 | 1.00 | 13.41 |
| ATOM | 2095 | CD2 | PHE | B | 117 | 24.594 | 1.752 | −1.139 | 1.00 | 13.43 |
| ATOM | 2096 | C | PHE | B | 117 | 28.583 | −1.046 | −1.667 | 1.00 | 11.92 |
| ATOM | 2097 | O | PHE | B | 117 | 29.497 | −0.262 | −1.414 | 1.00 | 12.30 |
| ATOM | 2485 | N | PHE | B | 164 | 20.554 | −10.249 | 3.036 | 1.00 | 10.13 |
| ATOM | 2486 | CA | PHE | B | 164 | 21.005 | −8.872 | 3.207 | 1.00 | 9.30 |
| ATOM | 2487 | CB | PHE | B | 164 | 19.903 | −7.944 | 2.685 | 1.00 | 8.96 |

TABLE 11-continued

Atomic coordinates of amino acid residues of hDcn1 Chain B essential for binding hUbc12.

| | Atom No. | Atom Name | | | X | Y | Z | Occupancy | B-factor |
|---|---|---|---|---|---|---|---|---|---|
| ATOM | 2488 | CG | PHE | B | 164 | 20.185 | −6.479 | 2.852 | 1.00 | 8.28 |
| ATOM | 2489 | CD1 | PHE | BB | 164 | 21.081 | −5.824 | 2.011 | 1.00 | 7.37 |
| ATOM | 2490 | CE1 | PHE | B | 164 | 21.325 | −4.458 | 2.152 | 1.00 | 7.93 |
| ATOM | 2491 | CZ | PHE | B | 164 | 20.663 | −3.732 | 3.132 | 1.00 | 7.52 |
| ATOM | 2492 | CE2 | PHE | B | 164 | 19.767 | −4.372 | 3.975 | 1.00 | 8.31 |
| ATOM | 2493 | CD2 | PHE | B | 164 | 19.524 | −5.739 | 3.831 | 1.00 | 7.61 |
| ATOM | 2494 | C | PHE | B | 164 | 21.330 | −8.579 | 4.673 | 1.00 | 8.93 |
| ATOM | 2495 | O | PHE | B | 164 | 22.328 | −7.921 | 4.972 | 1.00 | 8.93 |
| ATOM | 2510 | N | ASN | B | 167 | 25.423 | −11.883 | 8.254 | 1.00 | 17.88 |
| ATOM | 2511 | CA | AASN | B | 167 | 26.822 | −11.839 | 7.864 | 0.50 | 20.28 |
| ATOM | 2512 | CA | BASN | B | 167 | 26.827 | −11.858 | 7.892 | 0.50 | 20.24 |
| ATOM | 2513 | CB | AASN | B | 167 | 27.727 | −12.325 | 8.995 | 0.50 | 21.60 |
| ATOM | 2514 | CB | BASN | B | 167 | 27.634 | −12.433 | 9.057 | 0.50 | 21.55 |
| ATOM | 2515 | CG | AASN | B | 167 | 27.856 | −11.307 | 10.110 | 0.50 | 25.80 |
| ATOM | 2516 | CG | BASN | B | 167 | 29.119 | −12.423 | 8.809 | 0.50 | 25.38 |
| ATOM | 2517 | OD1 | AASN | B | 167 | 28.050 | −10.117 | 9.859 | 0.50 | 28.22 |
| ATOM | 2518 | OD1 | BASN | B | 167 | 29.601 | −12.981 | 7.826 | 0.50 | 27.79 |
| ATOM | 2519 | ND2 | AASN | B | 167 | 27.750 | −11.770 | 11.350 | 0.50 | 28.23 |
| ATOM | 2520 | ND2 | BASN | B | 167 | 29.863 | −11.810 | 9.722 | 0.50 | 27.67 |
| ATOM | 2521 | C | ASN | B | 167 | 27.010 | −12.683 | 6.608 | 1.00 | 20.72 |
| ATOM | 2522 | O | ASN | B | 167 | 26.555 | −13.829 | 6.549 | 1.00 | 20.44 |
| ATOM | 2589 | N | MET | B | 177 | 18.700 | −9.451 | 15.173 | 1.00 | 12.40 |
| ATOM | 2590 | CA | MET | B | 177 | 18.680 | −8.891 | 13.824 | 1.00 | 11.50 |
| ATOM | 2591 | CB | MET | B | 177 | 19.985 | −9.210 | 13.081 | 1.00 | 11.92 |
| ATOM | 2592 | CG | MET | B | 177 | 20.314 | −8.240 | 11.947 | 1.00 | 13.23 |
| ATOM | 2593 | SD | MET | B | 177 | 20.326 | −6.502 | 12.455 | 1.00 | 13.85 |
| ATOM | 2594 | CE | MET | B | 177 | 21.758 | −6.458 | 13.517 | 1.00 | 14.84 |
| ATOM | 2595 | C | MET | B | 177 | 17.465 | −9.394 | 13.045 | 1.00 | 10.79 |
| ATOM | 2596 | O | MET | B | 177 | 16.811 | −8.624 | 12.346 | 1.00 | 10.53 |
| ATOM | 2610 | N | ALA | B | 180 | 14.364 | −7.574 | 14.322 | 1.00 | 8.93 |
| ATOM | 2611 | CA | ALA | B | 180 | 14.340 | −6.219 | 13.771 | 1.00 | 8.75 |
| ATOM | 2612 | CB | ALA | B | 180 | 15.696 | −5.561 | 13.910 | 1.00 | 9.14 |
| ATOM | 2613 | C | ALA | B | 180 | 13.870 | −6.189 | 12.314 | 1.00 | 8.69 |
| ATOM | 2614 | O | ALA | B | 180 | 13.040 | −5.350 | 11.935 | 1.00 | 9.10 |
| ATOM | 2615 | N | TYR | B | 181 | 14.379 | −7.107 | 11.497 | 1.00 | 8.07 |
| ATOM | 2616 | CA | TYR | B | 181 | 13.968 | −7.133 | 10.097 | 1.00 | 7.64 |
| ATOM | 2617 | CB | TYR | B | 181 | 14.990 | −7.869 | 9.224 | 1.00 | 7.89 |
| ATOM | 2618 | CG | TYR | B | 181 | 16.138 | −6.973 | 8.845 | 1.00 | 6.99 |
| ATOM | 2619 | CD1 | TYR | B | 181 | 16.023 | −6.068 | 7.794 | 1.00 | 7.98 |
| ATOM | 2620 | CE1 | TYR | B | 181 | 17.075 | −5.234 | 7.450 | 1.00 | 7.54 |
| ATOM | 2621 | CZ | TYR | B | 181 | 18.255 | −5.297 | 8.173 | 1.00 | 8.50 |
| ATOM | 2622 | OH | TYR | B | 181 | 19.290 | −4.473 | 7.839 | 1.00 | 9.59 |
| ATOM | 2623 | CE2 | TYR | B | 181 | 18.390 | −6.176 | 9.224 | 1.00 | 8.12 |
| ATOM | 2624 | CD2 | TYR | B | 181 | 17.332 | −7.003 | 9.562 | 1.00 | 7.84 |
| ATOM | 2625 | C | TYR | B | 181 | 12.540 | −7.633 | 9.894 | 1.00 | 7.55 |
| ATOM | 2626 | O | TYR | B | 181 | 11.829 | −7.156 | 9.006 | 1.00 | 8.17 |
| ATOM | 2649 | N | LEU | B | 184 | 10.286 | −4.821 | 10.528 | 1.00 | 10.96 |
| ATOM | 2650 | CA | LEU | B | 184 | 10.311 | −3.937 | 9.370 | 1.00 | 11.71 |
| ATOM | 2651 | CB | LEU | B | 184 | 11.758 | −3.707 | 8.917 | 1.00 | 12.41 |
| ATOM | 2652 | CG | LEU | B | 184 | 12.048 | −2.593 | 7.910 | 1.00 | 13.96 |
| ATOM | 2653 | CD1 | LEU | B | 184 | 11.550 | −1.250 | 8.429 | 1.00 | 14.99 |
| ATOM | 2654 | CD2 | LEU | B | 184 | 13.543 | −2.532 | 7.604 | 1.00 | 14.64 |
| ATOM | 2655 | C | LEU | B | 184 | 9.466 | −4.465 | 8.207 | 1.00 | 11.44 |
| ATOM | 2656 | O | LEU | B | 184 | 8.546 | −3.785 | 7.754 | 1.00 | 12.30 |

TABLE 12

Additional contacts that contribute to, but are not essential, for contact between human Dcn1 and human Ubc12 with hUbc12 Chain E interactions with hDcn1$^P$ Chain B and hUbc12 Chain F interactions with hDcn1$^P$ Chain A shown.

| hUbc12 Atom | | hDcn1 Atom | | Distance (Å) |
|---|---|---|---|---|
| Leu | 7E | CB | Ile | 83B | CG2 | 4.14 |
| | | | Ile | 83B | CD1 | 4.33 |
| Leu | 7E | CD1 | Cys | 115B | CB | 3.61 |
| | | | Cys | 115B | SG | 3.78 |
| | | | Ile | 83B | CG2 | 3.94 |
| Leu | 7E | C | Ile | 83B | CD1 | 4.08 |
| Leu | 7E | O | Ile | 83B | CD1 | 4.15 |
| Lys | 8E | N | Ile | 83B | CD1 | 3.91 |
| Lys | 8E | CA | Ile | 83B | CD1 | 3.85 |
| Lys | 8E | CB | Ile | 83B | CD1 | 4.35 |

TABLE 12-continued

Additional contacts that contribute to, but are not essential, for contact between human Dcn1 and human Ubc12 with hUbc12 Chain E interactions with hDcn1^P Chain B and hUbc12 Chain F interactions with hDcn1^P Chain A shown.

| hUbc12 Atom | | hDcn1 Atom | | | Distance (Å) |
|---|---|---|---|---|---|
| Lys | 8E | CG | Ile | 83B | CB | 4.37 |
| | | | Ile | 83B | CG1 | 4.22 |
| | | | Ile | 83B | CD1 | 3.66 |
| Lys | 8E | CD | Asp | 84B | OD1 | 4.18 |
| Lys | 8E | CE | Gln | 87B | OE1 | 4.21 |
| Lys | 8E | NZ | Gln | 87B | CB | 3.97 |
| | | | Gln | 87B | OE1 | 3.02 |
| | | | Gln | 87B | CG | 3.92 |
| | | | Gln | 87B | CD | 3.85 |
| Lys | 11E | CE | Ile | 83B | CG1 | 3.97 |
| | | | Ile | 83B | CD1 | 3.27 |
| Lys | 11E | NZ | Ile | 83B | CG1 | 3.51 |
| | | | Ile | 83B | CD1 | 3.27 |
| | | | Asp | 84B | CG | 4.36 |
| | | | Asp | 84B | OD2 | 3.58 |
| Leu | 7F | CB | Ile | 83A | CD1 | 4.13 |
| | | | Ile | 83A | CG2 | 4.15 |
| Leu | 7F | CD1 | Cys | 115A | SG | 3.96 |
| | | | Cys | 115A | CB | 3.83 |
| | | | Ile | 83A | CG2 | 4.06 |
| Leu | 7F | C | Ile | 83A | CD1 | 3.82 |
| Leu | 7F | O | Ile | 83A | CD1 | 3.63 |
| Lys | 8F | N | Ile | 83A | CD1 | 4.02 |
| Lys | 8F | CA | Ile | 83A | CD1 | 4.08 |
| Lys | 8F | CD | Gln | 87A | CG | 4.46 |
| | | | Gln | 87A | CD | 4.5 |
| | | | Gln | 87A | OE1 | 3.73 |
| Lys | 8F | CE | Gln | 87A | CG | 4.42 |
| | | | Gln | 87A | CD | 3.95 |
| | | | Gln | 87A | OE1 | 2.91 |
| Lys | 8F | NZ | Gln | 87A | CB | 4.08 |
| | | | Gln | 87A | CG | 3.4 |
| | | | Gln | 87A | CD | 2.7 |
| | | | Gln | 87A | OE1 | 1.78 |
| | | | Gln | 87A | NE2 | 3.69 |
| Lys | 11F | CB | Ile | 83A | CD1 | 3.99 |
| Lys | 11F | CD | Asp | 84A | OD2 | 4.28 |
| | | | Ile | 83A | CG1 | 4.26 |
| | | | Ile | 83A | CD1 | 3.82 |
| Lys | 11F | CE | Asp | 84A | OD2 | 3.93 |
| Lys | 11F | NZ | Asp | 84A | CG | 3.65 |
| | | | Asp | 84A | OD1 | 4.2 |
| | | | Asp | 84A | OD2 | 2.91 |

TABLE 13

Atomic coordinates of residues that contribute to, but are not required for, binding of hDcn1 Chain A to hUbc12 from structure with stapled hUbc12 peptide.

| | Atom No. | Atom Name | | | | X | Y | Z | Occupancy | B-factor |
|---|---|---|---|---|---|---|---|---|---|---|
| ATOM | 206 | N | ASP | A | 84 | 15.064 | 41.735 | 5.788 | 1.00 | 10.17 |
| ATOM | 207 | CA | ASP | A | 84 | 16.219 | 42.546 | 6.174 | 1.00 | 10.55 |
| ATOM | 208 | CB | ASP | A | 84 | 17.461 | 41.675 | 6.366 | 1.00 | 11.23 |
| ATOM | 209 | CG | ASP | A | 84 | 17.375 | 40.805 | 7.603 | 1.00 | 13.04 |
| ATOM | 210 | OD1 | ASP | A | 84 | 16.531 | 41.113 | 8.522 | 1.00 | 16.41 |
| ATOM | 211 | OD2 | ASP | A | 84 | 18.111 | 39.803 | 7.658 | 1.00 | 15.83 |
| ATOM | 212 | C | ASP | A | 84 | 16.489 | 43.657 | 5.159 | 1.00 | 9.88 |
| ATOM | 213 | O | ASP | A | 84 | 16.754 | 44.791 | 5.545 | 1.00 | 9.65 |
| ATOM | 285 | N | ALA | A | 94 | 15.031 | 56.885 | 5.766 | 1.00 | 11.05 |
| ATOM | 286 | CA | ALA | A | 94 | 14.657 | 57.464 | 7.067 | 1.00 | 11.12 |
| ATOM | 287 | CB | ALA | A | 94 | 15.239 | 58.886 | 7.231 | 1.00 | 11.03 |
| ATOM | 288 | C | ALA | A | 94 | 13.133 | 57.443 | 7.302 | 1.00 | 11.47 |
| ATOM | 289 | O | ALA | A | 94 | 12.545 | 58.432 | 7.751 | 1.00 | 10.94 |
| ATOM | 290 | N | LEU | A | 95 | 12.504 | 56.311 | 6.972 | 1.00 | 11.82 |
| ATOM | 291 | CA | LEU | A | 95 | 11.064 | 56.133 | 7.181 | 1.00 | 12.39 |
| ATOM | 292 | CB | LEU | A | 95 | 10.330 | 55.975 | 5.843 | 1.00 | 12.25 |
| ATOM | 293 | CG | LEU | A | 95 | 10.424 | 57.112 | 4.823 | 1.00 | 12.44 |
| ATOM | 294 | CD1 | LEU | A | 95 | 9.967 | 56.631 | 3.452 | 1.00 | 12.15 |
| ATOM | 295 | CD2 | LEU | A | 95 | 9.632 | 58.326 | 5.278 | 1.00 | 12.56 |
| ATOM | 296 | C | LEU | A | 95 | 10.731 | 54.935 | 8.064 | 1.00 | 12.66 |
| ATOM | 297 | O | LEU | A | 95 | 11.381 | 53.895 | 7.995 | 1.00 | 13.03 |
| ATOM | 298 | N | ASP | A | 96 | 9.702 | 55.101 | 8.883 | 1.00 | 13.06 |
| ATOM | 299 | CA | ASP | A | 96 | 9.059 | 53.996 | 9.589 | 1.00 | 13.50 |
| ATOM | 300 | CB | ASP | A | 96 | 7.901 | 54.552 | 10.424 | 1.00 | 13.89 |
| ATOM | 301 | CG | ASP | A | 96 | 7.251 | 53.509 | 11.344 | 1.00 | 16.05 |
| ATOM | 302 | OD1 | ASP | A | 96 | 7.257 | 52.290 | 11.044 | 1.00 | 17.16 |
| ATOM | 303 | OD2 | ASP | A | 96 | 6.702 | 53.934 | 12.381 | 1.00 | 17.91 |
| ATOM | 304 | C | ASP | A | 96 | 8.539 | 53.014 | 8.531 | 1.00 | 12.97 |
| ATOM | 305 | O | ASP | A | 96 | 7.807 | 53.421 | 7.620 | 1.00 | 12.93 |

TABLE 14

Atomic coordinates of residues that contribute to, but are not required for, binding of hDcn1 Chain B to hUbc12 in structure of stapled hUbc12 peptide.

| | Atom No. | Atom Name | | | X | Y | Z | Occupancy | B-factor |
|---|---|---|---|---|---|---|---|---|---|
| ATOM | 2420 | N | ASP | B | 84 | −29.031 | 110.230 | −22.980 | 1.00 | 21.25 |
| ATOM | 2421 | CA | ASP | B | 84 | −28.182 | 111.358 | −23.383 | 1.00 | 21.22 |
| ATOM | 2422 | CB | ASP | B | 84 | −29.019 | 112.619 | −23.623 | 1.00 | 21.50 |
| ATOM | 2423 | CG | ASP | B | 84 | −29.913 | 112.501 | −24.842 | 1.00 | 22.06 |
| ATOM | 2424 | OD1 | ASP | B | 84 | −29.581 | 111.722 | −25.760 | 1.00 | 23.61 |
| ATOM | 2425 | OD2 | ASP | B | 84 | −30.952 | 113.192 | −24.884 | 1.00 | 23.44 |
| ATOM | 2426 | C | ASP | B | 84 | −27.088 | 111.651 | −22.365 | 1.00 | 20.88 |
| ATOM | 2427 | O | ASP | B | 84 | −25.970 | 112.013 | −22.735 | 1.00 | 20.81 |
| ATOM | 2499 | N | ALA | B | 94 | −14.009 | 109.936 | −22.759 | 1.00 | 22.67 |
| ATOM | 2500 | CA | ALA | B | 94 | −13.443 | 109.599 | −24.075 | 1.00 | 22.83 |
| ATOM | 2501 | CB | ALA | B | 94 | −12.005 | 110.127 | −24.218 | 1.00 | 22.75 |
| ATOM | 2502 | C | ALA | B | 94 | −13.517 | 108.097 | −24.360 | 1.00 | 22.93 |
| ATOM | 2503 | O | ALA | B | 94 | −12.552 | 107.489 | −24.826 | 1.00 | 22.99 |
| ATOM | 2504 | N | LEU | B | 95 | −14.680 | 107.514 | −24.076 | 1.00 | 23.01 |
| ATOM | 2505 | CA | LEU | B | 95 | −14.892 | 106.079 | −24.232 | 1.00 | 23.06 |
| ATOM | 2506 | CB | LEU | B | 95 | −15.078 | 105.407 | −22.863 | 1.00 | 23.00 |
| ATOM | 2507 | CG | LEU | B | 95 | −13.879 | 105.257 | −21.920 | 1.00 | 23.07 |
| ATOM | 2508 | CD1 | LEU | B | 95 | −14.348 | 104.751 | −20.567 | 1.00 | 23.09 |
| ATOM | 2509 | CD2 | LEU | B | 95 | −12.807 | 104.331 | −22.492 | 1.00 | 23.19 |
| ATOM | 2510 | C | LEU | B | 95 | −16.087 | 105.753 | −25.121 | 1.00 | 23.04 |
| ATOM | 2511 | O | LEU | B | 95 | −17.128 | 106.409 | −25.048 | 1.00 | 23.06 |
| ATOM | 2512 | N | ASP | B | 96 | −15.912 | 104.739 | −25.966 | 1.00 | 23.04 |
| ATOM | 2513 | CA | ASP | B | 96 | −17.017 | 104.098 | −26.670 | 1.00 | 23.21 |
| ATOM | 2514 | CB | ASP | B | 96 | −16.474 | 102.949 | −27.538 | 1.00 | 23.36 |
| ATOM | 2515 | CG | ASP | B | 96 | −17.524 | 102.342 | −28.477 | 1.00 | 24.22 |
| ATOM | 2516 | OD1 | ASP | B | 96 | −18.723 | 102.277 | −28.126 | 1.00 | 25.07 |
| ATOM | 2517 | OD2 | ASP | B | 96 | −17.132 | 101.898 | −29.578 | 1.00 | 24.66 |
| ATOM | 2518 | C | ASP | B | 96 | −17.984 | 103.568 | −25.603 | 1.00 | 22.87 |
| ATOM | 2519 | O | ASP | B | 96 | −17.567 | 102.833 | −24.704 | 1.00 | 22.78 |

TABLE 15

Atomic coordinates of residues that contribute to, but are not required for, binding of hDcn1 Chain A to hUbc12.

| | Atom No. | Atom Name | | | X | Y | Z | Occupancy | B-factor |
|---|---|---|---|---|---|---|---|---|---|
| ATOM | 204 | N | ASP | A | 84 | 37.117 | −17.398 | −21.586 | 1.00 | 15.30 |
| ATOM | 205 | CA | ASP | A | 84 | 36.947 | −18.847 | −21.612 | 1.00 | 15.98 |
| ATOM | 206 | CB | ASP | A | 84 | 38.173 | −19.558 | −21.028 | 1.00 | 17.35 |
| ATOM | 207 | CG | ASP | A | 84 | 39.362 | −19.558 | −21.982 | 1.00 | 21.48 |
| ATOM | 208 | OD1 | ASP | A | 84 | 39.184 | −19.251 | −23.181 | 1.00 | 24.51 |
| ATOM | 209 | OD2 | ASP | A | 84 | 40.482 | −19.872 | −21.530 | 1.00 | 24.38 |
| ATOM | 210 | C | ASP | A | 84 | 35.666 | −19.254 | −20.888 | 1.00 | 14.58 |
| ATOM | 211 | O | ASP | A | 84 | 34.915 | −20.101 | −21.374 | 1.00 | 14.36 |
| ATOM | 283 | N | ALA | A | 94 | 23.572 | −23.460 | −24.936 | 1.00 | 12.74 |
| ATOM | 284 | CA | ALA | A | 94 | 23.354 | −23.863 | −26.331 | 1.00 | 13.46 |
| ATOM | 285 | CB | ALA | A | 94 | 22.336 | −25.015 | −26.429 | 1.00 | 13.90 |
| ATOM | 286 | C | ALA | A | 94 | 22.937 | −22.668 | −27.195 | 1.00 | 13.29 |
| ATOM | 287 | O | ALA | A | 94 | 22.037 | −22.762 | −28.036 | 1.00 | 13.55 |
| ATOM | 288 | N | LEU | A | 95 | 23.604 | −21.540 | −26.966 | 1.00 | 12.35 |
| ATOM | 289 | CA | LEU | A | 95 | 23.344 | −20.312 | −27.704 | 1.00 | 11.64 |
| ATOM | 290 | CB | LEU | A | 95 | 22.743 | −19.238 | −26.788 | 1.00 | 11.73 |
| ATOM | 291 | CG | LEU | A | 95 | 21.370 | −19.454 | −26.147 | 1.00 | 12.12 |
| ATOM | 292 | CD1 | LEU | A | 95 | 21.138 | −18.429 | −25.053 | 1.00 | 12.54 |
| ATOM | 293 | CD2 | LEU | A | 95 | 20.245 | −19.399 | −27.176 | 1.00 | 13.08 |
| ATOM | 294 | C | LEU | A | 95 | 24.640 | −19.790 | −28.295 | 1.00 | 11.08 |
| ATOM | 295 | O | LEU | A | 95 | 25.702 | −19.886 | −27.675 | 1.00 | 11.12 |
| ATOM | 296 | N | ASP | A | 96 | 24.544 | −19.231 | −29.496 | 1.00 | 10.92 |
| ATOM | 297 | CA | ASP | A | 96 | 25.671 | −18.539 | −30.101 | 1.00 | 10.77 |
| ATOM | 298 | CB | ASP | A | 96 | 25.292 | −18.026 | −31.489 | 1.00 | 11.39 |
| ATOM | 299 | CG | ASP | A | 96 | 26.490 | −17.540 | −32.278 | 1.00 | 13.24 |
| ATOM | 300 | OD1 | ASP | A | 96 | 27.084 | −16.505 | −31.903 | 1.00 | 14.15 |
| ATOM | 301 | OD2 | ASP | A | 96 | 26.836 | −18.197 | −33.280 | 1.00 | 16.29 |
| ATOM | 302 | C | ASP | A | 96 | 26.060 | −17.373 | −29.187 | 1.00 | 9.82 |
| ATOM | 303 | O | ASP | A | 96 | 25.191 | −16.644 | −28.725 | 1.00 | 9.62 |

TABLE 16

Atomic coordinates of residues that contribute to, but are not required for, binding of hDcn1 Chain B to hUbc12.

|  | Atom No. | Atom Name |  |  | X | Y | Z | Occupancy | B-factor |
|---|---|---|---|---|---|---|---|---|---|
| ATOM | 1827 | N | ASP | B | 84 | 29.753 | 5.342 | 6.933 | 1.00 | 16.27 |
| ATOM | 1828 | CA | ASP | B | 84 | 29.678 | 6.800 | 6.878 | 1.00 | 16.75 |
| ATOM | 1829 | CB | ASP | B | 84 | 31.075 | 7.421 | 7.001 | 1.00 | 17.47 |
| ATOM | 1830 | CG | ASP | B | 84 | 31.691 | 7.209 | 8.374 | 1.00 | 19.75 |
| ATOM | 1831 | OD1 | ASP | B | 84 | 31.009 | 7.478 | 9.388 | 1.00 | 21.39 |
| ATOM | 1832 | OD2 | ASP | B | 84 | 32.863 | 6.777 | 8.441 | 1.00 | 21.09 |
| ATOM | 1833 | C | ASP | B | 84 | 28.984 | 7.274 | 5.602 | 1.00 | 16.12 |
| ATOM | 1834 | O | ASP | B | 84 | 28.155 | 8.184 | 5.640 | 1.00 | 16.27 |
| ATOM | 1906 | N | ALA | B | 94 | 16.681 | 12.075 | 2.790 | 1.00 | 15.25 |
| ATOM | 1907 | CA | ALA | B | 94 | 15.771 | 12.480 | 3.867 | 1.00 | 16.29 |
| ATOM | 1908 | CB | ALA | B | 94 | 14.856 | 13.631 | 3.416 | 1.00 | 16.50 |
| ATOM | 1909 | C | ALA | B | 94 | 14.962 | 11.288 | 4.394 | 1.00 | 16.33 |
| ATOM | 1910 | O | ALA | B | 94 | 13.767 | 11.399 | 4.687 | 1.00 | 16.79 |
| ATOM | 1911 | N | LEU | B | 95 | 15.642 | 10.148 | 4.503 | 1.00 | 15.53 |
| ATOM | 1912 | CA | LEU | B | 95 | 15.058 | 8.907 | 5.003 | 1.00 | 14.51 |
| ATOM | 1913 | CB | LEU | B | 95 | 15.049 | 7.834 | 3.907 | 1.00 | 14.56 |
| ATOM | 1914 | CG | LEU | B | 95 | 14.170 | 8.032 | 2.671 | 1.00 | 15.10 |
| ATOM | 1915 | CD1 | LEU | B | 95 | 14.550 | 7.008 | 1.608 | 1.00 | 15.62 |
| ATOM | 1916 | CD2 | LEU | B | 95 | 12.693 | 7.925 | 3.006 | 1.00 | 16.31 |
| ATOM | 1917 | C | LEU | B | 95 | 15.852 | 8.393 | 6.190 | 1.00 | 13.79 |
| ATOM | 1918 | O | LEU | B | 95 | 17.080 | 8.489 | 6.215 | 1.00 | 13.74 |
| ATOM | 1919 | N | ASP | B | 96 | 15.143 | 7.843 | 7.173 | 1.00 | 13.45 |
| ATOM | 1920 | CA | ASP | B | 96 | 15.789 | 7.160 | 8.286 | 1.00 | 13.09 |
| ATOM | 1921 | CB | ASP | B | 96 | 14.745 | 6.737 | 9.323 | 1.00 | 13.72 |
| ATOM | 1922 | CG | ASP | B | 96 | 15.365 | 6.262 | 10.624 | 1.00 | 15.39 |
| ATOM | 1923 | OD1 | ASP | B | 96 | 16.013 | 5.196 | 10.631 | 1.00 | 16.12 |
| ATOM | 1924 | OD2 | ASP | B | 96 | 15.186 | 6.952 | 11.648 | 1.00 | 17.96 |
| ATOM | 1925 | C | ASP | B | 96 | 16.518 | 5.939 | 7.721 | 1.00 | 12.21 |
| ATOM | 1926 | O | ASP | B | 96 | 15.954 | 5.217 | 6.904 | 1.00 | 12.01 |

In still other embodiments, the E2-binding pocket of a NEDD8 co-E3 protein comprises the atoms of Table 17, which are found in amino acid residues Glu108, Met111, Glu112, Pro122, Thr123, Glu124, Val127, Leu128, Ala131, Met139, Cys140, Phe142, Phe189, Ile204, Ala207, Leu208, and Leu211 of human Dcn3 (SEQ ID NO: 39), or a structural variant thereof. In particular embodiments, the E2-binding pocket of a NEDD8 co-E3 protein comprises at least one of the following amino acid residues: a glutamic acid corresponding to position 108 of SEQ ID NO: 39, a methionine corresponding to position 111 of SEQ ID NO: 39, a glutamic acid corresponding to position 112 of SEQ ID NO: 39, a proline corresponding to position 122 of SEQ ID NO: 39, a threonine corresponding to position 123 of SEQ ID NO: 39, a glutamic acid corresponding to position 124 of SEQ ID NO: 39, a valine corresponding to position 127 of SEQ ID NO: 39, a leucine corresponding to position 128 of SEQ ID NO: 39, an alanine corresponding to position 131 of SEQ ID NO: 39, a methionine corresponding to position 139 of SEQ ID NO: 39, a cysteine corresponding to position 140 of SEQ ID NO: 39, a phenylalanine corresponding to position 142 of SEQ ID NO: 39, a phenylalanine corresponding to position 189 of SEQ ID NO: 39, an isoleucine corresponding to position 204 of SEQ ID NO: 39, an alanine corresponding to position 207 of SEQ ID NO: 39, a leucine corresponding to position 208 of SEQ ID NO: 39, and a leucine corresponding to position 211 of SEQ ID NO: 39.

In some of these embodiments, the E2-binding pocket comprises the atomic coordinates of Table 18 or 19, or a structural variant thereof. In particular embodiments, the co-E3 protein has the amino acid sequence set forth in SEQ ID NO: 39.

In certain embodiments, the E2-binding pocket of a NEDD8 co-E3 protein comprises the atoms of Table 17 and 20. The atoms in Table 20 are found in amino acid residues Glu109, Val120, and Asp121. Thus, in some embodiments, the E2-binding pocket of a NEDD8 co-E3 protein comprises at least one of the following amino acid residues: a glutamic acid corresponding to position 108 of SEQ ID NO: 39, a methionine corresponding to position 111 of SEQ ID NO: 39, a glutamic acid corresponding to position 112 of SEQ ID NO: 39, a praline corresponding to position 122 of SEQ ID NO: 39, a threonine corresponding to position 123 of SEQ ID NO: 39, a glutamic acid corresponding to position 124 of SEQ ID NO: 39, a valine corresponding to position 127 of SEQ ID NO: 39, a leucine corresponding to position 128 of SEQ ID NO: 39, an alanine corresponding to position 131 of SEQ ID NO: 39, a methionine corresponding to position 139 of SEQ ID NO: 39, a cysteine corresponding to position 140 of SEQ ID NO: 39, a phenylalanine corresponding to position 142 of SEQ ID NO: 39, a phenylalanine corresponding to position 189 of SEQ ID NO: 39, an isoleucine corresponding to position 204 of SEQ ID NO: 39, an alanine corresponding to position 207 of SEQ ID NO: 39, a leucine corresponding to position 208 of SEQ ID NO: 39, a leucine corresponding to position 211 of SEQ ID NO: 39; a glutamic acid corresponding to position 109 of SEQ ID NO: 39; a valine corresponding to position 120 of SEQ ID NO: 39; and an aspartic acid at position 121 of SEQ ID NO: 39.

In some of these embodiments, the E2-binding pocket comprises the atomic coordinates of Tables 18 and 21; 19 and 22; or a structural variant thereof.

TABLE 17

Minimal contacts between human Dcn3 and human Ube2f with hUbe2f Chain F interactions with hDcn3$^P$ Chain A and hUbe2f Chain G interactions with hDcn3$^P$ Chain B shown.

| hUbe2f Atom | | | hDcn3 Atom | | Distance (Å) |
|---|---|---|---|---|---|
| Acetyl-Met | 1F | OT | Phe | 189A CZ | 3.75 |
| | | | Phe | 189A CE2 | 3.2 |
| | | | Phe | 189A CD2 | 4.22 |
| | | | Met | 139A CG | 3.96 |
| | | | Met | 139A SD | 3.8 |
| | | | Met | 139A CE | 3.47 |
| Acetyl-Met | 1F | CT1 | Phe | 189A CZ | 4.37 |
| | | | Phe | 189A CE2 | 3.94 |
| | | | Pro | 122A O | 3.76 |
| | | | Thr | 123A CA | 4.33 |
| Acetyl-Met | 1F | CT2 | Phe | 189A CE2 | 4.36 |
| | | | Glu | 124A O | 4.33 |
| | | | Leu | 128A N | 4.19 |
| | | | Leu | 128A CA | 4.42 |
| | | | Leu | 128A CB | 4.33 |
| | | | Leu | 211A CD2 | 3.48 |
| | | | Thr | 123A O | 3.78 |
| | | | Pro | 122A O | 3.88 |
| | | | Thr | 123A CA | 4.03 |
| | | | Thr | 123A C | 3.97 |
| Acetyl-Met | 1F | N | Val | 127A CG1 | 4.18 |
| | | | Pro | 122A C | 3.76 |
| | | | Pro | 122A O | 2.74 |
| | | | Thr | 123A N | 4.26 |
| | | | Thr | 123A CA | 3.88 |
| Acetyl-Met | 1F | CA | Pro | 122A O | 3.67 |
| Acetyl-Met | 1F | C | Met | 139A SD | 4.47 |
| | | | Cys | 140A SG | 4.43 |
| | | | Pro | 122A O | 4.36 |
| Acetyl-Met | 1F | O | Pro | 122A O | 4.34 |
| | | | Thr | 123A CG2 | 3.93 |
| Acetyl-Met | 1F | CB | Cys | 140A SG | 4.24 |
| | | | Pro | 122A CB | 4.47 |
| | | | Pro | 122A C | 4.36 |
| | | | Pro | 122A O | 3.53 |
| Acetyl-Met | 1F | CG | Met | 111A CG | 3.84 |
| | | | Met | 111A SD | 4.19 |
| | | | Val | 127A CG1 | 3.64 |
| | | | Pro | 122A O | 3.66 |
| Acetyl-Met | 1F | SD | Met | 139A C | 4.43 |
| | | | Phe | 189A CE1 | 4.45 |
| | | | Phe | 189A CZ | 3.73 |
| | | | Met | 111A CG | 4.27 |
| | | | Met | 111A SD | 4.17 |
| | | | Met | 111A CE | 4.22 |
| | | | Cys | 140A N | 3.38 |
| | | | Cys | 140A CA | 3.92 |
| | | | Val | 127A CG1 | 4.4 |
| Acetyl-Met | 1F | CE | Ala | 131A CB | 3.97 |
| | | | Phe | 142A CE1 | 3.9 |
| | | | Phe | 142A CZ | 3.67 |
| | | | Phe | 189A CE1 | 4.4 |
| | | | Phe | 189A CZ | 3.87 |
| | | | Met | 111A SD | 3.76 |
| | | | Met | 111A CE | 3.86 |
| | | | Cys | 140A N | 4.49 |
| | | | Val | 127A O | 4.46 |
| | | | Val | 127A CG1 | 3.89 |
| Leu | 2F | N | Met | 139A SD | 4.06 |
| | | | Thr | 123A CG2 | 4.33 |
| Leu | 2F | CA | Met | 139A SD | 4.46 |
| | | | Thr | 123A CG2 | 4.3 |
| Leu | 2F | CB | Met | 139A SD | 3.92 |
| | | | Met | 139A CE | 3.91 |
| | | | Ile | 204A CD1 | 4.16 |
| Leu | 2F | CG | Met | 139A CE | 4.47 |
| | | | Ala | 207A CB | 4.12 |
| Leu | 2F | CD1 | Leu | 211A CD2 | 4.4 |
| | | | Thr | 123A O | 4.2 |
| | | | Thr | 123A CA | 4.46 |
| | | | Thr | 123A CB | 4.18 |
| Leu | 2F | CD2 | Ile | 204A CG2 | 4.38 |
| | | | Met | 139A CE | 3.97 |
| | | | Ile | 204A CD1 | 4.21 |
| | | | Ile | 204A O | 4.08 |
| | | | Ala | 207A CB | 3.61 |
| | | | Ala | 207A C | 4.4 |
| | | | Leu | 208A N | 4.1 |
| | | | Leu | 208A CG | 3.56 |
| | | | Leu | 208A CD2 | 3.57 |
| Thr | 3F | N | Met | 139A SD | 4.08 |
| Thr | 3F | OG1 | Met | 139A CB | 3.82 |
| | | | Met | 139A CG | 4.45 |
| | | | Met | 139A SD | 3.76 |
| | | | Cys | 140A SG | 3.59 |
| Thr | 3F | CG2 | Met | 139A SD | 4.28 |
| | | | Ile | 204A CD1 | 3.82 |
| Thr | 3F | C | Cys | 140A SG | 3.89 |
| Thr | 3F | O | Cys | 140A SG | 4.22 |
| Leu | 4F | N | Cys | 140A SG | 3.56 |
| Leu | 4F | CA | Cys | 140A SG | 3.65 |
| Leu | 4F | CB | Cys | 140A SG | 3.93 |
| Leu | 4F | CG | Glu | 108A O | 4.44 |
| Leu | 4F | CD1 | Glu | 108A CB | 3.63 |
| | | | Cys | 140A CB | 4.21 |
| | | | Glu | 108A CA | 3.73 |
| | | | Glu | 108A C | 3.93 |
| | | | Met | 111A CB | 4.3 |
| | | | Met | 111A CG | 4.47 |
| | | | Cys | 140A SG | 4.04 |
| | | | Glu | 108A O | 3.31 |
| Leu | 4F | CD2 | Glu | 112A N | 4.28 |
| | | | Glu | 112A CA | 4.01 |
| | | | Glu | 112A CB | 3.92 |
| | | | Glu | 112A CG | 4.34 |
| | | | Pro | 122A CB | 3.54 |
| | | | Pro | 122A CG | 3.87 |
| Acetyl-Met | 1G | OT | Met | 139B CE | 3.53 |
| | | | Phe | 189B CZ | 3.91 |
| | | | Phe | 189B CE2 | 3.36 |
| | | | Phe | 189B CD2 | 4.4 |
| | | | Met | 139B CG | 4.22 |
| | | | Met | 139B SD | 3.92 |
| Acetyl-Met | 1G | CT1 | Pro | 122B O | 3.69 |
| | | | Thr | 123B CA | 4.42 |
| | | | Phe | 189B CZ | 4.46 |
| | | | Phe | 189B CE2 | 4.03 |
| Acetyl-Met | 1G | CT2 | Pro | 122B O | 3.91 |
| | | | Thr | 123B CA | 4.2 |
| | | | Thr | 123B C | 4.12 |
| | | | Val | 127B CG1 | 4.37 |
| | | | Thr | 123B O | 3.97 |
| | | | Glu | 124B O | 4.2 |
| | | | Leu | 211B CD2 | 3.6 |
| | | | Phe | 189B CE2 | 4.4 |
| | | | Leu | 128B N | 4.04 |
| | | | Leu | 128B CB | 4.26 |
| | | | Leu | 128B CA | 4.32 |
| Acetyl-Met | 1G | N | Pro | 122B C | 3.69 |
| | | | Pro | 122B O | 2.62 |
| | | | Thr | 123B N | 4.23 |
| | | | Thr | 123B CA | 3.95 |
| | | | Val | 127B CG1 | 4.16 |
| Acetyl-Met | 1G | CA | Pro | 122B O | 3.5 |
| | | | Cys | 140B SG | 4.5 |
| Acetyl-Met | 1G | C | Thr | 123B OG1 | 4.45 |
| | | | Pro | 122B O | 4.19 |
| | | | Cys | 140B SG | 4.38 |
| | | | Met | 139B SD | 4.49 |
| Acetyl-Met | 1G | O | Thr | 123B OG1 | 3.96 |
| | | | Pro | 122B O | 4.18 |
| | | | Cys | 140B SG | 4.47 |

TABLE 17-continued

Minimal contacts between human Dcn3 and human Ube2f with hUbe2f Chain F interactions with hDcn3$^P$ Chain A and hUbe2f Chain G interactions with hDcn3$^P$ Chain B shown.

| hUbe2f Atom | | | hDcn3 Atom | | | Distance (Å) |
|---|---|---|---|---|---|---|
| Acetyl-Met | 1G | CB | Pro | 122B | C | 4.31 |
| | | | Pro | 122B | O | 3.34 |
| | | | Cys | 140B | SG | 4.02 |
| Acetyl-Met | 1G | CG | Met | 111B | CG | 3.92 |
| | | | Met | 111B | SD | 4.32 |
| | | | Pro | 122B | O | 3.43 |
| | | | Val | 127B | CG1 | 3.6 |
| Acetyl-Met | 1G | SD | Met | 111B | CG | 4.29 |
| | | | Met | 111B | SD | 4.26 |
| | | | Met | 111B | CE | 4.35 |
| | | | Met | 139B | C | 4.46 |
| | | | Cys | 140B | N | 3.38 |
| | | | Cys | 140B | CA | 3.84 |
| | | | Val | 127B | CG1 | 4.31 |
| | | | Phe | 189B | CZ | 3.79 |
| Acetyl-Met | 1G | CE | Met | 111B | SD | 3.99 |
| | | | Met | 111B | CE | 4.1 |
| | | | Val | 127B | CG1 | 3.75 |
| | | | Ala | 131B | CB | 3.9 |
| | | | Phe | 142B | CE1 | 3.96 |
| | | | Phe | 142B | CZ | 3.83 |
| | | | Phe | 189B | CZ | 3.76 |
| | | | Phe | 189B | CE1 | 4.3 |
| Leu | 2G | N | Met | 139B | CE | 4.18 |
| | | | Met | 139B | SD | 3.68 |
| Leu | 2G | CA | Thr | 123B | OG1 | 4.14 |
| | | | Met | 139B | SD | 4.37 |
| Leu | 2G | CB | Met | 139B | CE | 4.09 |
| | | | Met | 139B | SD | 4.17 |
| Leu | 2G | CG | Met | 139B | CE | 3.98 |
| | | | Leu | 208B | CD2 | 4.16 |
| Leu | 2G | CD1 | Ala | 207B | CB | 3.61 |
| | | | Met | 139B | CE | 4.12 |
| | | | Leu | 208B | CD2 | 3.55 |
| | | | Ala | 207B | C | 4.32 |
| | | | Ile | 204B | O | 4 |
| | | | Leu | 208B | N | 4.14 |
| | | | Leu | 208B | CG | 3.7 |
| Leu | 2G | CD2 | Thr | 123B | CB | 4.48 |
| | | | Thr | 123B | OG1 | 3.87 |
| | | | Thr | 123B | CG2 | 4.41 |
| | | | Ala | 207B | CB | 4.49 |
| | | | Thr | 123B | O | 4.27 |
| Thr | 3G | N | Met | 139B | SD | 4.04 |
| Thr | 3G | OG1 | Met | 139B | CB | 3.84 |
| | | | Cys | 140B | SG | 3.5 |
| | | | Met | 139B | SD | 3.9 |
| Thr | 3G | CG2 | Met | 139B | SD | 4.24 |
| Thr | 3G | C | Cys | 140B | SG | 3.97 |
| Thr | 3G | O | Cys | 140B | SG | 4.42 |
| Leu | 4G | N | Cys | 140B | SG | 3.52 |
| Leu | 4G | CA | Cys | 140B | SG | 3.62 |
| Leu | 4G | CB | Cys | 140B | SG | 3.85 |
| Leu | 4G | CG | Cys | 140B | SG | 4.46 |
| Leu | 4G | CD1 | Glu | 108B | C | 4.11 |
| | | | Glu | 108B | O | 3.6 |
| | | | Met | 111B | CB | 4.3 |
| | | | Met | 111B | CG | 4.41 |
| | | | Glu | 108B | CA | 3.81 |
| | | | Glu | 108B | CB | 3.67 |
| | | | Cys | 140B | CB | 4.04 |
| | | | Cys | 140B | SG | 3.8 |
| Leu | 4G | CD2 | Glu | 112B | CG | 4.47 |
| | | | Pro | 122B | CG | 3.78 |
| | | | Glu | 112B | N | 4.42 |
| | | | Glu | 112B | CA | 4.19 |
| | | | Glu | 112B | CB | 4.17 |
| | | | Pro | 122B | CB | 3.39 |

TABLE 18

Atomic coordinates of amino acid residues essential for human Dcn3 Chain A to bind hUbe2F.

| | Atom No. | Atom Name | | | | X | Y | Z | Occupancy | B-factor |
|---|---|---|---|---|---|---|---|---|---|---|
| ATOM | 187 | N | GLU | A | 108 | 16.684 | 2.422 | 47.251 | 1.00 | 32.01 |
| ATOM | 188 | CA | GLU | A | 108 | 17.898 | 3.239 | 47.429 | 1.00 | 32.03 |
| ATOM | 189 | CB | GLU | A | 108 | 17.705 | 4.680 | 46.928 | 1.00 | 32.27 |
| ATOM | 190 | CG | GLU | A | 108 | 16.456 | 5.392 | 47.441 | 1.00 | 33.27 |
| ATOM | 191 | CD | GLU | A | 108 | 15.314 | 5.376 | 46.434 | 1.00 | 35.06 |
| ATOM | 192 | OE1 | GLU | A | 108 | 15.176 | 4.387 | 45.679 | 1.00 | 35.38 |
| ATOM | 193 | OE2 | GLU | A | 108 | 14.551 | 6.363 | 46.399 | 1.00 | 36.14 |
| ATOM | 194 | C | GLU | A | 108 | 18.476 | 3.251 | 48.851 | 1.00 | 31.77 |
| ATOM | 195 | O | GLU | A | 108 | 19.693 | 3.258 | 49.018 | 1.00 | 31.35 |
| ATOM | 209 | N | MET | A | 111 | 19.991 | -0.224 | 49.462 | 1.00 | 28.11 |
| ATOM | 210 | CA | MET | A | 111 | 21.137 | -0.378 | 48.570 | 1.00 | 27.16 |
| ATOM | 211 | CB | MET | A | 111 | 20.793 | 0.211 | 47.202 | 1.00 | 27.24 |
| ATOM | 212 | CG | MET | A | 111 | 21.843 | -0.028 | 46.128 | 1.00 | 27.61 |
| ATOM | 213 | SD | MET | A | 111 | 21.915 | -1.768 | 45.692 | 1.00 | 29.58 |
| ATOM | 214 | CE | MET | A | 111 | 20.390 | -1.963 | 44.779 | 1.00 | 25.97 |
| ATOM | 215 | C | MET | A | 111 | 22.400 | 0.294 | 49.111 | 1.00 | 26.60 |
| ATOM | 216 | O | MET | A | 111 | 23.516 | -0.231 | 48.985 | 1.00 | 26.39 |
| ATOM | 217 | N | GLU | A | 112 | 22.213 | 1.471 | 49.694 | 1.00 | 25.97 |
| ATOM | 218 | CA | GLU | A | 112 | 23.315 | 2.248 | 50.250 | 1.00 | 25.38 |
| ATOM | 219 | CB | GLU | A | 112 | 22.847 | 3.680 | 50.561 | 1.00 | 24.79 |
| ATOM | 220 | CG | GLU | A | 112 | 23.924 | 4.609 | 51.094 | 1.00 | 24.86 |
| ATOM | 221 | CD | GLU | A | 112 | 24.277 | 4.342 | 52.556 | 1.00 | 25.41 |
| ATOM | 222 | OE1 | GLU | A | 112 | 23.366 | 4.048 | 53.367 | 1.00 | 24.01 |
| ATOM | 223 | OE2 | GLU | A | 112 | 25.477 | 4.428 | 52.895 | 1.00 | 26.77 |
| ATOM | 224 | C | GLU | A | 112 | 23.899 | 1.524 | 51.480 | 1.00 | 25.08 |
| ATOM | 225 | O | GLU | A | 112 | 25.118 | 1.373 | 51.588 | 1.00 | 25.12 |
| ATOM | 299 | N | PRO | A | 122 | 29.322 | 2.686 | 46.412 | 1.00 | 26.00 |

TABLE 18-continued

Atomic coordinates of amino acid residues essential for human Dcn3 Chain A to bind hUbe2F.

| | Atom No. | Atom Name | | | X | Y | Z | Occupancy | B-factor |
|---|---|---|---|---|---|---|---|---|---|
| ATOM | 300 | CA | PRO | A 122 | 28.153 | 2.245 | 45.628 | 1.00 | 25.78 |
| ATOM | 301 | CB | PRO | A 122 | 27.022 | 3.162 | 46.120 | 1.00 | 25.58 |
| ATOM | 302 | CG | PRO | A 122 | 27.497 | 3.753 | 47.390 | 1.00 | 25.21 |
| ATOM | 303 | CD | PRO | A 122 | 28.986 | 3.786 | 47.338 | 1.00 | 25.69 |
| ATOM | 304 | C | PRO | A 122 | 28.301 | 2.388 | 44.099 | 1.00 | 25.85 |
| ATOM | 305 | O | PRO | A 122 | 27.590 | 1.718 | 43.354 | 1.00 | 25.98 |
| ATOM | 306 | N | THR | A 123 | 29.195 | 3.262 | 43.644 | 0.85 | 26.10 |
| ATOM | 307 | CA | THR | A 123 | 29.356 | 3.551 | 42.211 | 1.00 | 26.12 |
| ATOM | 308 | CB | THR | A 123 | 29.594 | 5.050 | 41.977 | 1.00 | 25.83 |
| ATOM | 309 | OG1 | THR | A 123 | 30.856 | 5.415 | 42.536 | 1.00 | 25.73 |
| ATOM | 310 | CG2 | THR | A 123 | 28.509 | 5.866 | 42.638 | 1.00 | 26.02 |
| ATOM | 311 | C | THR | A 123 | 30.510 | 2.765 | 41.573 | 1.00 | 26.40 |
| ATOM | 312 | O | THR | A 123 | 30.782 | 2.871 | 40.367 | 1.00 | 26.51 |
| ATOM | 313 | N | GLU | A 124 | 31.174 | 1.964 | 42.388 | 1.00 | 26.52 |
| ATOM | 314 | CA | GLU | A 124 | 32.391 | 1.277 | 41.977 | 1.00 | 27.12 |
| ATOM | 315 | CB | GLU | A 124 | 33.253 | 1.064 | 43.218 | 1.00 | 27.17 |
| ATOM | 316 | CG | GLU | A 124 | 34.192 | −0.090 | 43.152 | 1.00 | 31.54 |
| ATOM | 317 | CD | GLU | A 124 | 34.229 | −0.832 | 44.442 | 1.00 | 34.97 |
| ATOM | 318 | OE1 | GLU | A 124 | 33.153 | −0.981 | 45.040 | 1.00 | 38.54 |
| ATOM | 319 | OE2 | GLU | A 124 | 35.317 | −1.249 | 44.864 | 1.00 | 35.84 |
| ATOM | 320 | C | GLU | A 124 | 32.137 | −0.034 | 41.195 | 1.00 | 26.48 |
| ATOM | 321 | O | GLU | A 124 | 31.048 | −0.614 | 41.258 | 1.00 | 26.29 |
| ATOM | 344 | N | VAL | A 127 | 30.268 | −3.281 | 42.243 | 1.00 | 24.00 |
| ATOM | 345 | CA | VAL | A 127 | 28.822 | −3.096 | 42.392 | 1.00 | 23.84 |
| ATOM | 346 | CB | VAL | A 127 | 28.461 | −1.735 | 43.066 | 1.00 | 23.94 |
| ATOM | 347 | CG1 | VAL | A 127 | 26.957 | −1.516 | 43.092 | 1.00 | 23.56 |
| ATOM | 348 | CG2 | VAL | A 127 | 29.006 | −1.696 | 44.485 | 1.00 | 23.26 |
| ATOM | 349 | C | VAL | A 127 | 28.117 | −3.264 | 41.046 | 1.00 | 23.76 |
| ATOM | 350 | O | VAL | A 127 | 27.015 | −3.820 | 40.989 | 1.00 | 23.37 |
| ATOM | 351 | N | LEU | A 128 | 28.759 | −2.798 | 39.970 | 1.00 | 23.82 |
| ATOM | 352 | CA | LEU | A 128 | 28.271 | −3.081 | 38.618 | 1.00 | 24.05 |
| ATOM | 353 | CB | LEU | A 128 | 29.088 | −2.342 | 37.537 | 1.00 | 24.16 |
| ATOM | 354 | CG | LEU | A 128 | 28.768 | −2.629 | 36.055 | 1.00 | 23.92 |
| ATOM | 355 | CD1 | LEU | A 128 | 27.382 | −2.121 | 35.666 | 1.00 | 23.42 |
| ATOM | 356 | CD2 | LEU | A 128 | 29.834 | −2.033 | 35.131 | 1.00 | 23.07 |
| ATOM | 357 | C | LEU | A 128 | 28.230 | −4.597 | 38.360 | 1.00 | 23.85 |
| ATOM | 358 | O | LEU | A 128 | 27.226 | −5.111 | 37.861 | 1.00 | 24.40 |
| ATOM | 375 | N | ALA | A 131 | 25.273 | −6.175 | 40.307 | 1.00 | 24.30 |
| ATOM | 376 | CA | ALA | A 131 | 24.040 | −5.888 | 39.589 | 1.00 | 24.39 |
| ATOM | 377 | CB | ALA | A 131 | 23.979 | −4.414 | 39.234 | 1.00 | 23.85 |
| ATOM | 378 | C | ALA | A 131 | 23.907 | −6.751 | 38.330 | 1.00 | 25.10 |
| ATOM | 379 | O | ALA | A 131 | 22.824 | −7.264 | 38.030 | 1.00 | 25.10 |
| ATOM | 440 | N | MET | A 139 | 18.715 | 0.516 | 38.147 | 1.00 | 33.32 |
| ATOM | 441 | CA | MET | A 139 | 19.661 | 1.079 | 39.119 | 1.00 | 32.93 |
| ATOM | 442 | CB | MET | A 139 | 20.280 | 2.368 | 38.591 | 1.00 | 32.99 |
| ATOM | 443 | CG | MET | A 139 | 21.560 | 2.151 | 37.852 | 1.00 | 33.71 |
| ATOM | 444 | SD | MET | A 139 | 22.351 | 3.707 | 37.450 | 1.00 | 35.60 |
| ATOM | 445 | CE | MET | A 139 | 23.571 | 3.131 | 36.258 | 1.00 | 32.49 |
| ATOM | 446 | C | MET | A 139 | 19.038 | 1.357 | 40.483 | 1.00 | 32.55 |
| ATOM | 447 | O | MET | A 139 | 17.924 | 1.889 | 40.563 | 1.00 | 32.23 |
| ATOM | 448 | N | CYS | A 140 | 19.776 | 1.003 | 41.540 | 1.00 | 31.91 |
| ATOM | 449 | CA | CYS | A 140 | 19.395 | 1.286 | 42.930 | 1.00 | 31.63 |
| ATOM | 450 | CB | CYS | A 140 | 19.065 | 2.773 | 43.148 | 1.00 | 31.56 |
| ATOM | 451 | SG | CYS | A 140 | 20.261 | 3.913 | 42.469 | 1.00 | 31.88 |
| ATOM | 452 | C | CYS | A 140 | 18.235 | 0.433 | 43.412 | 1.00 | 31.60 |
| ATOM | 453 | O | CYS | A 140 | 17.563 | 0.780 | 44.391 | 1.00 | 31.76 |
| ATOM | 463 | N | PHE | A 142 | 17.106 | −3.895 | 43.853 | 1.00 | 29.28 |
| ATOM | 464 | CA | PHE | A 142 | 17.085 | −5.342 | 43.679 | 1.00 | 28.66 |
| ATOM | 465 | CB | PHE | A 142 | 18.143 | −6.045 | 44.543 | 1.00 | 28.19 |
| ATOM | 466 | CG | PHE | A 142 | 19.576 | −5.670 | 44.235 | 1.00 | 27.80 |
| ATOM | 467 | CD1 | PHE | A 142 | 20.035 | −5.556 | 42.922 | 1.00 | 26.71 |
| ATOM | 468 | CE1 | PHE | A 142 | 21.362 | −5.235 | 42.649 | 1.00 | 25.52 |
| ATOM | 469 | CZ | PHE | A 142 | 22.250 | −5.032 | 43.693 | 1.00 | 26.49 |
| ATOM | 470 | CE2 | PHE | A 142 | 21.815 | −5.161 | 45.013 | 1.00 | 26.54 |
| ATOM | 471 | CD2 | PHE | A 142 | 20.487 | −5.481 | 45.277 | 1.00 | 27.03 |
| ATOM | 472 | C | PHE | A 142 | 15.712 | −5.805 | 44.158 | 1.00 | 28.73 |
| ATOM | 473 | O | PHE | A 142 | 15.370 | −5.604 | 45.327 | 1.00 | 28.41 |
| ATOM | 849 | N | PHE | A 189 | 21.039 | −1.501 | 32.229 | 1.00 | 30.93 |
| ATOM | 850 | CA | PHE | A 189 | 21.160 | −1.056 | 33.617 | 1.00 | 31.54 |
| ATOM | 851 | CB | PHE | A 189 | 22.500 | −1.553 | 34.166 | 1.00 | 31.55 |
| ATOM | 852 | CG | PHE | A 189 | 22.696 | −1.333 | 35.643 | 1.00 | 31.93 |
| ATOM | 853 | CD1 | PHE | A 189 | 21.763 | −1.789 | 36.571 | 1.00 | 33.33 |
| ATOM | 854 | CE1 | PHE | A 189 | 21.968 | −1.598 | 37.943 | 1.00 | 33.69 |
| ATOM | 855 | CZ | PHE | A 189 | 23.126 | −0.973 | 38.387 | 1.00 | 32.63 |

TABLE 18-continued

Atomic coordinates of amino acid residues essential for human Dcn3 Chain A to bind hUbe2F.

| | Atom No. | Atom Name | | | X | Y | Z | Occupancy | B-factor |
|---|---|---|---|---|---|---|---|---|---|
| ATOM | 856 | CE2 | PHE | A | 189 | 24.069 | −0.532 | 37.470 | 1.00 | 32.60 |
| ATOM | 857 | CD2 | PHE | A | 189 | 23.853 | −0.718 | 36.110 | 1.00 | 32.46 |
| ATOM | 858 | C | PHE | A | 189 | 21.058 | 0.466 | 33.745 | 1.00 | 32.32 |
| ATOM | 859 | O | PHE | A | 189 | 20.321 | 0.974 | 34.589 | 1.00 | 32.66 |
| ATOM | 954 | N | ILE | A | 204 | 25.618 | 9.706 | 32.247 | 1.00 | 34.61 |
| ATOM | 955 | CA | ILE | A | 204 | 25.508 | 8.298 | 32.657 | 1.00 | 34.09 |
| ATOM | 956 | CB | ILE | A | 204 | 24.018 | 7.839 | 32.683 | 1.00 | 34.26 |
| ATOM | 957 | CG1 | ILE | A | 204 | 23.232 | 8.581 | 33.776 | 1.00 | 34.69 |
| ATOM | 958 | CD1 | ILE | A | 204 | 23.623 | 8.214 | 35.217 | 1.00 | 35.98 |
| ATOM | 959 | CG2 | ILE | A | 204 | 23.894 | 6.320 | 32.839 | 1.00 | 34.13 |
| ATOM | 960 | C | ILE | A | 204 | 26.319 | 7.391 | 31.725 | 1.00 | 33.50 |
| ATOM | 961 | O | ILE | A | 204 | 27.104 | 6.566 | 32.178 | 1.00 | 33.59 |
| ATOM | 975 | N | ALA | A | 207 | 29.988 | 7.778 | 32.451 | 1.00 | 29.61 |
| ATOM | 976 | CA | ALA | A | 207 | 30.345 | 7.131 | 33.705 | 1.00 | 29.37 |
| ATOM | 977 | CB | ALA | A | 207 | 29.407 | 7.586 | 34.815 | 1.00 | 29.46 |
| ATOM | 978 | C | ALA | A | 207 | 30.344 | 5.607 | 33.582 | 1.00 | 28.94 |
| ATOM | 979 | O | ALA | A | 207 | 31.266 | 4.929 | 34.063 | 1.00 | 28.63 |
| ATOM | 980 | N | LEU | A | 208 | 29.312 | 5.076 | 32.934 | 1.00 | 28.74 |
| ATOM | 981 | CA | LEU | A | 208 | 29.198 | 3.634 | 32.714 | 1.00 | 28.63 |
| ATOM | 982 | CB | LEU | A | 208 | 27.801 | 3.262 | 32.255 | 1.00 | 28.66 |
| ATOM | 983 | CG | LEU | A | 208 | 26.696 | 3.311 | 33.306 | 1.00 | 29.25 |
| ATOM | 984 | CD1 | LEU | A | 208 | 25.366 | 2.970 | 32.646 | 1.00 | 29.90 |
| ATOM | 985 | CD2 | LEU | A | 208 | 26.995 | 2.351 | 34.460 | 1.00 | 30.23 |
| ATOM | 986 | C | LEU | A | 208 | 30.233 | 3.097 | 31.725 | 1.00 | 28.50 |
| ATOM | 987 | O | LEU | A | 208 | 30.692 | 1.966 | 31.874 | 1.00 | 28.53 |
| ATOM | 1011 | N | LEU | A | 211 | 33.243 | 2.948 | 33.888 | 1.00 | 28.64 |
| ATOM | 1012 | CA | LEU | A | 211 | 33.102 | 1.803 | 34.773 | 1.00 | 28.57 |
| ATOM | 1013 | CB | LEU | A | 211 | 31.764 | 1.868 | 35.513 | 1.00 | 28.22 |
| ATOM | 1014 | CG | LEU | A | 211 | 31.691 | 1.163 | 36.865 | 1.00 | 27.92 |
| ATOM | 1015 | CD1 | LEU | A | 211 | 32.732 | 1.716 | 37.830 | 1.00 | 26.69 |
| ATOM | 1016 | CD2 | LEU | A | 211 | 30.304 | 1.334 | 37.429 | 1.00 | 26.94 |
| ATOM | 1017 | C | LEU | A | 211 | 33.255 | 0.447 | 34.064 | 1.00 | 28.71 |
| ATOM | 1018 | O | LEU | A | 211 | 34.032 | −0.405 | 34.510 | 1.00 | 28.67 |

TABLE 19

Atomic coordinates of amino acid residues essential for human Dcn3 Chain B to bind hUbe2F.

| | Atom No. | Atom Name | | | X | Y | Z | Occupancy | B-factor |
|---|---|---|---|---|---|---|---|---|---|
| ATOM | 1789 | N | GLU | B | 108 | −2.928 | −7.977 | 13.187 | 1.00 | 29.97 |
| ATOM | 1790 | CA | GLU | B | 108 | −2.667 | −8.790 | 11.989 | 1.00 | 30.11 |
| ATOM | 1791 | CB | GLU | B | 108 | −2.220 | −10.221 | 12.340 | 1.00 | 30.21 |
| ATOM | 1792 | CG | GLU | B | 108 | −3.139 | −10.971 | 13.304 | 1.00 | 32.70 |
| ATOM | 1793 | CD | GLU | B | 108 | −2.758 | −10.746 | 14.765 | 1.00 | 35.39 |
| ATOM | 1794 | OE1 | GLU | B | 108 | −1.786 | −9.993 | 15.029 | 1.00 | 36.06 |
| ATOM | 1795 | OE2 | GLU | B | 108 | −3.431 | −11.324 | 15.646 | 1.00 | 35.26 |
| ATOM | 1796 | C | GLU | B | 108 | −3.813 | −8.795 | 10.968 | 1.00 | 29.58 |
| ATOM | 1797 | O | GLU | B | 108 | −3.574 | −8.641 | 9.771 | 1.00 | 29.17 |
| ATOM | 1811 | N | MET | B | 111 | −3.873 | −5.424 | 9.369 | 1.00 | 26.60 |
| ATOM | 1812 | CA | MET | B | 111 | −2.622 | −5.223 | 8.640 | 1.00 | 26.08 |
| ATOM | 1813 | CB | MET | B | 111 | −1.434 | −5.761 | 9.444 | 1.00 | 25.97 |
| ATOM | 1814 | CG | MET | B | 111 | −0.084 | −5.508 | 8.793 | 1.00 | 26.18 |
| ATOM | 1815 | SD | MET | B | 111 | 0.323 | −3.749 | 8.840 | 1.00 | 28.45 |
| ATOM | 1816 | CE | MET | B | 111 | 0.542 | −3.511 | 10.610 | 1.00 | 25.99 |
| ATOM | 1817 | C | MET | B | 111 | −2.676 | −5.912 | 7.274 | 1.00 | 25.72 |
| ATOM | 1818 | O | MET | B | 111 | −2.175 | −5.375 | 6.272 | 1.00 | 25.80 |
| ATOM | 1819 | N | GLU | B | 112 | −3.269 | −7.106 | 7.250 | 1.00 | 24.77 |
| ATOM | 1820 | CA | GLU | B | 112 | −3.437 | −7.860 | 6.011 | 1.00 | 24.17 |
| ATOM | 1821 | CB | GLU | B | 112 | −3.954 | −9.276 | 6.294 | 1.00 | 23.71 |
| ATOM | 1822 | CG | GLU | B | 112 | −3.966 | −10.185 | 5.077 | 1.00 | 23.79 |
| ATOM | 1823 | CD | GLU | B | 112 | −5.214 | −10.001 | 4.225 | 1.00 | 24.84 |
| ATOM | 1824 | OE1 | GLU | B | 112 | −6.315 | −9.845 | 4.793 | 1.00 | 23.82 |
| ATOM | 1825 | OE2 | GLU | B | 112 | −5.100 | −10.013 | 2.982 | 1.00 | 25.84 |
| ATOM | 1826 | C | GLU | B | 112 | −4.352 | −7.104 | 5.033 | 1.00 | 23.85 |
| ATOM | 1827 | O | GLU | B | 112 | −4.036 | −6.998 | 3.851 | 1.00 | 24.18 |
| ATOM | 1901 | N | PRO | B | 122 | 2.307 | −8.239 | 1.798 | 1.00 | 23.06 |
| ATOM | 1902 | CA | PRO | B | 122 | 2.578 | −7.735 | 3.172 | 1.00 | 23.39 |
| ATOM | 1903 | CB | PRO | B | 122 | 1.678 | −8.608 | 4.056 | 1.00 | 23.19 |

TABLE 19-continued

Atomic coordinates of amino acid residues essential for human Dcn3 Chain B to bind hUbe2F.

| | Atom No. | Atom Name | | | X | Y | Z | Occupancy | B-factor |
|---|---|---|---|---|---|---|---|---|---|
| ATOM | 1904 | CG | PRO | B | 122 | 0.682 | −9.236 | 3.122 | 1.00 | 23.52 |
| ATOM | 1905 | CD | PRO | B | 122 | 1.369 | −9.376 | 1.804 | 1.00 | 23.09 |
| ATOM | 1906 | C | PRO | B | 122 | 4.037 | −7.894 | 3.620 | 1.00 | 23.35 |
| ATOM | 1907 | O | PRO | B | 122 | 4.438 | −7.374 | 4.661 | 1.00 | 23.55 |
| ATOM | 1908 | N | THR | B | 123 | 4.802 | −8.590 | 2.790 | 1.00 | 23.31 |
| ATOM | 1909 | CA | THR | B | 123 | 6.142 | −9.068 | 3.052 | 1.00 | 23.09 |
| ATOM | 1910 | CB | THR | B | 123 | 6.134 | −10.589 | 2.697 | 1.00 | 23.23 |
| ATOM | 1911 | OG1 | THR | B | 123 | 6.033 | −11.371 | 3.890 | 1.00 | 23.77 |
| ATOM | 1912 | CG2 | THR | B | 123 | 7.327 | −11.017 | 1.891 | 1.00 | 22.66 |
| ATOM | 1913 | C | THR | B | 123 | 7.189 | −8.294 | 2.211 | 1.00 | 23.32 |
| ATOM | 1914 | O | THR | B | 123 | 8.400 | −8.483 | 2.374 | 1.00 | 23.40 |
| ATOM | 1915 | N | GLU | B | 124 | 6.737 | −7.419 | 1.314 | 1.00 | 23.26 |
| ATOM | 1916 | CA | GLU | B | 124 | 7.663 | −6.765 | 0.384 | 1.00 | 23.57 |
| ATOM | 1917 | CB | GLU | B | 124 | 7.014 | −6.506 | −0.974 | 1.00 | 23.45 |
| ATOM | 1918 | CG | GLU | B | 124 | 6.055 | −5.334 | −1.019 | 1.00 | 25.47 |
| ATOM | 1919 | CD | GLU | B | 124 | 5.787 | −4.870 | −2.441 | 1.00 | 28.88 |
| ATOM | 1920 | OE1 | GLU | B | 124 | 4.946 | −5.505 | −3.136 | 1.00 | 29.24 |
| ATOM | 1921 | OE2 | GLU | B | 124 | 6.427 | −3.870 | −2.854 | 1.00 | 30.26 |
| ATOM | 1922 | C | GLU | B | 124 | 3.329 | −5.505 | 0.945 | 1.00 | 23.68 |
| ATOM | 1923 | O | GLU | B | 124 | 7.937 | −4.985 | 1.999 | 1.00 | 23.52 |
| ATOM | 1946 | N | VAL | B | 127 | 6.523 | −2.296 | 2.424 | 1.00 | 24.05 |
| ATOM | 1947 | CA | VAL | B | 127 | 5.875 | −2.439 | 3.725 | 1.00 | 23.81 |
| ATOM | 1948 | CB | VAL | B | 127 | 5.124 | −3.796 | 3.862 | 1.00 | 23.86 |
| ATOM | 1949 | CG1 | VAL | B | 127 | 4.638 | −4.015 | 5.282 | 1.00 | 22.40 |
| ATOM | 1950 | CG2 | VAL | B | 127 | 3.946 | −3.842 | 2.892 | 1.00 | 23.69 |
| ATOM | 1951 | C | VAL | B | 127 | 6.911 | −2.240 | 4.829 | 1.00 | 23.92 |
| ATOM | 1952 | O | VAL | B | 127 | 6.634 | −1.571 | 5.839 | 1.00 | 24.19 |
| ATOM | 1953 | N | LEU | B | 128 | 8.107 | −2.786 | 4.619 | 1.00 | 23.58 |
| ATOM | 1954 | CA | LEU | B | 128 | 9.239 | −2.482 | 5.489 | 1.00 | 23.70 |
| ATOM | 1955 | CB | LEU | B | 128 | 10.511 | −3.223 | 5.059 | 1.00 | 23.73 |
| ATOM | 1956 | CG | LEU | B | 128 | 11.749 | −2.865 | 5.898 | 1.00 | 23.84 |
| ATOM | 1957 | CD1 | LEU | B | 128 | 11.663 | −3.458 | 7.290 | 1.00 | 23.49 |
| ATOM | 1958 | CD2 | LEU | B | 128 | 13.010 | −3.333 | 5.209 | 1.00 | 25.14 |
| ATOM | 1959 | C | LEU | B | 128 | 9.495 | −0.971 | 5.567 | 1.00 | 23.52 |
| ATOM | 1960 | O | LEU | B | 128 | 9.653 | −0.440 | 6.668 | 1.00 | 23.85 |
| ATOM | 1977 | N | ALA | B | 131 | 6.644 | 0.572 | 7.623 | 1.00 | 21.94 |
| ATOM | 1978 | CA | ALA | B | 131 | 6.866 | 0.327 | 9.054 | 1.00 | 21.30 |
| ATOM | 1979 | CB | ALA | B | 131 | 7.166 | −1.143 | 9.295 | 1.00 | 20.73 |
| ATOM | 1980 | C | ALA | B | 131 | 7.991 | 1.213 | 9.620 | 1.00 | 21.62 |
| ATOM | 1981 | O | ALA | B | 131 | 7.889 | 1.731 | 10.736 | 1.00 | 21.42 |
| ATOM | 2042 | N | MET | B | 139 | 6.269 | −6.221 | 14.687 | 1.00 | 31.52 |
| ATOM | 2043 | CA | MET | B | 139 | 5.752 | −6.772 | 13.433 | 1.00 | 30.64 |
| ATOM | 2044 | CB | MET | B | 139 | 6.474 | −8.062 | 13.065 | 1.00 | 30.37 |
| ATOM | 2045 | CG | MET | B | 139 | 7.683 | −7.835 | 12.225 | 1.00 | 30.22 |
| ATOM | 2046 | SD | MET | B | 139 | 8.256 | −9.376 | 11.518 | 1.00 | 30.12 |
| ATOM | 2047 | CE | MET | B | 139 | 9.770 | −8.814 | 10.743 | 1.00 | 29.99 |
| ATOM | 2048 | C | MET | B | 139 | 4.250 | −7.036 | 13.490 | 1.00 | 30.11 |
| ATOM | 2049 | O | MET | B | 139 | 3.747 | −7.573 | 14.480 | 1.00 | 29.85 |
| ATOM | 2050 | N | CYS | B | 140 | 3.555 | −6.639 | 12.421 | 1.00 | 29.34 |
| ATOM | 2051 | CA | CYS | B | 140 | 2.118 | −6.876 | 12.238 | 1.00 | 28.75 |
| ATOM | 2052 | CB | CYS | B | 140 | 1.772 | −8.366 | 12.411 | 1.00 | 28.65 |
| ATOM | 2053 | SG | CYS | B | 140 | 2.841 | −9.467 | 11.455 | 1.00 | 29.16 |
| ATOM | 2054 | C | CYS | B | 140 | 1.239 | −5.994 | 13.126 | 1.00 | 28.39 |
| ATOM | 2055 | O | CYS | B | 140 | 0.065 | −6.302 | 13.357 | 1.00 | 28.43 |
| ATOM | 2065 | N | PHE | B | 142 | 0.389 | −1.667 | 13.943 | 1.00 | 25.66 |
| ATOM | 2066 | CA | PHE | B | 142 | 0.537 | −0.217 | 14.050 | 1.00 | 25.09 |
| ATOM | 2067 | CB | PHE | B | 142 | 0.094 | 0.503 | 12.767 | 1.00 | 24.60 |
| ATOM | 2068 | CG | PHE | B | 142 | 0.887 | 0.145 | 11.545 | 1.00 | 23.64 |
| ATOM | 2069 | CD1 | PHE | B | 142 | 2.264 | −0.020 | 11.606 | 1.00 | 21.72 |
| ATOM | 2070 | CE1 | PHE | B | 142 | 2.995 | −0.341 | 10.471 | 1.00 | 21.40 |
| ATOM | 2071 | CZ | PHE | B | 142 | 2.353 | −0.493 | 9.244 | 1.00 | 21.81 |
| ATOM | 2072 | CE2 | PHE | B | 142 | 0.971 | −0.315 | 9.159 | 1.00 | 23.34 |
| ATOM | 2073 | CD2 | PHE | B | 142 | 0.246 | 0.003 | 10.312 | 1.00 | 24.04 |
| ATOM | 2074 | C | PHE | B | 142 | −0.358 | 0.260 | 15.188 | 1.00 | 25.17 |
| ATOM | 2075 | O | PHE | B | 142 | −1.573 | 0.061 | 15.140 | 1.00 | 25.12 |
| ATOM | 2451 | N | PHE | B | 189 | 12.757 | −4.136 | 14.489 | 1.00 | 27.50 |
| ATOM | 2452 | CA | PHE | B | 189 | 11.486 | −4.532 | 13.896 | 1.00 | 27.79 |
| ATOM | 2453 | CB | PHE | B | 189 | 11.384 | −3.922 | 12.498 | 1.00 | 27.46 |
| ATOM | 2454 | CG | PHE | B | 189 | 10.085 | −4.177 | 11.802 | 1.00 | 26.05 |
| ATOM | 2455 | CD1 | PHE | B | 189 | 8.886 | −3.711 | 12.333 | 1.00 | 25.09 |
| ATOM | 2456 | CE1 | PHE | B | 189 | 7.680 | −3.937 | 11.675 | 1.00 | 24.46 |
| ATOM | 2457 | CZ | PHE | B | 189 | 7.668 | −4.619 | 10.463 | 1.00 | 24.31 |
| ATOM | 2458 | CE2 | PHE | B | 189 | 8.867 | −5.087 | 9.917 | 1.00 | 25.07 |
| ATOM | 2459 | CD2 | PHE | B | 189 | 10.064 | −4.855 | 10.588 | 1.00 | 24.93 |

TABLE 19-continued

Atomic coordinates of amino acid residues essential for human Dcn3 Chain B to bind hUbe2F.

| | Atom No. | Atom Name | | | X | Y | Z | Occupancy | B-factor |
|---|---|---|---|---|---|---|---|---|---|
| ATOM | 2460 | C | PHE | B | 189 | 11.335 | −6.053 | 13.847 | 1.00 | 28.94 |
| ATOM | 2461 | O | PHE | B | 189 | 10.249 | −6.580 | 14.093 | 1.00 | 29.14 |
| ATOM | 2559 | N | ILE | B | 204 | 14.094 | −15.322 | 10.184 | 1.00 | 29.32 |
| ATOM | 2560 | CA | ILE | B | 204 | 13.693 | −13.913 | 10.146 | 1.00 | 28.78 |
| ATOM | 2561 | CB | ILE | B | 204 | 13.179 | −13.406 | 11.518 | 1.00 | 28.99 |
| ATOM | 2562 | CG1 | ILE | B | 204 | 11.731 | −13.823 | 11.745 | 1.00 | 29.30 |
| ATOM | 2563 | CD1 | ILE | B | 204 | 11.591 | −15.090 | 12.517 | 1.00 | 31.74 |
| ATOM | 2564 | CG2 | ILE | B | 204 | 13.236 | −11.883 | 11.596 | 1.00 | 28.88 |
| ATOM | 2565 | C | ILE | B | 204 | 14.856 | −13.037 | 9.677 | 1.00 | 28.15 |
| ATOM | 2566 | O | ILE | B | 204 | 14.692 | −12.219 | 8.781 | 1.00 | 28.26 |
| ATOM | 2580 | N | ALA | B | 207 | 15.521 | −13.559 | 5.951 | 1.00 | 25.24 |
| ATOM | 2581 | CA | ALA | B | 207 | 14.484 | −12.882 | 5.189 | 1.00 | 25.15 |
| ATOM | 2582 | CB | ALA | B | 207 | 13.102 | −13.349 | 5.634 | 1.00 | 25.21 |
| ATOM | 2583 | C | ALA | B | 207 | 14.607 | −11.362 | 5.271 | 1.00 | 25.20 |
| ATOM | 2584 | O | ALA | B | 207 | 14.416 | −10.670 | 4.265 | 1.00 | 25.68 |
| ATOM | 2585 | N | LEU | B | 208 | 14.945 | −10.844 | 6.451 | 1.00 | 24.96 |
| ATOM | 2586 | CA | LEU | B | 208 | 15.113 | −9.394 | 6.626 | 1.00 | 24.85 |
| ATOM | 2587 | CB | LEU | B | 208 | 15.102 | −9.001 | 8.100 | 1.00 | 24.71 |
| ATOM | 2588 | CG | LEU | B | 208 | 13.746 | −9.038 | 8.809 | 1.00 | 25.14 |
| ATOM | 2589 | CD1 | LEU | B | 208 | 13.923 | −8.622 | 10.264 | 1.00 | 25.27 |
| ATOM | 2590 | CD2 | LEU | B | 208 | 12.710 | −8.147 | 8.123 | 1.00 | 24.28 |
| ATOM | 2591 | C | LEU | B | 208 | 16.355 | −8.848 | 5.923 | 1.00 | 24.52 |
| ATOM | 2592 | O | LEU | B | 208 | 16.313 | −7.779 | 5.329 | 1.00 | 24.45 |
| ATOM | 2616 | N | LEU | B | 211 | 15.564 | −8.585 | 2.472 | 1.00 | 25.74 |
| ATOM | 2617 | CA | LEU | B | 211 | 14.620 | −7.487 | 2.359 | 1.00 | 25.81 |
| ATOM | 2618 | CB | LEU | B | 211 | 13.474 | −7.660 | 3.359 | 1.00 | 25.74 |
| ATOM | 2619 | CG | LEU | B | 211 | 12.239 | −6.840 | 3.033 | 1.00 | 25.44 |
| ATOM | 2620 | CD1 | LEU | B | 211 | 11.726 | −7.220 | 1.637 | 1.00 | 25.06 |
| ATOM | 2621 | CD2 | LEU | B | 211 | 11.181 | −7.070 | 4.099 | 1.00 | 26.22 |
| ATOM | 2622 | C | LEU | B | 211 | 15.257 | −6.101 | 2.507 | 1.00 | 26.06 |
| ATOM | 2623 | O | LEU | B | 211 | 15.008 | −5.230 | 1.689 | 1.00 | 26.06 |

TABLE 20

Additional contacts that contribute to, but are not essential, for contact between human Dcn3 and human Ube2f with hUbe2f Chain F interactions with hDcn3$^P$ Chain A and hUbe2f Chain G interactions with hDcn3$^P$ Chain B shown.

| hUbe2f Atom | | | hDcn3 Atom | | | Distance (Å) |
|---|---|---|---|---|---|---|
| Lys | 7F | CB | Glu | 108A | CB | 4.3 |
| | | | Glu | 108A | CD | 4.2 |
| | | | Glu | 108A | OE2 | 4.14 |
| | | | Glu | 108A | CG | 4.31 |
| Lys | 7F | CD | Glu | 108A | OE1 | 4.42 |
| | | | Cys | 140A | CB | 4.12 |
| | | | Cys | 140A | SG | 3.84 |
| Lys | 7F | CE | Glu | 108A | CD | 4.17 |
| | | | Glu | 108A | OE1 | 3.79 |
| | | | Glu | 108A | OE2 | 4.26 |
| Lys | 7F | O | Glu | 108A | CD | 4.41 |
| | | | Glu | 108A | OE2 | 3.84 |
| | | | Glu | 108A | CG | 4.2 |
| Leu | 8F | CG | Glu | 108A | CB | 4.38 |
| Leu | 8F | CD1 | Glu | 108A | O | 4.29 |
| | | | Glu | 112A | CB | 3.96 |
| | | | Glu | 112A | CG | 3.98 |
| Leu | 8F | CD2 | Glu | 108A | CB | 4.03 |
| | | | Glu | 108A | CG | 3.88 |
| | | | Glu | 108A | C | 4.11 |
| | | | Glu | 109A | N | 4.18 |
| | | | Glu | 109A | CA | 4.26 |
| | | | Glu | 109A | CG | 4.16 |
| | | | Glu | 108A | O | 4.12 |
| Lys | 7G | CB | Glu | 108B | CG | 4.3 |
| | | | Glu | 108B | CD | 4.48 |
| | | | Glu | 108B | CB | 4.29 |

TABLE 20-continued

Additional contacts that contribute to, but are not essential, for contact between human Dcn3 and human Ube2f with hUbe2f Chain F interactions with hDcn3$^P$ Chain A and hUbe2f Chain G interactions with hDcn3$^P$ Chain B shown.

| hUbe2f Atom | | | hDcn3 Atom | | | Distance (Å) |
|---|---|---|---|---|---|---|
| Lys | 7G | CD | Glu | 108B | OE1 | 4.02 |
| | | | Cys | 140B | CB | 4.12 |
| | | | Cys | 140B | SG | 4.04 |
| Lys | 7G | NZ | Glu | 108B | OE1 | 4.21 |
| | | | Met | 139B | O | 3.95 |
| Lys | 7G | O | Glu | 108B | CG | 4.36 |
| Leu | 8G | CG | Glu | 108B | CB | 4.41 |
| Leu | 8G | CD1 | Glu | 112B | CG | 3.84 |
| | | | Glu | 112B | CB | 3.89 |
| Leu | 8G | CD2 | Glu | 109B | CG | 4.39 |
| | | | Glu | 109B | CA | 3.94 |
| | | | Glu | 109B | N | 3.88 |
| | | | Glu | 108B | CG | 4.02 |
| | | | Glu | 108B | C | 3.95 |
| | | | Glu | 108B | O | 4.01 |
| | | | Glu | 108B | CB | 4.12 |

TABLE 21

Atomic coordinates of amino acid residues of hDcn3 Chain A that contribute to, but are not required, for binding hUbe2F.

| | Atom No. | Atom Name | | | X | Y | Z | Occupancy | B-factor |
|---|---|---|---|---|---|---|---|---|---|
| ATOM | 196 | N | GLU | A | 109 | 17.607 | 3.250 | 49.863 | 1.00 | 31.59 |
| ATOM | 197 | CA | GLU | A | 109 | 18.060 | 3.299 | 51.247 | 1.00 | 31.75 |
| ATOM | 198 | CB | GLU | A | 109 | 16.902 | 3.575 | 52.213 | 1.00 | 32.09 |
| ATOM | 199 | CG | GLU | A | 109 | 16.229 | 4.933 | 52.026 | 1.00 | 34.47 |
| ATOM | 200 | CD | GLU | A | 109 | 15.075 | 4.915 | 51.007 | 1.00 | 37.77 |
| ATOM | 201 | OE1 | GLU | A | 109 | 14.960 | 3.957 | 50.200 | 1.00 | 37.79 |
| ATOM | 202 | OE2 | GLU | A | 109 | 14.273 | 5.878 | 51.023 | 1.00 | 39.47 |
| ATOM | 203 | C | GLU | A | 109 | 18.775 | 1.997 | 51.598 | 1.00 | 31.35 |
| ATOM | 204 | O | GLU | A | 109 | 19.923 | 2.016 | 52.059 | 1.00 | 31.47 |
| ATOM | 284 | N | VAL | A | 120 | 32.343 | −1.152 | 50.143 | 1.00 | 28.04 |
| ATOM | 285 | CA | VAL | A | 120 | 32.370 | −0.816 | 48.732 | 1.00 | 27.63 |
| ATOM | 286 | CB | VAL | A | 120 | 31.772 | −2.024 | 47.945 | 1.00 | 27.52 |
| ATOM | 287 | CG1 | VAL | A | 120 | 30.862 | −1.607 | 46.834 | 1.00 | 26.88 |
| ATOM | 288 | CG2 | VAL | A | 120 | 32.884 | −2.959 | 47.468 | 1.00 | 27.58 |
| ATOM | 289 | C | VAL | A | 120 | 31.644 | 0.511 | 48.420 | 1.00 | 27.54 |
| ATOM | 290 | O | VAL | A | 120 | 30.512 | 0.733 | 48.872 | 1.00 | 27.62 |
| ATOM | 291 | N | ASP | A | 121 | 32.307 | 1.388 | 47.662 | 1.00 | 26.97 |
| ATOM | 292 | CA | ASP | A | 121 | 31.673 | 2.594 | 47.134 | 1.00 | 26.54 |
| ATOM | 293 | CB | ASP | A | 121 | 32.683 | 3.431 | 46.341 | 1.00 | 26.32 |
| ATOM | 294 | CG | ASP | A | 121 | 32.118 | 4.781 | 45.877 | 1.00 | 26.75 |
| ATOM | 295 | OD1 | ASP | A | 121 | 32.719 | 5.831 | 46.203 | 1.00 | 25.81 |
| ATOM | 296 | OD2 | ASP | A | 121 | 31.087 | 4.801 | 45.167 | 1.00 | 27.68 |
| ATOM | 297 | C | ASP | A | 121 | 30.539 | 2.125 | 46.236 | 1.00 | 26.35 |
| ATOM | 298 | O | ASP | A | 121 | 30.760 | 1.257 | 45.389 | 1.00 | 26.75 |

TABLE 22

Atomic coordinates of amino acid residues of hDcn3 Chain B that contribute to, but are not required, for binding hUbe2F.

| | Atom No. | Atom Name | | | X | Y | Z | Occupancy | B-factor |
|---|---|---|---|---|---|---|---|---|---|
| ATOM | 1798 | N | GLU | B | 109 | −5.041 | −8.978 | 11.450 | 1.00 | 29.25 |
| ATOM | 1799 | CA | GLU | B | 109 | −6.225 | −8.988 | 10.595 | 1.00 | 29.12 |
| ATOM | 1800 | CB | GLU | B | 109 | −7.510 | −9.163 | 11.425 | 1.00 | 29.53 |
| ATOM | 1801 | CG | GLU | B | 109 | −7.538 | −10.384 | 12.392 | 1.00 | 31.83 |
| ATOM | 1802 | CD | GLU | B | 109 | −6.793 | −10.146 | 13.734 | 1.00 | 34.71 |
| ATOM | 1803 | OE1 | GLU | B | 109 | −6.585 | −8.973 | 14.138 | 1.00 | 34.75 |
| ATOM | 1804 | OE2 | GLU | B | 109 | −6.423 | −11.148 | 14.392 | 1.00 | 36.82 |
| ATOM | 1805 | C | GLU | B | 109 | −6.295 | −7.707 | 9.753 | 1.00 | 28.56 |
| ATOM | 1806 | O | GLU | B | 109 | −6.361 | −7.773 | 8.523 | 1.00 | 28.30 |
| ATOM | 1886 | N | VAL | B | 120 | 0.008 | −4.308 | −2.141 | 1.00 | 21.20 |
| ATOM | 1887 | CA | VAL | B | 120 | 1.355 | −4.805 | −1.885 | 1.00 | 20.97 |
| ATOM | 1888 | CB | VAL | B | 120 | 2.209 | −3.786 | −1.090 | 1.00 | 21.14 |
| ATOM | 1889 | CG1 | VAL | B | 120 | 2.557 | −2.574 | −1.957 | 1.00 | 21.30 |
| ATOM | 1890 | CG2 | VAL | B | 120 | 1.518 | −3.371 | 0.210 | 1.00 | 20.07 |
| ATOM | 1891 | C | VAL | B | 120 | 1.321 | −6.131 | −1.124 | 1.00 | 21.03 |
| ATOM | 1892 | O | VAL | B | 120 | 0.463 | −6.332 | −0.273 | 1.00 | 20.30 |
| ATOM | 1893 | N | ASP | B | 121 | 2.243 | −7.032 | −1.462 | 1.00 | 21.30 |
| ATOM | 1894 | CA | ASP | B | 121 | 2.501 | −8.218 | −0.657 | 1.00 | 21.87 |
| ATOM | 1895 | CB | ASP | B | 121 | 3.604 | −9.058 | −1.304 | 1.00 | 21.84 |
| ATOM | 1896 | CG | ASP | B | 121 | 3.835 | −10.394 | −0.597 | 1.00 | 22.12 |
| ATOM | 1897 | OD1 | ASP | B | 121 | 4.155 | −10.394 | 0.603 | 1.00 | 25.73 |
| ATOM | 1898 | OD2 | ASP | B | 121 | 3.727 | −11.446 | −1.239 | 1.00 | 19.92 |
| ATOM | 1899 | C | ASP | B | 121 | 2.939 | −7.731 | 0.719 | 1.00 | 22.56 |
| ATOM | 1900 | O | ASP | B | 121 | 3.844 | −6.897 | 0.811 | 1.00 | 22.97 |

As will be apparent to those of ordinary skill in the art, the atomic structures presented herein are independent of their orientation, and the atomic co-ordinates identified herein merely represent one possible orientation of a particular E2 or E3 polypeptide. The atomic coordinates are a relative set of points that define a shape in three dimensions. Thus, it is possible that a different set of coordinates could define a similar or identical shape. Therefore, slight variations in the individual coordinates will have little effect on overall shape. It is apparent, therefore, that the atomic co-ordinates identified herein may be mathematically rotated, translated, scaled, or a combination thereof, without changing the relative positions of atoms or features of the respective structure. The variations in coordinates discussed may be generated because of mathematical manipulations of the structure coordinates. For example, the structure coordinates could be manipulated by crystallographic permutations of the structure coordinates, fractionalization of the structure coordinates, integer additions or subtractions to sets of the structure coordinates, inversion of the structure coordinates or any combination of the above.

As used herein, a "structural variant" comprises a three-dimensional molecular structure that is similar to another three-dimensional molecular structure. In some embodiments, the structural variant comprises a root mean square deviation (RMSD) from the back-bone atoms of the amino acids of listed in a particular table (e.g., Table 2, 3, 5, 6, 8, 9, 10, 11, 13, 14, 15, 16, 18, 19, 21, 22) of riot more than about 4 Å, including but not limited to about 3.5 Å, 3 Å, 2.5 Å, 2 Å, 1.9 Å, 1.8 Å, 1.7 Å, 1.6 Å, 1.5 Å, 1.4 Å, 1.3 Å, 1.2 Å, 1.1 Å, 1.0 Å, 0.9 Å, 0.8 Å, 0.7 Å, 0.6 Å, 0.5 Å, 0.4 Å, 0.3 Å, 0.2 Å, and 0.1 Å. In some of these embodiments, the structural variant comprises a root mean square deviation from the back-bone atoms of the amino acids listed in a particular table (e.g., Table 2, 3, 5, 6, 8, 9, 10, 11, 13, 14, 15, 16, 18, 19, 21, 22) of not more than about 2.0 Å. Modifications in the crystal structure due to mutations, additions, substitutions and/or deletions of amino acids, or other changes in any of the components that make up the crystal could also account for variations in the structure coordinates.

The novel E2-binding pocket of NEDD8 co-E3 proteins can be exploited to discover compounds that bind to the pocket and in some embodiments, inhibit the activity of the NEDD8 co-E3 protein. Such compounds can be identified using computational techniques or various in vitro or in vivo binding assays.

Computational techniques can be used to screen, identify, select and/or design compounds (i.e., small molecules, peptides) capable of associating with the E2-binding pocket of co-E3 proteins. Knowledge of the structure coordinates for the E2-binding pocket of co-E3 proteins permits the design and/or identification of synthetic compounds and/or other molecules which have a shape complementary to the conformation of the E2-binding pocket of co-E3 proteins. In particular, computational techniques can be used to identify or design compounds, such as inhibitors (also referred to herein as antagonists), that associate with a co-E3 protein E2-binding pocket. Potential inhibitors may bind to or interfere with all or a portion of the E2-binding pocket, and can be competitive, non-competitive, or uncompetitive inhibitors. Once identified and screened for biological activity, these inhibitors may be used therapeutically or prophylactically to inhibit co-E3 activity and, thus, prevent the onset and/or further progression of diseases or conditions associated with, for example, cell hyperproliferation (e.g., cancer, inflammatory disorders). Structure-activity data for inhibitors that bind to or interfere with the E2-binding pocket of co-E3 proteins can also be obtained computationally.

The design of compounds with particular structural relationships to part of a protein molecule are well established and described in the literature (see for example Cochran (2000) Chem. Biol. 7:85-94; Grzybowski et al. (2002) Acc. Chem. Res 35:261-269; Vejasquez-Campoy et al. (2001) Arch. Biochem. Biophys. 380:169-175; D'Aquino et al. (2000) Proteins: Struc. Func. Genet. Suppl. 4:93-107). Any of these "molecular modeling" methods for rational drug design can be used to find antagonists of the E2-binding pocket of co-E3 proteins. Most of these molecular modeling methods take into consideration the shape, charge distribution and the distribution of hydrophobic groups, ionic groups and hydrogen bonds in the binding site of the protein molecule. Using this information derived from the crystal structure of proteins and protein complexes, these methods suggest improvements to existing proposed compounds, construct new compounds on their own that are expected to have good binding affinity, screen through virtual compound libraries for such molecules, or otherwise support the interactive design of new drug compounds in silico. Programs such as GOLD (Jones et al. (1997) J. Mol. Biol. 267:727-748); FLEXX (Kramer et al. (1999) Structure, Functions, and Genetics 37:228-241); FLEXE (Rarey et al. (1996) JMB 261:470-489) DOCK (Kuntz (1992) Science 257:1078-1082); and AUTODOCK (Morris et al. (1998) J. Computational Chemistry 19:1639-1662) are virtual screening programs designed to calculate the binding position and conformation as well as the corresponding binding energy of an organic compound to a protein. These programs are specially trimmed to allow a great number of "dockings", that is, calculations of the conformation with the highest binding energy of a compound to a binding site, per time unit. The binding energy is not always a real value, but can be statistically related to a real binding energy through a validation procedure.

In one embodiment, the method for identifying compounds that bind to the presently disclosed E2-binding pocket of NEDD8 co-E3 proteins comprises comparing the three-dimensional structure of a test compound and the three-dimensional molecular structure of the E2-binding pocket to determine if at least one atom of the test compound will interact with at least one atoms of the E2-binding pocket. As used herein, "interact" refers to both covalent and non-covalent interactions, including but not limited to hydrogen bonds, van der Waals interactions, hydrophobic interactions, and electrostatic interactions.

The term "test compound" refers to the molecule that is being assayed using the presently disclosed methods to determine if the test compound is capable of binding the E2-binding pocket of a NEDD8 co-E3 protein. The test compound can be naturally-occurring or non-naturally occurring and can be purified from a biological sample or synthetically derived. The structure of the test compound may be known or unknown. The test compound need not have a known biological activity or a known ability to interact with proteins. The compound may be solubilized in a solution, such as an aqueous solution or an organic solvent (e.g., dimethyl sulfoxide) prior to addition of the molecule to a sample comprising a NEDD8 co-E3 protein.

In some embodiments, the test compound is a member of a chemical library. A chemical library refers to a plurality of molecules. The components of the chemical library can be well-defined, containing known mixtures of molecules. For example, each molecule of a well-defined chemical library can be catalogued. Alternatively, the components of the library can be poorly defined, as is often the case with combinatorial libraries. Likewise, the structures of the molecules within the chemical library can be known or unknown.

In particular embodiments, the test compound is a member of a combinatorial chemical library. A combinatorial chemical library is a plurality of molecules or compounds which are formed by selectively combining a particular set of chemical building blocks. Combinatorial libraries can be constructed according to methods familiar to those skilled in the art. For example, see Rapoport et al., (1995) Immunology Today 16:43-49; Sepetov, N. F. et al., (1995) Proc. Natl. Acad. Sci. U.S.A. 92:5426-5430; Gallop, M. A. et al., (1994) J. Med. Chem. 9:1233-1251; Gordon, E. M. et al., (1994) J. Med. Chem. 37:1385-1401; Stankova, M. et al., (1994) Peptide Res. 7:292-298; Erb, E. et al., (1994) Proc. Natl. Acad. Sci. U.S.A. 91:11422-11426; DeWitt, S. H. et al., (1993) Proc. Natl. Acad. Sci. U.S.A. 90:6909-6913; Barbas, C. F. et al., (1992) Proc. Natl. Acad. Sci. U.S.A. 89:4457-4461; Brenner, S. et al. (1992) Proc. Natl. Acad. Sci. U.S.A.

89:5381-5383; Lam, K. S. et al., (1991) *Nature* 354:82-84; Devlin, J. J. et al., (1990) *Science* 245:404-406; Cwirla, S. E. et al., (1990) *Proc. Natl. Acad. Sci, U.S.A.* 87:6378-6382; Scott, J. K. et al., (1990) *Science* 249:386-390, and U.S. Pat. No. 5,463,564, each of which is herein incorporated by reference in its entirety.

To be a viable drug candidate, the compound identified or designed according to the method must be capable of structurally associating with at least part of the E2-binding pocket on co-E3 proteins, and must be able, sterically and energetically, to assume a conformation that allows it to associate with the E2-binding pocket of co-E3 proteins. Non-covalent molecular interactions important in this association include hydrogen bonding, van der Waals interactions, hydrophobic interactions, and electrostatic interactions. Conformational considerations include the overall three-dimensional structure and orientation of the compound in relation to the binding pocket, and the spacing between various functional groups of a compound that directly interact with the E2-binding pocket.

One embodiment of the method involves evaluating the potential association of a known compound with the E2-binding pocket of co-E3 proteins. The method of drug design thus includes computationally evaluating the potential of a selected compound to associate with any of the molecules or molecular complexes set forth above. This method includes the steps of (a) employing computational means to perform a fitting operation between the selected chemical entity and the E2-binding pocket; and (b) analyzing the results of said fitting operation to quantify the association between the compound and the binding pocket.

Specialized computer programs may also assist in the process of selecting compounds. Examples include GRID (Goodford (1985) *J. Med. Chem.* 28:849-57); available from Oxford University, Oxford, UK); MCSS (Miranker et al. (1991) *Proteins: Struct. Funct. Gen.* 11:29-34); available from Molecular Simulations, San Diego, Calif.); AUTODOCK (Goodsell et al. (1990) *Proteins: Struct. Funct. Genet.* 8:195-202; available from Scripps Research Institute, La Jolla, Calif.); and DOCK (Kuntz et al. (1982) *J. Mol. Biol.* 161:269-88); available from University of California, San Francisco, Calif.).

If these computational experiments suggest insufficient interaction and association between the test compound and the E2-binding pocket of co-E3 proteins, testing of the compound is obviated. However, if computer modeling indicates a strong interaction, the molecule may then be synthesized and tested for its ability to bind to or interfere with the E2-binding pocket of co-E3 proteins as disclosed elsewhere herein. In some cases, it may be advantageous to develop new inhibitors de novo, i.e. not on the basis and as a modification of a pre-existing compound. The term "de novo compound design" refers to a process whereby the binding pocket of the target macromolecule (e.g., the E2-binding pocket of co-E3 proteins) is determined; and its surfaces is used as a platform or basis for the rational design of compounds that will interact with those surfaces. The molecular modeling steps used in the methods may use the atomic coordinates of the E2-binding pocket disclosed herein and models or structures derived therefrom, to determine binding surfaces. Any such structure will preferably reveal van der Waals contacts, electrostatic interactions, and/or hydrogen bonding opportunities. Said binding surfaces will typically be used by grid-based techniques (e.g. GRID, CERIUS², [Goodford (1985) *J. Med. Chem.* 28: 849-857]) and/or multiple copy simultaneous search (MCSS) techniques to map favorable interaction positions for functional groups. This preferably reveals positions in the E2-binding pocket of the co-E3 protein for interactions such as, but not limited to, those with protons, hydroxyl groups, amine groups, hydrophobic groups (e.g. methyl, ethyl, benzyl) and/or divalent cations.

Computer-based approaches to de novo compound design that can be used with the atomic co-ordinates of the E2-binding pocket of co-E3 proteins include LUDI(15 Bohm (1992) *J. Comp. X ed Molec. Design* 6: 61-78), SPROUT (Available from chem.leeds.ac. uk/ICAMS/SPROUT.html) and LEAPFROG (available from Tripos Inc (www.tripos.com)). Suitable in silico libraries include the Available Chemical Directory (MDL Inc), the Derwent World Drug Index (WDI), BioByteMasterFile, the National Cancer Institute database (NCl), and the Maybridge catalog. Compounds in these in silico libraries can also be screened for their ability to interact with the E2-binding pocket of co-E3 proteins by using their respective atomic coordinates in automated docking algorithms. An automated docking algorithm is one which permits the prediction of interactions of a number of compounds with a molecule having a given atomic structure. Suitable docking algorithms include: DOCK (Kuntz et al. (1982) *J. Mol. Biol.* 161: 269-288)), AUTODOCK (Goodsell et al. (1990) *Proteins: Structure, Function and Genetics* 8: 195-202), MOE-DOCK (Available from Chemical Computing Group Inc. (www.chemcomp.com/)) or FLEXX (Available from Tripos Inc (www.tripos.com)). Docking algorithms can also be used to verify interactions with ligands designed de novo.

Another approach encompassed by methods provided herein is the computational screening of small molecule databases for compounds that can bind in whole, or in part, to the E2-binding pocket of co-E3 proteins. In this screening, the quality of fit of such entities to the binding site may be judged either by shape complementarity or by estimated interaction energy (Meng et al. (1992) *J. Comp. Chem.* 13:505-24).

A compound that is identified or designed as a result of any of these methods can be obtained (or synthesized) and tested for its biological activity, e.g., inhibition of co-E3 activity. Binding assays to determine if a compound (e.g., an inhibitor) actually binds to or interferes with the E2-binding pocket on co-E3 enzymes can also be performed and are well known in the art and are described herein.

Further methods for identifying compounds that bind to an E2-binding pocket in a NEDD8 co-E3 protein disclosed herein comprise contacting a NEDD8 co-E3 protein with a test compound and determining if the test compound binds to the E2-binding pocket. The test compound may be contacted with the NEDD8 co-E3 protein in a cell-free system, in cells, or in vivo.

Binding assays to determine if the test compound binds the NEDD8 co-E3 protein may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. One can determine if a test compound binds to the E2-binding pocket of a co-E3 enzyme using, for example, assays such as mutational analyses wherein residues that comprise the E2-binding pocket are mutated and the effect on test compound binding is assessed; and competitive binding assays, wherein a compound known to bind to the E2-binding pocket (for example, one of the peptides disclosed herein) is added to a binding reaction with the test compound to determine if the test compound is able to compete with the peptide for binding to the co-E3 protein.

In some of these embodiments, the compound known to bind to the E2-binding pocket can be coupled with a detectable label, such as a radioisotope, fluorescent label, or enzymatic label, such that binding of the test compound to the E2-binding pocket can be determined by detecting a reduction in the labeled compound in a complex. For example, compounds known to bind to the E2-binding pocket (e.g., one of the peptides disclosed herein) can be labeled with $^{125}$I, $^{35}$S, $^{14}$C, or $^{3}$H, either directly or indirectly, and the radioisotope detected by direct counting of radio emmission or by scintillation counting. Alternatively, compounds known to bind to the E2-binding pocket can be enzymatically labeled with, for example, horseradish peroxidase, alkaline phosphatase, or luciferase, and the enzymatic label detected by determination of conversion of an appropriate substrate to product.

As another example, the compound known to bind to an E2-binding pocket can be coupled with a fluorescent label to allow for detection of binding using, for example, fluorescence polarization. In some embodiments, the NEDD8 co-E3 protein is also fluorescently labeled. The fluororescent molecules (i.e., fluorophores) on the compound and the NEDD8 co-E3 protein can have an overlapping excitation and emission spectra such as those generally used in fluorescence resonance energy transfer (FRET) technology assays, wherein the excitation of a first fluorescent molecule (donor fluorophore) at a first wavelength of light causes the first fluorescent molecule to emit light at a second wavelength, and wherein the second fluorescent molecule (acceptor fluorophore) is excited by the second wavelength of light if the two fluorescent molecules are in close enough proximity to one another, and subsequently, the second fluorescent molecule emits light at a third wavelength, which can be detected using any method or apparatus known in the art. Non-limiting examples of fluorophores that can be conjugated to antibodies include Cy3, Cy5, Cy5.5, Cy7, Alexa488, Alexa555, FITC, and rhodamine (TRITC). It is to be noted that the selection of the donor fluorophore depends on the excitation and emission spectra of the acceptor fluorophore and vice versa. Frequently used fluorophore pairs for FRET include but are not limited to, Cy3 and Cy5, Alexa488 and Alexa555, Alexa488 and Cy3, and FITC and rhodamine. In such an assay, the compound known to bind to an E2-binding pocket can be coupled to a donor fluorophore (in an alternative embodiment, to an acceptor fluorophore) and the NEDD8 co-E3 protein (e.g., at or near the E2-binding pocket) can be coupled to an acceptor fluorophore (in the alternative embodiment, to a donor fluorophore). If the two come in close contact with another, the acceptor fluorophore will emit light. One can determine if the test compound that is added to the assay binds to the E2-binding pocket of the NEDD8 co-E3 protein if the emission of the acceptor fluorophore is diminished due to competition with the tabled compound known to bind to the pocket.

In some assays, it may be desirable to immobilize either the NEDD8 co-E3 protein or a portion thereof or the compound known to bind to the E2-binding pocket to facilitate automation of the assay. For example, the NEDD8 co-E3 protein could be produced as a fusion protein that adds a domain that allows the NEDD8 co-E3 protein to be bound to a matrix. A non-limiting example of such a domain is glutathione-S-transferase, which can be adsorbed onto glutathione sepharose beads (Sigma Chemical, St. Louis, Mo.) or glutathione-derivatized microtitre plates. In other embodiments, the co-E3 protein or compounds can be immobilized utilizing conjugation of biotin and streptavidin. Biotinylated co-E3 proteins or compounds can be prepared from biotin-NHS(N-hydroxy-succinimide) using techniques well known in the art (e.g., biotinylation kit, Pierce Chemicals, Rockford, Ill.), and immobilized in the wells of a plate.

This invention further pertains to novel compounds identified by the above-described screening assays and uses thereof as described herein.

Further, the three-dimensional molecular structure of the test compound bound to the co-E3 protein can be determined using methods known in the art to determine if the test compound is binding within the presently disclosed E2-binding pocket of the NEDD8 co-E3 protein.

Methods known in the art and disclosed elsewhere herein can be used to determine if the test compound inhibits the co-E3 activity of NEDD8 co-E3 proteins (see Examples 1 and 4). Such binding assays can also be used to screen compounds or compound libraries for those that bind to the E2-binding pocket. Compounds that are found to bind can be further characterized for inhibition of co-E3 activity.

Compounds (e.g., small molecules and peptides) that bind to the E2-binding pocket of co-E3 proteins are provided herein. The term "compound" refers to any chemical molecule, including organic and inorganic molecules. In some embodiments, the compound is a small molecule. As used herein, the term "small molecule" refers to a chemical molecule that in some embodiments is a small organic compound, having a molecular weight of more than 100 and less than about 2,500 Daltons, including but not limited to less than 2000, or less than 1500 or less than 1000 or less than 500 D. The term "small molecule" does not encompass a peptide.

As used herein, the terms "peptide," "polypeptide," or "protein" are used interchangeably herein and are intended to encompass a singular "polypeptide" as well as plural "polypeptides," and refers to a molecule composed of monomers (amino acids) linearly linked by amide bonds (also known as peptide bonds). The terms "peptide" and "polypeptide" refer to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "peptide" and "polypeptide". The terms apply to amino acid polymers in which one or more amino acid residues is an artificial chemical analogue of a corresponding naturally occurring amino acid, as well as to naturally occurring amino acid polymers. Non-limiting examples of artificial amino acid residues include norleucine and selenomethionine. An amino acid residue is a molecule having a carboxyl group, an amino group, and a side chain and having the generic formula $H_2NCHRCOOH$, where R is an organic substituent, forming the side chain. An amino acid residue, whether it is artificial or naturally occurring, is capable of forming a peptide bond with a naturally occurring amino acid residue.

An "isolated" or "purified" peptide is substantially or essentially free from components that normally accompany or interact with the peptide as found in its naturally occurring environment. Thus, an isolated or purified peptide is substantially free of other cellular material, or culture medium when produced by recombinant techniques, or substantially free of chemical precursors or other chemicals when chemically synthesized. A peptide that is substantially free of cellular material includes preparations of peptide having less than about 30%, 20%, 10%, 5%, or 1% (by dry weight) of contaminating protein. When the peptide is recombinantly produced, optimally culture medium represents less than about 30%, 20%, 10%, 5%, or 1% (by dry weight) of chemical precursors or non-peptide-of-interest chemicals.

In some embodiments of the presently disclosed invention, peptides that bind to the E2-binding pocket of a NEDD8 co-E3 protein comprise the first 4, 5, 6, 7, 8, 9, 10, 11, 12, 13, 14, 15, 16, 17, 18, 19, 20, 21, 22, 23, 24, 25, 26, 27, 28, 29, 30, or greater amino acid residues of a naturally-occurring NEDD8 E2 protein or a variant thereof. In particular embodiments, the peptide has the sequence set forth in SEQ ID NO: 7, 12, 13, 14, 15, or 16 or a fragment or variant thereof capable of binding to the E2-binding pocket, including but not limited to an amino acid sequence having at least 40%, at least about 50%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 7, 12, 13, 14, 15, or 16. In certain embodiments, the variant peptide may differ from SEQ ID NO: 7, 12, 13, 14, 15, or 16 by 1, 2, 3, 4, 5, 6, 7, 8, 9, 10, or 11 amino acid residues or greater.

It was disclosed herein that N-terminal acetylation of yeast Ubc12 enhances its interaction with Dcn1 and that N-terminal acetylation of human Ubc12 is essential for its interaction with Dcn1. Acetylation of the nitrogen atom of the N-terminal methioinine of Ubc12 contributed to the binding of Ubc12 to Dcn1 by eliminating the N-terminal positive charge that otherwise would impede burial in the Dcn1 hydrophobic pocket, and the methyl group of the acetyl provides hydrophobic interactions with the hydrophobic pocket. Therefore, in some embodiments, the peptides of the invention that bind to the E2-binding pocket of a NEDD8 co-E3 protein are N-terminally acetylated; that is, the nitrogen atom in the amino-terminal amino acid residue is covalently bound to an acetyl group. An acetyl group has the formula

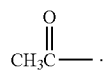

Amino acid residues referred to herein with N-acetyl-preceding the name of the amino acid residue comprise an acetyl group covalently bound to the backbone nitrogen atom. In other embodiments, the nitrogen atom of the amino-terminal amino acid residue of the peptide is covalently bound to at least one —R group so that the nitrogen is not ionizable, wherein the —R group is any functional group that is not a hydrogen and is uncharged or non-ionizable under physiological conditions when bound to the backbone nitrogen atom. Non-limiting examples of appropriate —R groups include an alkyl (including, but not limited to, a $C_2$ to a $C_{20}$ chain), alkenyl, alkynyl, aryl, or heteroaryl, optionally substituted.

Alkyl refers to both straight, branched carbon chains and cyclic hydrocarbon groups; references to individual alkyl groups are specific for the straight chain (e.g. butyl=n-butyl). In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-4 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyls, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Third Edition, 1999, hereby incorporated by reference.

Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10 or 2-8. In yet another embodiment of alkenyl, the number of carbon atoms is 2-4. Other ranges of carbon-carbon double bonds and carbon numbers are also contemplated depending on the location of the alkenyl moiety on the molecule;

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2- dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10 or 2-8. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

Aryl refers to a $C_6$-$C_{14}$ aromatic carbocyclic ring structure having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl. Arylo refers to an aryl substituted at two adjacent sites.

Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

In all embodiments, it is preferred that the R group is uncharged under physiological conditions.

Preferred hydrophobic moieties include substituted and unsubstituted alkyl, alkenyl, alkynyl, aryl and heteroaryl groups. More preferably, the hydrophobic moiety is a $C_4$-$C_{20}$ alkyl, alkenyl or alkynyl group. Most preferably, the hydrophobic moiety is a $C_6$-$C_{12}$ alkyl, alkenyl or alkynyl group.

In those embodiments wherein the nitrogen is bound to more than one —R group (e.g., 2 —R groups), the —R groups may be the same or distinct from one another. In particular embodiments, the —R group is not an acetyl group. In other embodiments, the —R group has Formula (I), wherein Formula (I) is:

wherein the —$R_2$ group is any functional group that is uncharged under physiological conditions and is not a hydrogen. Non-limiting examples of appropriate —$R_2$ groups include an alkyl (including, but not limited to, a $C_2$ to a $C_{20}$ chain), aryl, or heteroaryl. In certain embodiments, the —R group is a formyl group, wherein a formyl group has the formula

In particular embodiments, the amino-terminal methionine (at position 1) of the peptide that binds to the E2-binding pocket of a NEDD8 co-E3 protein (e.g., SEQ ID NO: 7, 12, 13, 14, 15, or 16) is substituted with an artificial amino acid residue having an unbranched hydrophobic side chain. As used herein, the term "hydrophobic" is a physical property of a molecule that is repelled from a mass of water and can be referred to as "nonpolar," or "apolar," all of which are terms that can be used interchangeably with "hydrophobic." Non-limiting examples of an unbranched hydrophobic side chain include an alkyl (e.g., $C_2$ to $C_{20}$), an alkenyl, or alkynyl. In particular embodiments, peptides of the invention that bind to the E2-binding pocket of a NEDD8 co-E3 protein comprise a norleucine or selenomethionine at the first position of the peptide in place of a methioinine.

Analysis of the presently disclosed crystal structures revealed that in order to place the hydrophobic side chains of amino acid residues at positions 2 and 4 within the Ubc12 N-terminal extension on opposite sides of the amino-terminal acetylated methioinine to aid in binding, a helical structure is required. Thus, in certain embodiments, the peptide that binds to the E2-binding pocket of a NEDD8 co-E3 protein has an alpha-helical structure. As used herein, an "alpha helix" refers to the most abundant helical conformation found in globular proteins and the term is used in accordance with the standard meaning of the art. In an alpha helix, all amide protons point toward the N-terminus and all carbonyl oxygens point toward the C-terminus. Hydrogen bonds within an alpha helix also display a repeating pattern in which the backbone C=O of residue X (wherein X refers to any amino acid) hydrogen bonds to the backbone H—N of residue X+4. The alpha helix is a coiled structure characterized by 3.6 residues per turn, and translating along its axis 1.5 Å per amino acid. Thus the pitch is 3.6×1.5 or 5.4 Å. The screw sense of alpha helices is always right-handed.

In some of those embodiments wherein the peptide has an alpha helical structure, the peptide comprises a hydrophobic staple (such as those described in Bird et al. (2008) *Methods Enzymol* 446:369-386; Houston et al. (1995) *J Pept Sci* 1(4)274-282; Taylor (2002) *Biopolymers* 66(1):49-75; and Houston et al. (1996) *Biochemistry* 35(31):10041-50, each of which is herein incorporated by reference in its entirety), which is herein incorporated by reference in its entirety. As used herein, a "hydrophobic staple" refers to the presence of two amino acid residues having hydrophobic side chains that are covalently bound to one another. A hydrophobic staple is generated when the peptide comprises artificial amino acid residues comprising hydrophobic staple-forming amino acid residues at positions X and X+4 within the peptide, wherein X is any amino acid residue within any position of the peptide. One of skill in the art will appreciate that in order for a hydrophobic staple-forming amino acid residue to be present at positions X and X+4, X can not be any of the last four residues (i.e., the four most carboxy residues) within a peptide chain. In particular embodiments, the hydrophobic staple-forming amino acid residues are present at positions 4 and 8, 5 and 9, 6 and 10, or 7 and 11 of the peptide. Additional hydrophobic staple-forming amino acid residues can be present within the peptide as long as they are at least four amino acid residues away from another hydrophobic staple-forming amino acid residue.

As used herein a "hydrophobic staple-forming amino acid residue" is an amino acid residue as defined herein that comprises a side chain capable of forming a covalent bond with the side chain of another amino acid residue to form a hydrophobic staple. Non-limiting examples of hydrophobic staple-forming amino acid residues include (S)-2-(4-pentenyl)alanine, (R)-2-(4-pentenyl)alanine, (S)-2-(3-butenyl)alanine, (S)-2-(7-octenyl)alanine, lysine, and glutamic acid.

Further, in particular embodiments, the carboxy terminus of the peptide that binds to the E2-binding pocket of a NEDD8 co-E3 protein is amidated, wherein the carbon atom of the backbone carboxyl group in the most carboxyl amino acid residue is covalently bound to an optionally substituted nitrogen. In other embodiments, the carbon atom of the carboxyl group in the most carboxyl amino acid residue is bound to at least one —R group, as defined elsewhere herein.

In particular embodiments, the peptide that binds to the E2-binding pocket has the sequence set forth in SEQ ID NO: 10, 11, 17, 18, 19, 20, 21, 22, 23, 24, 25, 26, 27, 28, 29, 30, 31, 87, 88, 89, 90, 91, 92, 93, or 94, or a fragment or variant thereof.

In some embodiments, the small molecule or peptide that binds to the E2-binding pocket of a NEDD8 co-E3 protein inhibits the co-E3 activity of the co-E3 protein. Therefore, the small molecule or peptide is capable of inhibiting the neddylation of at least one NEDD8 target proteins, including but not limited to, a cullin protein. Such a molecule is referred to herein as an antagonist or an inhibitor. In some embodiments, the co-E3 inhibitor inhibits the co-E3 activity of the co-E3 protein by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or greater. The ability of a small molecule or peptide to inhibit the activity of a co-E3 protein can be measured in vitro or in vivo or in cells in culture using any method known in the art, including those assays disclosed elsewhere herein (see, for example, Example 4). The compound may be assessed for its ability to inhibit co-E3 activity by measuring co-E3 activity directly or indirectly by assaying downstream effects of NEDD8 co-E3 proteins (e.g., inhibition of cullin-dependent ubiquitination and proteolysis). For example, activity may be assessed by detection of downstream protein substrate stabilization (e.g., stabilization of p27, of IκB, NFκB or p27 reporter assays).

In addition to NEDD8 co-E3 proteins, the amino terminal extension of NEDD8 E2 enzymes (e.g., Ubc12) also binds to NEDD8 E1 proteins (Huang et al. (2004) *Nat Struct Mol Biol* 11:927-935, which is herein incorporated by reference in its entirety). Therefore, in some embodiments, the NEDD8 co-E3 inhibitor that binds to the E2-binding pocket of the co-E3 protein also inhibits the activity of a NEDD8 E1 protein. In order to generate an inhibitor molecule that is more specific for co-E3 proteins, in some embodiments, the phenylalanine corresponding to position 5 and leucine corresponding to position 7 of Ubc12 (SEQ ID NO: 2), which contribute to the bulk of the binding energy of Ubc12 to E1, are substituted with another amino acid residue, such as a hydrophobic staple-forming residue. Further, the addition of a hydrophobic staple to a peptide, locking it into an alpha helical conformation, prevents binding to NEDD8 E1 proteins (see Example 1).

Further, the peptide binding assays disclosed elsewhere herein (see Example 3 and Table 13) demonstrate that the assayed peptides exhibit binding specificity for particular co-E3 proteins (e.g., Dcn1, Dcn2, Dcn3, Dcn4, Dcn5). For example, SEQ ID NO: 8 (hUbc12Ac1-26) and SEQ ID NO: 87 (yUbc12Ac1-24) have greatest affinity for Dcn1 and 2, whereas SEQ ID NO: 88 (hUbe2fAcl-25) has greatest affinity for Dcn3 and is fairly specific for this particular co-E3 protein. The affinity of hUbc12Ac1-12 for Dcn3 and 5 can be enhanced by substituting amino acid residues at positions 6 and 10 with (S)-2-(3-butenyl)alanine and (S)-2-(7-octenyl)alanine, respectively, to form a hydrophobic staple. Similarly, the affinity of yUbc12Ac1-24 for Dcn1, 2, and 3 can be enhanced by substituting the first methionine with norleucine and amino acid residues at positions 6 and 10 with (S)-2-(4-pentenyl)alanine to form a hydrophobic staple. Interestingly, the affinity of yUbc12Ac1-24 for Dcn4 and Dcn5 is reduced with these modifications. Using this information, in combination with the disclosed crystal structures of the E2-binding pocket, one of skill in the art could generate a peptide that has enhanced specificity for one NEDD8 co-E3 protein over another.

The presently disclosed NEDD8 co-E3 inhibitors may be used to inhibit co-E3 activity and cellular growth and therefore, find use in treating disorders associated with unregulated cell growth. Further, as IκB, the inhibitor of the inflammatory mediator NFκB, is a target of the cullin-comprising SCF complex, the presently disclosed NEDD8 co-E3 inhibitors also find use in treating inflammatory disorders.

NEDD8 co-E3 proteins can be inhibited by the presently disclosed NEDD8 co-E3 inhibitors by contacting a NEDD8 co-E3 protein (e.g., Dcn1, Dcn2, Dcn3, Dcn4, Dcn5) with a NEDD8 co-E3 inhibitor, such as those described herein, in vivo or in vitro or in cells in culture.

In some embodiments, the NEDD8 co-E3 protein is contacted by a NEDD8 co-E3 inhibitor in a biological sample. As used herein, the phrase "biological sample" refers to a sample obtained from or comprising a cell, tissue, organ, or organism. Non-limiting examples of biological samples include cellular organelles, cells (e.g., mammalian cells, bacterial cells, cultured cells), a biological fluid, such as blood, plasma, serum, urine, bile, saliva, tears, cerebrospinal fluid, aqueous or vitreous humor, or any bodily secretion), a transudate or exudate (e.g. fluid obtained from an abscess or other site of infection or inflammation), a fluid obtained from a joint (e.g. a normal joint or a joint affected by disease such as rheumatoid arthritis, osteoarthritis, gout or septic arthritis), or the like, and a lysate or extract of an organelle, cell, tissue, organ, or organism.

Biological samples may be obtained from any organ or tissue (normal or diseased, including a biopsy or autopsy specimen) or may comprise cells or a lysate or extract thereof (including primary cells, passaged or cultured primary cells, cell lines, cells conditioned by a specific medium or grown under a particular set of environmental conditions) or medium conditioned by cells. In some embodiments, the biological sample (e.g., cell, tissue, organism or extract thereof) after exposure to a hormone or other biological or pharmacological agent. If desired, the biological sample may be subjected to processing, such as lysis, extraction, subcellular fractionation, or other standard biochemical procedures known in the art to solubilize proteins. See, Deutscher (ed.) (1990) *Methods in Enzymology* 182:147-238, which is herein incorporated by reference in its entirety. For example, tissues or cells can be ground and homogenized in buffers appropriate for solubilizing proteins and retaining their native conformations, followed by clarification by centrifugation. Other methods known in the art can be used to process the biological sample to obtain the protein with co-E3 activity, including but not limited to osmotic lysis, detergent lysis, sonication, heat, and rapid decompression. In general, methods used to obtain the Nedd8 co-E3 protein are performed under non-denaturing conditions, allowing the majority of proteins to retain their native conformations.

The Nedd8 pathway is involved in the regulation of cell cycle progression and cell proliferation. Thus, the various inhibitors of the E2 binding pocket of the co-E3 enzymes provided herein may be useful for inhibiting cell growth and in the treatment of diseases or disorders that are associated with hyperproliferation (e.g., cancers, inflammatory disorders, pathogenic infections). As used herein, "cell growth" refers to cell proliferation, cell division, or progression through the cell cycle.

Methods for inhibiting cell growth comprise introducing into a cell a NEDD8 co-E3 inhibitor, such as those disclosed herein. As used herein, the terms "introduce" and "introducing" when referring to a compound refers to the presentation of the compound to a cell in such a manner that the compound gains access to the intracellular region of the cell. The compound can be introduced into the cell via any means known in the art.

Any method known in the art can be used to measure the growth rate of a cell, including, but not limited to, optical density ($OD_{600}$), $CO_2$ production, $O_2$ consumption, assays that measure mitochondrial function, such as those utilizing tetrazolium salts (e.g., MTT, XTT), or other colorimetric reagents (e.g., the WST-1 reagent available from Roche), assays that measure or estimate DNA content, including, but not limited to fluorometric assays such as those utilizing the fluorescent dye Hoechst 33258, assays that measure or estimate protein content, including, but not limited to, the sulforhodamine B (SRB) assay, manual or automated cell counts (with or without the Trypan Blue stain to distinguish live cells), and clonogenic assays with manual or automated colony counts. In some embodiments, the growth rate of a cell is inhibited by a NEDD co-E3 inhibitor by at least 5%, at least 10%, at least 20%, at least 30%, at least 40%, at least 50%, at least 60%, at least 70%, at least 80%, at least 90%, at least 95%, at least 96%, at least 97%, at least 98%, at least 99%, or greater.

The NEDD8 co-E3 inhibitors disclosed herein can be used to treat disorders that are associated with hyperproliferation, such as cancers, inflammatory disorders, and pathogenic infections.

As used herein, "treatment" is an approach for obtaining beneficial or desired clinical results. For purposes of this invention, beneficial or desired clinical results include, but are not limited to, alleviation of symptoms, partial or complete restoration of eyesight (e.g., central vision, visual acuity), diminishment of extent of the disorder, stabilized (i.e., not worsening) state of the disorder (e.g., degeneration of cone photoreceptors), delaying or slowing of progression of the disorder, amelioration or palliation of the disorder, and prevention of, inhibition of, or reduction of risk of developing a retinal disorder. "Treatment" refers to both therapeutic treatment and prophylactic or preventative measures. Those in need of treatment include those already with the disorder (to prevent further degeneration) as well as those in which the disorder is to be prevented. "Palliating" a disorder means that the extent and/or undesirable clinical manifestations of the disorder are lessened and/or the time course of the progression is slowed or lengthened, as compared to a situation without treatment.

Methods for treating a disorder associated with hyperproliferation (e.g., cancer, inflammatory disorder, pathogenic infection) comprise administering a therapeutically effective amount of a NEDD co-E3 inhibitor, such as those disclosed herein, to a subject in need thereof.

By "therapeutically effective amount" is intended an amount that is useful in the treatment, prevention or diagnosis of a disease or condition. As used herein, a therapeutically effective amount of a NEDD8 co-E3 enzyme inhibitor is an amount which, when administered to a subject, is sufficient to achieve a desired effect, such as inhibiting NEDD8 co-E3 activity or cell growth in a subject being treated with that composition. The effective amount of a NEDD8 co-E3 protein inhibitor useful for inhibiting cell growth will depend on the subject being treated, the severity of the affliction, and the manner of administration of the NEDD8 co-E3 protein inhibitor.

By "subject" is intended an animal, including but not limited to, mammals, e.g., primates, humans, agricultural and domesticated animals such as, but not limited to, dogs, cats, cattle, horses, pigs, sheep, and the like. In some embodiments, the subject undergoing treatment with the pharmaceutical formulations of the invention is a human.

Given the involvement of NEDD8 in the regulation of cell cycle progression, NEDD8 co-E3 inhibitors, such as those disclosed herein, can be used to treat disorders that are associated with unregulated cell growth, such as cancer. Components of the Nedd8 pathway have been implicated in various types of cancer, including, but not limited to, gliomas, cancers of the lung, head and neck, esophagus, tongue, urinary tract, cervix, vulva, vagina and ovary (Broderick et al. (2010) *Neoplasia* 12(6):476-84; Sarkaria et al. (2006) *Cancer Res* 66(19): 9437-44; and Sarkaria et al. (2004) *Ann Thorac Surg* 78:1734-41, each of which are herein incorporated by reference in its entirety). In fact, human DCUN1D1 is also known as squamous cell carcinoma-related oncogene (SCCRO) due to its overexpression in various squamous cell carcinomas of mucosal origin, including, for example, oral tongue squamous cell carcinoma (Estilo et al. (2003) *Clin Can Res* 9:2300-06, which is herein incorporated by reference in its entirety).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, sarcomas, gliomas, lymphomas and leukemias, including without limitation, lung cancer, head and neck cancer, esophageal cancer, tongue cancer, cancers of the urinary tract, cervical cancer, vulval cancer, vaginal cancer, ovarian cancer. In particular embodiments, the cancer that is being treated with the presently disclosed NEDD8 co-E3 inhibitors is a squamous cell carcinoma, such as an oral tongue squamous cell carcinoma.

The neddylation of cullin proteins promotes the ubiquitination of IκB and subsequent activation of the inflammatory mediator NFκB. Therefore, NEDD8 co-E3 inhibitors can be used to treat inflammatory disorders.

As used herein, an "inflammatory disorder" is a condition characterized by inflammation and tissue destruction, or a combination thereof. An "inflammatory disorder" includes any inflammatory immune-mediated process where the initiating event or target of the immune response involves non-self antigen(s), including, for example, alloantigens, xenoantigens, viral antigens, bacterial antigens, unknown antigens, or allergens.

Further, for purposes of the present invention, the term "inflammatory disorder(s)" includes "autoimmune disease(s)." As used herein, the term "autoimmunity" is generally understood to encompass inflammatory immune-mediated processes involving "self" antigens. In autoimmune diseases, self antigen(s) trigger host immune responses. The term "inflammatory disorder" also refers to inflammation associated with tissue transplant rejection, such as graft versus host disease. "Transplant rejection" or "graft rejection" refers to any host-mounted immune response against a graft including but not limited to HLA antigens, blood group antigens, and the like.

Non-limiting examples of inflammatory disorders that can be treated with the NEDD8 co-E3 inhibitors disclosed herein include systemic lupus erythematosus (SLE), CREST syndrome, inflammatory myositis, Sjogren's syndrome, mixed connective tissue disease, multiple sclerosis, inflammatory bowel disease, acute respiratory distress syndrome, pulmonary inflammation, idiopathic pulmonary fibrosis, osteoporosis, delayed type hypersensitivity, asthma, primary biliary cirrhosis, and idiopathic thrombocytopenic purpura, discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1,2, 3, and 4 delayed-type hypersensitivity, allergy or allergic disorders, unwanted/unintended immune responses to therapeutic proteins (see for example, U.S. Patent Application No. US 2002/0119151 and Koren, et al. (2002) *Curr. Pharm. Biotechnol.* 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like.

Given the conservation of the NEDD8 signaling pathway in all eukaryotes, including fungal species, the presently disclosed NEDD8 co-E3 inhibitors inhibit the growth of pathogens and can be used to treat pathogenic infections, such as fungal infections. Further, viruses and bacterial pathogens routinely hijack the cullin-RING ligase machinery for ubiquitination and degradation of specific host factors. For example, HIV-1 Vif targets a RNA-editing enzyme (APOBEC3G) for Cu15-mediated degradation in a manner that reportedly depends on the NEDD8 pathway (see, for example, Barry and Fruh (2006) *Sci STKE* 335:21; Ribert and Cossart (2010) *Cell* 143:694-702). Therfore, the growth of viruses and bacterial pathogens that target host proteins for cullin RING ligase-dependent degradation can also be inhibited by the presently disclosed NEDD8 co-E3 inhibitors and these inhibitors find further use in treating infections of these viral and bacterial pathogens. Non-limiting examples of pathogenic organisms whose growth can be attenuated by the NEDD8 co-E3 inhibitors disclosed herein include fungal species within the genus *Candida, Aspergillus, Cryptococcus, Histoplasma, Pneumocystis, Stachybotrys*, and *Paracoccidioides*, including but not limited to, *Candida albicans, Aspergillus fumigatus, Aspergillus flavus, Cryptococcus neoformans, Cryptococcus gattii, Histoplasma capsulatum, Pneumocystis jirovecii, Stachybotrys chartarum*, and *Paracoccidioides brasiliensis* (see, for example, San-Blas and Calderone (2008) Pathogenic Fungi Insights in Molecular Biology. Caister Academic Press. 264 pages; and Chen et al. (2010) *Curr Opin Pharmacol* 10(5): 522-30, each of which is herein incorporated by reference in its entirety); viral pathogens such as human immunodeficiency virus (HIV) and other lentiviruses; and bacterial pathogens that target host proteins for cullin RING ligase-dependent degradation.

When administration is for the purpose of treatment, administration may be for either a prophylactic (i.e., preventative) or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

It will be understood by one of skill in the art that the treatment modalities described herein may be used alone or in conjunction with other therapeutic modalities (i.e., as adjuvant therapy), including, but not limited to, surgical therapy, radiotherapy, chemotherapy (e.g., with any chemotherapeutic agent well known in the art) or immunotherapy.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a NEDD8 co-E3 inhibitor can include a single treatment or, preferably, can include a series of treatments. It will also be appreciated that the effective dosage of a NEDD8 co-E3 inhibitor used for treatment may increase or decrease over the course of a particular treatment. Changes in dosage may result and become apparent from the results of diagnostic assays as described herein.

It is understood that appropriate doses of such active compounds depends upon a number of factors within the knowledge of the ordinarily skilled physician, veterinarian, or researcher. The dose(s) of the active compounds will vary, for example, depending upon the identity, size, and condition of the subject or sample being treated, further depending upon the route by which the composition is to be administered, if applicable. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of an active agent depend upon the potency of the active agent with respect to the expression or activity to be modulated. Such appropriate doses may be determined using the assays described herein. When one or more of these molecules is to be administered to an animal (e.g., a human) in order to reduce the activity of the NEDD8 co-E3 protein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Therapeutically effective amounts of a NEDD8 co-E3 inhibitor can be determined by animal studies. When animal assays are used, a dosage is administered to provide a target tissue concentration similar to that which has been shown to be effective in the animal assays. It is recognized that the method of treatment may comprise a single administration of a therapeutically effective amount or multiple administrations of a therapeutically effective amount of the NEDD8 co-E3 inhibitor.

The inhibitors of the E2 binding pocket of the co-E3 enzyme disclosed herein can be incorporated into pharmaceutical compositions suitable for administration. Such compositions typically comprise the compound (e.g., peptide, small molecule) and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. In addition, it may be desirable to administer a therapeutically effective amount of the pharmaceutical composition locally to an area in need of treatment (e.g., to an area of the body where inhibiting a $T_R$ cell function is desired). This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In one embodiment, administration can be by direct injection at the site (or former site) of a cancer that is to be treated. In another embodiment, the therapeutically effective amount of the pharmaceutical composition is delivered in a vesicle, such as liposomes (see, e.g., Langer (1990) Science 249:1527-33; and Treat et al., in *Liposomes in the Therapy of Infectious Disease and Cancer*, Lopez Berestein and Fidler (eds.), Liss, N.Y., pp. 353-65, 1989).

In another embodiment, the peptide NEDD8 co-E3 inhibitors can be formulated with a cell-penetrating peptide, including but not limited to the HIV tat protein, that is either covalently bound to the peptide or otherwise associated therewith (see, for example, Okuyama et al. (2007) *Nature Methods* 4:153-159).

In yet another embodiment, the therapeutically effective amount of the pharmaceutical composition can be delivered in a controlled release system. In one example, a pump can be used (see, e.g., Langer (1990) *Science* 249:1527-33; Sefton (1987) *Crit. Rev. Biomed. Eng.* 14:201-40; Buchwald et al. (1980) *Surgery* 88:507-16; Saudek et al. (1989) *N. Engl. J. Med.* 321:574-79). In another example, polymeric materials can be used (see, e.g., Levy et al. (1985) *Science* 228:190-92; During et al. (1989) *Ann. Neurol.* 25:351-56; Howard et al. (1989) *J. Neurosurg.* 71:105-12). Other controlled release systems, such as those discussed by Langer (1990) *Science* 249:1527-33, can also be used.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor® EL (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

It is to be noted that the term "a" or "an" entity refers to one or more of that entity; for example, "a peptide" is understood to represent one or more peptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The following examples are offered by way of illustration and not by way of limitation.

EXPERIMENTAL

Example 1

Activation of Ubiquitin-Like Protein Ligation by Acetylation-Dependent E2-E3 Interaction Exogenously expressed C-terminally tagged and/or untagged human or yeast Ubc12 were purified from 293T cells, yeast, and/or SF9 cells (hereafter human proteins denoted with "h", and yeast with "y"). Endogenous hUbc12 was co-immunoprecipitated with TAPhNedd8 expressed in 293T cells. Tandem mass spectrometry (LC-MS/MS) identified exogenous yeast and human, and endogenous human Ubc12 as retaining the amino-terminal (N-terminal) methionine (Met) and being N-terminally acetylated (data not shown). N-terminal acetylation has been well-characterized in budding yeast: N-terminal Acetyltransferase (Nat) enzyme specificities depend upon a combination of: (1) whether or not the N-terminal Met is removed by methionine-aminopeptidase; and (2) the second residue in a protein's sequence (Polevoda and Sherman (2003) *J Mol Biol* 325(4):595-622). yUbc12's N-terminal sequence, Met-Leu, is predicted to retain the Met and be acetylated by NatC, a heterotrimeric enzyme consisting of Mak3p, Mak10p and Mak31p (Polevoda and Sherman (2001) *J Biol Chem* 276 (23):20154-20159). Indeed, deletion of the yeast Mak3 gene prevents yUbc12 N-terminal acetylation. Furthermore, coexpression with NatC subunits is sufficient for yUbc12 N-terminal acetylation in bacteria (FIG. 1A). Thus, yeast NatC performs yUbc12 N-terminal acetylation.

Figure 1B:
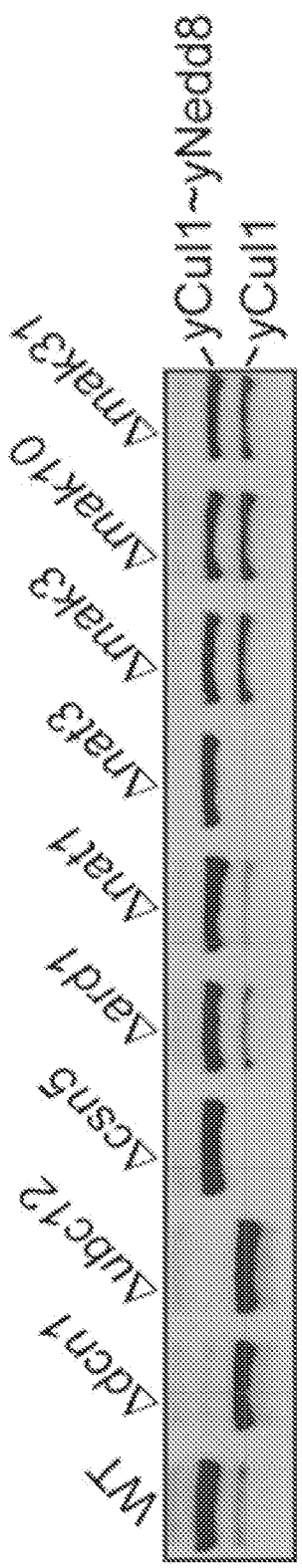
FIG. 1B provides a Western blot of yCul1 (aka Cdc53p) from WT yeast and the indicated deletion strains.

To address the question of whether Ubc12 N-terminal acetylation influences Nedd8 ligation to cullins such as Cul1, levels of yNedd8~yCul1 (aka Rub1p~Cdc53p, but here human nomenclature used for simplification) complexes in yeast were examined with gene deletions for subunits of the major N-terminal Acetyltransferases, NatA, NatB, and NatC. Only yeast deleted for genes encoding NatC subunits displayed decreased levels of yNedd8~yCul1 (FIG. 1B), indicating a correlation between yUbc12 N-terminal acetylation and yNedd8 modification of yCul1 in vivo. Furthermore, loss of NatC activity was synthetically lethal in combination with the cdc34-2 temperature-sensitive allele (data not shown)—a hallmark for Nedd8 pathway components due to roles in yCul1/SCF-regulated cell division (Kurz et al. (2008) *Mol Cell* 29:33; Lammer et al. (1998) *Genes Dev* 12:914).

Figure 2A:
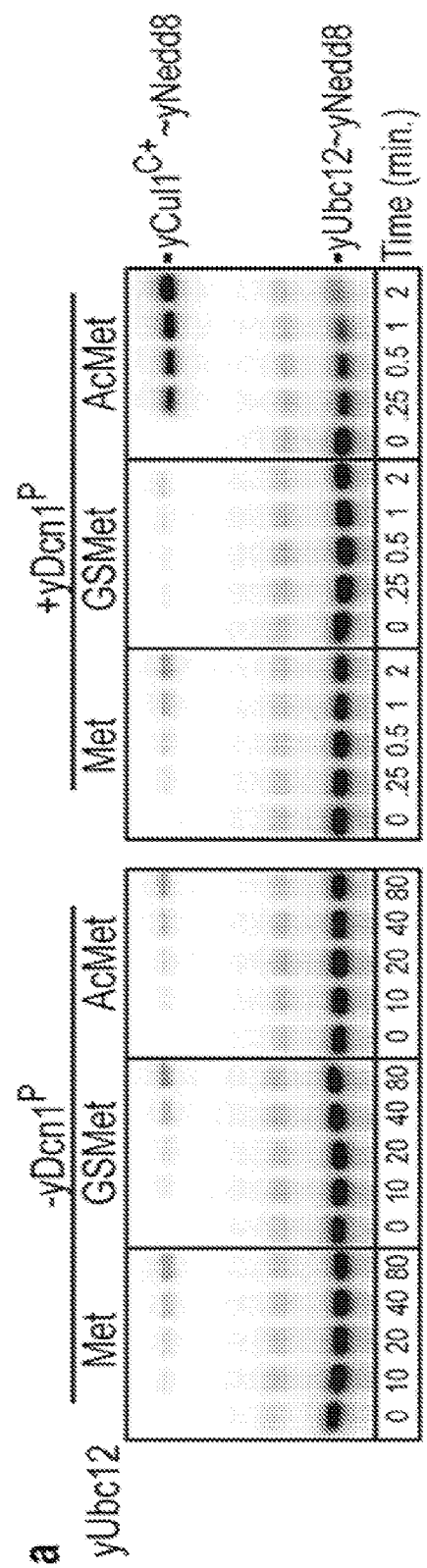
FIGS. 2A and 2B provide results of a pulse-chase assay monitoring [$^{32}$P]~yNEDD8 transfer from the indicated variants of yUbc12 to yCul1$^{C+}$-yRbx1 (FIG. 2A) or hUbc12 to hCul1$^{C+}$-hRbx1 (FIG. 2B) in the absence (left panel) or presence (right panel) of yDcn1$^P$ (FIG. 2A) or hDcn1$^P$ (FIG. 2B). Note the differences in times between left and right, with longer times required to observe activity without yDcn1$^P$.
Figure 2B:
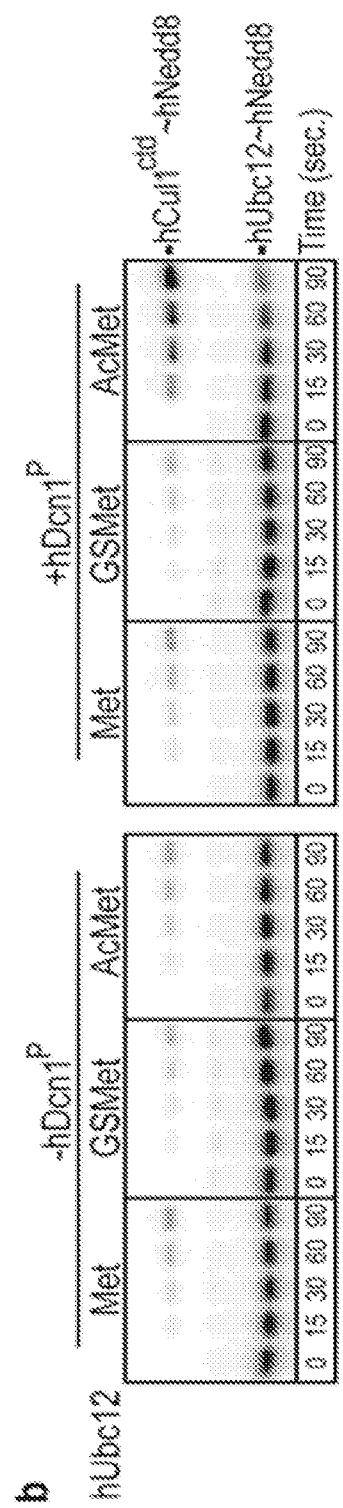
Figure 3A:
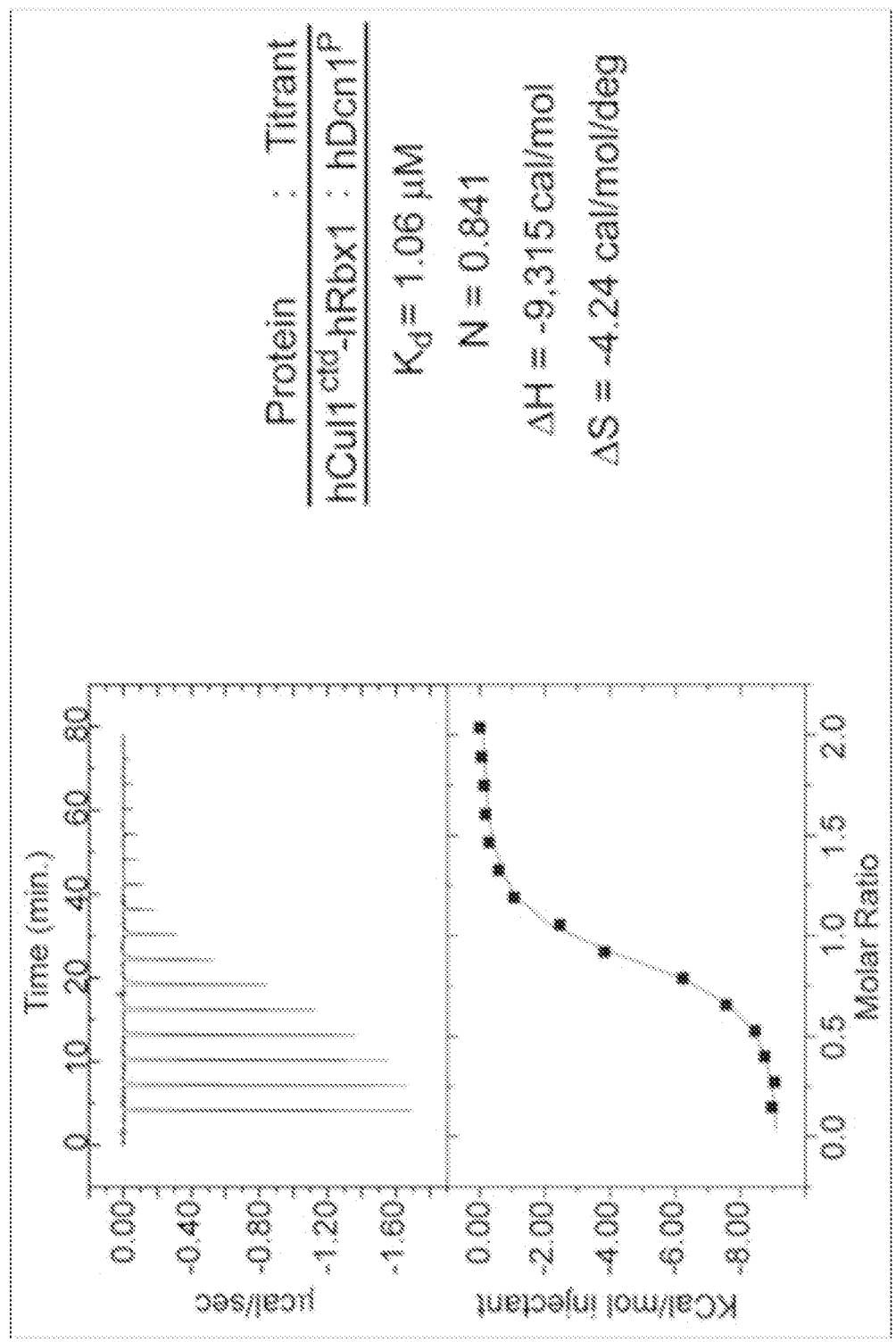
FIG. 3A provides raw isothermal titration calorimetry (ITC) data for titration of hDcn1$^P$ binding to hCul1$^{ctd}$-hRbx1 (left panel) and thermodynamic parameters for hDcn1$^P$ binding to hCul1$^{ctd}$-hRbx1 (right panel). The measured binding Kd of 1 µM for human proteins is approximately 30-fold worse than for the yeast counterparts (yCul1$^{C+}$-yRbx1:yDcn1$^P$, Kd=28 nM$^3$).
Figure 3B:
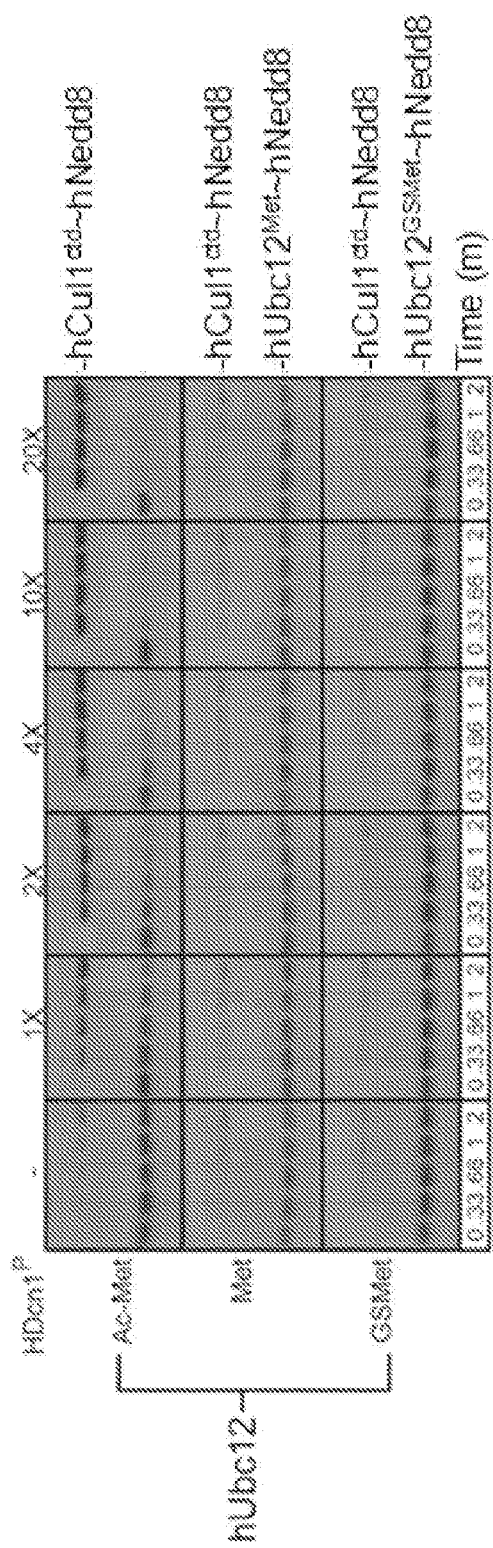
FIG. 3B provides an autoradiograph of pulse-chase assays monitoring [$^{32}$]~hNEDD8 transfer from hUbc12$^{AcMet}$ to 125 nM hCul1$^{ctd}$-hRbx1 in the absence or presence of the indicated fold molar excess of hDcn1$^P$. hDcn1$^P$ concentration-dependence in pulse-chase assays demonstrates activation while maintaining the absolute requirement for N-terminal acetylation of hUbc12. At saturating hDcn1$^P$ concentrations based on Kd measured above, hDcn1$^P$ demonstrates a striking co-E3 activity for hNEDD8 only with hUbc12$^{AcMet}$.
Figure 3C:
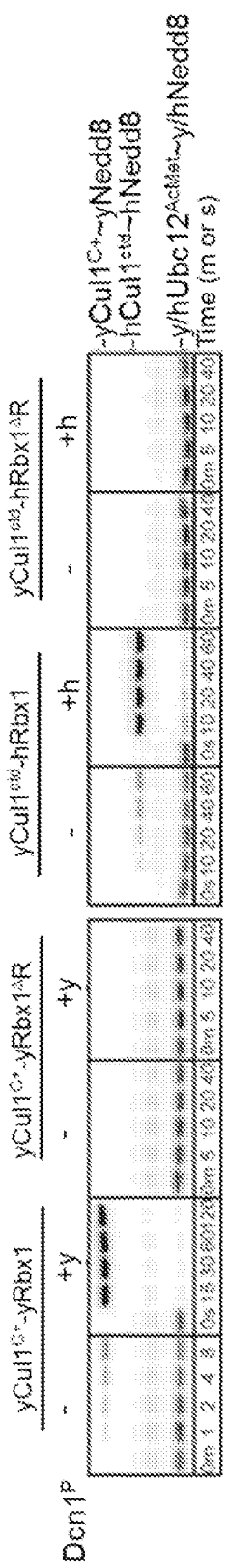
FIG. 3C demonstrates that Cul1 neddylation requires Rbx1 RING domain, even in the presence of Dcn1$^P$ and N-terminally acetylated Ubc12$^{AcMet}$ and provides phosphorimager data for a time course of pulse-chase assays monitoring [$^{32}$P]~yNEDD8 transfer from yUbc12$^{AcMet}$ to yCul1$^{C+}$-yRbx1 and yCul1$^{C+}$-yRbx1$^R$ in the absence or presence of yDcn1$^P$ (left panel) or [$^{32}$P]~-hNEDD8 transfer from hUbc12$^{AcMet}$ to hCul1$^{C+}$-hRbx1 and hCul1$^{C+}$-hRbx1$^R$ in the absence or presence of hDcn1$^P$ (right panel). Assays were carried out at a final concentration of 500 nM y or hCul1 or a 500 nM mix of y or hCul1 with y or hDcn1$^P$. Experiments with yeast proteins were performed at 18° C. instead of 4° C. as in other experiments. These differences in experimental design were implemented to highlight the necessity of the RING domain for cullin neddylation. Note differences in time-scales as some chase timepoints are on the order of seconds, and others minutes.

In vitro, Ubc12 N-terminal acetylation strikingly and specifically dictates Dcn1$^P$-mediated Nedd8 transfer to Cul1, as revealed by assays with three forms of Ubc12: Ubc12$^{AcMet}$ is N-terminally acetylated; Ubc12$^{Met}$ is identical to Ubc12$^{AcMet}$ sequence but lacks N-terminal acetylation; and yUbc12$^{GSMet}$ is not acetylated and has Gly-Ser N-terminal of Met (Scott et al. (2010) *Mol Cell* 39(5):784-795). Although yDcn1$^P$ enhances yNedd8 transfer to yCul1 even from yUbc12$^{Met}$ or yUbc12$^{GSMet}$, consistent with the partial defect observed in NatC null yeast (FIG. 1B), yDcn1$^P$ E3 activity is substantially magnified for yUbc12$^{AcMet}$ (FIG. 2A). For human proteins, hUbc12 N-terminal acetylation is absolutely required to observe any hDcn1$^P$ mediated potentiation of neddylation (FIG. 2B). With apparently saturating concentrations of hDcn1$^P$, hNedd8 transfer to hCul1 from hUbc12$^{AcMet}$ is complete in less than 20 seconds under conditions where we estimate the reaction would take ~8 minutes either in the absence of hDcn1$^P$, or with hDcn1$^P$ but without Ubc12 N-terminal acetylation (FIGS. 2B and 3C). The effect of Ubc12 N-terminal acetylation is specific for Dcn1$^P$, because Rbx1-mediated transfer of Nedd8 to Cul1 is independent of the state of Ubc12's N-terminus (FIGS. 2A and 2B). Nonetheless, even in the presence of Dcn1$^P$ and Ubc12 N-terminal acetylation, Cul1 neddylation still requires Rbx1's RING E3 activity and is blocked by an inhibitor, CAND1 (FIG. 3).

To gain insights into mechanistic roles of Ubc12 N-terminal acetylation, isothermal titration calorimetry (ITC) was used to quantify interactions with peptides corresponding to the N-termini of yeast or human Ubc12. Strikingly, N-terminal acetylation increases affinity for Dcn1$^P$ by roughly two orders-of-magnitude (Table 23). Ubc12's N-terminal Met is also required for Dcn1$^P$-binding. For comparison, N-terminal acetylation has little effect on Ubc12 peptide binding to E1, although the role of the Met differs between yeast and human, likely due to idiosynchratic Nedd8 E1-E2 interactions in yeast (FIG. 4) (Huang et al. (2009) *Mol Cell* 33(4):483-495).

TABLE 23

Thermodynamic parameters determined by isothermal titration calorimetry (ITC) for binding between the indicated Ubc12 peptides and Dcn1$^P$ and E1.

| Protein | Titrant | Kd (µM) | ΔH (cal/mol) | ΔS (cal/mol/deg) | N |
|---|---|---|---|---|---|
| yDcn1$^P$ (44) | yUbc12$^{1-24}$ (10) | >40 | 3,777 | 33.4 | 1.16 |
| yDcn1$^P$ (44) | Acetyl-yUbc12$^{1-24}$ | 0.444 | 4,145 | 43.6 | 0.99 |
| yDcn1$^P$ | Acetyl-yUbc12$^{2-24}$ | >37 | 3,761 | 33.4 | 0.92 |
| hDcn1$^P$ | hUbc12$^{1-26}$ | >130 | 1,259 | 22.2 | 0.75 |
| hDcn1$^P$ | Acetyl-hUbc12$^{1-26}$ | 1.11 | −6,107 | 5.84 | 0.92 |
| hDcn1$^P$ | Acetyl-hUbc12$^{2-26}$ | >100 | 1,719 | 24.1 | 0.52 |
| yE1 | yUbc12$^{1-24}$ | 0.070 | −8,571 | 2.65 | 1.05 |
| yE1 | Acetyl-yUbc12$^{1-24}$ | 0.016 | −11,260 | −3.8 | 0.99 |
| yE1 | Acetyl-yUbc12$^{2-24}$ | 1.58 | −9,625 | −7.21 | 0.92 |
| hE1 | hUbc12$^{1-26}$ | 0.585 | −8,881 | −1.99 | 1.29 |
| hE1 | Acetyl-hUbc12$^{1-26}$ | 0.943 | −9,425 | −4.79 | 1.14 |
| hE1 | Acetyl-hUbc12$^{2-26}$ | 0.390 | −8,899 | −1.24 | 1.04 |

Figure 5A:
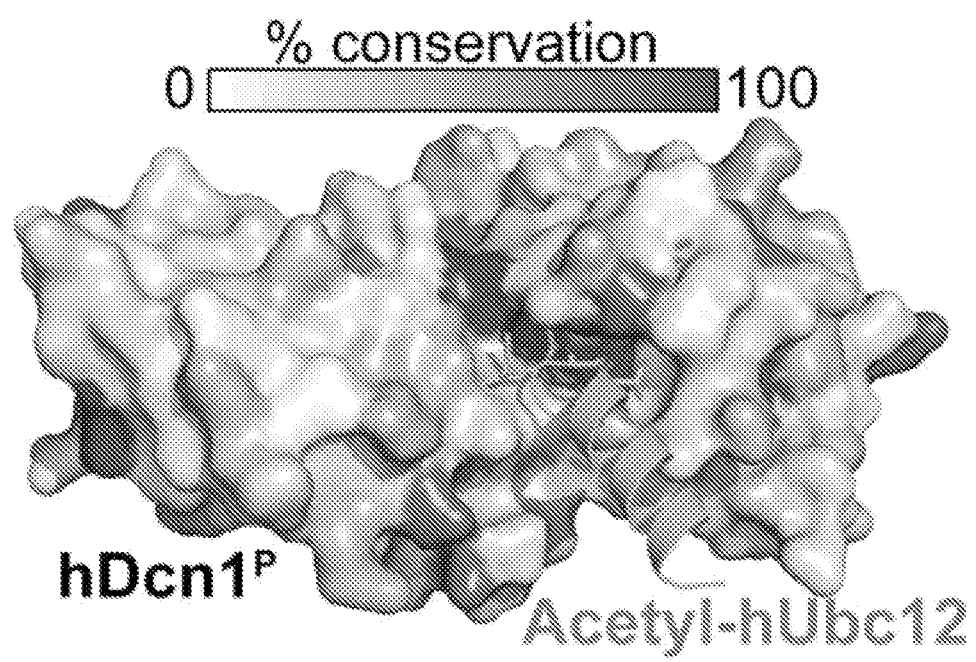
FIG. 5A provides a depiction of the structure of hCul1$^{WHB}$-hDcn1$^P$-AcetylhUbc12$^{1-15}$. hDcn1$^P$ is displayed in surface-mode, colored according to conservation between 5 human and yeast Dcn1$^P$ orthologs (white—not conserved; black—100% conserved). Acetyl-hUbc12$^{1-15}$ peptide is shown as a helix and stick figure. hCul1$^{WHB}$ is not shown for simplification.
Figure 5B:
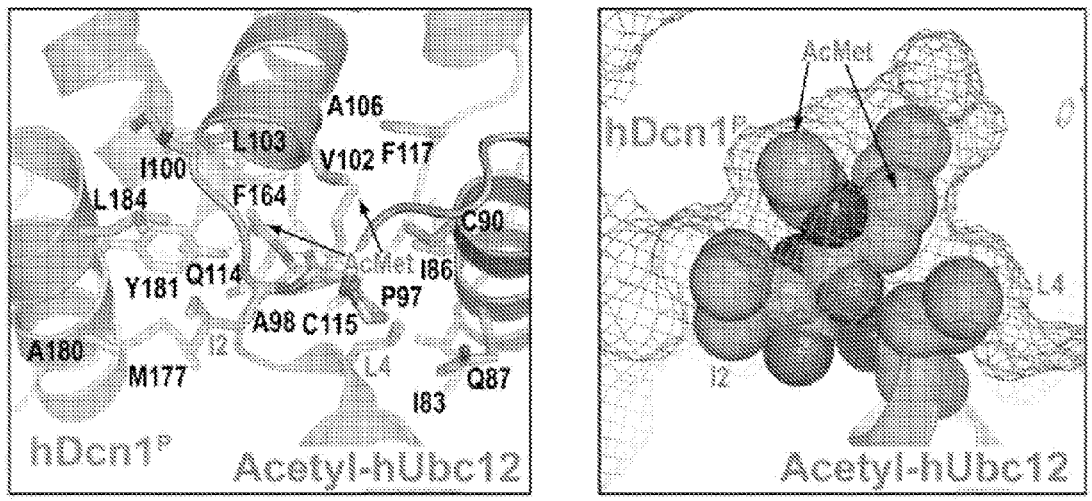
FIG. 5B provides a close-up depiction of Acetyl-hUbc12$^{1-15}$ peptide N-terminus binding to hDcn1$^P$. Left— interacting residues are shown as sticks with electrostatic interactions as dashes. Right—hUbc12's N-acetyl-methionine and residues 2 and 4 as spheres in a mesh view of the hDcn1$^P$ crevasse.

Kd: dissociation constant; ΔH: change in enthalpy; ΔS: change in entropy; N: stoichiometry, number of molecules of titrant the protein binds To understand how N-acetyl-methionine mediates interactions, the crystal structures of yeast and human Dcn1$^P$ bound to Ubc12 peptides were determined (Table 24). The structure with human proteins is also in complex with a domain of the Nedd8 target, Cul1. hDcn1$^P$-hCul1 interactions superimpose with the prior structure of yeast counterparts (Scott et al. (2010) *Mol Cell* 39(5):784-796), and are not discussed in detail here. Overall, Dcn1$^P$ superimposes with prior structures, forming a helical domain containing 2 EFhand-like folds (Kurz et al. (2008) *Mol Cell* 29(1):23-25; Scott et al. (2010) *Mol Cell* 39(5):784-796; and Yang et al. (2007) *J Biol Chem* 282(34):24490-24494). The Ubc12 N-terminal peptides are α-helical, as in full-length yUbc12$^{GSMet}$ (Scott et al. (2010) *Mol Cell* 39(5):784-796). A Dcn1$^P$ groove at the junction between the two EF-hand-like subdomains cradles Ubc12's helix, culminating in Ubc12's N-acetyl-methionine filling a conserved, hydrophobic crevasse in Dcn1$^P$ (FIGS. 5 and 6).

TABLE 24

Data collection and refinement statistics for three crystal structures.

| | yDcn1$^P$:Acetyl-yUbc12$^{1-24}$ | hCul1$^{WHB}$:hDcn1$^P$:Acetyl-hUbc12$^{1-15}$ | hCut1$^{WHB}$:hDcn1$^P$:Acetyl-hUbc12$^{1-12}$(5:9 Staple) | hDcn3$^P$:Acetyl-hUbe2f$^{1-25}$ |
|---|---|---|---|---|
| DATA COLLECTION | | | | |
| Space group | C222$_1$ | C2 | C222$_1$ | P2$_1$ |
| Cell dimensions | | | | |
| a, b, c (Å) | 72.906, 98.421, 143.923 | 135.431, 65.454, 64.182 | 131.790, 190.210, 67.506 | 83.464, 44.579, 101.216 |
| α, β, γ (°) | 90.0, 90.0, 90.0 | 90.0, 104.73, 90.0 | 90.0, 90.0, 90.0 | 90.000, 103.305, 90.000 |
| Resolution (Å) | 40.0-2.3 (2.38-2.3) | 50.0-1.5 (1.55-1.5) | 50.0-2.0 | 50.0-2.4 |
| R$_{merge}$ | 0.123 (0.370) | 0.090 (0.413) | 0.078 (0.439) | 0.110 (0.474) |
| I/σ| | 13.5 (2.6) | 27.2 (2.6) | 24.9 (2.5) | 1.857 |
| Completeness (%) | 89.9 (65.8) | 96.2 (88.0) | 96.7 (77.2) | 91.6 (70.0) |
| Redundancy | 5.4 (3.4) | 3.7 (3.3) | 6.6 (3.5) | 3.6 (3.2) |
| REFINEMENT | | | | |
| Resolution (Å) | 35-2.3 | 50.0-1.5 | 50.0-2.0 | 40.0-2.4 |
| No. reflections | 19967 | 78739 | 53080 | 27355 |
| R$_{work}$/R$_{free}$ | 21.3/26.9 | 21.0/23.7 | 19.89/22.77 | 21.52/23.93 |
| No. atoms | 3788 | 5365 | 5131 | 3437 |
| Protein | 3651 | 4776 | 4646 | |
| Water | 137 | 589 | 485 | 135 |
| B-factors | | | | |
| Protein | 27.06 | 19.56 | 17.2 | 34.381 |
| Water | 33.3 | 30.75 | 26.0 | 37.21 |
| R.m.s deviations | | | | |
| Bond lengths (Å) | 0.009 | 0.006 | 0.008 | 0.009 |
| Bond angles (°) | 1.021 | 0.914 | 0.992 | 1.297 |
| RAMACHANDRAN PLOT STATISTICS (%) | | | | |
| Preferred regions | 97.1 | 97.8 | 97.5 | 94.62 |
| Allowed regions | 2.9 | 2.2 | 2.5 | 4.1 |
| Disallowed regions | 0 | 0 | 0 | 1.28 |

Data for highest resolution shell is shown in parentheses. Rwork = Σ|F$_0$-F$_c$|/ΣF$_{0*Rfree}$ is the cross-validation of R-factor, with 5-10% of the total reflections omitted in model refinement.

N-acetyl-methionine recognition consists of three major components (FIG. 5). First, the methyl portion of the acetyl group fits snuggly in a hydrophobic pocket consisting of the α-carbon from yDcn1's Glu105 (hDcn1's Ala98) and side-chains from yDcn1's Leu107, Leu 110, and Leu193 (hDcn1's Ile100, Val102, Leu103, and Leu184). Second, the amide makes a hydrogen bond with the carbonyl oxygen from yDcn1's Leu104 (hDcn1's Pro97). Third, the Met side-chain packs in an extensive hydrophobic channel formed by side-chains from yDcn1's Leu93, Ile97, Leu104, Thr109, Leu112, Ala113, Tyr118, Leu121, and Leu173 (hDcn1's Ile86, Cys90, Pro97, Val102, Ile105, Ala106, Cys115, Phe117, Leu121, and Phe164).

Four additional structural elements, two each from Dcn1$^P$ and Ubc12, secure Ubc12's N-acetyl-methionine in place. First, yDcn1's Tyr190 (hDcn1's Tyr181) clamps between Ubc12's N-acetyl-Met1 and yDcn1-Leu2/hDcn1-Ile2 to press the N-acetyl-Met into the hydrophobic crevasse in Dcn1$^P$. Second, the loop between Dcn1$^P$'s E- and F-á-helices acts as an additional clamp, closing down on top of Ubc12's N-acetyl-methionine. Notably, in 7 prior structures of yDcn1$^P$ (Kurz et al. (2008) Mol Cell 29(1):23-35; Scott et al. (2010) Mol Cell 39(5):784-796; and Yang et al. (2007) J Biol Chem 282(34):24490-24494), none of which are bound to Ubc12, both of these elements are repositioned and partially occupy and occlude access to the hydrophobic crevasse (data not shown). It seems likely that yDcn1$^P$ is sufficiently flexible to initially engage Ubc12's acetylated N-terminus, and subsequently clamps down around the hydrophobic yUbc12 N-acetyl-methionine. Such conformational flexibility may allow structural rearrangement accounting for yDcn1$^P$'s ability to mediate low-level activation of yUbc12 even in the absence of N-terminal acetylation.

Figure 5C:
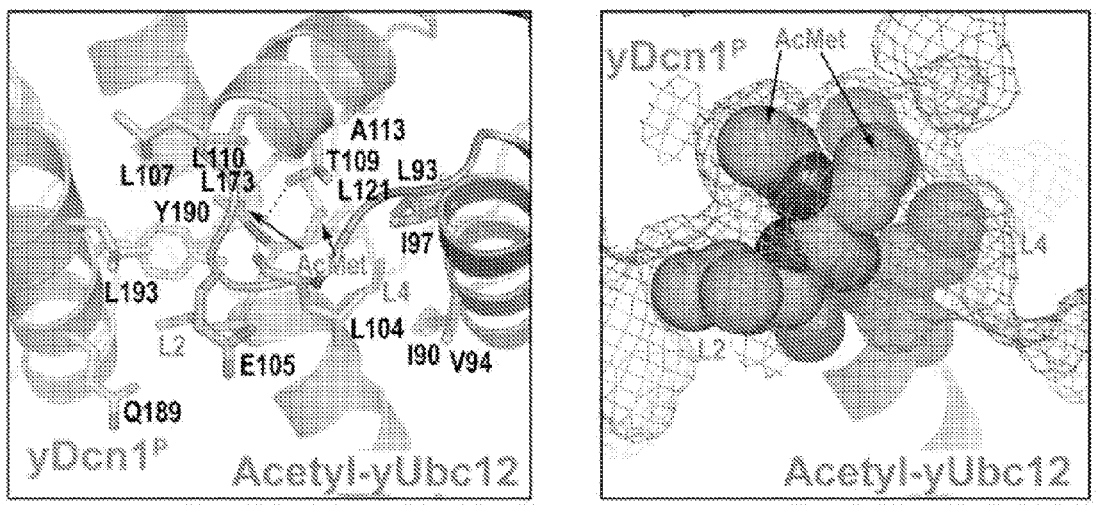
FIG. 5C provides a close-up depiction of Acetyl-yUbc12$^{1-24}$ peptide N-terminus binding to yDcn1$^P$. Left— interacting residues are shown as sticks with electrostatic interactions as dashes. Right—yUbc12's N-acetyl-methionine and residues 2 and 4 as spheres in a mesh view of the yDcn1$^P$ crevasse.
Figure 6:
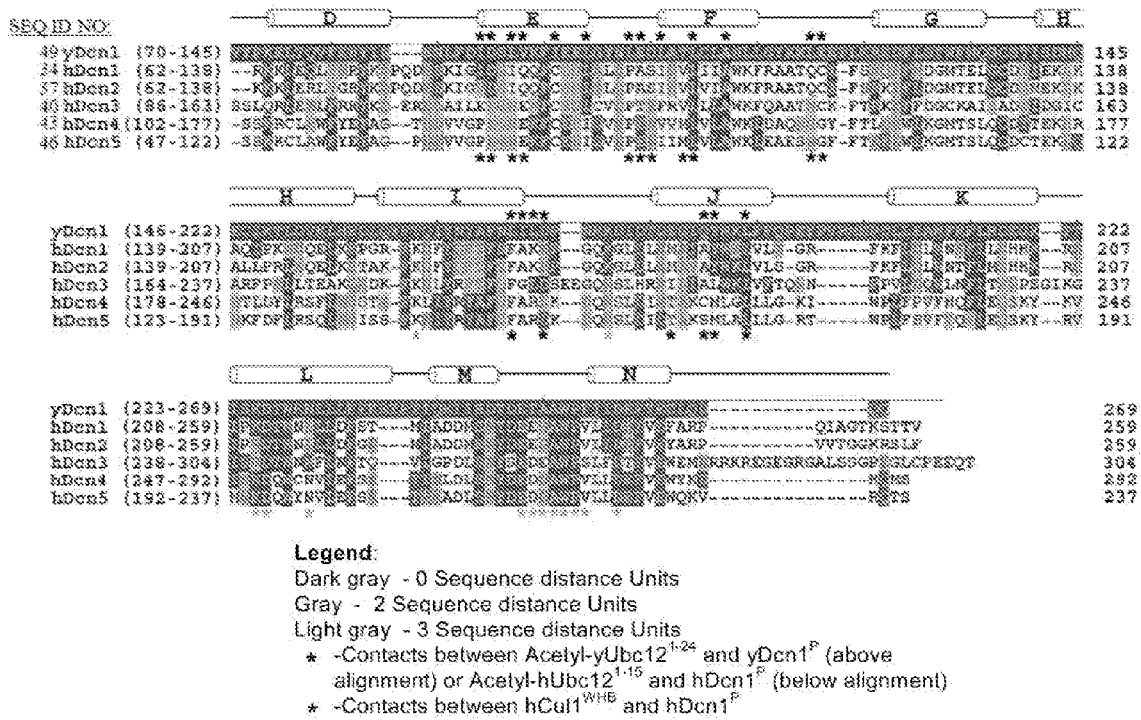
FIG. 6 provides a sequence alignment of Dcn1$^P$ family members. Structure-based sequence alignment of Dcn1$^P$ (also called "PONY" (Kurz et al. (2007) *Nature* 445(7126): 394-398)) domains from yeast Dcn1 (SEQ ID NO: 49) and human Dcn1 family members 1-5 (also called DCUND1-DCUND5; SEQ ID NOs: 34, 37, 40, 43, and 46, respectively). Secondary structural elements are indicated above (Kurz et al. (2007) *Nature* 445(7126):394-398). Black asterisks above the alignment indicate contact sites between yDcn1$^P$ and the N-terminally acetylated yUbc12 peptide. Black asterisks below the alignment indicate contact sites between hDcn1$^P$ and the N-terminally acetylated hUbc12 peptide. Gray asterisks below the alignment indicate contact sites between hDcn1$^P$ and the hCul1$^{WHB}$ sub-domain.

Ubc12's N-acetyl-methionine is further sealed into the hydrophobic crevasse by interactions involving hydrophobic residues at positions 2 and 4 in Ubc12 (FIGS. 5C and 5D). This requires the helical structure, which places these side-chains on opposite sides of the N-acetyl-methionine. On one side, yUbc12's Leu2 (hUbc12's Ile2) buries the acetyl moiety via interacting with the aliphatic portion of yDcn1's Glu105 and Gln189 side-chains, Tyr190, and Leu193. The interaction is more extensive for the human proteins, with interactions with hDcn1's Ala98, Met177, Ala180, Tyr181, and Leu184. On the other side, Ubc12's Leu4 side-chain seals the Met1 side-chain into place via interactions with yDcn1's Ile90, Val94, Leu104, and Leu121 (hDcn1's Ile83, Ile86, Gln87, Pro97, and Cys115). Furthermore, there are numerous additional, species-specific interactions between other downstream residues from both faces of the Ubc12 helix and surrounding residues from the Dcn1$^P$ groove. For example, yUbc12's Lys3 fits in an anionic pocket formed by side-chains from yDcn1$^P$'s Glu122 and Asp 176, and carbonyls from Ile174 and Leu175. Other interactions include the following: yUbc12's Arg5 forms a salt-bridge with yDcn1$^P$'s Glu105; yUbc12's Leu7 makes hydrophobic contacts with yDcn1$^P$'s Ile90 and Leu121; and yUbc12's Lys11 fits in an anionic pocket formed by side-chains from yDcn1$^P$'s Asp89 and Asp91. Examples of interactions between hUbc12 and hDcn1 include the following: hUbc12's Lys3 makes a salt-bridge with hDcn1$^P$'s Asn167; hUbc12's Leu7 makes hydrophobic contacts with hDcn1$^P$'s Ile83 and Cys115; hUbc12's Lys8 forms a hydrogen bond with hDcn1$^P$'s Gln87; and hUbc12's Lys11 forms a salt-bridge with hDcn1$^P$'s Asp84.

Although yUbc12$^{Met}$'s N-terminal extension is helical in a prior structure (Scott et al. (2010) Mol Cell 39(5):784-796), experiments were performed to confirm a role for the helix with human proteins because hUbc12$^{Met}$'s N-terminal region is extended in complex with E1 (Huang et al, (2004) Nat Struct Mol Biol 11(10):927-935; Huang et al. (2007) Nature 445(7126):394-398). Specifically, Phe5 and Gln9 were replaced with (S)-2-(4'-pentenyl) alanine and these side-chains were covalently linked to test the effect of "stapling" an acetylated Ubc12 peptide into a helix (Bird et al. (2008) Methods Enzymol 446:369-386). The stapled helical peptide no longer binds E1 (data not shown), consistent with prior structures (Huang et al. (2004) Nat Struct Mol Biol 11(10):927-935; and Huang et al. (2007) Nature 445(7126):394-398). Moreover, a 2.0 Å resolution structure with the stapled peptide superimposes with the unstapled hUbc12$^{AcMet}$ complex with hDcn1$^P$, confirming that the staple is completely solvent-exposed (data not shown). The helical staple improves binding to hDcn1$^P$ 14-fold (Table 25). This is largely due to decreasing the entropic cost of binding, supporting the notion that locking the flexible hUbc12 N-terminal region into a helical conformation is important for the hDcn1$^P$ interaction.

TABLE 25

Thermodynamic parameters determined by isothermal titration calorimetry (ITC) for binding between hDcn1$^P$ or HE1 to control or hydrocarbon-stapled Ubc12 peptides.

| Protein | Titrant | Kd (μM) | ΔH (cal/mol) | ΔS (cal/mol/deg) | N |
|---|---|---|---|---|---|
| hDcn1P | Acetyl-hUbc12$^{1-12}$ | 2.15 | −4,992 | 8.79 | 0.99 |
| hDcn1P | Acetyl-hUbc12$^{1-12}$ (5:9Staple) | 0.15 | −3,386 | 19.3 | 1.18 |
| hE1 | Acetyl-hUbc12$^{1-12}$ | 0.63 | −11,490 | −11.0 | 0.78 |
| hE1 | Acetyl-hUbc12$^{1-12}$ (5:9Staple) | NB | NB | NB | NB |

The structures suggest two primary mechanisms by which Ubc12's N-terminal acetylation dictates binding to Dcn1$^P$. First, the acetyl group interacts directly with Dcn1$^P$. Second, acetylation eliminates an N-terminal positive charge, which would impede burial in the Dcn1$^P$ hydrophobic crevasse. To test these concepts, Dcn1$^P$ binding to Ubc12 peptides that were N-terminally formylated was examined by ITC (Table 26). The formylated peptides lack the methyl portion of an acetyl, but retain the amide and are uncharged. Indeed, the formylated peptides bind better than those with a free N-terminus. Furthermore, the Kds were decreased ~9- and ~17-fold compared with the acetylated human and yeast peptides, respectively, highlighting the importance of the acetyl methyl for mediating Ubc12-Dcn1$^P$ interactions.

TABLE 26

Thermodynamic parameters determined by isothermal titration calorimetry (ITC) for binding between N-terminally formylated Ubc12 peptides and Dcn1$^P$.

| Protein | Titrant | Kd (μM) | ΔH (cal/mol) | ΔS (cal/mol/deg) | N |
|---|---|---|---|---|---|
| yDcn1P | Formyl-yUbc12$^{1-24}$ | 7.46 | 2,824 | 33.4 | 0.90 |
| hDcn1P | Formyl-hUbcU$^{126}$ | 9.71 | −4,893 | 5.79 | 1.00 |

Figure 7A:
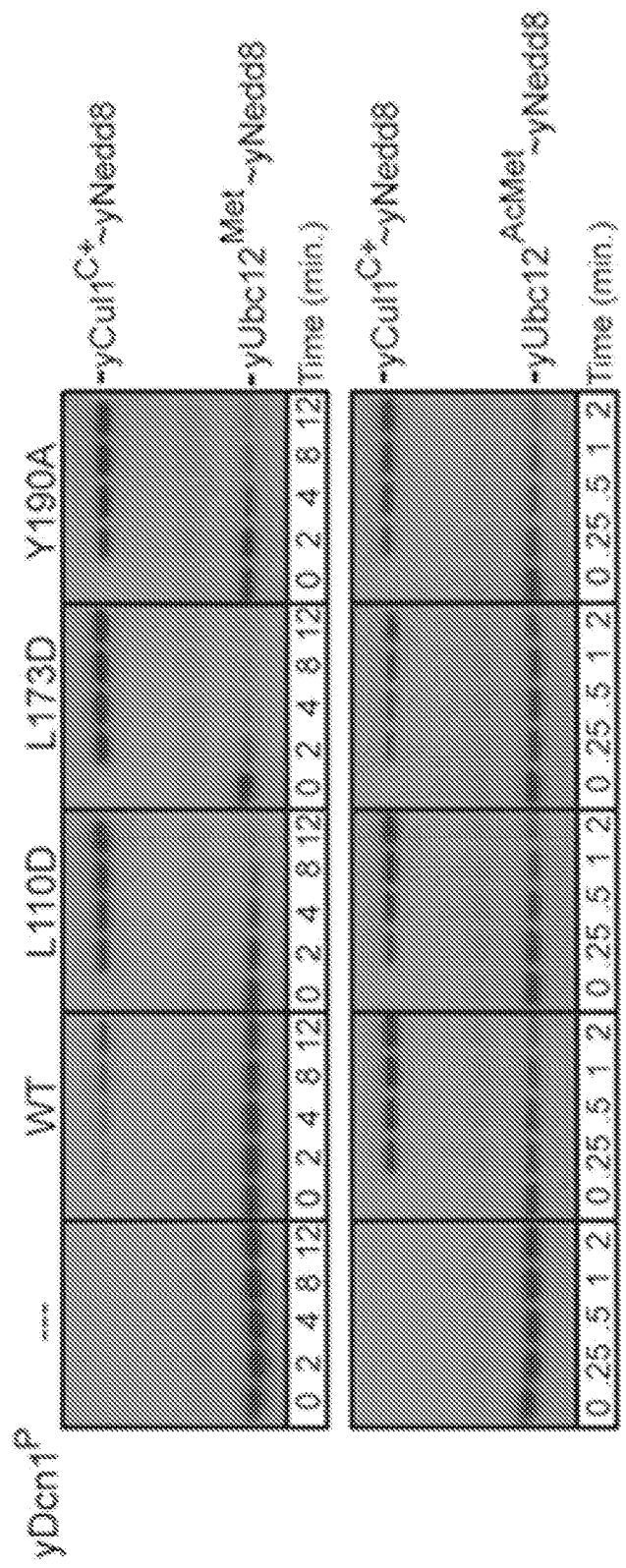
FIG. 7A provides an autoradiograph of pulse-chase assays monitoring [$^{32}$P]-yNEDD8 transfer from yUbc12$^{Met}$ (top) or yUbc12$^{AcMet}$ (bottom) to yCul1$^{C+}$-yRbx1 in the absence or presence of the indicated yDcn1$^P$ variants (note differences in times between top and bottom panels).
Figure 7B:
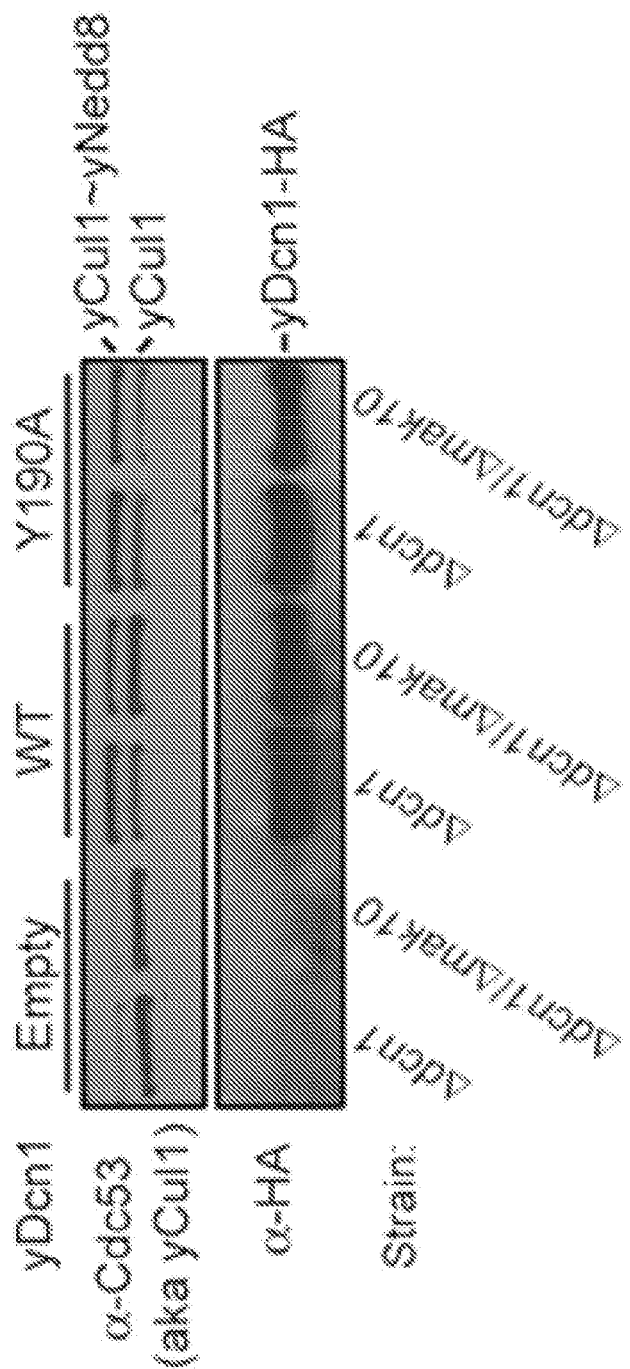
FIG. 7B provides Western blots for yCul1 (aka Cdc53p, top) or HA-tag (bottom) from mid-log whole cell extracts from Δdcn1 or Δdcn1/Δmak10 yeast harboring empty or WT Dcn1-HA, or Y190A mutant Dcn1-HA expression vectors.

The ultimate test of understanding the structural role of Ubc12 N-terminal acetylation would be to design Dcn1$^P$ mutants that potentiate neddylation with unacetylated Ubc12. Given the structural malleability of yDcn1$^P$, it was reasoned that mutations alleviating repulsion of yUbc12's N-terminal charge might enhance the low-level yDcn1$^P$ E3 activity toward yUbc12$^{Met}$. The structure indicated that aspartate substitutions for yDcn1$^P$ Leu110 or Leu173 would approach yUbc12$^{Met}$'s N-terminus to balance the positive charge. Also, an Ala replacement for the Tyr190 "clamp" would not force a charged yUbc12$^{Met}$'s N-terminus directly into the hydrophobic pocket. Indeed, the three Dcn1$^P$ mutants showed enhanced activity specifically toward unacetylated yUbc12 in potentiating yNedd8 transfer to yCul1 (FIG. 7A). To address whether a mutation could compensate for loss of NatC-mediated yUbc12 acetylation in vivo, HA-tagged versions of either wild-type or mutant yDcn1 were expressed in strains deleted for either Dcn1, or both Dcn1 and the NatC subunit Mak10. Although Leu110Asp or Leu173Asp mutants were not expressed at levels comparable to the wild-type, strains expressing the Tyr190Ala mutant were obtained. Consistent with the in vitro results, relative to wild-type Dcn1, the Tyr190Ala mutant partially rescued the defect in yCul1~yNedd8 conjugate formation in the absence of NatC activity (FIG. 7B).

Methods

Constructs, Protein Preparation, Antibodies, and Peptides

Constructs for expression and purification of hUbc12, yUbc12$^{GSMet}$ (also referred to as Ubc12), yDcn1$^P$, hNedd8, yNedd8 (also referred to as Rub1), hCul1$^{ctd}$-hRbx1, yCul1$^{C+}$-yRbx1 (also referred to as Cdc53$^{C+}$-Hrt1), yCul1$^{C+}$-yRbx1$^R$ (also referred to as Cdc53$^{C+}$-Hrt1$^R$), hE1 for Nedd8 (also referred to as APPBP1-UBA3 and NAE1-UBA3), yE1 for yNedd8 (also referred to as Ula1Uba3), and hCAND1 were expressed in E. coli and purified as described previously (Walden et al. (2003) Nature 422(6929):330-334; Duda et al. (2008) Cell 134(6):995-1006; Scott et al. (2010) Mol Cell 39(5):784-796). hCul1-hRbx1 was expressed in insect cells and purified as described previously (Duda et al. (2008) Cell 134(6):995-1006).

hCul1ctd-hRbx1$^R$ contains a stop mutation introduced after residue 36 in hRbx1 to delete the RING domain, and was expressed and purified as previously described for hCul1$^{ctd}$hRbx1 (Duda et al. (2008) Cell 134(6):995-1006). Expression constructs generated for this study were prepared by standard molecular biology techniques and coding sequences were entirely verified. Mutant versions used in this study were generated by QuickChange (Stratagene). hCul1$^{WHB}$ corresponds to residues 702 to the C-terminal residue 776 of hCul1 (SEQ ID NO: 79). hDcn1$^P$ corresponds to residues 62 to the C-terminal residue 259 of hDcn1 (aka SCCRO or DCUN1D1 (Sarkaria et al. (2006) Cancer Res 66(19):9437-9444); SEQ ID NO: 33).

hCul1$^{WHB}$, hDcn1$^P$, and hDcn1$^{FL}$ were expressed as GST fusions in BL21(DE3)Gold E. coli and purified by glutathione affinity chromatography. After TEV protease treatment to release GST, proteins were further purified by ion exchange and gel filtration chromatography in 25 mM Tris, 125 mM NaCl, 5 mM DTT, pH 7.6 (Buffer A), concentrated (Amicon Ultra), aliquotted, flash-frozen and stored at −80° C.

For expression and purification of hUbc12$^{Met}$ and yUbc12$^{Met}$ proteins, His-SUMO-1 fusions were generated in pRSF-Duet, in which the Met start codon of hUbc12 or yUbc12 was directly fused to follow the GlyGly SUMO-1 C-terminus. His-SUMO-1 fusions were expressed in BL21 (DE3)Gold $E.\ coli$ and purified by Ni$^{+2}$ affinity chromatography. After treatment with the SUMO protease SENP2, hUbc12$^{Met}$ and yUbc12$^{Met}$ were further purified by gel filtration and passed back over a Ni$^{+2}$ affinity resin to remove any residual His-SUMO-1 that co-purified over sizing.

For purification of hUbc12$^{AcMet}$, hUbc12 was expressed untagged in insect cells. The Ubc12 coding sequence was cloned into pFastbac1, and baculoviruses were prepared using the Bac-to-Bac system (Invitrogen). Insect cell expression of hUbc12$^{AcMet}$ was performed at 24° C. for 1 day, followed by incubation at 18° C. for 2 days, with lysates initially purified over gravity S-Sepharose with a step gradient elution. Fractions containing hUbc12$^{AcMet}$ were diluted and reapplied to a Source-S column via FPLC, and eluted with a linear salt gradient. Fractions were pooled and concentrated (Amicon Ultra), and further purified by gel filtration chromatography in Buffer A.

For expression and purification of yUbc12$^{AcMet}$, the yUbc12 ORF was fused to a C-terminal hexahistidine tag and cloned into pRS426-Gal1 (Mumberg et al. (1994) *Nucleic Acids Res* 22(25):5767-5768). Proteins expressed from this vector are referred to as "yUbc12-His6", but subsequently the N-terminally acetylated version is referred to as "yUbc12$^{ACMet}$". BY4742, or mak3 (i.e., strain Y15470) yeast cells harboring pRS426-Gal1-yUbc12-His6 under control of the galactose-inducible promoter were grown at 30° C. in SD-Ura 2% Raffinose 0.1% Glucose media to mid-log phase (OD600=0.4-0.6). Cells were pelleted and resuspended at a density of 0.1 OD/ml in pre-warmed SD-Ura 2% Galactose media and induced at 30° C. for 14-16 hours. Cell pellets were resuspended in Phosphate-Buffer Saline containing Aprotonin, Leupeptin, PMSF, and protease inhibitor tablets (Sigma). Cells were lysed by three passages through a cell disruptor at 15,000 psi and protein subsequently purifed by Ni$^{+2}$ affinity chromatography. Ni$^{+2}$ column eluates were further purified over gel filtration chromatography in Buffer A.

N-terminal acetylation of bacterially expressed yUbc12 was achieved by co-expression of Mak3, Mak10, Mak31, and yUbc12-His6, followed by Ni$^{+2}$ affinity and gel filtration chromatography. Briefly, untagged Mak10 and Mak3 were cloned into site 1 and 2, respectively, of pET-Duet (EMD Biosciences), and untagged Mak31 and yUbc12-His6 were cloned into site 1 and 2, respectively, of pRSF-Duet (EMD Biosciences).

For wild type and mutant rescue of dcn1 yeast cells, yDcn1-HA was built by overlap PCR from yeast genomic DNA and cloned into the CEN/Leu vector pRS315. The resultant clone contains approximately 600 nucleotides 5' and 3' of the start and stop codon, respectively, in order to preserve the natural regulatory elements of genomic yDcn1.

Antibodies against Cdc53 (sc-50444) and HA tag (H6908) were obtained from Santa Cruz Biotechnology and Sigma, respectively, and used according to the manufacturer's instructions. Peptides were synthesized and purified by reversed-phase HPLC by the Hartwell Center for Bioinformatics and Biotechnology at St. Jude. All peptides were C-terminally amidated. For helical hydrocarbon stapling, residues 5 and 9 of Ac-hUbc12$^{1-12}$ were substituted with (S)—N-Fmoc-2-(4-pentenyl)alanine, and the staple generated as described (Schafineister et al. (2000) *J Am Chem Soc* 122:5891-5892). Sequences of peptides used in this study are provided in Table 27.

TABLE 27

Sequences of peptides used in Example 1.

| SEQ ID NO: | Peptide name | Sequence |
|---|---|---|
| 15 | yUbc12$^{1-24}$ | MLKLRQLQKKKQKENENSSSIQPN-NH2 |
| 87 | Acetyl-yUbc12$^{1-24}$ | Ac-MLKLRQLQKKKQKENENSSSIQPN- |
| 89 | Acetyl-yUbc12$^{2-24}$ | Ac-LKLRQLQKKKQKENENSSSIQPN- |
| 7 | hUbc12$^{1-26}$ | MIKLFSLKQQKKEEESAGGTKGSSKK- |
| 8 | Acetyl-hUbc12$^{1-26}$ | Ac- |
| 9 | Acetyl-hUbc12$^{2-26}$ | Ac-IKLFSLKQQKKEEESAGGTKGSSKK- |
| 90 | Acetyl-hUbc12$^{1-12}$ | Ac-MIKLFSLKQQKK-NH2 |
| 20 | Acetyl-hUbc12$^{1-12}$(5:9Staple) | Ac-MIKLXSLKXQKK-NH2 X = 2-(4-pentenyl)alanine- |
| 91 | Formyl-yUbc12$^{1-24}$ | Formyl-MLKLRQLQKKKQKENENSSSIQPN-NH2 |
| 10 | Formyl-hUbc12$^{1-26}$ | Formyl-MIKLFSLKQQKKEEESAGGTKGSSKK- |
| 92 | Acetyl-hUbc12$^{1-15}$ | Ac-MIKLFSLKQQKKEEE-NH2 |

Cell Line Generation and Sample Preparation 293T cells with stable expression of C-terminally Flag-HA tagged hUbc12 were generated using lentiviral-mediated transduction. Puromycin-resistant cells were grown in DMEM supplemented with L-glutamine, 10% FBS, and pen/strep. TAP-Nedd8 cells were generated as described previously (Bennett et al. (2010) *Cell* 143(6):951-965). Cells were harvested and lysed in buffer containing 50 mM Tris pH 7.8, 150 mM NaCl, 0.5% NP40, and protease inhibitors (Roche). Cell lysates were then immunoprecipitated with HA conjugated resin. Complexes were washed, eluted with HA peptide, precipitated with TCA, and digested with GluC (NEB).

Yeast Strains Used in this Study

Yeast strains for expression and purification of C-terminally His6-tagged yUbc12 ("yUbc12$^{AcMet}$") and for monitoring the yNedd8 modification status of yCul1 were obtained from the EUROScarf collection (Brachmann et al. (1998) *Yeast* 14(2):115-132). YBS001 was constructed by PCR-mediated gene disruption using pUG72 as a template for generation of a loxP-His3-loxP Dcn1 deletion cassette. Correct integration was confirmed by PCR screening of purified genomic DNA utilizing two primers that anneal internal to the His3 cassette and 5' and 3' primers flanking the intended disruption gene. Marker rescue was achieved as described with pSH47 (a kind gift from Randy Schekman's lab). After counter-selection on 5-FOA, YBS001 was subsequently used to generate YBS002 and correct integration verified as described above. Yeast strains used in this study are described in Table 28.

TABLE 28

Yeast strains used in Example 1.

| Strain name or proccession Number | Genotype | Reference |
|---|---|---|
| BY4742 | MAT his3- 1 leu2- 0 lys2- 0 ura3- 0 | * |
| Y14085 | Same as B Y4742 but also dcn1::kanMX4 | * |
| Y15214 | Same as B Y4742 but also ubc12::kanMX4 | * |
| Y13914 | Same as B Y4742 but also csn5::kanMX4 | * |
| Y10976 | Same as B Y4742 but also ard1::kanMX4 | * |
| Y13736 | Same as B Y4742 but also nat1::kanMX4 | * |
| Y15546 | Same as B Y4742 but also nat3::kanMX4 | * |
| Y15470 | Same as B Y4742 but also mak3::kanMX4 | * |
| Y10294 | Same as B Y4742 but also mak10::kanMX4 | * |
| Y13501 | Same as B Y4742 but also mak31::kanMX4 | * |
| YBS001 | Same as B Y4742 but also dcn1::loxP | This study |
| YBS002 | Same as B Y4742 but also mak10::loxP-His3-IoxP | This study |

* Brachmann et al (1998) Yeast 14: 115-132

Yeast Extract Preparation for Western Blotting

For FIG. 1, cells were inoculated into YPD media and grown overnight at 30° C. After OD600 measurements, cells were subcultured into fresh YPD media at 0.2 OD/ml and grown at 30° C. until OD600=0.9-1.0. Cells were pelleted from 2 ml of media and extracts made by the NaOH/BME/TCA method as described (Knop et al. (1999) *Yeast* 15(10B):963-972). For western blots from cell extracts in FIG. 7, cells were treated as described above except they were grown in SD-Leu 2% glucose for plasmid maintenance. Cell extracts corresponding to approximately 0.3 OD's of cells were run on 10% NuPAGE gels (Invitrogen). After western transfer, nitrocellulose membranes were probed with anti-Cdc53 (referred to here as yCul1) or anti-HA antibodies as indicated and visualized by enhanced chemiluminescence.

Mass Spectrometry

Peptides generated from GluC digestion of sample proteins were desalted offline using C18 stage tips. Peptides were eluted from the stage tip, dried down using a speed vac, and resuspended in 10 μl 5% formic acid, 5% acetonitrile. Peptide mixtures were separated by in line reverse phase using an 18 cm×150 μm (ID) column packed with C18 (MAGIC C18 5 μm particle, 200 angstrom pore size) using a 50-minute 8%-26% acetonitrile gradient. MS/MS data was generated using an LTQ-Velos mass spectrometer (Thermo), a data-dependent top 10 instrument method, and zoom scan for MS1 assignments. Data was acquired using CID with the normalized collision energy set to 35% with activation times of 10 ms. MS/MS triggering thresholds were set to 2000 and a 30s dynamic exclusion was used with an exclusion list size of 500. All of the mass spec data was validated using an LTQ-Orbitrap (Thermo) instrument to obtain high mass accuracy MS1 assignments for all Ubc12 peptides. Resultant MS/MS spectra were searched using Sequest against a concatenated forward and reverse human IPI database (v3.6), or a *Saccharomyces cerevisiae* database as needed. Methionine oxidation (+15.99), acetylation (+42.01), and the combined modification (+58.09) were set as dynamic modifications.

For intact mass analyses, protein was desalted using a reverse phase C8 Zip Tip and eluted in 50% acetonitrile, 2% formic acid. The eluent was ionized by static nanospray on Waters LCT Premier XE mass spectrometer using positive mode to obtain MaxEnt LC-TOF spectra.

Isothermal Titration calorimetry (ITC)

Protein samples were buffer matched by desalting over a NAP-5 column (GE Healthcare) into 50 mM Hepes, 125 mM NaCl, 1 mM BME, pH 7.0 (ITC buffer). Peptides were dissolved by weight to a final concentration of 10 mM in ITC buffer and diluted further in ITC buffer as required for the experiments. Measurements were performed using a MicroCal ITC200. hDcn1$^P$ or yDcn1$^P$ were placed into the sample cell at a final concentration of 400 μM at 18° C. The peptide ligands (4 mM) were constantly injected (1.5 μl). The interval time between each injection was 3 minutes and the duration of each injection was 3 seconds. For titrations involving hE1 and yE1, proteins were placed into the sample cell at a final concentration of 25 μM at 22° C. Peptide ligands (250 μM) were constantly injected (2.5 μl). The interval time between each injection was three minutes and the duration of each injection was 5 seconds. For hCul1$^{ctd}$-Rbx1:hDcn1$^P$ binding, proteins were buffer matched by desalting over a NAP-5 column in 25 mM Tris, 0.1 M NaCl, 1 mM BME, pH 7.6. hCul1$^{ctd}$-Rbx1 was placed into the sample cell at a final concentration of 55 μM at 22° C. hDcn1$^P$ (550 μM) was constantly injected (2.5 μl). The interval time between each injection was 3 minutes and the duration of each injection was 5 seconds. Obtained spectra were evaluated using Origin (V 7.0) to determine heats of binding and Kd values.

Crystallography

Crystals were grown by the hanging-drop vapor-diffusion method. Crystals of yDcn1$^P$-Acetyl-yUbc12$^{1-24}$ grew as plate clusters at room temperature in 19-22% PEG3350, 0.1 M Bis-Tris Propane, 0.2 M sodium/potassium tartrate, pH 8.5. Single crystals were obtained by streak seeding into 16% PEG 3350, 0.1 M Bis-Tris Propane, 0.2 M sodium/potassium tartrate, pH 7.9. The crystals were harvested from mother liquor supplemented with 25% glycerol prior to flash-freezing in liquid nitrogen. Reflection data were collected at NECAT ID-24-E at the Advanced Photon Source.

The crystals belong to space group C2221 with two yDcn1$^P$-Acetyl-yUbc12$^{1-24}$ complexes in the asymmetric unit.

Crystals of hCul1$^{WHB}$-hDcn1$^P$-Acetyl-hUbc12$^{1-15}$ were grown at 4° C. in 27% PEG1500, 0.1 M MIB buffer (Qiagen), pH 4.0. The crystals grew as multiple clusters. Single crystals of the complex were obtained by streak-seeding into 17% PEG1500, 0.1 M MIB pH 4.0. The crystals were soaked in step gradients for 1-5 minutes, with sequential soaks containing well solution supplemented with 10%, 20%, and 30% ethylene glycol prior to flash-freezing in liquid nitrogen. Reflection data were collected at beamline 8.2.2 at the Advanced Light Source. Even after seeding, reflections from data for both the yDcn1$^P$-Acetyl-yUbc12$^{1-24}$ and hCul1$^{WHB}$-hDcn1$^P$-Acetyl-hUbc12$^{1-15}$ complexes were streaky.

Crystals of hCul1$^{WHB}$-hDcn1$^P$-AcetylhUbc12$^{Ac1-12}$(5,9 Staple) contained a selenomethionine version of the peptide used for convenience in crystallography that binds hDcn1$^P$ with essentially the same Kd as the methionine-containing peptide (not shown), and were grown at 4° C. in 21% PEG3350, 0.2 M KCl. The crystals were soaked in step gradients for 1-5 minutes, with sequential soaks containing well solution supplemented with 10%, 20%, and 30% of a 50:50 mixture of glycerol:ethylene glycol prior to flash-freezing in liquid nitrogen. Reflection data were collected at SERCAT 22-ID beamline at the Advanced Photon Source. All reflection data were processed with HKL2000 (Otwinowski and Minor (1997) *Methods in Enzymology, Macromolecular Crystallography, part A* 276:307-326).

Phases for all structures were obtained by molecular replacement using PHASER (Storoni et al. (2004) *Acta Crystallogr D Biol Crystallogr* 60(Pt 3):432-438) using the following search models: (1) for yDcn1$^P$-Acetyl-yUbc12$^{1-24}$ structure, 2 copies of yDcn1$^P$ (3); (2) for hCul1$^{WHB}$-hDcn1$^P$-Acetyl-hUbc12$^{1-15}$ structure, 2 copies each of (a) a model of hDcn1$^P$ generated by Modeller (Eswar et al. (2006) *Curr Protoc Bioinformatics* Chapter 5, Unit 5 6) and (b) residues 707-776 from a prior structure of hCul1 (SEQ ID NO: 79) (Zheng et al. (2002) *Nature* 416(6882):703-709); (3) for hCul1$^{WHB}$-hDcn1$^P$-Acetyl-hUbc12$^{Ac1-12}$(5,9 Staple) structure, 2 copies of hCul1$^{WHB}$-hDcn1$^P$ from the hCul1$^{WHB}$-hDcn1$^P$-Acetyl-hUbc12$^{1-15}$ structure. In all cases, the peptides were built manually, and general manual rebuilding was performed with COOT (Emsley et al. (2004) *Acta Crystallogr D Biol Crystallogr* 60(Pt12Pt1):2126-2132). Refinement was performed using Phenix (Adams et al. (2010) *Acta Crystallogr D Biol Crystallogr* 66(Pt2):213-221) and Refmac (Murshudov et al. (1997) *Acta Crystallogr D Biol Crystallogr* D53:240-255). Details of Refinement are provided in Table 24.

Biochemical Assays

Dcn1$^P$-mediated co-E3 activity was monitored using pulse-chase assays to exclusively monitor effects of acetylation on Nedd8 transfer to Cul1 without sensing earlier steps in the reaction. For the "pulse", 10 μM of the indicated versions of yUbc12 were charged with [$^{32}$P]-yNedd8 (also referred to as [$^{32}$P]-Rub1) as described previously (Scott et al. (2010) *Mol Cell* 39(5):784-796), resulting in formation of a thiolester-linked yUbc12-[$^{32}$P]-yNedd8 intermediate. 10 μM of the indicated versions of hUbc12 were charged similarly with [$^{32}$P]-hNedd8, for 15 minutes at room temperature using 0.1 μM hE1, 15 μM [$^{32}$P]-hNedd8, in 50 mM Hepes, 100 mM NaCl, 1.25 mM ATP, 2.5 mM MgCl2, pH 7.5. Formation of a yUbc12-[$^{32}$P]-yNedd8 or hUbc12-[$^{32}$P]-hNedd8 intermediate was quenched with 50 mM EDTA on ice for 5 minutes. Other than in FIG. 3, where additional details are provided, chase reactions with hUbc12 and yUbc12 variants involved dilution of the Ubc12-[$^{32}$P]-Nedd8 thioester conjugate to 40 nM in 50 mM BisTris, 100 mM NaCl, 50 mM EDTA, 0.5 mg/ml BSA, pH 6.7. Chase reactions were initiated at 0° C. by the addition of hCul1$^{ctd}$-hRbx1, yCul1$^{C+}$-yRbx1, hDcn1$^P$-hCul1$^{ctd}$-hRbx1, or yDcn1$^P$-yCul1$^{C+}$-yRbx1 at a final concentration of 125 nM. Aliquots were removed at the indicated times and quenched with 2×SDS-PAGE sample buffer. Reaction products were heated at 70° C. for 1.5 minutes and separated on 4-12% NuPAGE gels (Invitrogen). Dried gels were exposed, as indicated in the figure legends, to a Storm (GE) Phosphorimager screen or film (Kodak).

Example 2

Figure 8A:
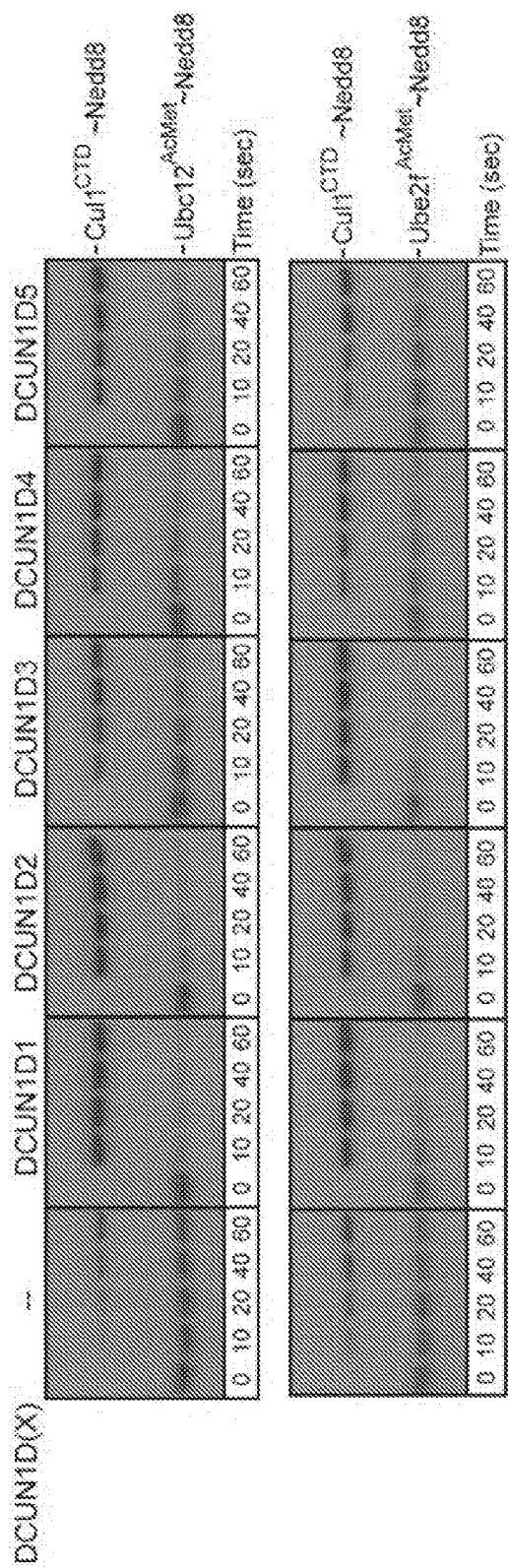
FIG. 8A provides an autoradiograph of pulse-chase assays in the absence or presence (500 nM) of the indicated DCUN1D family members monitoring tranfer of NEDD8 from 40 nM Ubc12$^{AcMet}$~NEDD8 (upper panel) or 40 nM Ube2f$^{AcMet}$~NEDD8 (lower panel) to 500 nM Cul1$^{CTD}$-Rbx1, demonstrating that DCUN1D(1-5) family members stimulate Ubc12$^{AcMet}$ and Ube2f$^{AcMet}$NEDD8 transfer to Cul1$^{CTD}$-Rbx1.
Figure 8B:
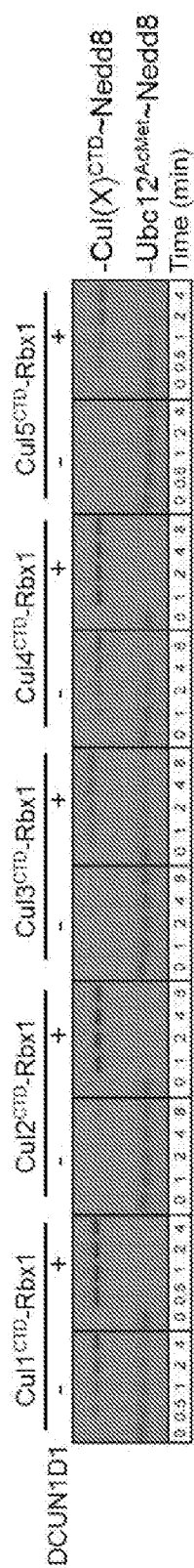
FIG. 8B provides an autoradiograph of pulse-chase assays in the absence or presence of 500 nM DCUN1D1 monitoring transfer of NEDD8 from 40 nM Ubc12$^{AcMet}$~NEDD8 to 500 nM Cul(1-5)CTD-Rbx1, demonstrating that DCUN1D1 potentiates NEDD8 transfer from Ubc12$^{AcMet}$ to Cul(1-5) family members.

DCUND1D(1-5) Family Members Stimulate Ubc12$^{AcMet}$ and Ube2f$^{AcMet}$ Nedd8 Transfer to Cul1-5 Family Members Pulse-chase assays similar to those described in Example 1 were used to determine if the DCUN1D family members, DCUN1D1, DCUN1D2, DCUN1D3, DCUN1D4, and DCUN1D5 could stimulate Nedd8 transfer to cullin family members, Cul1, Cul2, Cul3, Cul4, and Cul5. Results are shown in FIGS. 8A and 8B.

Example 3

Peptide Binding Assays

The affinity of various peptides for hDcn1$^P$, hDcn2$^P$, hDcn3$^P$, hDcn4$^P$, and hDcn5$^P$ was tested using isothermal titration calorimetry as described in Example 1 and is provided in Table 29.

TABLE 29

Binding Kd (in μM) of peptides for hDcn1$^P$, hDcn2$^P$, hDcn3$^P$, hDcn4$^P$, and hDcn5$^P$.

| SEQ ID NO*: | Peptide | hDcn1$^P$ | hDcn2$^P$ | hDcn3$^P$ | hDcn4$^P$ | hDcn5$^P$ |
|---|---|---|---|---|---|---|
| 8 | hUbc12$^{Ac1-26}$ | 1.5 | 0.735 | 10.8 | 10 | 8.6 |
| 7 | hUbc12$^{1-26}$ | >200 | — | — | — | — |
| 9 | hUbc12$^{Ac-2-26}$ | >150 | — | — | — | — |
| 10 | hUbc12$^{Formyl-1-26}$ | 9.7 | — | — | — | — |
| 11 | hUbc12$^{Ac1-Ac3-26}$ | 4.6 | — | — | — | — |
| 12 | hUbc12$^{Ac1-12}$ | 2.1 | — | 6.3 | 13.1 | >30 |
| 17 | hUbc12$^{Ac1-12}$ (NorLeu) | 5.6 | — | — | — | — |
| 93 | hUbc12$^{1-12}$ (NorLeu) | >400 | — | — | — | — |

TABLE 29-continued

Binding Kd (in μM) of peptides for hDcn1$^P$, hDcn2$^P$, hDcn3$^P$, hDcn4$^P$, and hDcn5$^P$.

| SEQ ID NO*: | Peptide | hDcn1$^P$ | hDcn2$^P$ | hDcn3$^P$ | hDcn4$^P$ | hDcn5$^P$ |
|---|---|---|---|---|---|---|
| 18 | hUbc12$^{Ac1-12}$ (NorLeu) 5, 9 | 0.440 | — | — | — | — |
| 19 | hUbc12$^{Ac1-12}$ (NorLeu) 6, 10 | 0.8/1.2** | — | — | — | — |
| 20 | hUbc12$^{Ac1-12}$ (Met) 5, 9 | 0.153 | — | — | — | — |
| 21 | hUbc12$^{Ac1-12}$ (Met) SS 6, 10 | 0.0018/0.187** | — | — | — | — |
| 22 | hUbc12$^{Ac1-12}$ (Met) RR 6, 10 | 0.34/1 × 10$^-$29** | — | — | — | — |
| 23 | hUbc12$^{Ac1-12}$ (SeMet) 5, 9 | 0.182 | — | — | — | — |
| 24 | hUbc12$^{Ac1-12}$ (SeMet) 6, 10 | 0.00093/0.361** | — | — | — | — |
| 25 | hUbc12$^{Ac1-12}$ (Met) Oct:But 6, 10 | 0.129 | — | — | — | — |
| 26 | hUbc12$^{Ac1-12}$ (Met) But:Oct 6, 10 | 0.120 | — | 1.52 | — | 0.781 |
| 27 | hUbc12$^{Ac1-12}$ (Met) KE 5, 9 | 1.06 | — | — | — | — |
| 94 | hUbc12$^{Ac1-12}$ (Met) KE 6, 10 | 0.483 | — | — | — | — |
| 88 | hUbe2f$^{Ac1-25}$ | >500 | >400 | 2 | >40 | >30 |
| 14 | hUbe2f$^{1-25}$ | — | — | >400 | — | — |
| 87 | yUbc12$^{Ac1-24}$ | 0.311 | 0.204 | 3.4 | *1.2/13 | 2.4 |
| 88 | yUbc12$^{Ac1-12}$ (NorLeu) | 0.628 | 0.793 | — | — | — |
| 29 | yUbc12$^{Ac1-12}$ (NorLeu) 5, 9 | 0.418 | 0.515 | — | — | — |
| 30 | yUbc12$^{Ac1-12}$ (NorLeu) 6, 10 | 0.068 | 0.075 | 1.76 | 4.3 | 4.78 |
| 31 | yUbc12$^{Ac1-12}$ (Met) 6, 10 | 0.038/0.037** | — | — | — | — |

*Each of the peptides had an amidated carboxy-terminus.
**The binding isotherm from the titration best fit a two-site model for binding, but the stoichiometry of binding is additive to approximately one.

Example 4

Peptide Inhibition

Figure 9A:
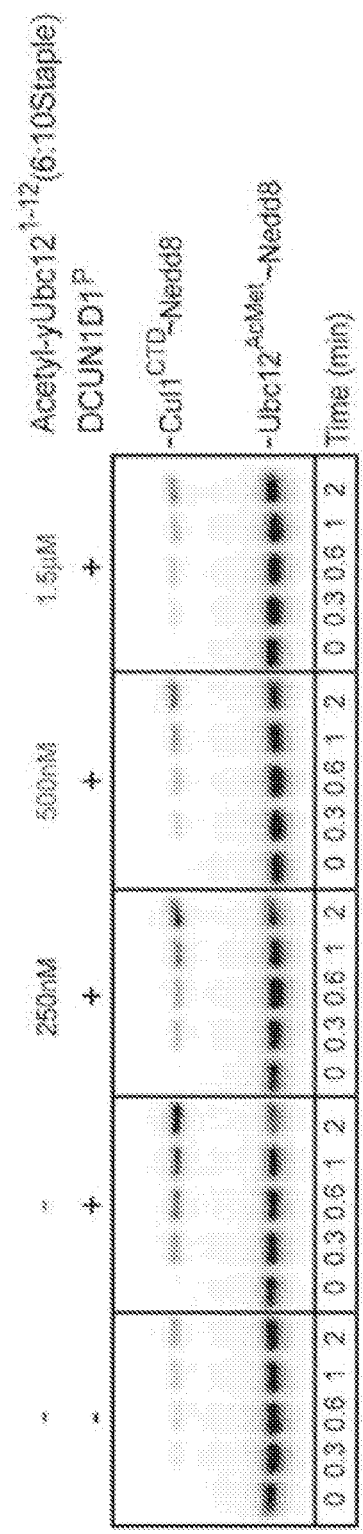
FIGS. 9A and 9B demonstrate the inhibition of DCUN1D1 potentiated NEDD8 modification of Cul1$^{CTD}$-Rbx1.
Figure 9B:
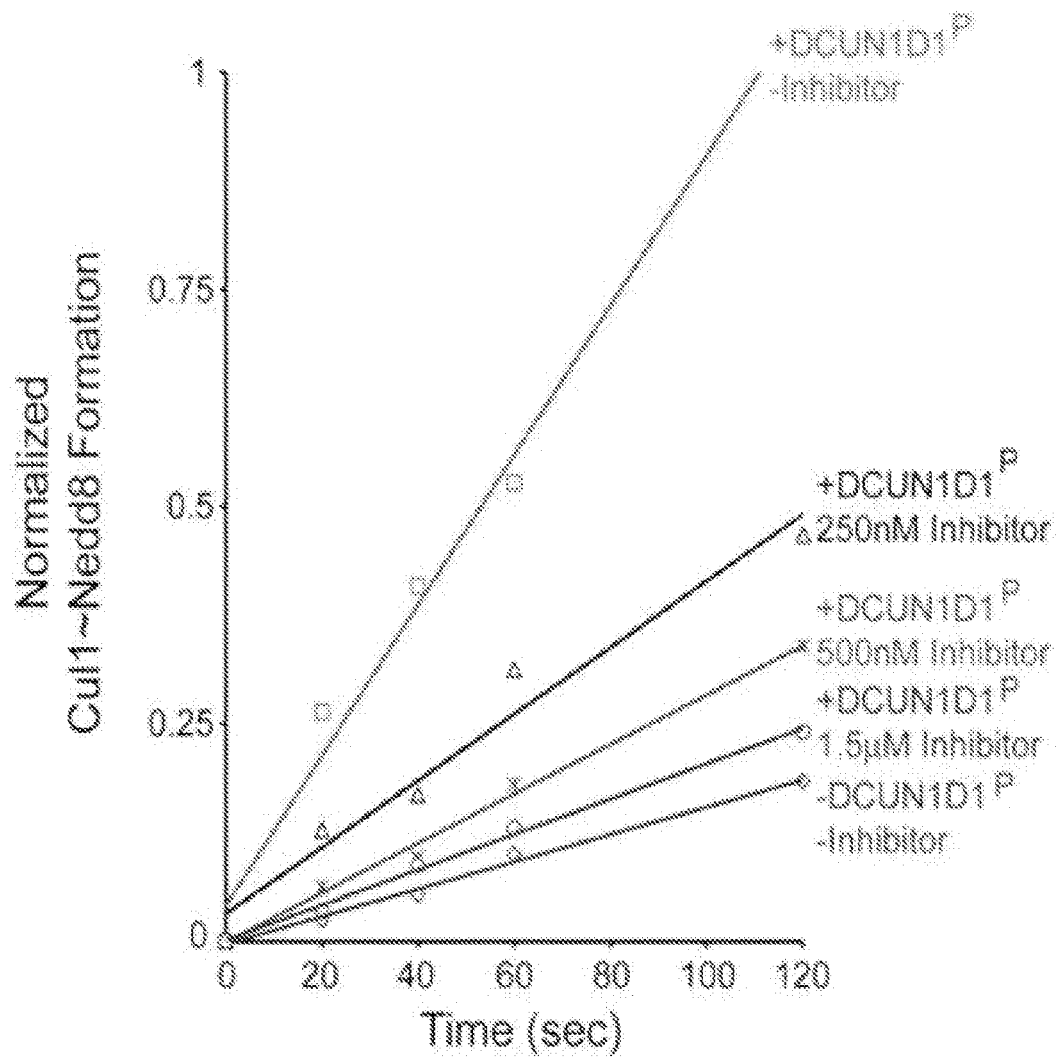

Pulse chase assays were used to monitor the transfer of Nedd8 from Ubc12$^{AcMet}$~Nedd8 to Cul1$^{CTD}$-Rbx1 in the absence or presence of DCUN1D1$^P$ and the indicated amounts of the peptide inhibitor Acetyl-yUbc12$^{1-12}$(6:10Staple). Results are provided in FIGS. 9A and 9B.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. This application hereby incorporates by reference in its entirety U.S. Provisional Application No. 61/486,972, filed May 17, 2011.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for identifying compounds that bind to an E2-binding pocket in a NEDD8 co-E3 protein, said method comprising performing a competitive binding assay using a peptide selected from the group consisting of:
 a peptide having the sequence set forth in SEQ ID NO: 7, 12, 13, 14, 15, or 16,
 wherein the nitrogen atom of the amino terminus of said peptide is covalently bound to at least one —R group, wherein said —R group is a substituted or unsubstituted alkyl, alkenyl, alkynyl, aryl, heteroaryl or has Formula (I):

wherein said —R$_2$ group is a hydrophobic moiety or hydrogen, wherein the methionine corresponding to position 1 of SEQ ID NO: 7, 12, 13, 14, 15, or 16 can be substituted with another amino acid residue having an unbranched hydrophobic side chain,
 wherein said peptide can comprise a hydrophobic staple, and
 wherein said peptide binds to an E2-binding pocket of Dcn1, DCUN1D1, DCUN1D2, DCUN1D3, DCUN1D4, or DCUN1D5.

2. The method of claim 1, wherein said —R group is a substituted or unsubstituted alkyl, alkenyl, alkynyl, aryl, or heteroaryl.

3. The method of claim 1, wherein said —R group is a formyl group.

4. The method of claim 1, wherein said —R group is not an acetyl group.

5. The method of claim 1, wherein said —R group has Formula (I):

wherein said —R$_2$ group is a hydrophobic moiety.

6. The method of claim 5, wherein said —R$_2$ group is alkyl or aryl.

7. The method of claim 1, wherein said unbranched hydrophobic side chain is an alkyl, alkenyl, or alkynyl.

8. The method of claim 1, wherein the methionine corresponding to position 1 in SEQ ID NO: 7, 12, 13, 14, 15, or 16 is substituted with a selenomethionine or a norleucine.

9. The method of claim 1, wherein said peptide comprises a hydrophobic staple.

10. The method of claim 9, wherein amino acid residues at positions X and X+4 are substituted with hydrophobic staple-forming amino acid residues, wherein X is not the first amino acid residue of the peptide.

11. The method of claim 10, wherein said hydrophobic staple-forming amino acid residues are selected from the group consisting of: (S)-2-(4-pentenyl)alanine, (R)-2-(4-pentenyl)alanine, (S)-2-(3-butenyl)alanine, (S)-2-(7-octenyl)alanine, lysine, and glutamic acid.

12. The method of claim 1, wherein the carboxy terminus of said peptide is amidated.

13. The method of claim 1, wherein said peptide inhibits co-E3 activity of said Dcn1, DCUN1D1, DCUN1D2, DCUN1D3, DCUN1D4, or DCUN1D5.

14. The method of claim 13, wherein said peptide inhibits the neddylation of a cullin.

15. The method of claim 1, wherein said method further comprises assaying the ability of said compound to inhibit the co-E3 activity of said Dcn1, DCUN1D1, DCUN1D2, DCUN1D3, DCUN1D4, or DCUN1D5.

* * * * *

UNITED STATES PATENT AND TRADEMARK OFFICE
CERTIFICATE OF CORRECTION

PATENT NO. : 9,447,156 B2
APPLICATION NO. : 14/118132
DATED : September 20, 2016
INVENTOR(S) : Monda et al.

It is certified that error appears in the above-identified patent and that said Letters Patent is hereby corrected as shown below:

In the Specification

At Column 1, under the heading "FEDERALLY SPONSORED RESEARCH OR DEVELOPMENT," at Lines 16-19, the text "This invention was made with United States Government support under grant number R01GM069530 awarded by the National Institutes of Health. The United States Government has certain rights in the invention." should be changed to --This invention was made with government support under grant GM069530 awarded by the National Institutes of Health. The government has certain rights in the invention.--

Signed and Sealed this
Twenty-second Day of January, 2019

Andrei Iancu
*Director of the United States Patent and Trademark Office*

SEQUENCE LISTING

<160> NUMBER OF SEQ ID NOS: 94

<210> SEQ ID NO 1
<211> LENGTH: 1540
<212> TYPE: DNA
<213> ORGANISM: Homo Sapiens
<220> FEATURE:
<221> NAME/KEY: CDS
<222> LOCATION: (596)...(1147)

<400> SEQUENCE: 1

```
aggcgcacaa cgcaggccgg gcgggaagag ccaaagcggg caggcggcgg aaatatccga      60
agcggcgggg cgcccgaggc cgttgccgac ctccgcgcta agccgctgc tgccgcggaa      120 gacgatcctc cagtacccgc ccgccgtcac cgcagctgcc gtgtcctcct cccaccccta     180
gccgcacccc ctcgcggagg gatcagctga gcggccaaac ggcacggtcg ggggagcccc     240
gagtccgcag ctgcagcggg gcctgagacc agagttggcg agggcaagga aggagcggcc     300 ccggcagtg ggggcgggc cgggcgggcc cgagaacagc cgaatttggc cgagcgctgc      360
cgagcgagtc cgaggcgctg gccaggccg agccggact acgggagccg aggcgggccg      420
cgcggtgggc gcggagagga gcggagcggc gcggcaggcc gggcgggtgg cggcagcagc     480
ggaggaggcc gcagctgcgg gtccgaggag cggaggcgac gcgggcggcg cgggggcc       540 gggtggccgg ggtcccgggc cccgcggcgg cggcagcggc ggcggcggcg gcagg atg      598
                                                                Met
                                                                 1 atc aag ctg ttc tcg ctg aag cag cag aag aag gag gag gag tcg gcg      646
Ile Lys Leu Phe Ser Leu Lys Gln Gln Lys Lys Glu Glu Glu Ser Ala
      5                  10                   15 ggc ggc acc aag ggc agc agc aag aag gcg tcg gcg gcg cag ctg cgg      694
Gly Gly Thr Lys Gly Ser Ser Lys Lys Ala Ser Ala Ala Gln Leu Arg
 20                  25                   30 atc cag aag gac ata aac gag ctg aac ctg ccc aag acg tgt gat atc      742
Ile Gln Lys Asp Ile Asn Glu Leu Asn Leu Pro Lys Thr Cys Asp Ile
 35                  40                   45 agc ttc tca gat cca gac gac ctc ctc aac ttc aag ctg gtc atc tgt      790
Ser Phe Ser Asp Pro Asp Asp Leu Leu Asn Phe Lys Leu Val Ile Cys
 50                  55                   60                  65 cct gat gag ggc ttc tac aag agt ggg aag ttt gtg ttc agt ttt aag      838
Pro Asp Glu Gly Phe Tyr Lys Ser Gly Lys Phe Val Phe Ser Phe Lys
              70                  75                  80 gtg ggc cag ggt tac ccg cat gat ccc ccc aag gtg aag tgt gag aca      886
Val Gly Gln Gly Tyr Pro His Asp Pro Pro Lys Val Lys Cys Glu Thr
         85                  90                  95 atg gtc tat cac ccc aac att gac ctc gag ggc aac gtc tgc ctc aac      934
Met Val Tyr His Pro Asn Ile Asp Leu Glu Gly Asn Val Cys Leu Asn
    100                 105                 110 atc ctc aga gag gac tgg aag cca gtc ctt acg ata aac tcc ata att      982
Ile Leu Arg Glu Asp Trp Lys Pro Val Leu Thr Ile Asn Ser Ile Ile
115                 120                 125 tat ggc ctg cag tat ctc ttc ttg gag ccc aac ccc gag gac cca ctg     1030
Tyr Gly Leu Gln Tyr Leu Phe Leu Glu Pro Asn Pro Glu Asp Pro Leu
130                 135                 140                 145 aac aag gag gcc gca gag gtc ctg cag aac aac cgg cgg ctg ttt gag     1078
Asn Lys Glu Ala Ala Glu Val Leu Gln Asn Asn Arg Arg Leu Phe Glu
             150                 155                 160 cag aac gtg cag cgc tcc atg cgg ggt ggc tac atc ggc tcc acc tac     1126
Gln Asn Val Gln Arg Ser Met Arg Gly Gly Tyr Ile Gly Ser Thr Tyr
         165                 170                 175 ttt gag cgc tgc ctg aaa tag ggttggcgca tacccacccc cgccacggcc        1177
Phe Glu Arg Cys Leu Lys
180 acaagccctg gcatcccctg caaatattta ttggggggcca tgggtagggg tttgggggc    1237 ggccggtggg ggaatcccct gccttggcct tgcctcccct tcctgccacg tgcccctagt   1297 tatttttttt ttttaacac catgtgatta aggtcggcgc tgcctccccc gacccactca    1357
```

```
gcgatgggaa atgaattggc ttgtctagcc cccctgctgg gtgcttgttc agcccccact   1417
ctgggctgtg gagtgggtgg gcaacgggcc tgggtagctg gcccaggca acccacccct    1477 ccacctctgg aggtcccacc aggctattaa aggggaatgt tactgcaaaa aaaaaaaaa    1537 aaa                                                                 1540

<210> SEQ ID NO 2
<211> LENGTH: 183
<212> TYPE: PRT
<213> ORGANISM: Homo Sapiens

<400> SEQUENCE: 2

Met Ile Lys Leu Phe Ser Leu Lys Gln Gln Lys Glu Glu Glu Ser
 1               5                  10                  15

Ala Gly Gly Thr Lys Gly Ser Ser Lys Lys Ala Ser Ala Ala Gln Leu
            20                  25                  30

Arg Ile Gln Lys Asp Ile Asn Glu Leu Asn Leu Pro Lys Thr Cys Asp
        35                  40                  45

Ile Ser Phe Ser Asp Pro Asp Leu Leu Asn Phe Lys Leu Val Ile
    50                  55                  60

Cys Pro Asp Glu Gly Phe Tyr Lys Ser Gly Lys Phe Val Phe Ser Phe
65                  70                  75                  80

Lys Val Gly Gln Gly Tyr Pro His Asp Pro Pro Lys Val Lys Cys Glu
                85                  90                  95

Thr Met Val Tyr His Pro Asn Ile Asp Leu Glu Gly Asn Val Cys Leu
            100                 105                 110

Asn Ile Leu Arg Glu Asp Trp Lys Pro Val Leu Thr Ile Asn Ser Ile
        115                 120                 125

Ile Tyr Gly Leu Gln Tyr Leu Phe Leu Glu Pro Asn Pro Glu Asp Pro
    130                 135                 140

Leu Asn Lys Glu Ala Ala Glu Val Leu Gln Asn Asn Arg Arg Leu Phe
145                 150                 155                 160

Glu Gln Asn Val Gln Arg Ser Met Arg Gly Tyr Ile Gly Ser Thr
                165                 170                 175

Tyr Phe Glu Arg Cys Leu Lys
            180

<210> SEQ ID NO 3
<211> LENGTH: 2206
<212> TYPE: DNA
<213> ORGANISM: Homo Sapiens
<220> FEATURE:
<221> NAME/KEY: CDS
<222> LOCATION: (205)...(762)

<400> SEQUENCE: 3 ttttttttt aaagcgcccg ctgctgtctc ggctgccgcg ggcgagagcg gccgagtccc   60
cgccccgcca cttccggtcc cgccgccggg agcggtgcg gctgtgaggg gccgcgtctc   120
gcagcagccg cccggaccgg gcatggtgtt gggcgccggg cccgcctcgc ctgtctcggg   180
gagcccaggg taaaggcagc agta atg cta acg cta gca agt aaa ctg aag    231
                        Met Leu Thr Leu Ala Ser Lys Leu Lys
                         1               5 cgt gac gat ggt ctc aaa ggg tcc cgg acg gca gcc aca gcg tcc gac    279
Arg Asp Asp Gly Leu Lys Gly Ser Arg Thr Ala Ala Thr Ala Ser Asp
 10              15                  20                  25 tcg act cgg agg gtt tct gtg aga gac aaa ttg ctt gtt aaa gag gtt    327
Ser Thr Arg Arg Val Ser Val Arg Asp Lys Leu Leu Val Lys Glu Val
```

|  |  |  |  |  |  |  |  |  |  |  |  |  |  |  |  |
|---|---|---|---|---|---|---|---|---|---|---|---|---|---|---|---|
|  |  | 30 |  |  |  | 35 |  |  |  |  | 40 |  |  |  |  |
| gca | gaa | ctt | gaa | gct | aat | tta | cct | tgt | aca | tgt | aaa | gtg | cat | ttt | cct | 375 |
| Ala | Glu | Leu | Glu | Ala | Asn | Leu | Pro | Cys | Thr | Cys | Lys | Val | His | Phe | Pro |
|  |  | 45 |  |  |  | 50 |  |  |  |  | 55 |  |  |  |  |
| gat | cca | aac | aag | ctt | cat | tgt | ttt | cag | cta | aca | gta | acc | cca | gat | gag | 423 |
| Asp | Pro | Asn | Lys | Leu | His | Cys | Phe | Gln | Leu | Thr | Val | Thr | Pro | Asp | Glu |
|  |  |  | 60 |  |  |  | 65 |  |  |  |  | 70 |  |  |  |
| ggt | tac | tac | cag | ggt | gga | aaa | ttt | cag | ttt | gaa | act | gaa | gtt | ccc | gat | 471 |
| Gly | Tyr | Tyr | Gln | Gly | Gly | Lys | Phe | Gln | Phe | Glu | Thr | Glu | Val | Pro | Asp |
|  | 75 |  |  |  |  | 80 |  |  |  |  | 85 |  |  |  |  |
| gcg | tac | aac | atg | gtg | cct | ccc | aaa | gtg | aaa | tgc | ctg | acc | aag | atc | tgg | 519 |
| Ala | Tyr | Asn | Met | Val | Pro | Pro | Lys | Val | Lys | Cys | Leu | Thr | Lys | Ile | Trp |
| 90 |  |  |  |  | 95 |  |  |  |  | 100 |  |  |  |  | 105 |
| cac | ccc | aac | atc | aca | gag | aca | ggg | gaa | ata | tgt | ctg | agt | tta | ttg | aga | 567 |
| His | Pro | Asn | Ile | Thr | Glu | Thr | Gly | Glu | Ile | Cys | Leu | Ser | Leu | Leu | Arg |
|  |  |  |  | 110 |  |  |  |  | 115 |  |  |  |  | 120 |  |
| gaa | cat | tca | att | gat | ggc | act | ggc | tgg | gct | ccc | aca | aga | aca | tta | aag | 615 |
| Glu | His | Ser | Ile | Asp | Gly | Thr | Gly | Trp | Ala | Pro | Thr | Arg | Thr | Leu | Lys |
|  |  |  | 125 |  |  |  |  | 130 |  |  |  |  | 135 |  |  |
| gat | gtc | gtt | tgg | gga | tta | aac | tct | ttg | ttt | act | gat | ctt | ttg | aat | ttt | 663 |
| Asp | Val | Val | Trp | Gly | Leu | Asn | Ser | Leu | Phe | Thr | Asp | Leu | Leu | Asn | Phe |
|  |  | 140 |  |  |  |  | 145 |  |  |  |  | 150 |  |  |  |
| gat | gat | cca | ctg | aat | att | gaa | gct | gca | gaa | cat | cat | ttg | cgg | gac | aag | 711 |
| Asp | Asp | Pro | Leu | Asn | Ile | Glu | Ala | Ala | Glu | His | His | Leu | Arg | Asp | Lys |
|  | 155 |  |  |  |  | 160 |  |  |  |  | 165 |  |  |  |  |
| gag | gac | ttc | cgg | aat | aaa | gtg | gat | gac | tac | atc | aaa | cgt | tat | gcc | aga | 759 |
| Glu | Asp | Phe | Arg | Asn | Lys | Val | Asp | Asp | Tyr | Ile | Lys | Arg | Tyr | Ala | Arg |
| 170 |  |  |  | 175 |  |  |  |  | 180 |  |  |  |  | 185 |  |

|  |  |  |  |  |
|---|---|---|---|---|
|  | tga | taaaagggga | cgattgcagg | cccatggact | gtgttacagt | tgtctctaa | 812 |
| catgaaacag | caagaggtag | cccctctcc | cgtcctcatg | ctccctctca | gtccctggga | 872 |
| ttgccccagt | cctgtgacca | tgttgccctg | aagaagacca | tcttcatgac | tgctcattgt | 932 |
| agatggagaa | ttcaacataa | atacagcaag | aaaatgtgtt | tgggcttctg | aagagttgtc | 992 |
| tgcttacctt | aacatgttta | cttttttgaa | cttgtactgt | ataggctgtt | ggtgaaattc | 1052 |
| ttaagaagtt | gtaatgaact | caaaattgag | gccagagctt | gctttccctt | ttcccaaaca | 1112 |
| aaattggttt | tctgcacaag | cgatgctaat | gatgtgttca | gtgtaactcg | cagattggca | 1172 |
| ataagatacc | cgctacaaac | tgtgattgga | tgcaaaatct | cttagcttct | ttcacgaatg | 1232 |
| ttggccctgc | ctagatgttg | tgaagcctcc | cagaatgcat | agagtcattc | actgtagatc | 1292 |
| tcttattgaa | atgcgtattt | tatttaatgt | aagtatattt | tggaacagat | tgtaatttg | 1352 |
| tacaattcaa | tgctttaatt | attttttcta | ttctcattta | gtttgtattt | tcattgtata | 1412 |
| gagcagacag | aaagatgttg | ggtcaagcaa | ctattgaaga | gaaatacaaa | gaaaatatga | 1472 |
| aaggcacatt | attcattttg | tccaaatgca | atgagaatct | cactcttaaa | aatcagctct | 1532 |
| tgctttcggg | tccggatgtg | gtgagcacat | ttttggagccc | tttgaagcta | gatttggatg | 1592 |
| atcaaaacaa | aaaggcaggg | agcccattct | aacatgctgc | ccagaggaaa | ctggctggag | 1652 |
| cctggaccag | ctggggttga | tgcttttgca | gtggtcatgt | gattgtgacc | tggtagctac | 1712 |
| ttatcagaga | gccagaccct | gctgtcctgg | gagacaggag | cgatgcctca | ggaatcagcc | 1772 |
| caatgtctga | tgtcactgag | actgtacctg | tggccttctt | ctgagtttgc | tatggctcca | 1832 |
| ggccctgccg | gtggggtgag | cctcctaggc | cttggaggac | caggagtcaa | cagtggcata | 1892 |
| tgccatcctc | ggccaggtta | atatactgca | gaggaaaagc | cctgaagaga | ggcaagtgga | 1952 |
| tttactccag | catgtagaca | tttgaaccag | tgaaatcaaa | cacaaaataa | atgtctgtct | 2012 |

```
agtttcattt gctgcctgcc taacactctc aaacttaact gccagcttcc ttagacctct    2072
ggattccccc atctgccatc tactgggttt agtttgtttt tcttaattta tagaatctct    2132
gattgtgaga tcagtctgtc acggagaccc agcaggtgag gaatgtaggc cttgcttcct    2192
ctttgcaccc atta                                                      2206
```

```
<210> SEQ ID NO 4
<211> LENGTH: 185
<212> TYPE: PRT
<213> ORGANISM: Homo Sapiens

<400> SEQUENCE: 4

Met Leu Thr Leu Ala Ser Lys Leu Lys Arg Asp Asp Gly Leu Lys Gly
 1               5                  10                  15

Ser Arg Thr Ala Ala Thr Ala Ser Asp Ser Thr Arg Arg Val Ser Val
                20                  25                  30

Arg Asp Lys Leu Leu Val Lys Glu Val Ala Glu Leu Glu Ala Asn Leu
            35                  40                  45

Pro Cys Thr Cys Lys Val His Phe Pro Asp Pro Asn Lys Leu His Cys
    50                  55                  60

Phe Gln Leu Thr Val Thr Pro Asp Glu Gly Tyr Tyr Gln Gly Gly Lys
65                  70                  75                  80

Phe Gln Phe Glu Thr Glu Val Pro Asp Ala Tyr Asn Met Val Pro Pro
                85                  90                  95

Lys Val Lys Cys Leu Thr Lys Ile Trp His Pro Asn Ile Thr Glu Thr
            100                 105                 110

Gly Glu Ile Cys Leu Ser Leu Leu Arg Glu His Ser Ile Asp Gly Thr
        115                 120                 125

Gly Trp Ala Pro Thr Arg Thr Leu Lys Asp Val Val Trp Gly Leu Asn
    130                 135                 140

Ser Leu Phe Thr Asp Leu Leu Asn Phe Asp Asp Pro Leu Asn Ile Glu
145                 150                 155                 160

Ala Ala Glu His His Leu Arg Asp Lys Glu Asp Phe Arg Asn Lys Val
                165                 170                 175

Asp Asp Tyr Ile Lys Arg Tyr Ala Arg
            180                 185

<210> SEQ ID NO 5
<211> LENGTH: 567
<212> TYPE: DNA
<213> ORGANISM: Saccharomyces cerevisiae
<220> FEATURE:
<221> NAME/KEY: CDS
<222> LOCATION: (1)...(567)

<400> SEQUENCE: 5 atg ttg aaa tta cgc caa tta caa aag aaa aag caa aaa gaa aat gaa    48
Met Leu Lys Leu Arg Gln Leu Gln Lys Lys Lys Gln Lys Glu Asn Glu
 1               5                  10                  15 aac agc agt tct att cag cct aat tta tcg gca gca aga att cgt ttg    96
Asn Ser Ser Ser Ile Gln Pro Asn Leu Ser Ala Ala Arg Ile Arg Leu
                20                  25                  30 aaa agg gac ctt gat tcg ctg gac ctc cca cca aca gtg act ttg aat    144
Lys Arg Asp Leu Asp Ser Leu Asp Leu Pro Pro Thr Val Thr Leu Asn
            35                  40                  45 gta ata aca tca cca gat agt gcg gat aga tca caa tcg ccg aaa ttg    192
Val Ile Thr Ser Pro Asp Ser Ala Asp Arg Ser Gln Ser Pro Lys Leu
    50                  55                  60
```

```
gag gta att gtt agg cct gat gaa gga tat tat aat tat gga tct att      240
Glu Val Ile Val Arg Pro Asp Glu Gly Tyr Tyr Asn Tyr Gly Ser Ile
 65                  70                  75                  80 aat ttc aat ttg gat ttt aac gaa gtt tat ccg att gaa cca cca aaa      288
Asn Phe Asn Leu Asp Phe Asn Glu Val Tyr Pro Ile Glu Pro Pro Lys
                 85                  90                  95 gtt gta tgt ttg aag aag atc ttt cat cca aat atc gat tta aag ggg      336
Val Val Cys Leu Lys Lys Ile Phe His Pro Asn Ile Asp Leu Lys Gly
            100                 105                 110 aac gtt tgc cta aat att ctt cga gaa gac tgg tcg cca gct cta gat      384
Asn Val Cys Leu Asn Ile Leu Arg Glu Asp Trp Ser Pro Ala Leu Asp
        115                 120                 125 ttg cag agt att ata acc ggg ctt ctt ttc ttg ttc ttg gag cct aat      432
Leu Gln Ser Ile Ile Thr Gly Leu Leu Phe Leu Phe Leu Glu Pro Asn
    130                 135                 140 ccc aat gac ccg tta aac aag gat gca gca aag tta ctg tgt gag ggt      480
Pro Asn Asp Pro Leu Asn Lys Asp Ala Ala Lys Leu Leu Cys Glu Gly
145                 150                 155                 160 gag aaa gaa ttt gct gaa gct gtg aga ttg acc atg tct gga ggt tca      528
Glu Lys Glu Phe Ala Glu Ala Val Arg Leu Thr Met Ser Gly Gly Ser
                165                 170                 175 att gaa cat gtc aaa tat gat aac ata gtt tct cct tga                  567
Ile Glu His Val Lys Tyr Asp Asn Ile Val Ser Pro
                180                 185

<210> SEQ ID NO 6
<211> LENGTH: 188
<212> TYPE: PRT
<213> ORGANISM: Saccharomyces cerevisiae

<400> SEQUENCE: 6

Met Leu Lys Leu Arg Gln Leu Gln Lys Lys Gln Lys Glu Asn Glu
 1               5                  10                  15

Asn Ser Ser Ser Ile Gln Pro Asn Leu Ser Ala Ala Arg Ile Arg Leu
                 20                  25                  30

Lys Arg Asp Leu Asp Ser Leu Asp Leu Pro Pro Thr Val Thr Leu Asn
            35                  40                  45

Val Ile Thr Ser Pro Asp Ser Ala Asp Arg Ser Gln Ser Pro Lys Leu
 50                  55                  60

Glu Val Ile Val Arg Pro Asp Glu Gly Tyr Tyr Asn Tyr Gly Ser Ile
 65                  70                  75                  80

Asn Phe Asn Leu Asp Phe Asn Glu Val Tyr Pro Ile Glu Pro Pro Lys
                 85                  90                  95

Val Val Cys Leu Lys Lys Ile Phe His Pro Asn Ile Asp Leu Lys Gly
            100                 105                 110

Asn Val Cys Leu Asn Ile Leu Arg Glu Asp Trp Ser Pro Ala Leu Asp
        115                 120                 125

Leu Gln Ser Ile Ile Thr Gly Leu Leu Phe Leu Phe Leu Glu Pro Asn
    130                 135                 140

Pro Asn Asp Pro Leu Asn Lys Asp Ala Ala Lys Leu Leu Cys Glu Gly
145                 150                 155                 160

Glu Lys Glu Phe Ala Glu Ala Val Arg Leu Thr Met Ser Gly Gly Ser
                165                 170                 175

Ile Glu His Val Lys Tyr Asp Asn Ile Val Ser Pro
                180                 185

<210> SEQ ID NO 7
```

```
<211> LENGTH: 26
<212> TYPE: PRT
<213> ORGANISM: Homo Sapiens

<400> SEQUENCE: 7

Met Ile Lys Leu Phe Ser Leu Lys Gln Gln Lys Lys Glu Glu Glu Ser
1               5                   10                  15

Ala Gly Gly Thr Lys Gly Ser Ser Lys Lys
            20                  25

<210> SEQ ID NO 8
<211> LENGTH: 26
<212> TYPE: PRT
<213> ORGANISM: Artificial Sequence
<220> FEATURE:
<223> OTHER INFORMATION: Fragment of amino-terminally acetylated Homo
      sapiens Ubc12 (residues 1-26)
<220> FEATURE:
<221> NAME/KEY: ACETYLATION
<222> LOCATION: (1)...(1)
<223> OTHER INFORMATION: The acetyl group is covalently bound to the
      backbone nitrogen of methionine

<400> SEQUENCE: 8

Met Ile Lys Leu Phe Ser Leu Lys Gln Gln Lys Lys Glu Glu Glu Ser
1               5                   10                  15

Ala Gly Gly Thr Lys Gly Ser Ser Lys Lys
            20                  25

<210> SEQ ID NO 9
<211> LENGTH: 25
<212> TYPE: PRT
<213> ORGANISM: Artificial Sequence
<220> FEATURE:
<223> OTHER INFORMATION: Fragment of amino-terminally acetylated Homo
      sapiens Ubc12 (residues 2-26)
<220> FEATURE:
<221> NAME/KEY: ACETYLATION
<222> LOCATION: (1)...(1)
<223> OTHER INFORMATION: The acetyl group is covalently bound to the
      backbone nitrogen of Isoleucine

<400> SEQUENCE: 9

Ile Lys Leu Phe Ser Leu Lys Gln Gln Lys Lys Glu Glu Glu Ser Ala
1               5                   10                  15

Gly Gly Thr Lys Gly Ser Ser Lys Lys
            20                  25

<210> SEQ ID NO 10
<211> LENGTH: 26
<212> TYPE: PRT
<213> ORGANISM: Artificial Sequence
<220> FEATURE:
<223> OTHER INFORMATION: Fragment of amino-terminally formylated Homo
      sapiens Ubc12 (residues 1-26)
<220> FEATURE:
<221> NAME/KEY: FORMYLATION
<222> LOCATION: (1)...(1)
<223> OTHER INFORMATION: The formyl group is covalently bound to the
      backbone nitrogen of methionine

<400> SEQUENCE: 10

Met Ile Lys Leu Phe Ser Leu Lys Gln Gln Lys Lys Glu Glu Glu Ser
1               5                   10                  15

Ala Gly Gly Thr Lys Gly Ser Ser Lys Lys
            20                  25
```

```
<210> SEQ ID NO 11
<211> LENGTH: 26
<212> TYPE: PRT
<213> ORGANISM: Artificial Sequence
<220> FEATURE:
<223> OTHER INFORMATION: Fragment of amino-terminally acetylated Homo
      sapiens Ubc12 (residues 1-26) with an
      acetyl-lysine at position 3
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: (3)...(3)
<223> OTHER INFORMATION: Xaa= acetyl-lysine

<400> SEQUENCE: 11

Met Ile Xaa Leu Phe Ser Leu Lys Gln Gln Lys Glu Glu Glu Ser
 1               5                  10                  15

Ala Gly Gly Thr Lys Gly Ser Ser Lys Lys
            20                  25

<210> SEQ ID NO 12
<211> LENGTH: 12
<212> TYPE: PRT
<213> ORGANISM: Homo sapiens

<400> SEQUENCE: 12

Met Ile Lys Leu Phe Ser Leu Lys Gln Gln Lys Lys
 1               5                  10

<210> SEQ ID NO 13
<211> LENGTH: 12
<212> TYPE: PRT
<213> ORGANISM: Homo sapiens

<400> SEQUENCE: 13

Met Leu Thr Leu Ala Ser Lys Leu Lys Arg Asp Asp
 1               5                  10

<210> SEQ ID NO 14
<211> LENGTH: 25
<212> TYPE: PRT
<213> ORGANISM: Homo sapiens

<400> SEQUENCE: 14

Met Leu Thr Leu Ala Ser Lys Leu Lys Arg Asp Asp Gly Leu Lys Gly
 1               5                  10                  15

Ser Arg Thr Ala Ala Thr Ala Ser Asp
            20                  25

<210> SEQ ID NO 15
<211> LENGTH: 24
<212> TYPE: PRT
<213> ORGANISM: Saccharomyces cerevisiae

<400> SEQUENCE: 15

Met Leu Lys Leu Arg Gln Leu Gln Lys Lys Lys Gln Lys Glu Asn Glu
 1               5                  10                  15

Asn Ser Ser Ser Ile Gln Pro Asn
            20

<210> SEQ ID NO 16
<211> LENGTH: 12
```

```
<212> TYPE: PRT
<213> ORGANISM: Saccharomyces cerevisiae

<400> SEQUENCE: 16

Met Leu Lys Leu Arg Gln Leu Gln Lys Lys Lys Gln
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Fragment of Homo sapiens Ubc12 (residues 1-12)
      with N-acetyl-norleucine at position 1
<220> FEATURE:
<221> NAME/KEY: VARIANT
<222> LOCATION: (1)...(1)
<223> OTHER INFORMATION: Xaa= N-acetyl-norleucine

<400> SEQUENCE: 17

Xaa Ile Lys Leu Phe Ser Leu Lys Gln Gln Lys Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Fragment of Homo sapiens Ubc12 (residues 1-12)
      with N-acetyl-norleucine at position 1 and
      (S)-2-(4-pentenyl)alanine at positions 5 and 9
<220> FEATURE:
<221> NAME/KEY: VARIANT
<222> LOCATION: (1)...(1)
<223> OTHER INFORMATION: Xaa at position 1= N-acetyl-norleucine
<220> FEATURE:
<221> NAME/KEY: VARIANT
<222> LOCATION: 5, 9
<223> OTHER INFORMATION: Xaa at positions 5 and 9=
      (S)-2-(4-pentenyl)alanine

<400> SEQUENCE: 18

Xaa Ile Lys Leu Xaa Ser Leu Lys Xaa Gln Lys Lys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Fragment of Homo sapiens Ubc12 (residues 1-12)
      with N-acetyl-norleucine at postion 1 and
      (S)-2-(4-pentenyl)alanine at positions 6 and 10
<220> FEATURE:
<221> NAME/KEY: VARIANT
<222> LOCATION: (1)...(1)
<223> OTHER INFORMATION: Xaa= N-acetyl-norleucine
<220> FEATURE:
<221> NAME/KEY: VARIANT
<222> LOCATION: 6, 10
<223> OTHER INFORMATION: Xaa at positions 6 and 10=
      (S)-2-(4-pentenyl)alanine

<400> SEQUENCE: 19

Xaa Ile Lys Leu Phe Xaa Leu Lys Gln Xaa Lys Lys
1               5                   10

<210> SEQ ID NO 20
<211> LENGTH: 12
<212> TYPE: PRT
<213> ORGANISM: Artificial Sequence
```

```
<220> FEATURE:
<223> OTHER INFORMATION: Fragment of N-terminally acetylated Homo
      sapiens Ubc12 (residues 1-12)  with
      (S)-2-(4-pentenyl)alanine at positions 5 and 9
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: 5, 9
<223> OTHER INFORMATION: Xaa at postions 5 and 9= (S)-2-
      (4-pentenyl)alanine

<400> SEQUENCE: 20

Met Ile Lys Leu Xaa Ser Leu Lys Xaa Gln Lys Lys
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-12)  with
      (S)-2-(4-pentenyl)alanine at positions 6 and 10
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: 6, 10
<223> OTHER INFORMATION: Xaa at positions 6 and 10=
      (S)-2-(4-pentenyl)alanine

<400> SEQUENCE: 21

Met Ile Lys Leu Phe Xaa Leu Lys Gln Xaa Lys Lys
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-12)  with
      (R)-2-(4-pentenyl)alanine at positions 6 and 10
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: 6, 10
<223> OTHER INFORMATION: Xaa at positions 6 and 10=
      (R)-2-(4-pentenyl)alanine

<400> SEQUENCE: 22

Met Ile Lys Leu Phe Xaa Leu Lys Gln Xaa Lys Lys
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-12)  with
      N-acetyl-selenomethionine at position 1 and
```

```
        (S)-2-(4-pentenyl)alanine at positions 5 and 9
<220> FEATURE:
<221> NAME/KEY: VARIANT
<222> LOCATION: (1)...(1)
<223> OTHER INFORMATION: Xaa at position 1= N-acetyl-selenomethionine
<220> FEATURE:
<221> NAME/KEY: VARIANT
<222> LOCATION: 5, 9
<223> OTHER INFORMATION: Xaa at positions 5 and 9=
        (S)-2-(4-pentenyl)alanine

<400> SEQUENCE: 23

Xaa Ile Lys Leu Xaa Ser Leu Lys Xaa Gln Lys Lys
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Fragment of N-terminally acetylated Homo
        sapiens Ubc12 (residues 1-12)  with
        N-acetyl-selenomethionine at position 1 and
        (S)-2-(4-pentenyl)alanine at positions 6 and 10
<220> FEATURE:
<221> NAME/KEY: VARIANT
<222> LOCATION: (1)...(1)
<223> OTHER INFORMATION: Xaa at position 1= N-acetyl-selenomethionine
<220> FEATURE:
<221> NAME/KEY: VARIANT
<222> LOCATION: 6, 10
<223> OTHER INFORMATION: Xaa at positions 6 and 10=
        (S)-2-(4-pentenyl)alanine

<400> SEQUENCE: 24

Xaa Ile Lys Leu Phe Xaa Leu Lys Gln Xaa Lys Lys
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Fragment of N-terminally acetylated Homo
        sapiens Ubc12 (residues 1-12)  with
        (S)-2-(7-octenyl)alanine at position 6 and
        (S)-2-(3-butenyl)alanine at position 10
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: (6)...(6)
<223> OTHER INFORMATION: Xaa at position 6= (S)-2-(7-octenyl)alanine
<220> FEATURE:
<221> NAME/KEY: VARIANT
<222> LOCATION: (10)...(10)
<223> OTHER INFORMATION: Xaa at position 10= (S)-2-(3-butenyl)alanine

<400> SEQUENCE: 25

Met Ile Lys Leu Phe Xaa Leu Lys Gln Xaa Lys Lys
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Fragment of N-terminally acetylated Homo
        sapiens Ubc12 (residues 1-12)  with
        (S)-2-(3-butenyl)alanine at position 6 and
```

```
      (S)-2-(7-octenyl)alanine at position 10
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: (6)...(6)
<223> OTHER INFORMATION: Xaa at position 6= (S)-2-(3-butenyl)alanine
<220> FEATURE:
<221> NAME/KEY: VARIANT
<222> LOCATION: (10)...(10)
<223> OTHER INFORMATION: Xaa at position 10 (S)-2-(7-octenyl)alanine

<400> SEQUENCE: 26

Met Ile Lys Leu Phe Xaa Leu Lys Gln Xaa Lys Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-12)  with lysine at position 5
      and glutamic acid at postion 9
<220> FEATURE:
<221> NAME/KEY: ACETYLATION
<222> LOCATION: (1)...(1)
<223> OTHER INFORMATION: The acetyl group is covalently bound to the
      backbone nitrogen of methionine

<400> SEQUENCE: 27

Met Ile Lys Leu Lys Ser Leu Lys Glu Gln Lys Lys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Fragment of N-terminally acetylated
      Saccharomyces cerevisiae Ubc12 (residues 1-12)  with
      N-acetyl-norleucine at position 1
<220> FEATURE:
<221> NAME/KEY: VARIANT
<222> LOCATION: (1)...(1)
<223> OTHER INFORMATION: Xaa at position 1= N-acetyl-norleucine

<400> SEQUENCE: 28

Xaa Leu Lys Leu Arg Gln Leu Gln Lys Lys Lys Gln
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Fragment of Saccharomyces cerevisiae Ubc12
      (residues 1-12)  with N-acetyl-norleucine at
      position 1, and (S)-2-(4-pentenyl)alanine at
      postions 5 and 9
<220> FEATURE:
<221> NAME/KEY: VARIANT
<222> LOCATION: (1)...(1)
<223> OTHER INFORMATION: Xaa at position 1= N-acetyl-norleucine
<220> FEATURE:
<221> NAME/KEY: VARIANT
<222> LOCATION: 5, 9
<223> OTHER INFORMATION: Xaa at positions 5 and 9=
      (S)-2-(4-pentenyl)alanine
```

<400> SEQUENCE: 29

Xaa Leu Lys Leu Xaa Gln Leu Gln Xaa Lys Lys Gln
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Fragment of Saccharomyces cerevisiae Ubc12
      (residues 1-12) with N-acetyl-norleucine at
      position 1, and (S)-2-(4-pentenyl)alanine at
      postions 6 and 10
<220> FEATURE:
<221> NAME/KEY: VARIANT
<222> LOCATION: (1)...(1)
<223> OTHER INFORMATION: Xaa at position 1= N-acetyl-norleucine
<220> FEATURE:
<221> NAME/KEY: VARIANT
<222> LOCATION: 6, 10
<223> OTHER INFORMATION: Xaa at positions 6 and 10=
      (S)-2-(4-pentenyl)alanine

<400> SEQUENCE: 30

Xaa Leu Lys Leu Arg Xaa Leu Gln Lys Xaa Lys Gln
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Fragment of N-terminally acetylated
      Saccharomyces cerevisiae Ubc12 (residues 1-12) with
      (S)-2-(4-pentenyl)alanine at postions 6 and 10
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
<220> FEATURE:
<221> NAME/KEY: VARIANT
<222> LOCATION: 6, 10
<223> OTHER INFORMATION: Xaa at positions 6 and 10=
      (S)-2-(4-pentenyl)alanine

<400> SEQUENCE: 31

Met Leu Lys Leu Arg Xaa Leu Gln Lys Xaa Lys Gln
1               5                   10

<210> SEQ ID NO 32
<211> LENGTH: 3192
<212> TYPE: DNA
<213> ORGANISM: Homo sapiens
<220> FEATURE:
<221> NAME/KEY: CDS
<222> LOCATION: (50)...(829)

<400> SEQUENCE: 32
attcgctgcg gagccggagg aggagggag aggcctggag gacaccaac atg aac aag      58
                                                     Met Asn Lys
                                                      1 ttg aaa tca tcg cag aag gat aaa gtt cgt cag ttt atg atc ttc aca      106
Leu Lys Ser Ser Gln Lys Asp Lys Val Arg Gln Phe Met Ile Phe Thr
 5                  10                  15 caa tct agt gaa aaa aca gca gta agt tgt ctt tct caa aat gac tgg      154
Gln Ser Ser Glu Lys Thr Ala Val Ser Cys Leu Ser Gln Asn Asp Trp
         20                 25                  30              35 aag tta gat gtt gca aca gat aat ttt ttc caa aat cct gaa ctt tat      202

```
                Lys Leu Asp Val Ala Thr Asp Asn Phe Phe Gln Asn Pro Glu Leu Tyr
                            40                  45                  50 ata cga gag agt gta aaa gga tca ttg gac agg aag aag tta gaa cag              250
Ile Arg Glu Ser Val Lys Gly Ser Leu Asp Arg Lys Lys Leu Glu Gln
            55                  60                  65 ctg tac aat aga tac aaa gac cct caa gat gag aat aaa att gga ata              298
Leu Tyr Asn Arg Tyr Lys Asp Pro Gln Asp Glu Asn Lys Ile Gly Ile
        70                  75                  80 gat ggc ata cag cag ttc tgt gat gac ctg gca ctc gat cca gcc agc              346
Asp Gly Ile Gln Gln Phe Cys Asp Asp Leu Ala Leu Asp Pro Ala Ser
    85                  90                  95 att agt gtg ttg att att gcg tgg aag ttc aga gca gca aca cag tgc              394
Ile Ser Val Leu Ile Ile Ala Trp Lys Phe Arg Ala Ala Thr Gln Cys
100                 105                 110                 115 gag ttc tcc aaa cag gag ttc atg gat ggc atg aca gaa tta gga tgt              442
Glu Phe Ser Lys Gln Glu Phe Met Asp Gly Met Thr Glu Leu Gly Cys
                120                 125                 130 gac agc ata gaa aaa cta aag gcc cag ata ccc aag atg gaa caa gaa              490
Asp Ser Ile Glu Lys Leu Lys Ala Gln Ile Pro Lys Met Glu Gln Glu
            135                 140                 145 ttg aaa gaa cca gga cga ttt aag gat ttt tac cag ttt act ttt aat              538
Leu Lys Glu Pro Gly Arg Phe Lys Asp Phe Tyr Gln Phe Thr Phe Asn
        150                 155                 160 ttt gca aag aat cca gga caa aaa gga tta gat cta gaa atg gcc att              586
Phe Ala Lys Asn Pro Gly Gln Lys Gly Leu Asp Leu Glu Met Ala Ile
    165                 170                 175 gcc tac tgg aac tta gtg ctt aat gga aga ttt aaa ttc tta gac tta              634
Ala Tyr Trp Asn Leu Val Leu Asn Gly Arg Phe Lys Phe Leu Asp Leu
180                 185                 190                 195 tgg aat aaa ttt ttg ttg gaa cat cat aaa cga tca ata cca aaa gac              682
Trp Asn Lys Phe Leu Leu Glu His His Lys Arg Ser Ile Pro Lys Asp
                200                 205                 210 act tgg aat ctt ctt tta gac ttc agt acg atg att gca gat gac atg              730
Thr Trp Asn Leu Leu Leu Asp Phe Ser Thr Met Ile Ala Asp Asp Met
            215                 220                 225 tct aat tat gat gaa gaa gga gca tgg cct gtt ctt att gat gac ttt              778
Ser Asn Tyr Asp Glu Glu Gly Ala Trp Pro Val Leu Ile Asp Asp Phe
        230                 235                 240 gtg gaa ttt gca cgc cct caa att gct ggg aca aaa agt aca aca gtg              826
Val Glu Phe Ala Arg Pro Gln Ile Ala Gly Thr Lys Ser Thr Thr Val
    245                 250                 255 tag cactaaagga accttctaga atgtacatag tctgtacaat aaatacaaca       879
gaaaattgca cagtcaattt ctgctggctg gactgaactg aagatcaatc ctcacaattc           939
agactgaggg ttgagacaaa actttaagga tacatcttgg accatatcgt atttcattct           999
tctaatggtg gtttgggctt gtcttctagt ctgggccgct ctaaacattt ataattccaa           1059
cattgtggat ttcatcttat atctgtggac catcctagtt tattctccca taagtcttag           1119
aagctttatg gtgattattt tgaggttttc attctcgcat aaagcacaat gctgtcttca           1179
tcagaaaaca gttggcataa gaattaaaca tatgaacatc acaaaacaat ttataaaaac           1239
ttcttaaata tacgctttgg gctagttgca aagactatgc taatagcact tccagtgaga           1299
gtgatatatt taagtgtact ggatctggaa tggtgttttg gtttgggggg aattttttt            1359 ttttcctggc aaatcacatg tgttgttgat gtgagtatct gatgaaaaaa caatgtcaga           1419
ataaccgaca tgaaattttt ttaggataac ttggtgccta cctgaaaaat gtattgtgtt           1479
ttagactctt gatttcaaaa ggttccacag aactagtctg cgcttacctt acccatgttt          1539
```

```
atatatagct gtcctacagg gagctttttat ttagaaaatg tctgcataat gttagattct   1599
tctcctgtct acattatgca ctacataatt ggacttcatt atgcttttga aatgcttatc   1659
tgcctgtcac ataagttaaa ctatttaatt tgttttgaat gttttggatt gctacacaat   1719
acaatattct aaatttaggc atgagggttt ttttgttttg tttttacttt ttttttgtca   1779
tcgcactatg gaacacaaat ggaattctct taatttataa gaagatagtt gcagttaaat   1839
tttgaaaatg gttgtaatga gccatgaagt tcaatcttta taatataggt actgctcttt   1899
cagacaaata gtccattttc gatgacttat tattttgttg aaattgcttt aactgctaat   1959
cactgtggtt gccaaatatt tacttcagga gcaaagattt tcaaacaagc atacacgatg   2019
caaaatacca atctggcttc tagtctcttt actgttttcg tttcactcag attagctcag   2079
ttttctcatc aaagcagaat gctatcttgt atgtattttt ttcattacaa gccccatgag   2139
ctgcttttat gctgaaaatg gtcatttccc tgttcactta ctgacatgtg aagaagggtt   2199
tcttgctttc ttaaacattt ccgtaaggca ggctagaaat gtaatacttc aaatgtttga   2259
tgattatggt cttttgatag aatagattc tgcttgggat atatatccag gcactctcta   2319
aggtctaggg ttgatattaa caaggaatg tacttagaat agcagtacat tttatgcaaa   2379
tatgaaaatt atttttaagaa acaatgacat atcaaaactg cttttttacat gattttgaaa   2439 tagactagaa agcttttccct atagacatat taatattcca atcataactt taattcaaga   2499
atgcagtttt accaaaagaa aaatttgaaa atttctattc aggctactgg aattggttat   2559
taaaagaaaa aggaaaaaga agaatcttgc tgctttcagt atttcctgat ttttttgtaa   2619
atataaagag gaacttcaat tatgaaaaat ttttaaaaga tatatatatc tatatatcta   2679
tatatatgta ctgttttgtt tcctgtcttg aagattttga gttatggtta ttggtttcag   2739
attgattaat tcacatatgc tgtgttttga aatgagatcc cattagcttt tttttttttt   2799 ttttttttc aatataaagt gttttcttta aaagtcatat tggttcgtgg cctagtgcct   2859 tggatttttac atattttttct ttttaaatgc aaaaccttttt caacaaaata gtgtttgtca   2919
tcaggttggt actaaacatt tataattact gtgtaattat aaacaaaaat acataaagct   2979
ttgaatataa ttatgtagca taaaagttaa ggttgttcac tatgatggca tcttagaatt   3039
aaacaaaact tttactaggg ctgaaaagag aagactgatt taatgtggtg tgattattct   3099
gaagataaat gtctggctac agggaatatt ttgtactaaa aaatgattac acaaaaaaaa   3159
aaaaaaaaaa aaaaaaaaaa aaaaaaaaaa aaa                                3192
```

<210> SEQ ID NO 33
<211> LENGTH: 259
<212> TYPE: PRT
<213> ORGANISM: Homo sapiens

<400> SEQUENCE: 33

```
Met Asn Lys Leu Lys Ser Ser Gln Lys Asp Lys Val Arg Gln Phe Met
1               5                   10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asp Asn Phe Phe Gln Asn Pro
        35                  40                  45

Glu Leu Tyr Ile Arg Glu Ser Val Lys Gly Ser Leu Asp Arg Lys Lys
    50                  55                  60

Leu Glu Gln Leu Tyr Asn Arg Tyr Lys Asp Pro Gln Asp Glu Asn Lys
65                  70                  75                  80
```

Ile Gly Ile Asp Gly Ile Gln Gln Phe Cys Asp Asp Leu Ala Leu Asp
            85                  90                  95

Pro Ala Ser Ile Ser Val Leu Ile Ile Ala Trp Lys Phe Arg Ala Ala
        100                 105                 110

Thr Gln Cys Glu Phe Ser Lys Gln Glu Phe Met Asp Gly Met Thr Glu
        115                 120                 125

Leu Gly Cys Asp Ser Ile Glu Lys Leu Lys Ala Gln Ile Pro Lys Met
    130                 135                 140

Glu Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Lys Phe
            180                 185                 190

Leu Asp Leu Trp Asn Lys Phe Leu Leu Glu His His Lys Arg Ser Ile
        195                 200                 205

Pro Lys Asp Thr Trp Asn Leu Leu Leu Asp Phe Ser Thr Met Ile Ala
    210                 215                 220

Asp Asp Met Ser Asn Tyr Asp Glu Gly Ala Trp Pro Val Leu Ile
225                 230                 235                 240

Asp Asp Phe Val Glu Phe Ala Arg Pro Gln Ile Ala Gly Thr Lys Ser
                245                 250                 255

Thr Thr Val

<210> SEQ ID NO 34
<211> LENGTH: 198
<212> TYPE: PRT
<213> ORGANISM: Homo sapiens

<400> SEQUENCE: 34

Arg Lys Lys Leu Glu Gln Leu Tyr Asn Arg Tyr Lys Asp Pro Gln Asp
 1               5                  10                  15

Glu Asn Lys Ile Gly Ile Asp Gly Ile Gln Gln Phe Cys Asp Asp Leu
                20                  25                  30

Ala Leu Asp Pro Ala Ser Ile Ser Val Leu Ile Ile Ala Trp Lys Phe
            35                  40                  45

Arg Ala Ala Thr Gln Cys Glu Phe Ser Lys Gln Glu Phe Met Asp Gly
        50                  55                  60

Met Thr Glu Leu Gly Cys Asp Ser Ile Glu Lys Leu Lys Ala Gln Ile
65                  70                  75                  80

Pro Lys Met Glu Gln Glu Leu Lys Glu Pro Gly Arg Phe Lys Asp Phe
                85                  90                  95

Tyr Gln Phe Thr Phe Asn Phe Ala Lys Asn Pro Gly Gln Lys Gly Leu
                100                 105                 110

Asp Leu Glu Met Ala Ile Ala Tyr Trp Asn Leu Val Leu Asn Gly Arg
            115                 120                 125

Phe Lys Phe Leu Asp Leu Trp Asn Lys Phe Leu Leu Glu His His Lys
        130                 135                 140

Arg Ser Ile Pro Lys Asp Thr Trp Asn Leu Leu Leu Asp Phe Ser Thr
145                 150                 155                 160

Met Ile Ala Asp Asp Met Ser Asn Tyr Asp Glu Gly Ala Trp Pro
                165                 170                 175

Val Leu Ile Asp Asp Phe Val Glu Phe Ala Arg Pro Gln Ile Ala Gly
            180                 185                 190

```
Thr Lys Ser Thr Thr Val
        195

<210> SEQ ID NO 35
<211> LENGTH: 3046
<212> TYPE: DNA
<213> ORGANISM: Homo sapiens
<220> FEATURE:
<221> NAME/KEY: CDS
<222> LOCATION: (40)...(819)

<400> SEQUENCE: 35
gaaggccggg gccggccaga agcgggcggc gcggggag atg cat aag ctt aaa         54
                                         Met His Lys Leu Lys
                                           1               5 tcg tct cag aag gac aag gtc cgc cag ttt atg gcg tgc act cag gct    102
Ser Ser Gln Lys Asp Lys Val Arg Gln Phe Met Ala Cys Thr Gln Ala
             10                  15                  20 ggc gag aga act gct atc tac tgc tta acg cag aat gag tgg aga cta    150
Gly Glu Arg Thr Ala Ile Tyr Cys Leu Thr Gln Asn Glu Trp Arg Leu
         25                  30                  35 gac gag gcc acg gac agc ttc ttc caa aac cca gac tcg ctc cac agg    198
Asp Glu Ala Thr Asp Ser Phe Phe Gln Asn Pro Asp Ser Leu His Arg
 40                  45                  50 gag tcc atg cgg aac gct gtg gac aag aag aag ctg gag cgg ctg tac    246
Glu Ser Met Arg Asn Ala Val Asp Lys Lys Lys Leu Glu Arg Leu Tyr
     55                  60                  65 ggc agg tac aaa gat cca caa gat gaa aac aaa att gga gtc gat ggg    294
Gly Arg Tyr Lys Asp Pro Gln Asp Glu Asn Lys Ile Gly Val Asp Gly
 70                  75                  80                  85 att caa cag ttt tgt gat gat ctg agc ctg gat cct gcc agt atc agt    342
Ile Gln Gln Phe Cys Asp Asp Leu Ser Leu Asp Pro Ala Ser Ile Ser
                 90                  95                 100 gta ttg gtc ata gcg tgg aag ttc agg gca gca act cag tgt gaa ttt    390
Val Leu Val Ile Ala Trp Lys Phe Arg Ala Ala Thr Gln Cys Glu Phe
            105                 110                 115 agc aga aag gaa ttt cta gat ggc atg aca gaa ctt ggg tgt gac agc    438
Ser Arg Lys Glu Phe Leu Asp Gly Met Thr Glu Leu Gly Cys Asp Ser
        120                 125                 130 atg gag aag cta aag gct ctt ctg cca aga ctg gag cag gag ctg aag    486
Met Glu Lys Leu Lys Ala Leu Leu Pro Arg Leu Glu Gln Glu Leu Lys
    135                 140                 145 gac aca gcc aag ttt aaa gat ttt tat cag ttt acc ttc acc ttc gct    534
Asp Thr Ala Lys Phe Lys Asp Phe Tyr Gln Phe Thr Phe Thr Phe Ala
150                 155                 160                 165 aag aac cca ggg cag aaa ggt tta gac tta gaa atg gct gtt gcg tat    582
Lys Asn Pro Gly Gln Lys Gly Leu Asp Leu Glu Met Ala Val Ala Tyr
                170                 175                 180 tgg aaa tta gtg tta tct gga agg ttt aaa ttt tta gat ctc tgg aac    630
Trp Lys Leu Val Leu Ser Gly Arg Phe Lys Phe Leu Asp Leu Trp Asn
            185                 190                 195 aca ttc tta atg gaa cat cac aaa aga tca att cca agg gac acc tgg    678
Thr Phe Leu Met Glu His His Lys Arg Ser Ile Pro Arg Asp Thr Trp
        200                 205                 210 aac ctc ctg ctg gac ttt gga aac atg att gcg gat gat atg tct aac    726
Asn Leu Leu Leu Asp Phe Gly Asn Met Ile Ala Asp Asp Met Ser Asn
    215                 220                 225 tac gat gaa gaa gga gct tgg ccc gtt ctt ata gat gat ttt gta gaa    774
Tyr Asp Glu Glu Gly Ala Trp Pro Val Leu Ile Asp Asp Phe Val Glu
230                 235                 240                 245 tat gca cgg cca gta gtc aca ggt gga aaa cgc agc ctt ttc tag        819
Tyr Ala Arg Pro Val Val Thr Gly Gly Lys Arg Ser Leu Phe
```

```
Tyr Ala Arg Pro Val Val Thr Gly Gly Lys Arg Ser Leu Phe
            250                 255 gcagcaagtt aagcaggagt aagattatga aatgatttgt atcctgcaag gagattgcag      879
tcagttcctg ggtgcattgt cgctgattcc agaagtcatt cttgaccagc catgaaacca      939
gaggcgccat cccattctgc cggaggacag ccagcggctg ctttgtggac accgcaggaa      999
gttcctcggg acacggctgc tttgggatgt ttggagattt gtcatcatag cttttgcgtt     1059
aggaaatttc tgcatgattt tttaatattt acaaaatact aaggtagagc atagcgccg      1119 cctgtgggac cgcagagcat gctgcgtagc tcgcgcgtca ggcgaaccag cgtccggcag     1179
cgtcccgccg aatgacgttg cggtggcact ggcaacacgg catgtgtcct ctgcagggcg     1239
ctgcgttttt atacacgtca aagctgttaa gaatgtgccc taagggagag gatcttgtcg     1299
tagagtctaa tgttttttaa aattggtgcc agcaattcac gatttatatt ttttgaatta     1359
ccaaatatct agatttacca gctctatttt tgttttcatt ttctctagac attcatctga     1419
aaatcatttt atggttctca atccccatgt agctttgcat agcaacggca cacgtggcac     1479
gattccagca gagtttatct cacaccgttt atatatcact gggcctctct tacttaaata     1539
ttatttgacc tgcctgagaa gcttcataaa gtatgttttt ttaaaatata ttttaattac     1599
atttaaaaag acatttttcc atgaaaaaca tttattttat gagtgatgaa ttatagattt     1659
taaaatcaag gccgggcgtg gtggctcaca cctgtaatcc cagcattttg ggaggccgag     1719
gcaggtggat cacctgaggt caggagtttg agaccagcct ggccaacatg gtgaaaccct     1779
gtctctacta aaaatacaaa aattagccgg gcatggtggc acatgcctgt aatcccagct     1839
actcaggagg ctgaggcagg agattcgctt gaactcagga gacggaggtt acagtgagtc     1899
gagatcgcgc cactgcactc cagcctggac gacagagtga gattctgtct caaaataaat     1959
acatacatac atacaataaa accgaatgag ctggttcttt ccatcctctt gtggtacccg     2019
tagtgcccag catccagacc tttgtgcccc tgtgcacatt tggaagctaa aatgtacatc     2079
gttgtctgaa aaacccaac cccaaaacct tcatctgatt ggtgagctga agtctgtcct      2139
tgcaccatgt tatcatctgt ttctcgtgtc cgcctggttg aggaggaccc acgagtgctg     2199
ccgaggtgtg gagggctggt attgagttgt ggacatcact gttgacccta cctcacgtgc     2259
cgagactctc atgtcacagg cgtgccttgc tgcccccctg cagcactgtg caggacgtgg     2319
accagctgga gctgctgccc agcacagagg agagtcgccg cagatgacct agctgcggtg     2379
tgagagagca tgcccagac aagcagctgg gttggcttct gagaacagga cttaccctgg      2439
gcttcaggaa catctgatgg ctgaggttag tgtgcttgga ggctgcagga cgaactgtcg     2499
atgtttctta gcagagatgg tcacagaggg cagcagggac aggactggaa gggacctgca     2559
gcctgcagac cccgcctggc cccgctggc ttctggctgg tccagtgatg ggcaagtgac      2619
agaccttccc caggctctgc ttccagaact ctaatgggaa actgggcctg tctacctta     2679 gaagtcttcg attctcagag agcatttgtc taatacaata aaaactggca ttaatacaaa     2739
cctcaaaaac gtgagcgtat cttccaggct tcatggattc ttgacatgta attgttttgt     2799
tcagaaaagt ttatagaatt cacataattc tgtataaact atggagatcc acagtacttt     2859
tttgtttttg agatttaaag ttctaaggga ttgtcaatag atatcaaaat attaatcatt     2919
ggacaaaggc ttttccaaaa attgtgggtt ttttcttct gttgtatcca tttgagtcct      2979
gcatgctgtg aaatgctgag aacagaagca ttaaattggt ttttctcggg aaaaaaaaa     3039 aaaaaaa                                                               3046
```

<210> SEQ ID NO 36
<211> LENGTH: 259
<212> TYPE: PRT
<213> ORGANISM: Homo sapiens

<400> SEQUENCE: 36

```
Met His Lys Leu Lys Ser Ser Gln Lys Asp Lys Val Arg Gln Phe Met
1               5                   10                  15

Ala Cys Thr Gln Ala Gly Glu Arg Thr Ala Ile Tyr Cys Leu Thr Gln
            20                  25                  30

Asn Glu Trp Arg Leu Asp Glu Ala Thr Asp Ser Phe Phe Gln Asn Pro
        35                  40                  45

Asp Ser Leu His Arg Glu Ser Met Arg Asn Ala Val Asp Lys Lys Lys
    50                  55                  60

Leu Glu Arg Leu Tyr Gly Arg Tyr Lys Asp Pro Gln Asp Glu Asn Lys
65                  70                  75                  80

Ile Gly Val Asp Gly Ile Gln Gln Phe Cys Asp Asp Leu Ser Leu Asp
                85                  90                  95

Pro Ala Ser Ile Ser Val Leu Val Ile Ala Trp Lys Phe Arg Ala Ala
            100                 105                 110

Thr Gln Cys Glu Phe Ser Arg Lys Glu Phe Leu Asp Gly Met Thr Glu
        115                 120                 125

Leu Gly Cys Asp Ser Met Glu Lys Leu Lys Ala Leu Leu Pro Arg Leu
    130                 135                 140

Glu Gln Glu Leu Lys Asp Thr Ala Lys Phe Lys Asp Phe Tyr Gln Phe
145                 150                 155                 160

Thr Phe Thr Phe Ala Lys Asn Pro Gly Gln Lys Gly Leu Asp Leu Glu
                165                 170                 175

Met Ala Val Ala Tyr Trp Lys Leu Val Leu Ser Gly Arg Phe Lys Phe
            180                 185                 190

Leu Asp Leu Trp Asn Thr Phe Leu Met Glu His His Lys Arg Ser Ile
        195                 200                 205

Pro Arg Asp Thr Trp Asn Leu Leu Leu Asp Phe Gly Asn Met Ile Ala
    210                 215                 220

Asp Asp Met Ser Asn Tyr Asp Glu Glu Gly Ala Trp Pro Val Leu Ile
225                 230                 235                 240

Asp Asp Phe Val Glu Tyr Ala Arg Pro Val Val Thr Gly Gly Lys Arg
                245                 250                 255

Ser Leu Phe
```

<210> SEQ ID NO 37
<211> LENGTH: 198
<212> TYPE: PRT
<213> ORGANISM: Homo sapiens

<400> SEQUENCE: 37

```
Lys Lys Lys Leu Glu Arg Leu Tyr Gly Arg Tyr Lys Asp Pro Gln Asp
1               5                   10                  15

Glu Asn Lys Ile Gly Val Asp Gly Ile Gln Gln Phe Cys Asp Asp Leu
            20                  25                  30

Ser Leu Asp Pro Ala Ser Ile Ser Val Leu Val Ile Ala Trp Lys Phe
        35                  40                  45

Arg Ala Ala Thr Gln Cys Glu Phe Ser Arg Lys Glu Phe Leu Asp Gly
    50                  55                  60

Met Thr Glu Leu Gly Cys Asp Ser Met Glu Lys Leu Lys Ala Leu Leu
```

```
              65                  70                  75                  80
Pro Arg Leu Glu Gln Glu Leu Lys Asp Thr Ala Lys Phe Lys Asp Phe
                        85                  90                  95

Tyr Gln Phe Thr Phe Thr Phe Ala Lys Asn Pro Gly Gln Lys Gly Leu
            100                 105                 110

Asp Leu Glu Met Ala Val Ala Tyr Trp Lys Leu Val Leu Ser Gly Arg
                115                 120                 125

Phe Lys Phe Leu Asp Leu Trp Asn Thr Phe Leu Met Glu His His Lys
    130                 135                 140

Arg Ser Ile Pro Arg Asp Thr Trp Asn Leu Leu Leu Asp Phe Gly Asn
145                 150                 155                 160

Met Ile Ala Asp Asp Met Ser Asn Tyr Asp Glu Gly Ala Trp Pro
                165                 170                 175

Val Leu Ile Asp Asp Phe Val Glu Tyr Ala Arg Pro Val Val Thr Gly
                180                 185                 190

Gly Lys Arg Ser Leu Phe
            195

<210> SEQ ID NO 38
<211> LENGTH: 2886
<212> TYPE: DNA
<213> ORGANISM: Homo sapiens
<220> FEATURE:
<221> NAME/KEY: CDS
<222> LOCATION: (142)...(1056)

<400> SEQUENCE: 38
agaaagggtt tgactggagg aacctctgga gcagctgttg gctggctcct ctggctgatg      60
gcatgttgag gtacatgggc cagcggcagc gagggcatcc aatccagagg ggtccactct    120
agaggccagg ccaccagcac c atg ggc cag tgt gtc acc aag tgt aag aat      171
                        Met Gly Gln Cys Val Thr Lys Cys Lys Asn
                          1               5                   10 ccc tca tcg acc ctg ggc agc aaa aat gga gac cgt gag ccc agc aac      219
Pro Ser Ser Thr Leu Gly Ser Lys Asn Gly Asp Arg Glu Pro Ser Asn
              15                  20                  25 aag tca cat agc agg agg ggt gca ggc cac cgt gag gag cag gta cca      267
Lys Ser His Ser Arg Arg Gly Ala Gly His Arg Glu Glu Gln Val Pro
         30                  35                  40 ccc tgt ggc aag cca ggt gga gat atc ctc gtc aac ggg acc aag aag      315
Pro Cys Gly Lys Pro Gly Gly Asp Ile Leu Val Asn Gly Thr Lys Lys
         45                  50                  55 gcc gag gct gcc act gag gcc tgc cag ctg cca acg tcc tcg gga gat      363
Ala Glu Ala Ala Thr Glu Ala Cys Gln Leu Pro Thr Ser Ser Gly Asp
 60                  65                  70 gct ggg agg gag tcc aag tcc aat gcc gag gag tct tcc ttg caa aga      411
Ala Gly Arg Glu Ser Lys Ser Asn Ala Glu Glu Ser Ser Leu Gln Arg
 75                  80                  85                  90 ttg gaa gaa ctg ttc agg cgc tac aag gat gag cgg gaa gat gca att      459
Leu Glu Glu Leu Phe Arg Arg Tyr Lys Asp Glu Arg Glu Asp Ala Ile
                 95                 100                 105 ttg gag gaa ggc atg gag cgc ttt tgc aat gac ctg tgt gtt gac ccc      507
Leu Glu Glu Gly Met Glu Arg Phe Cys Asn Asp Leu Cys Val Asp Pro
            110                 115                 120 aca gaa ttt cga gtg ctg ctc ttg gct tgg aag ttc cag gct gca acc      555
Thr Glu Phe Arg Val Leu Leu Leu Ala Trp Lys Phe Gln Ala Ala Thr
             125                 130                 135 atg tgc aaa ttc acc agg aag gag ttt ttt gat ggc tgc aaa gca ata      603
Met Cys Lys Phe Thr Arg Lys Glu Phe Phe Asp Gly Cys Lys Ala Ile
         140                 145                 150
```

```
            140                 145                 150
agt gca gac agc att gac gga atc tgt gca cgg ttc cct agc ctc tta          651
Ser Ala Asp Ser Ile Asp Gly Ile Cys Ala Arg Phe Pro Ser Leu Leu
155                 160                 165                 170 aca gaa gcc aaa caa gag gat aaa ttc aag gat ctc tac cgg ttt aca          699
Thr Glu Ala Lys Gln Glu Asp Lys Phe Lys Asp Leu Tyr Arg Phe Thr
                175                 180                 185 ttt cag ttt ggc ctg gac tct gaa gaa ggg cag cgg tca ctg cat cgg          747
Phe Gln Phe Gly Leu Asp Ser Glu Glu Gly Gln Arg Ser Leu His Arg
            190                 195                 200 gaa ata gcc att gcc ctg tgg aaa cta gtc ttt acc cag aac aat cct          795
Glu Ile Ala Ile Ala Leu Trp Lys Leu Val Phe Thr Gln Asn Asn Pro
        205                 210                 215 ccg gta ttg gac caa tgg cta aac ttc cta aca gag aac ccc tcg ggg          843
Pro Val Leu Asp Gln Trp Leu Asn Phe Leu Thr Glu Asn Pro Ser Gly
    220                 225                 230 atc aag ggc atc tcc cgg gac act tgg aac atg ttc ctt aac ttc act          891
Ile Lys Gly Ile Ser Arg Asp Thr Trp Asn Met Phe Leu Asn Phe Thr
235                 240                 245                 250 cag gtg att ggc cct gac ctc agc aac tac agt gaa gat gag gcc tgg          939
Gln Val Ile Gly Pro Asp Leu Ser Asn Tyr Ser Glu Asp Glu Ala Trp
                255                 260                 265 cca agt ctc ttt gac acc ttt gtg gag tgg gaa atg gag cga agg aaa          987
Pro Ser Leu Phe Asp Thr Phe Val Glu Trp Glu Met Glu Arg Arg Lys
            270                 275                 280 aga gaa ggg gaa ggg aga ggt gca ctc agc tca ggg cct gag ggc ttg         1035
Arg Glu Gly Glu Gly Arg Gly Ala Leu Ser Ser Gly Pro Glu Gly Leu
        285                 290                 295 tgt ccc gag gag cag act tag tggctctgtc ccaggagcag cagcaaggat            1086
Cys Pro Glu Glu Gln Thr
    300 ctgccagctg ccctgcagcc aactgaggaa ttggaccatt ttggaaatta ctgaagatcc       1146 ggatattttc tactttacac ctttctctgc cttgtatctg aaagggctct aaaatgctgt       1206 atcatgtttt aggcactttc ttcatttttt tggttatttt ggttatttcc ttttggggg        1266 gatctcccag aatatttgaa cctggttaca tgttgtgtat cttttttga  agccttcaga       1326 tagaataagc ctgccatttc ttgcacaaat ttaggttttt ttttgttttt ttttgtttt        1386 tttttttttt tttttggtag gggagggcat agagcagggc gggggatgg  gactgttagg       1446 ttgaattaac attacaaaat gatacagtgc cagatctcag tttcgcatat tgttttcag       1506 ggcaggtctg tactgtgtgt agtgctgttt acatagatga atttaggttg taataattat      1566 ttttaaagat ttacacagat ttgaatagca gtgttaactg ttaaccacat tgcattaatt      1626 cccaggcgat ttagagctct tggagagcca aggccagcca agagcatttg tagtctggtg      1686 acaacccct tttaagctaa tttatccaga acctgatttt ccctcacttc ttgctcattc       1746 cttctttgac ctattgcatt tcatgttgag ttttttccatc aacatgctgc acctgtcagt     1806 caagtgagca ttttttaaga acacattgta ctgagaacca cttaagcatt gaatgcggag     1866 aaagcagtgc tacctcagtt ttgctggaag tagacttctt tgatagtttt ctttctttga     1926 tgaagtttct gtattttcat gttgtaagtg gaaatacttt ttttgtttg  tttgtttcat     1986 ttgccttgga gccaaagttt ctgttcctgg tggtcgggaa actgcctgcc ggccaactga     2046 cttgaaggaa aactgtggta tggagctctg cttgaatttt ttttttttta atattttat     2106 ttttttcttt gaatatcatc agcttacttg tctggcaagg gcagaagcct ggggttggcc    2166 tgaactctgc caaacaaata tcaaagtgta tttaatagtt aaatttgtgc cctttccctt    2226
```

-continued

```
cttgctgcac ccatgttgtc acttaacccc caggagttat ttattatctt tttgttaaag    2286
tcaggctcat ttggggtaat gtgatgactg tttaggttta catgaccctc ctctcctttc    2346
cctaccccca aatatgtata tatacatata taaaatatgt atatatttta cctatataaa    2406
atatatatat atacacatat atgtatctat attcctttgt ttctttgcct gcttatactg    2466
gccataaaag agggagctgc cttcaatgta taaagtataa gaagagtgcc agggaatgcc    2526
ataatggagg cttttggatc tgaatttgga ccatttcact aaagagaaca tgagtttgct    2586 cagcccttc ctcacaagag ggagggcccc ggttccccag acttctccac gcgctggctc    2646
cataaaggcc agctttggcc aggctgccac aggggcctga ggagctcact ctgggcctac    2706
ctggtttcag ttagagggtc ctcctgttat ttttccattt aaaaagtatg tcctcagaaa    2766
actgtactgg aaggatgggt ggcaggaact tgtatagttc agcttccaac actttggaac    2826
agattaaaaa gggaatcttt taaataaaaa cgtataaaaa taaaaaaaaa aaaaaaaaa     2886
```

<210> SEQ ID NO 39
<211> LENGTH: 304
<212> TYPE: PRT
<213> ORGANISM: Homo sapiens

<400> SEQUENCE: 39

```
Met Gly Gln Cys Val Thr Lys Cys Lys Asn Pro Ser Ser Thr Leu Gly
  1               5                  10                  15

Ser Lys Asn Gly Asp Arg Glu Pro Ser Asn Lys Ser His Ser Arg Arg
             20                  25                  30

Gly Ala Gly His Arg Glu Glu Val Pro Pro Cys Gly Lys Pro Gly
         35                  40                  45

Gly Asp Ile Leu Val Asn Gly Thr Lys Lys Ala Glu Ala Ala Thr Glu
     50                  55                  60

Ala Cys Gln Leu Pro Thr Ser Ser Gly Asp Ala Gly Arg Glu Ser Lys
 65                  70                  75                  80

Ser Asn Ala Glu Glu Ser Ser Leu Gln Arg Leu Glu Glu Leu Phe Arg
                 85                  90                  95

Arg Tyr Lys Asp Glu Arg Glu Asp Ala Ile Leu Glu Glu Gly Met Glu
            100                 105                 110

Arg Phe Cys Asn Asp Leu Cys Val Asp Pro Thr Glu Phe Arg Val Leu
        115                 120                 125

Leu Leu Ala Trp Lys Phe Gln Ala Ala Thr Met Cys Lys Phe Thr Arg
    130                 135                 140

Lys Glu Phe Phe Asp Gly Cys Lys Ala Ile Ser Ala Asp Ser Ile Asp
145                 150                 155                 160

Gly Ile Cys Ala Arg Phe Pro Ser Leu Leu Thr Glu Ala Lys Gln Glu
                165                 170                 175

Asp Lys Phe Lys Asp Leu Tyr Arg Phe Thr Phe Gln Phe Gly Leu Asp
            180                 185                 190

Ser Glu Glu Gly Gln Arg Ser Leu His Arg Glu Ile Ala Ile Ala Leu
        195                 200                 205

Trp Lys Leu Val Phe Thr Gln Asn Asn Pro Pro Val Leu Asp Gln Trp
    210                 215                 220

Leu Asn Phe Leu Thr Glu Asn Pro Ser Gly Ile Lys Gly Ile Ser Arg
225                 230                 235                 240

Asp Thr Trp Asn Met Phe Leu Asn Phe Thr Gln Val Ile Gly Pro Asp
                245                 250                 255
```

```
Leu Ser Asn Tyr Ser Glu Asp Glu Ala Trp Pro Ser Leu Phe Asp Thr
            260                 265                 270

Phe Val Glu Trp Glu Met Glu Arg Arg Lys Arg Glu Gly Glu Gly Arg
            275                 280                 285

Gly Ala Leu Ser Ser Gly Pro Glu Gly Leu Cys Pro Glu Glu Gln Thr
            290                 295                 300

<210> SEQ ID NO 40
<211> LENGTH: 219
<212> TYPE: PRT
<213> ORGANISM: Homo sapiens

<400> SEQUENCE: 40

Ser Ser Leu Gln Arg Leu Glu Glu Leu Phe Arg Arg Tyr Lys Asp Glu
  1               5                  10                  15

Arg Glu Asp Ala Ile Leu Glu Glu Gly Met Glu Arg Phe Cys Asn Asp
             20                  25                  30

Leu Cys Val Asp Pro Thr Glu Phe Arg Val Leu Leu Leu Ala Trp Lys
         35                  40                  45

Phe Gln Ala Ala Thr Met Cys Lys Phe Thr Arg Lys Glu Phe Phe Asp
     50                  55                  60

Gly Cys Lys Ala Ile Ser Ala Asp Ser Ile Asp Gly Ile Cys Ala Arg
 65                  70                  75                  80

Phe Pro Ser Leu Leu Thr Glu Ala Lys Gln Glu Asp Lys Phe Lys Asp
                 85                  90                  95

Leu Tyr Arg Phe Thr Phe Gln Phe Gly Leu Asp Ser Glu Glu Gly Gln
            100                 105                 110

Arg Ser Leu His Arg Glu Ile Ala Ile Ala Leu Trp Lys Leu Val Phe
        115                 120                 125

Thr Gln Asn Asn Pro Pro Val Leu Asp Gln Trp Leu Asn Phe Leu Thr
    130                 135                 140

Glu Asn Pro Ser Gly Ile Lys Gly Ile Ser Arg Asp Thr Trp Asn Met
145                 150                 155                 160

Phe Leu Asn Phe Thr Gln Val Ile Gly Pro Asp Leu Ser Asn Tyr Ser
                165                 170                 175

Glu Asp Glu Ala Trp Pro Ser Leu Phe Asp Thr Phe Val Glu Trp Glu
            180                 185                 190

Met Glu Arg Arg Lys Arg Glu Gly Glu Gly Arg Gly Ala Leu Ser Ser
        195                 200                 205

Gly Pro Glu Gly Leu Cys Pro Glu Glu Gln Thr
    210                 215

<210> SEQ ID NO 41
<211> LENGTH: 4278
<212> TYPE: DNA
<213> ORGANISM: Homo sapiens
<220> FEATURE:
<221> NAME/KEY: CDS
<222> LOCATION: (134)...(1012)

<400> SEQUENCE: 41
aaggcgagat gggcgggctg ggagtgcccg gcggcgggtc ctcagcttcg agccgaggtg      60
cagtgagctg gtgggggac cgcgaggcga gcgcgggagc ctgggcggcg agccgggtgt     120
gagctgcctg aaa atg cac tcg gat gcc gcc gct gtc aat ttt cag ctg       169
            Met His Ser Asp Ala Ala Ala Val Asn Phe Gln Leu
              1               5                  10 aac tct cat ctc tca aca ctg gca aat att cat aag atc tac cac acc     217
```

```
              Asn Ser His Leu Ser Thr Leu Ala Asn Ile His Lys Ile Tyr His Thr
                          15                  20                  25 ctt aat aag ctg aac cta aca gaa gac att ggc caa gac gat cac caa       265
Leu Asn Lys Leu Asn Leu Thr Glu Asp Ile Gly Gln Asp Asp His Gln
         30                  35                  40 aca gga agt ctg cgg tct tgc agt tct tca gac tgc ttt aat aaa gtg       313
Thr Gly Ser Leu Arg Ser Cys Ser Ser Ser Asp Cys Phe Asn Lys Val
 45                  50                  55                  60 atg cca cca agg aaa aag aga aga cct gcc tct gga gat gat tta tct       361
Met Pro Pro Arg Lys Lys Arg Arg Pro Ala Ser Gly Asp Asp Leu Ser
                 65                  70                  75 gcc aag aaa agt aga cat gat agc atg tat aga aaa tat gat tcg act       409
Ala Lys Lys Ser Arg His Asp Ser Met Tyr Arg Lys Tyr Asp Ser Thr
         80                  85                  90 aga ata aag act gaa gaa gaa gcc ttt tca agt aaa agg tgc ttg gaa       457
Arg Ile Lys Thr Glu Glu Glu Ala Phe Ser Ser Lys Arg Cys Leu Glu
             95                 100                 105 tgg ttc tat gaa tat gca gga act gat gat gtt gta ggc cct gaa ggc       505
Trp Phe Tyr Glu Tyr Ala Gly Thr Asp Asp Val Val Gly Pro Glu Gly
110                 115                 120 atg gag aaa ttt tgt gaa gac att ggt gtt gaa cca gaa aac gta gtt       553
Met Glu Lys Phe Cys Glu Asp Ile Gly Val Glu Pro Glu Asn Val Val
125                 130                 135                 140 atg ctt gtc cta gct tgg aaa ttg gat gca caa aac atg ggt tat ttt       601
Met Leu Val Leu Ala Trp Lys Leu Asp Ala Gln Asn Met Gly Tyr Phe
                145                 150                 155 act cta cag gag tgg tta aaa gga atg act tct ctc caa tgt gat aca       649
Thr Leu Gln Glu Trp Leu Lys Gly Met Thr Ser Leu Gln Cys Asp Thr
            160                 165                 170 aca gaa aaa ctc aga aat act ttg gat tac tta aga tca ttc tta aat       697
Thr Glu Lys Leu Arg Asn Thr Leu Asp Tyr Leu Arg Ser Phe Leu Asn
        175                 180                 185 gat tct aca aac ttt aaa ctt att tac aga tat gcg ttt gac ttt gca       745
Asp Ser Thr Asn Phe Lys Leu Ile Tyr Arg Tyr Ala Phe Asp Phe Ala
190                 195                 200 cgg gaa aag gac cag cgc agc cta gac ata aac act gcc aag tgc atg       793
Arg Glu Lys Asp Gln Arg Ser Leu Asp Ile Asn Thr Ala Lys Cys Met
205                 210                 215                 220 ttg gga ctg tta tta gga aaa atc tgg ccc ctt ttt cca gtt ttt cac       841
Leu Gly Leu Leu Leu Gly Lys Ile Trp Pro Leu Phe Pro Val Phe His
                225                 230                 235 caa ttc tta gag caa tca aaa tac aaa gtt att aat aaa gac cag tgg       889
Gln Phe Leu Glu Gln Ser Lys Tyr Lys Val Ile Asn Lys Asp Gln Trp
            240                 245                 250 tgc aat gtc cta gag ttt agc aga aca att aat ctt gac ctc agc aac       937
Cys Asn Val Leu Glu Phe Ser Arg Thr Ile Asn Leu Asp Leu Ser Asn
        255                 260                 265 tat gat gaa gat gga gca tgg cca gtt ttg ttg gac gag ttt gtg gag       985
Tyr Asp Glu Asp Gly Ala Trp Pro Val Leu Leu Asp Glu Phe Val Glu
270                 275                 280 tgg tat aaa gac aaa cag atg tcc tag gactttatgc atagcagcga            1032
Trp Tyr Lys Asp Lys Gln Met Ser
285                 290 gagagtcact gttaccacag ttttgtcacc cattagccat aaattgctgt tgtatcaaa     1092 gcgcatgctg cttctcttgc actgtttccc tttcgcaggg acatgttggt gtttgctatt    1152
gaattggcca gctctgcttg ctgtgtggca ttgttctctt ggaaggctgc tttgcagttt    1212
gtatttacac tacagattgg tgaatttgcc aacgtcctca ctgtgattat gtgtatattg    1272
```

```
ctgtttaaat tttgtatatg tgtataaaag gaaaaaggtt cacctagaga ttatttctga    1332
aaaatgtatt gtaaaaataa ttttgtggca tttctagtcc cttttttga atgaaccaat     1392
tatactttat ttggtctcct atgtagcatt tcagaaaaca agagaaaact gttaccatga    1452
acaaacattg ccagaattaa ccttactgtt taagaggcca acttctggaa ggaggtagga    1512
gtcataactt tttagaggca tatgccaaat atcatttggt atacttaaca atattagtgt    1572
tttaaaatga tgagttataa ttatttgaac atatagatat gtaacatgcc acaaatcatt    1632
tctaccatgc aaggtgtata agttgtttat tttttagtgt taaaactata atagcttgaa    1692
tataggtacc aatgaacaaa ttcaaattgc acctcttttc ttaaaagaat gggatttaaa    1752
ctcttataaa cattctttaa cttttttgtt tgtttgttct cttttttcc ttttgcattc     1812
ttctagccag tgattgatct gctaatgctt tctttgccac tctaagtaaa atttatttca    1872
cctcctcaat gaaaacctca tggttttgct ggctgtttat aactgcatcg cacttctagt    1932
tgtggcttga attttcagtt aagctttcat ggtatgtaat tttccagcct tttgagaaaa    1992
caagcatact ataagtgaga gctgttttgt tttccttgtt tgtttgtttc atgctaggct    2052
tttcctggca gcatgtccat tgcaggcagt ggacaagaaa ccaccagcat tgagctaacc    2112
cagtacatgc taggacctgt cctagagggg ccacttttca ttacctgagt tatttgtaca    2172
gaagggcaat agccattatt tttgtggatg aggaaacaag aataaacaga atggtatttt    2232
taggttttgta ttttatgtct tttttttttt tttttttgc cattcttgag gaaatataga    2292
gatgacatgt tttcaccca actatctggt gctattgaat gactaattca gtccctaaag     2352
ttctgtgaaa acacaaaagt ctaatgattt gagtgagtaa aaggtaatgg tgcatttgaa    2412
caagtaaatg ctgtcgtggt cagcaagatc cgtgatttga acatgtgatg actggaaaaa    2472
ggtttgggtt atttggaact ctggctaaaa cttctttcgg gtgacatgtg atcgtttaaa    2532
tggcattaag tgaataaagc acacagacag tgctactctt gaccactatt ttaccatttc    2592
tttgcaaaca gtgttcacat tttcatattt tttccctaac taaaccacca agaaagaaa    2652
ttttgtatgt atatacagtg tgtgtgtata caaaatcatg atatagtaga atgcaactac    2712
tttcttttc taccaaacga aaggttttat ttgctgtgaa ataaaccaga agtttaaaaa    2772
accctgtagt gattaagcat acttaaccac tccttatttg tagattcact ttcaacctta    2832
aaaattaata ccagtttgca taaaccaata tctgaaaaga acaggaaatg ttaatggcaa    2892
gcaacagcta ttaatactga tgtgatggat gcatttgttt tgcagtggtg actggcctag    2952
gcaggtttgg atctgtgaag aattgattca ttttcaaaat tattccataa agttaaaaag    3012
ttacacttta aaggcaacag gtcatacagt tctttaaatc tgatcaactg tagctttatt    3072
taaagcaaat ataaatcata gatgaagtta tttttaaacac tatgttagaa tatagagatt    3132
tttaaaaaat gctgataagc acagttaatt ctaaaatgag aggattgtta caggagggag    3192
atgttacagt taatccacaa tcaacatttt gatggtaggg aaaaaactgc gtaaaaacta    3252
ttgcattatg tatgataaga aagtaagtat tccaagggaa taatcttgca tattaagaaa    3312
actccaaata atctttaaac tgccttgaaa aataaacctc tttgactgct gagcggcaga    3372
gtgcttaccc ttgattgtct tgattttata tatttatttc taaggggaga aaaaggggtc    3432
agacagagta atatgataca ttttcttaaa aacttctcta agttgcacaa aactgaacaa    3492
tcatcaagca cttatttact ggctaatgtt gaataaatta gggtgccttc atctgggttt    3552
tctttagtac ctaagtctac aacccttct ctttttctat tgtgtttcga actccacatt     3612
gcaatactct gttgtcatgg aatacaacct ttagatgttt actgctgaag taggtcagaa    3672
```

```
attgtattat ttgatttgcc tcaaacatcc actgtaatgt tacatgcacc ttttttgaag    3732
catgaactct gaattatgtt tttataaatc tgactaggca aacctagatt ctggtttcac    3792
aatggattta ttttctctct cagtctccat tttaacagtg cttttgaagt ttatacagaa    3852
agctttaaaa gttagtttgt gcccttggtt tttattctta aaactgctaa aatacctctg    3912
taagccttat cctttattct ttcatatgtt gtataataaa tgtatagatt tcattgacca    3972
actaaaatgt tgggtgtctg taaatgagac caaaacgtgg gttgcttttt tcataaaata    4032
atttctattg ggggttactg ttcaatgaca gcaggtaacc tataactgtg aatgcttcgt    4092
gtcgtcagta tttgcattac attcataaaa gtgtgcaagt cctgtgactc ccagcttaac    4152
tgaaatactg ttatgccacc taacttgagt acagcaaact ggttttaggt ttcaatgaca    4212
ttgatgtaaa atgatatccc atgaataaaa agtatttgtg tttggtttca gaaaaaaaaa    4272
aaaaaa                                                               4278
```

<210> SEQ ID NO 42
<211> LENGTH: 292
<212> TYPE: PRT
<213> ORGANISM: Homo sapiens

<400> SEQUENCE: 42

```
Met His Ser Asp Ala Ala Val Asn Phe Gln Leu Asn Ser His Leu
 1               5                  10                  15

Ser Thr Leu Ala Asn Ile His Lys Ile Tyr His Thr Leu Asn Lys Leu
                20                  25                  30

Asn Leu Thr Glu Asp Ile Gly Gln Asp His Gln Thr Gly Ser Leu
            35                  40                  45

Arg Ser Cys Ser Ser Asp Cys Phe Asn Lys Val Met Pro Pro Arg
 50                  55                  60

Lys Lys Arg Arg Pro Ala Ser Gly Asp Leu Ser Ala Lys Lys Ser
 65                  70                  75                  80

Arg His Asp Ser Met Tyr Arg Lys Tyr Asp Ser Thr Arg Ile Lys Thr
                85                  90                  95

Glu Glu Glu Ala Phe Ser Ser Lys Arg Cys Leu Glu Trp Phe Tyr Glu
                100                 105                 110

Tyr Ala Gly Thr Asp Asp Val Val Gly Pro Glu Gly Met Glu Lys Phe
            115                 120                 125

Cys Glu Asp Ile Gly Val Glu Pro Glu Asn Val Val Met Leu Val Leu
130                 135                 140

Ala Trp Lys Leu Asp Ala Gln Asn Met Gly Tyr Phe Thr Leu Gln Glu
145                 150                 155                 160

Trp Leu Lys Gly Met Thr Ser Leu Gln Cys Asp Thr Thr Glu Lys Leu
                165                 170                 175

Arg Asn Thr Leu Asp Tyr Leu Arg Ser Phe Leu Asn Asp Ser Thr Asn
            180                 185                 190

Phe Lys Leu Ile Tyr Arg Tyr Ala Phe Asp Phe Ala Arg Glu Lys Asp
        195                 200                 205

Gln Arg Ser Leu Asp Ile Asn Thr Ala Lys Cys Met Leu Gly Leu Leu
210                 215                 220

Leu Gly Lys Ile Trp Pro Leu Phe Pro Val Phe His Gln Phe Leu Glu
225                 230                 235                 240

Gln Ser Lys Tyr Lys Val Ile Asn Lys Asp Gln Trp Cys Asn Val Leu
                245                 250                 255
```

```
Glu Phe Ser Arg Thr Ile Asn Leu Asp Leu Ser Asn Tyr Asp Glu Asp
                260                 265                 270

Gly Ala Trp Pro Val Leu Leu Asp Glu Phe Val Glu Trp Tyr Lys Asp
            275                 280                 285

Lys Gln Met Ser
        290

<210> SEQ ID NO 43
<211> LENGTH: 191
<212> TYPE: PRT
<213> ORGANISM: Homo sapiens

<400> SEQUENCE: 43

Ser Ser Lys Arg Cys Leu Glu Trp Phe Tyr Glu Tyr Ala Gly Thr Asp
 1               5                  10                  15

Asp Val Val Gly Pro Glu Gly Met Glu Lys Phe Cys Glu Asp Ile Gly
             20                  25                  30

Val Glu Pro Glu Asn Val Val Met Leu Val Leu Ala Trp Lys Leu Asp
         35                  40                  45

Ala Gln Asn Met Gly Tyr Phe Thr Leu Gln Glu Trp Leu Lys Gly Met
     50                  55                  60

Thr Ser Leu Gln Cys Asp Thr Thr Glu Lys Leu Arg Asn Thr Leu Asp
 65                  70                  75                  80

Tyr Leu Arg Ser Phe Leu Asn Asp Ser Thr Asn Phe Lys Leu Ile Tyr
                 85                  90                  95

Arg Tyr Ala Phe Asp Phe Ala Arg Glu Lys Asp Gln Arg Ser Leu Asp
            100                 105                 110

Ile Asn Thr Ala Lys Cys Met Leu Gly Leu Leu Leu Gly Lys Ile Trp
        115                 120                 125

Pro Leu Phe Pro Val Phe His Gln Phe Leu Glu Gln Ser Lys Tyr Lys
    130                 135                 140

Val Ile Asn Lys Asp Gln Trp Cys Asn Val Leu Glu Phe Ser Arg Thr
145                 150                 155                 160

Ile Asn Leu Asp Leu Ser Asn Tyr Asp Glu Asp Gly Ala Trp Pro Val
                165                 170                 175

Leu Leu Asp Glu Phe Val Glu Trp Tyr Lys Asp Lys Gln Met Ser
            180                 185                 190

<210> SEQ ID NO 44
<211> LENGTH: 12732
<212> TYPE: DNA
<213> ORGANISM: Homo sapiens
<220> FEATURE:
<221> NAME/KEY: CDS
<222> LOCATION: (344)...(1057)

<400> SEQUENCE: 44
gattgcgtca cttccgggcc tcagcgattc gcctccgggt taggctgagc ctcttgcttg      60
ctgtgactgg tggagctgcc gcgctgtccg cgttatctcc tcccggtgag aacgaaccgc     120
agtgtccacc ggcgaggagc cagccctgtc ccggtcagag aaagacgacg aggatacctg     180
ggagcgggcg gcgccgggc tgggccgcgc cggtgcgggc tggcgactct gctcctccgc      240
ttgctgctgt ctctgggaac tgggtgccag cgctgagggg cttccagcgg acagggaccc     300
ccttccccgg ctcccctgcc caccctgccg gggagggcgg aag atg ccg gtg aag       355
                                              Met Pro Val Lys
                                                1 aag aag aga aaa tcc cct ggg gtg gca gca gca gta gcg gaa gac gga       403
```

```
                    Lys Lys Arg Lys Ser Pro Gly Val Ala Ala Val Ala Glu Asp Gly
                     5                  10                  15                  20 ggc ctc aaa aag tgt aaa atc tcc agc tat tgc aga tcc caa ccc cct      451
Gly Leu Lys Lys Cys Lys Ile Ser Ser Tyr Cys Arg Ser Gln Pro Pro
                25                  30                  35 gct aga cta ata agt gga gag gaa cat ttt tca agc aag aag tgc ctg      499
Ala Arg Leu Ile Ser Gly Glu Glu His Phe Ser Ser Lys Lys Cys Leu
                40                  45                  50 gct tgg ttt tat gaa tat gca ggt cct gat gaa gtt gta ggg cca gaa      547
Ala Trp Phe Tyr Glu Tyr Ala Gly Pro Asp Glu Val Val Gly Pro Glu
                55                  60                  65 gga atg gaa aaa ttt tgt gaa gac att ggt gtt gaa cct gaa aat att      595
Gly Met Glu Lys Phe Cys Glu Asp Ile Gly Val Glu Pro Glu Asn Ile
         70                  75                  80 att atg tta gtt tta gcg tgg aaa ttg gag gct gaa agc atg gga ttt      643
Ile Met Leu Val Leu Ala Trp Lys Leu Glu Ala Glu Ser Met Gly Phe
     85                  90                  95                 100 ttt acc aag gaa gaa tgg tta aag gga atg act tca tta cag tgt gac      691
Phe Thr Lys Glu Glu Trp Leu Lys Gly Met Thr Ser Leu Gln Cys Asp
                105                 110                 115 tgc aca gaa aag tta caa aac aaa ttt gac ttt ttg cgc tca cag ttg      739
Cys Thr Glu Lys Leu Gln Asn Lys Phe Asp Phe Leu Arg Ser Gln Leu
                120                 125                 130 aat gat att tcg tca ttt aag aat atc tac aga tat gcc ttt gat ttt      787
Asn Asp Ile Ser Ser Phe Lys Asn Ile Tyr Arg Tyr Ala Phe Asp Phe
                135                 140                 145 gca agg gat aaa gat cag aga agc ctt gat att gat act gct aaa tct      835
Ala Arg Asp Lys Asp Gln Arg Ser Leu Asp Ile Asp Thr Ala Lys Ser
         150                 155                 160 atg tta gct ctt ctg ctt ggg agg aca tgg cca ctg ttt tca gta ttt      883
Met Leu Ala Leu Leu Leu Gly Arg Thr Trp Pro Leu Phe Ser Val Phe
165                 170                 175                 180 tac cag tac ctg gag caa tca aag tat cgt gtt atg aac aaa gat caa      931
Tyr Gln Tyr Leu Glu Gln Ser Lys Tyr Arg Val Met Asn Lys Asp Gln
                185                 190                 195 tgg tac aat gta tta gaa ttc agc aga aca gtc cat gct gat ctt agt      979
Trp Tyr Asn Val Leu Glu Phe Ser Arg Thr Val His Ala Asp Leu Ser
         200                 205                 210 aac tat gat gaa gat ggt gct tgg cct gtt ctt ctt gat gaa ttt gtt     1027
Asn Tyr Asp Glu Asp Gly Ala Trp Pro Val Leu Leu Asp Glu Phe Val
                215                 220                 225 gag tgg caa aaa gtc cgt cag aca tca tag caagaactat gtgaagaaaa       1077
Glu Trp Gln Lys Val Arg Gln Thr Ser
         230                 235 tgcaaacctt tcaattccca cgtgtataca agctaatgtg atgagggggga aaaaaatcca  1137 acgggtgcat tttcattcat atgaaagact tctcatagta ctttttttc ctttttttaa   1197 aggaggtttt tcttgttaca tgtgatgggc attgagccac acctcttctt agactgaata  1257
ttgaagtttt tgttttgagt tatgtttata acatttattt cagaacaata aagattcaga  1317
tttgtgacaa aggccttaaa gtgaagatgt cccttgagtg tcagagtggt atttattttt  1377
gtaaatttga attttttgat ttttgaggtt ccaattcacc gtgaatttac agaattttca  1437
agattttaaa cagtcttaat atttggcaac atagtctgct gatggtatgg ctcattatag  1497
tcatctctgc acaatttgga agactgttgg ccttgacttc tgggataatg atttgctgat  1557
gcagctaata aacatttcta ggtattgaa aaatgctcct actttagct ctgggtttct   1617 ataaaagctg ccaaggtctt atgcagatgt cttatctcag agagcttaga attggaaaga  1677
```

```
ttatgtccag ttgttttgtt ttctaaaaaa gttgtattat aagttgtat  catcattatt  1737 attgttgata atagcatatt tatatttta  actgtcatta tatagggaat tttgtttaaa  1797
gcactttttt tttttttttt tgccttaaga aacgttagc  tgtgatatgg atttaattaa  1857
gatacacata ggaaaagaag acaatagaat aaggaatcat gagagaactc tgggtataat  1917
taattgtgca caactcaata gagccattta cgttggtagt attgcagctt gctaattatc  1977
acaattttct gcctgttggt aatcaagtgt cttgaggaaa gggaaggctt tcctaattca  2037
tgtaaaaggc acttttgtac tagcagcagg cctgtttgta cattccttt  caaaccatcc  2097 agtatcccag tgatatgaaa actttgttca tattcatagc ccagtcacaa cttcagaaac  2157
atttctagtg tcattgtttg agtagagaga agtaaagagg ttatttttcc ataataaggg  2217
agtgtttcta ttaggattta aggtaaaggt tgattttca  gtggtgaatt tgtttaaaga  2277
atgatttctc catattgatt acctaagaga atgacatttt aaagtgtttt attgtttgct  2337
ttttagttaa tcagctggga aaaaatgat  tgccactgtt ttacttgcct tcttaataag  2397
attactttgt acagttttct gaaacaccca taatagtggg agacagtttt cctaaatgtc  2457
ttatagaaaa ggataataca gaatgctcct cttaagtatt agaatcactg agttatgaac  2517
tgagcatacc agtggtgtta ggatttaata ttatgaatga tgttttaata tcaaatttat  2577
tataaggaaa gcatttagat ttgtagacct ttaaattat  aatttagttg actcttcaag  2637
gcacatctga actgaagaac atatccactt ttgttaaatt ccaaaacata taagcaaaat  2697
cttataaatt gtccatttgt aacctgaact aatggtaata tcttttcat  cttcagtatt  2757 tgagtaaaat agggaacact taaagcttat agatgacatg ttttttaaaa ggtatattta  2817
tgaaagcaca ggcatccttg gtatacgcag gagattgata ccaggaccct tgtgtatacc  2877
caaatctgtg catacttaag tcctacagtc atccctgtgg aacctgcctg tataaaaagt  2937
cagccctccc cgtgtatgta ggtgtcgcat cccgggaata ctgtattttc aatccatgtt  2997
tggtttaaaa aaatctgcgt ataagcagac ccacacagtt caaactcatg ctgttcaagg  3057
gtcaacagta tttactttgc atacttatcc aaagatacct ttaagacttt ttgagtctga  3117 aaaatgaaatt tactttattt tttcccttaa agtcaactgt cctatcctac cctagccata  3177
ctttggagtc cagtaccact gaggccacgc ttgctttact ctattgctcc atctatttct  3237
cttaccttct taaagttata acatttgcct actttgaagg caaatttact ctgcctaatt  3297
catcagtcag ggtgtgggct gtgtcccttc ctgtctttcc tttgttaatt tgaatagca   3357 tttaatttac tgggaaattt atgatcaaaa atgttaagtg atataaacaa tacaatatta  3417
aggaccctgc agtataaaaa agtctaactg ttgtggttcc tttttgact  agttagcttt  3477 aagtgccttc ccacgaaccc tgttgtaaaa ttttcagaac tacttccctt tgtacaggat  3537
gaaataccgt atggtgcttt ataacatgga gttgagttgt ttctataaga atattataca  3597
aatgtaatac tactgggaga agtagagcc  agatgttgat tggacagatt gcaaccccc   3657 caccccccca ctcctcgggg ccaataattc ttaataaggt atgatgttaa tacctctagg  3717
aaattgccag ggattcaggt gacagtgtgt gatgaaaacg gtgtattgtg tgctggcctg  3777
actgcattac catgtttgtc ttctattgtc taatgatttc ttatttctta aatgctgctg  3837
ataaaattat tgatataata cattttgac  agtagtagca ttttgtgta  taatgtatag  3897 attttattgg ttttttactca gaagcactct agattagtgt ttcttgaact gcaatttgaa  3957
gccttctttg ggaatgttag attgaggagt atttctctta aatacaaatg ccttttcatc  4017
tagcaaacca aaaattatat cttaatattg aatgccatca ctcggggtcg ggtgggagt   4077
```

```
aaattctgag ataactccag agttttcaag gcatacaagg tatgtggaat agcacagatt    4137
cagaatacat gatacatacg tataaaatga aacatttcac tttgaagtat ttcttcaaca    4197
aaacatgtcc tgtctgccta cttgctaatg tgaaattatg aaaggattta ttgaaatata    4257
tgttcagttt gaggtgtaat tggtaagaat gccaggtgtt gttcttctgc cctcttaaag    4317
aagtgtactt aaaactattg tgataattca tctctgataa aactttgttc tggccttcaa    4377
ggctcttaca gcttaatgtt ttaaatgtct aaggcatcaa ataaattgag gcattttaa     4437 taaaaaaaa aaaggaaaac taaatgcctt tctttgttaa agcaaaaggc caaaataaa      4497 aaataaaatt aaaaccccc ccaaaaaaac ccaaaagtct tactcctaaa gaagaattct     4557
tacctctaag gaggaatcct tccctcttga ggaaatacca cttttttgagt gacattagaa   4617 atcatcacaa ggaaacattt caagaaaagg atcattttt tttcaggaga aagaggaata     4677
acaatttcat taacttcctc aataggaaag gctagtctga attattaaat attctggatt    4737
atatcttttt ttaatgatat agttttatta cttcaggaat atttggtaag aaccaggtaa    4797
acctattgtt taagatttgt tctttttgt taatagacct atgattagta tggtggaagc     4857
ccaaaaagca gtctaatttt tatgataaac ttacagactg tggaaagatg aatttctgcc    4917
ccaaaccttg gataagttgt cattaattta attgtagaga ttttctagt gaacttgtac     4977 ttcactggaa caaatcttta gatcttttaa agcacaattt atttatgttt ttaaaaacag    5037
tcttaaaact gatcgatcat acatttgctg tgtccacctt acaatctttt acattctatt    5097
agtacagata gtgtttcctt tgctcctttt cctgaccagt tgttattggt gtgaccattt    5157 tcttttttagg atcgatgaaa cattttgctg tgtatgctgt gtcatgtatt agaacctctt   5217
ataatatggc tcattttac atggtttctg atttaccatg tgttaaatat tccttaaaat     5277
acatctagta acactatata gtaaggttag attttaacct aagtattgaa tcttgtctta   5337
taatgccaat tttattggag cttttgttgca tttattttg gctctatggt ccataaatgg   5397
gagttaatag caaacgtttt attaaaaatg tcttagcttt cccccaaatt atatcatttt    5457
ttagaagttt tatccttctg gggtgttttt ggctttctga gctttaagat attaatgaat    5517 ttttttccaca tacttcatgg gtttggtttt aagtatgagg ttaaaattgt ggatttaaa    5577 aagctaataa atacttgaag tgaatatata gagagagcca gatttcccca aaactctgtg   5637
agctgtgtgt gttttgtgta gaatattagc cataattaac ttttcccttt tttttttgg     5697 agacagggtc ttactctgtc acccaggatg gagtgcagtg gtgcggtctc agctcactgc   5757
agcctcgacc tcctgggttc aagagattct cgtgcgtcaa cctcccaagt agctgggatt   5817
acagatgcct gccaccatgc ccagctaagt tttgtatttt ttttttttgtt tgttttagta   5877 aagatgggat ttcaccatgt tggccaggct ggtctcaaac tcctgcctc aagtgatccc     5937 acccacctca gactcccaaa gtgctgggat tacaggtgtg agccaccact cctgggaaat    5997
aattaacttt tcacataga aaatagatca cagataaaag ctcctcacat attttgaagg    6057 tcaaaaaaa atttgctgtt gctaacaatt gcctttgaac catgaaagag gaaaaactaa    6117
ctttatttga gcaacttgtc atttgagact taaactaact tatcaaactt agcagaatta    6177
acttgtgagt attgacttaa gtgaagttag tttatatact ttactattct gtcatgcaaa   6237
taaaatggct tagagcaagt tcatacacag ttactttat ctacaaatgt agaaatctta    6297
cctatttgaa atttacatta ttccctgaaa ctatgcctat tgagagagag tttatagaag   6357
tattatctga gaaacctgag tttgatttc ttttttgtgac attcctgtta atgtcacttt    6417
```

```
taaacaagcc acttaaccta tgtcattttc agtttcttct gtaaaatggc gataatgata    6477
cctaccagta ttgttacgaa gttcaaatag gccctatcca cagcacttag taggtgttaa    6537
atgaatgcgt cttgttactt gaacaagaag tggttagtta tgatagttta ttttttttctg   6597
acaaatttac tgtcttttat aaaagaaat agctaggatt tcctgtgtta tcctgccatt     6657
tttataatca aacaaaatta ttaatattct ccttagacta aatcattaat ttaacaaatc    6717
tcaagcatct actatatgcc aagaagtatt ctaggcctga atatattgca gggcacgaag    6777
caagacagta atttcgaacc tttatgggat ttttatttta attggttagt aaaatagttt    6837
atcatttggt gacaaggtta tatgggaaa gtaagttgag gaaggggccc agagagtgtg     6897
tgaggatagg attactatta agtagcatgt acactgatat gtgacattga gcagaggcct    6957
gaggaggtga atggttgtgc agtgtggata tctgggagga gagcattcca ggcagaagga    7017
atattacatg ctaaggccct gagctggtac agagtgtaaa gaaacagtaa agagatcagt    7077
gtgactgtag tgaacaataa tagcatttta gggagaatta gaaaatgaac tgagagagat    7137
tgggagtaat aatcctgcct gattgtaggt aattacgtag ggcattatag ccctttctca    7197
agagtaggac tttactgagt gagctagcaa gcaattagga ttcagatcaa agcaaggatg    7257
gaagcaggta gtagtaggaa gataaatatgg taaatccagg tgacaaatgg tacaatttga   7317
gattaagagt aatggaaata ataagtggtc agattctgaa tgtattttgg tggtagcacc    7377
aaaaggatat gctgatagaa tggatgtgag gtatgaaaaa agaatgatc aaggtttttg     7437
gcttgaagaa tgaagtgggc attaataaga tggcgaagac tcagaggagc aggcttaagc    7497
gggtagattg agagtttact tttgatatg ttatggtaga cttgtctgtc agacgtccaa     7557
aggaaaatgt agagtgggca gttggatatt tgaacctgga aaagtagagg tctgggctgg    7617
agataaatat atttggaagt catcagtgtg taatcttatt ttaagtcagg acatggatga    7677
aaccacttag agagtaagtg tagccagagg atagaactta attgaagaca tatgatcgat    7737
gaaattcaag gccaacttttt gtgattttttc aaatagaaat aaaatgttaa catttttctac  7797
cacacatata caaaccatta ctttctatag tgttgtagaa gcactaagat ttaaaaagca    7857
agattgataa tagttgccaa atatgtaaac aaatggcaaa ttaaattgag gagggagtgt    7917
cactttattc ttggaataaa gttttttgttt tgaagtaata cagttttttta tattaagaat  7977
aacaacatct ggagtgctag tttctttttc tcattgttgg aaattgctat tccaattcaa    8037
tttgacagtt ttagcactag agggcaggct tgcttctaga ttgtgaagag ttctacatga    8097
attaatatag ccaaacagcg caggttgaac atccttaact tgaaaatctg aaattcaaaa    8157
tgcttcaaaa tccaaaactt tttgagtgtt gacatgatgc cacaagtgga aaattccaca   8217
cctgacctca tatgatgggt cacagtcaaa atgcaggtgt acaacagttt actctgttcc   8277
caagagaaaa ataaaattag ctgcaggcta tgtgtaaaaa gtgtatatga aacataaatg    8337
aatttcatgt ttagacttgg gtcccatccc caaggtatct tattatgaat atgcaaatat    8397
tcaaagatca aaaaaagaa atctaaaaca cttccggtcc caagcatttt ggataagaga     8457
tattcaacct gcacctacat tcaatctcaa ttaatgaatg cagttgtttc ttatgtgaca    8517
ggtttgccat ctactatgtt ttttttctagt gctaggaaag cataaaataa ggctaattga   8577
ttttagtaca tctaggactg gcagttgacg ctaatataca tttgaatata aatgtatatt    8637
tatattccaa ggagttttcca aggaaactca agtgtagctt aattatactc agatttgata   8697
tagagggtct tccaccacat atatgaatat taaagccagt cagaagaaat cctggacatg   8757
aaaacatttt ttcaggaaat aattaactat gtgctgggta ttattatatg agcgtggcta   8817
```

```
caaagatgaa taaaatatag tccctgccta aataagcttt gttgtagcat cttacagcac   8877
ttaatatctt gtgctgtatc tatttaaatg tcttttccc ttcaataata gaaatcctga   8937
ctcacttatt tttggtgcct ccaagtgccc atcacacaat tcagtttaca gtgtttgaac   8997
atgtgaataa tgagagagag aaaaataaga aaacggtcag ggaattgggg cctttgaaaa   9057
aacttatttt cacatttta cccttagaga gatgcttttc ctattaacac gtctaaagat    9117
tatgagagaca attctaacct tctatctttg ctcccactac ttcttcaagc agactttaac   9177
cccattcctc aagagcagtt attggcagcc atagagagtg ggaggtcaag cctttttag    9237
tcattggagt aaacaggaga catagatgtg gaaattggga ggttctctct atctggctta   9297
cgtcagtttg agaagtttga catgaaatgg aaccttctgg aatgaggttc tttttcctgc   9357
ttttcacctg gaaagttttc ccatacatgg tcctcttgca ccctagtcc ttttagggta    9417
cctatttctg tgtgctagtt cttcattc cttgtctgta acatgaggat aataatagtc     9477
cttatctaat agcattattt tgaggatgaa atgaaataca ggcagtaaat attagttact   9537
ctttgctatc tggaaaaaca tcaattgaac ctcataggat ggacttgtgt tcaataagtg   9597
ttatatatag tagagtcaaa tggaaaaatt gaaccactca gatacatttt tttcattgat   9657
acataataga tgtatttatt tgggggggtac atgtgataat atgatatatt catataatta  9717
aaattcattg atacatgatg tatttatttg ggggtacatg tgatagtatg atatattcat  9777
ataattaaaa ttcattgata cataatgtat ttatttgggg ggtacatgtg atagtatgat  9837
atattcatat aattaaatga agataattgg gatatccatc accttaaata tttatgtttt  9897
ctttacacta ggaacattcg aattctcttt agctatttg aaatgtacaa tagtttagtg   9957
ttaatagatc agtcatccta ctgatatatc gaacaccagg tcttatttct tctgtctaca  10017
tagacatatt tagaaatgca aatctcttag gaaattaatc tgtaatgtca atgatgcaca  10077
ctgatttgta ttacttgctt tcttttgtagg cagtatagtg aaatggttca ttaaatggat 10137
gctaaatatg actaaatgat caatttacag tgtagttggc accaagtaat aaatgctcag  10197
taacatagct actatggctg tctttaaaag tggattggtt tgacttcata ggaaggactc  10257
tattttaaa aagagaaat attaaaaat aaaagccaa aattctatga tgtcttatta      10317
cattgagtct cttaaatcag tttttttta attaagtagc aggaccctat tgcaaaataa   10377
gttttaccta gaagcacagt attaaaaaca gaaagctaaa atactctggt taagtgggaa  10437
gctccctgtc ttcctcgctg ctagtattat ttctgaaaaa cctcaaagga actccttgct   10497
ctctgaatag caggttttaa aaaccactac ttgcacattt gcaccttgac atcaaacatg  10557
tgaacaaagt aatagagtga gaaaactgaa tttctattta ggaatttcta ttttattctc  10617
tctataaaaa gccaagaagt ggttggtgtt tggaataaca tgaaaaatat tccaagtatc  10677
tttggaaata cttacactag aactataagg tttatgataa ttctatctta gattcattat  10737
ctagagctgg tctaaaaag gatgatatgt aagaactacc aagagagact tggagtagat   10797
acaagaatga aggaatgaat caatatccaa taaatatcca taggcccagg ctttgctatg  10857
ccctcttatt acacaggata aaacagtgta gttgttagtt ctacctttg aagattatga   10917
tccttaaaaa ggaaacagct ctgtgaacag agaccatgtt attcataggt gttcctcact  10977
tgtttccacc acataatagg tatttaatga atgaaaaaat tcacgtctct ctttgatcct  11037
agactgcaag ttacttaaaa gaaatggacc gtatttact tatctctcat ggcctgcaaa   11097
ttgagtttgc ttactgaatt aatgaatgaa tgaccaattg tacacatatg tctgtaaaac  11157
```

```
gtttacatat ccacattccc attagactga gattcttgag ggcagaaacc atgtcttcag    11217
ctctcagcat ggtgcctgac tcatggtagg ttgtcaaaag catttgcaga actgaataaa    11277
acttacgttt aagtagtact ggagcagtct cacataaccg ggcacagtgt cttctaaata    11337
gacactaaaa ttatttcata attaaagaca gatctcacta agcattttct gagttagtgc    11397
cagttgaata atatgacaat aagctatagg agttcagagg agagtgagtt ctgtggactg    11457
aaatagtcaa agtggatttt cagagcagat gagacgcgat gaaggctggg gctactttgg    11517
tgttttaaga acattaatta ggcagcagga aaatctgagg acagggagac tagtaaggaa    11577
ggctggaaag agccctgggt ttggagttca gagatctgtg ttcagagtcc tttgcttctt    11637
agtgactatg tgaccttgag aagataactt gagctcccct ttttcctcttc tgtgaggtag   11697
aggtaagatt gatgtgcata ttgatattgt acttaaaagt gttttgtaaaa tgctaagtaa   11757
aacctaatgc tatgctttga atgtagtggg ttccaaatat ttgtttaatg acaaagaata    11817
aatgatattg actaatgaaa ataatggagc cactggaatg tcacctcctg catctgccag    11877
taaacctgtt aacacagggg tggcggggggg ggggggaag taaatatgtg aagccaccaa    11937
atctcatgat caggagaaaa actttggaac tcccatgaga ctccaaagtt atgtcacagg    11997
tgaataagtc atgaactttt catgctgata tcatttctaa ggttgctgcc ttgtcagaag    12057
aagcaaacca caagataaac catgcagaaa atctttttttt aaaaaagttt cctgaaggat   12117
ggatggttca tttgttctgc ttgtcacttt acttactaat gagtcatttt tttccttaac    12177
cagtaatttg ttttaaattt ggtcataaga tggtatgttg actagtccaa tgttacaaaa    12237
taattggaaa aaagatgaca gaccaccaac tgaataaggg aaatctggtt cttgaacttc    12297
caatgtatga attggtgatg gtaagcttag tctttatgat gtaagattgg atttattgga    12357
acttctttat gtccagaagt tgcagcacct ttctttgtct ctggaatgcc caagatctct    12417
actgcatcct gtagacatgg agggtttccc cccttattct gggtctgatt attttttaaag   12477
aaacacccctt tccttaccca tcatggagac actactaacc ttgtatatac ttttattaga    12537
gtgctgataa caccatatta cagtagcata cttacatatc tgttttctta actgtgagct    12597
ccttgagagc agggactgtg tgtttttgct tttatttcac cagtactcag aactatccac    12657
agtatagaaa agcactcaat aaatggaata aatgaaaatg aatagataaa taatgatttt    12717
cacttgtata agatg                                                     12732
```

<210> SEQ ID NO 45
<211> LENGTH: 237
<212> TYPE: PRT
<213> ORGANISM: Homo sapiens

<400> SEQUENCE: 45

```
Met Pro Val Lys Lys Arg Lys Ser Pro Gly Val Ala Ala Ala Val
  1               5                  10                  15

Ala Glu Asp Gly Gly Leu Lys Lys Cys Lys Ile Ser Ser Tyr Cys Arg
                 20                  25                  30

Ser Gln Pro Pro Ala Arg Leu Ile Ser Gly Glu Glu His Phe Ser Ser
             35                  40                  45

Lys Lys Cys Leu Ala Trp Phe Tyr Glu Tyr Ala Gly Pro Asp Glu Val
         50                  55                  60

Val Gly Pro Glu Gly Met Glu Lys Phe Cys Glu Asp Ile Gly Val Glu
 65                  70                  75                  80

Pro Glu Asn Ile Ile Met Leu Val Leu Ala Trp Lys Leu Glu Ala Glu
                 85                  90                  95
```

```
Ser Met Gly Phe Phe Thr Lys Glu Glu Trp Leu Lys Gly Met Thr Ser
            100                 105                 110

Leu Gln Cys Asp Cys Thr Glu Lys Leu Gln Asn Lys Phe Asp Phe Leu
            115                 120                 125

Arg Ser Gln Leu Asn Asp Ile Ser Ser Phe Lys Asn Ile Tyr Arg Tyr
130                 135                 140

Ala Phe Asp Phe Ala Arg Asp Lys Asp Gln Arg Ser Leu Asp Ile Asp
145                 150                 155                 160

Thr Ala Lys Ser Met Leu Ala Leu Leu Leu Gly Arg Thr Trp Pro Leu
                165                 170                 175

Phe Ser Val Phe Tyr Gln Tyr Leu Glu Gln Ser Lys Tyr Arg Val Met
            180                 185                 190

Asn Lys Asp Gln Trp Tyr Asn Val Leu Glu Phe Ser Arg Thr Val His
            195                 200                 205

Ala Asp Leu Ser Asn Tyr Asp Glu Asp Gly Ala Trp Pro Val Leu Leu
            210                 215                 220

Asp Glu Phe Val Glu Trp Gln Lys Val Arg Gln Thr Ser
225                 230                 235

<210> SEQ ID NO 46
<211> LENGTH: 191
<212> TYPE: PRT
<213> ORGANISM: Homo sapiens

<400> SEQUENCE: 46

Ser Ser Lys Lys Cys Leu Ala Trp Phe Tyr Glu Tyr Ala Gly Pro Asp
1               5                   10                  15

Glu Val Val Gly Pro Glu Gly Met Glu Lys Phe Cys Glu Asp Ile Gly
            20                  25                  30

Val Glu Pro Glu Asn Ile Ile Met Leu Val Leu Ala Trp Lys Leu Glu
        35                  40                  45

Ala Glu Ser Met Gly Phe Phe Thr Lys Glu Glu Trp Leu Lys Gly Met
50                  55                  60

Thr Ser Leu Gln Cys Asp Cys Thr Glu Lys Leu Gln Asn Lys Phe Asp
65                  70                  75                  80

Phe Leu Arg Ser Gln Leu Asn Asp Ile Ser Ser Phe Lys Asn Ile Tyr
                85                  90                  95

Arg Tyr Ala Phe Asp Phe Ala Arg Asp Lys Asp Gln Arg Ser Leu Asp
            100                 105                 110

Ile Asp Thr Ala Lys Ser Met Leu Ala Leu Leu Leu Gly Arg Thr Trp
        115                 120                 125

Pro Leu Phe Ser Val Phe Tyr Gln Tyr Leu Glu Gln Ser Lys Tyr Arg
130                 135                 140

Val Met Asn Lys Asp Gln Trp Tyr Asn Val Leu Glu Phe Ser Arg Thr
145                 150                 155                 160

Val His Ala Asp Leu Ser Asn Tyr Asp Glu Asp Gly Ala Trp Pro Val
                165                 170                 175

Leu Leu Asp Glu Phe Val Glu Trp Gln Lys Val Arg Gln Thr Ser
            180                 185                 190

<210> SEQ ID NO 47
<211> LENGTH: 810
<212> TYPE: DNA
<213> ORGANISM: Saccharomyces cerevisiae
<220> FEATURE:
<221> NAME/KEY: CDS
```

<222> LOCATION: (1)...(810)

<400> SEQUENCE: 47

| | | | | | | | | | | | | | | | | |
|---|---|---|---|---|---|---|---|---|---|---|---|---|---|---|---|---|
| atg | agt | aat | aat | aaa | ata | aaa | aga | aag | gat | gca | agc | ccg | gaa | caa | gag | 48 |
| Met | Ser | Asn | Asn | Lys | Ile | Lys | Arg | Lys | Asp | Ala | Ser | Pro | Glu | Gln | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gca | att | gaa | tca | ttc | acc | tca | tta | acc | aaa | tgt | gac | ccc | aag | gta | tcc | 96 |
| Ala | Ile | Glu | Ser | Phe | Thr | Ser | Leu | Thr | Lys | Cys | Asp | Pro | Lys | Val | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| agg | aag | tac | ctg | cag | cgt | aat | cac | tgg | aac | atc | aat | tac | gct | ctc | aat | 144 |
| Arg | Lys | Tyr | Leu | Gln | Arg | Asn | His | Trp | Asn | Ile | Asn | Tyr | Ala | Leu | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| gat | tat | tat | gac | aag | gaa | ata | ggg | acg | ttt | act | gac | gag | gtt | tca | act | 192 |
| Asp | Tyr | Tyr | Asp | Lys | Glu | Ile | Gly | Thr | Phe | Thr | Asp | Glu | Val | Ser | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| gtg | gct | cat | cca | ccc | gta | tac | ccg | aag | gag | cta | aca | cag | gta | ttt | gaa | 240 |
| Val | Ala | His | Pro | Pro | Val | Tyr | Pro | Lys | Glu | Leu | Thr | Gln | Val | Phe | Glu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cac | tat | atc | aat | aac | aac | ttg | ttt | gat | ata | gac | tca | ctg | gtc | aag | ttc | 288 |
| His | Tyr | Ile | Asn | Asn | Asn | Leu | Phe | Asp | Ile | Asp | Ser | Leu | Val | Lys | Phe | |
| | | | 85 | | | | | 90 | | | | | 95 | | | |

| | | | | | | | | | | | | | | | | |
|---|---|---|---|---|---|---|---|---|---|---|---|---|---|---|---|---|
| att | gag | gag | cta | ggc | tac | aat | ctt | gaa | gat | tta | gcg | aca | tta | tgc | tta | 336 |
| Ile | Glu | Glu | Leu | Gly | Tyr | Asn | Leu | Glu | Asp | Leu | Ala | Thr | Leu | Cys | Leu | |
| | | 100 | | | | | 105 | | | | | 110 | | | | |

| | | | | | | | | | | | | | | | | |
|---|---|---|---|---|---|---|---|---|---|---|---|---|---|---|---|---|
| gcc | cat | tta | ctg | ggg | tac | aag | aaa | cta | gaa | gaa | ccc | tta | aaa | cga | gag | 384 |
| Ala | His | Leu | Leu | Gly | Tyr | Lys | Lys | Leu | Glu | Glu | Pro | Leu | Lys | Arg | Glu | |
| | 115 | | | | | 120 | | | | | 125 | | | | | |

| | | | | | | | | | | | | | | | | |
|---|---|---|---|---|---|---|---|---|---|---|---|---|---|---|---|---|
| gac | ttc | ctg | tca | aca | tgg | ttt | atg | caa | ggc | tgt | tcc | acc | att | tca | gac | 432 |
| Asp | Phe | Leu | Ser | Thr | Trp | Phe | Met | Gln | Gly | Cys | Ser | Thr | Ile | Ser | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | caa | gag | tgc | atc | aag | acg | tta | gat | gtt | aaa | tta | cat | gaa | gac | tta | 480 |
| Met | Gln | Glu | Cys | Ile | Lys | Thr | Leu | Asp | Val | Lys | Leu | His | Glu | Asp | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| caa | tat | ttc | aca | cag | att | tat | aac | tat | gct | ttc | aat | ttg | att | ctg | gac | 528 |
| Gln | Tyr | Phe | Thr | Gln | Ile | Tyr | Asn | Tyr | Ala | Phe | Asn | Leu | Ile | Leu | Asp | |
| | | | 165 | | | | | 170 | | | | | 175 | | | |

| | | | | | | | | | | | | | | | | |
|---|---|---|---|---|---|---|---|---|---|---|---|---|---|---|---|---|
| cca | aat | cga | aag | gat | ata | gat | aca | gac | gaa | ggc | atc | cag | tat | tgg | aag | 576 |
| Pro | Asn | Arg | Lys | Asp | Ile | Asp | Thr | Asp | Glu | Gly | Ile | Gln | Tyr | Trp | Lys | |
| | | 180 | | | | | 185 | | | | | 190 | | | | |

| | | | | | | | | | | | | | | | | |
|---|---|---|---|---|---|---|---|---|---|---|---|---|---|---|---|---|
| cta | ttt | ttc | caa | cca | gag | tac | cca | gtg | cgt | atg | gaa | cca | gat | ttg | ctt | 624 |
| Leu | Phe | Phe | Gln | Pro | Glu | Tyr | Pro | Val | Arg | Met | Glu | Pro | Asp | Leu | Leu | |
| | 195 | | | | | 200 | | | | | 205 | | | | | |

| | | | | | | | | | | | | | | | | |
|---|---|---|---|---|---|---|---|---|---|---|---|---|---|---|---|---|
| gag | gca | tgg | ttc | cgt | ttc | ctt | cgc | gat | gag | ggg | aaa | acc | act | ata | agt | 672 |
| Glu | Ala | Trp | Phe | Arg | Phe | Leu | Arg | Asp | Glu | Gly | Lys | Thr | Thr | Ile | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| aaa | gac | acc | tgg | cgt | atg | ctg | ctc | ctc | ttt | ttc | aaa | cga | tac | ccc | act | 720 |
| Lys | Asp | Thr | Trp | Arg | Met | Leu | Leu | Leu | Phe | Phe | Lys | Arg | Tyr | Pro | Thr | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| att | cag | aaa | ata | ata | agc | gat | tac | gac | gaa | act | gca | gcc | tgg | cca | ttt | 768 |
| Ile | Gln | Lys | Ile | Ile | Ser | Asp | Tyr | Asp | Glu | Thr | Ala | Ala | Trp | Pro | Phe | |
| | | | 245 | | | | | 250 | | | | | 255 | | | |

| | | | | | | | | | | | |
|---|---|---|---|---|---|---|---|---|---|---|---|
| att | atc | gat | gag | ttc | tat | gag | tgc | tta | cag | gat | cag | caa | taa | | | 810 |
| Ile | Ile | Asp | Glu | Phe | Tyr | Glu | Cys | Leu | Gln | Asp | Gln | Gln | | | | |
| | | 260 | | | | | 265 | | | | | | | | | |

<210> SEQ ID NO 48
<211> LENGTH: 269
<212> TYPE: PRT
<213> ORGANISM: Saccharomyces cerevisiae

<400> SEQUENCE: 48

```
Met Ser Asn Asn Lys Ile Lys Arg Lys Asp Ala Ser Pro Glu Gln Glu
1               5                   10                  15

Ala Ile Glu Ser Phe Thr Ser Leu Thr Lys Cys Asp Pro Lys Val Ser
            20                  25                  30

Arg Lys Tyr Leu Gln Arg Asn His Trp Asn Ile Asn Tyr Ala Leu Asn
        35                  40                  45

Asp Tyr Tyr Asp Lys Glu Ile Gly Thr Phe Thr Asp Glu Val Ser Thr
    50                  55                  60

Val Ala His Pro Pro Val Tyr Pro Lys Glu Leu Thr Gln Val Phe Glu
65              70                  75                  80

His Tyr Ile Asn Asn Asn Leu Phe Asp Ile Asp Ser Leu Val Lys Phe
                85                  90                  95

Ile Glu Glu Leu Gly Tyr Asn Leu Glu Asp Leu Ala Thr Leu Cys Leu
                100                 105                 110

Ala His Leu Leu Gly Tyr Lys Lys Leu Glu Glu Pro Leu Lys Arg Glu
            115                 120                 125

Asp Phe Leu Ser Thr Trp Phe Met Gln Gly Cys Ser Thr Ile Ser Asp
    130                 135                 140

Met Gln Glu Cys Ile Lys Thr Leu Asp Val Lys Leu His Glu Asp Leu
145                 150                 155                 160

Gln Tyr Phe Thr Gln Ile Tyr Asn Tyr Ala Phe Asn Leu Ile Leu Asp
            165                 170                 175

Pro Asn Arg Lys Asp Ile Asp Thr Asp Glu Gly Ile Gln Tyr Trp Lys
        180                 185                 190

Leu Phe Phe Gln Pro Glu Tyr Pro Val Arg Met Glu Pro Asp Leu Leu
    195                 200                 205

Glu Ala Trp Phe Arg Phe Leu Arg Asp Glu Gly Lys Thr Thr Ile Ser
210                 215                 220

Lys Asp Thr Trp Arg Met Leu Leu Leu Phe Phe Lys Arg Tyr Pro Thr
225             230                 235                 240

Ile Gln Lys Ile Ile Ser Asp Tyr Asp Glu Thr Ala Ala Trp Pro Phe
            245                 250                 255

Ile Ile Asp Glu Phe Tyr Glu Cys Leu Gln Asp Gln Gln
        260                 265
```

<210> SEQ ID NO 49
<211> LENGTH: 200
<212> TYPE: PRT
<213> ORGANISM: Saccharomyces cerevisiae

<400> SEQUENCE: 49

```
Val Tyr Pro Lys Glu Leu Thr Gln Val Phe Glu His Tyr Ile Asn Asn
1               5                   10                  15

Asn Leu Phe Asp Ile Asp Ser Leu Val Lys Phe Ile Glu Glu Leu Gly
            20                  25                  30

Tyr Asn Leu Glu Asp Leu Ala Thr Leu Cys Leu Ala His Leu Leu Gly
        35                  40                  45

Tyr Lys Lys Leu Glu Glu Pro Leu Lys Arg Glu Asp Phe Leu Ser Thr
    50                  55                  60

Trp Phe Met Gln Gly Cys Ser Thr Ile Ser Asp Met Gln Glu Cys Ile
65              70                  75                  80

Lys Thr Leu Asp Val Lys Leu His Glu Asp Leu Gln Tyr Phe Thr Gln
            85                  90                  95

Ile Tyr Asn Tyr Ala Phe Asn Leu Ile Leu Asp Pro Asn Arg Lys Asp
```

```
                  100                 105                 110
Ile Asp Thr Asp Glu Gly Ile Gln Tyr Trp Lys Leu Phe Phe Gln Pro
            115                 120                 125

Glu Tyr Pro Val Arg Met Glu Pro Asp Leu Leu Glu Ala Trp Phe Arg
            130                 135                 140

Phe Leu Arg Asp Glu Gly Lys Thr Thr Ile Ser Lys Asp Thr Trp Arg
145                 150                 155                 160

Met Leu Leu Leu Phe Phe Lys Arg Tyr Pro Thr Ile Gln Lys Ile Ile
                165                 170                 175

Ser Asp Tyr Asp Glu Thr Ala Ala Trp Pro Phe Ile Ile Asp Glu Phe
            180                 185                 190

Tyr Glu Cys Leu Gln Asp Gln Gln
            195                 200

<210> SEQ ID NO 50
<211> LENGTH: 625
<212> TYPE: DNA
<213> ORGANISM: Homo sapiens
<220> FEATURE:
<221> NAME/KEY: CDS
<222> LOCATION: (104)...(349)

<400> SEQUENCE: 50
agtagaagtg gcccttgcag gcaagagtgc tggagggcgg cagcggcgac cggagcggta      60
ggagcagcaa tttatccgtg tgcagcccca aactggaaag aag atg cta att aaa      115
                                              Met Leu Ile Lys
                                                1 gtg aag acg ctg acc gga aag gag att gag att gac att gaa cct aca      163
Val Lys Thr Leu Thr Gly Lys Glu Ile Glu Ile Asp Ile Glu Pro Thr
  5                  10                  15                  20 gac aag gtg gag cga atc aag gag cgt gtg gag gag aaa gag gga atc      211
Asp Lys Val Glu Arg Ile Lys Glu Arg Val Glu Glu Lys Glu Gly Ile
                 25                  30                  35 ccc cca caa cag cag agg ctc atc tac agt ggc aag cag atg aat gat      259
Pro Pro Gln Gln Gln Arg Leu Ile Tyr Ser Gly Lys Gln Met Asn Asp
             40                  45                  50 gag aag aca gca gct gat tac aag att tta ggt ggt tca gtc ctt cac      307
Glu Lys Thr Ala Ala Asp Tyr Lys Ile Leu Gly Gly Ser Val Leu His
         55                  60                  65 ctg gtg ttg gct ctg aga gga gga ggt ggt ctt agg cag tga              349
Leu Val Leu Ala Leu Arg Gly Gly Gly Gly Leu Arg Gln
 70                  75                  80 tggaccctcc attttacctc tttacccgtgt cgctcataat gaggcatcat atatcctctc    409
actctctggg acaccatagc cactgccccc tccctggat gcccagtaat gtatgtctac      469
tggtgggaga ctgtgaggat cccaggattc agtattcctg gcccagaggg cccttgctgg    529
ctactgggtg ttagtttgca gtcctgtgtg cttccctctc ttatgactgt gtccctggtt    589
gtcaataaaa tatttcctgg cctcctggaa tctttc                              625

<210> SEQ ID NO 51
<211> LENGTH: 81
<212> TYPE: PRT
<213> ORGANISM: Homo sapiens

<400> SEQUENCE: 51

Met Leu Ile Lys Val Lys Thr Leu Thr Gly Lys Glu Ile Glu Ile Asp
  1                   5                  10                  15

Ile Glu Pro Thr Asp Lys Val Glu Arg Ile Lys Glu Arg Val Glu Glu
```

```
                    20                  25                  30

Lys Glu Gly Ile Pro Pro Gln Gln Gln Arg Leu Ile Tyr Ser Gly Lys
            35                  40                  45

Gln Met Asn Asp Glu Lys Thr Ala Ala Asp Tyr Lys Ile Leu Gly Gly
        50                  55                  60

Ser Val Leu His Leu Val Leu Ala Leu Arg Gly Gly Gly Leu Arg
65                  70                  75                  80

Gln

<210> SEQ ID NO 52
<211> LENGTH: 602
<212> TYPE: DNA
<213> ORGANISM: Mus musculus
<220> FEATURE:
<221> NAME/KEY: CDS
<222> LOCATION: (95)...(340)

<400> SEQUENCE: 52
cttgccgtgg agtgctggga agcggcagcg gcagcagcga ccacagcggg agaagcagca        60
ctctagccgc ctgcaacccc aacctgggaa gaag atg cta att aaa gtg aag acg      115
                                    Met Leu Ile Lys Val Lys Thr
                                      1               5 ctg act ggg aag gag att gag ata gac atc gaa ccc aca gac aag gtg        163
Leu Thr Gly Lys Glu Ile Glu Ile Asp Ile Glu Pro Thr Asp Lys Val
        10                  15                  20 gag cga atc aag gag cgt gtg gaa gaa aaa gaa ggg att ccc ccc cag        211
Glu Arg Ile Lys Glu Arg Val Glu Glu Lys Glu Gly Ile Pro Pro Gln
            25                  30                  35 cag cag cgg ctc atc tac agt ggc aag caa atg aat gat gag aag aca        259
Gln Gln Arg Leu Ile Tyr Ser Gly Lys Gln Met Asn Asp Glu Lys Thr
        40                  45                  50                  55 gca gct gat tac aag att cta ggt ggt tcc gtc ctc cac ctg gtg ttg        307
Ala Ala Asp Tyr Lys Ile Leu Gly Gly Ser Val Leu His Leu Val Leu
                60                  65                  70 gct ctt aga gga gga ggt ggt ctt ggg cag tga agaaacttgg ttccgtttac      360
Ala Leu Arg Gly Gly Gly Gly Leu Gly Gln
            75                  80 ctccttgccc tgccaatcat aatgtggcat cacatatcct ctcactctct gggacaccag      420
agccactgcc ccctctcttg gatgcccaat cttgtgtgtc tactggtggg agaatgtgag      480
gaccccaggg tgcagtgttc ctggcccaga tggcccctgc tggctattgg gttttagttt      540
gcagtcatgt gtgcttccct gtcttatggc tgtatccttg gttatcaata aaatatttcc      600
tg                                                                    602

<210> SEQ ID NO 53
<211> LENGTH: 81
<212> TYPE: PRT
<213> ORGANISM: Mus musculus

<400> SEQUENCE: 53

Met Leu Ile Lys Val Lys Thr Leu Thr Gly Lys Glu Ile Glu Ile Asp
  1               5                  10                  15

Ile Glu Pro Thr Asp Lys Val Glu Arg Ile Lys Glu Arg Val Glu Glu
                20                  25                  30

Lys Glu Gly Ile Pro Pro Gln Gln Gln Arg Leu Ile Tyr Ser Gly Lys
            35                  40                  45

Gln Met Asn Asp Glu Lys Thr Ala Ala Asp Tyr Lys Ile Leu Gly Gly
        50                  55                  60
```

```
Ser Val Leu His Leu Val Leu Ala Leu Arg Gly Gly Gly Leu Gly
 65                  70                  75                  80

Gln

<210> SEQ ID NO 54
<211> LENGTH: 1918
<212> TYPE: DNA
<213> ORGANISM: Homo sapiens
<220> FEATURE:
<221> NAME/KEY: CDS
<222> LOCATION: (194)...(1780)

<400> SEQUENCE: 54
agtgcgcctg cgcgcttgtg gagctggtgg cggcgctccg caggggctcg gctgttttcc      60
gcgcggcagg cgcggccatg gcgcagctgg gaaagctgct caaggagcag aagtacgacc     120
ggcagctgag gcgattcctc catacatttg acagctgtct gggcccttat ggagcataca     180
gtggagtgga aag atg gat gct cag caa aca aaa aca aat gaa gcc agg       229
            Met Asp Ala Gln Gln Thr Lys Thr Asn Glu Ala Arg
             1               5                  10 ttg tgg ggt gat cat ggg caa gag gct tta gaa tct gct cat gtt tgc       277
Leu Trp Gly Asp His Gly Gln Glu Ala Leu Glu Ser Ala His Val Cys
         15                  20                  25 cta ata aat gca aca gcc aca gga act gaa att ctt aaa aac ttg gta       325
Leu Ile Asn Ala Thr Ala Thr Gly Thr Glu Ile Leu Lys Asn Leu Val
 30                  35                  40 cta cca ggt att ggt tcg ttt aca att att gat gga aat cag gtc agc       373
Leu Pro Gly Ile Gly Ser Phe Thr Ile Ile Asp Gly Asn Gln Val Ser
 45                  50                  55                  60 gga gaa gat gct gga aac aat ttc ttc ctt caa aga agc agt atc ggc       421
Gly Glu Asp Ala Gly Asn Asn Phe Phe Leu Gln Arg Ser Ser Ile Gly
                 65                  70                  75 aag aac cga gct gaa gct gcc atg gaa ttc tta caa gaa tta aat agc       469
Lys Asn Arg Ala Glu Ala Ala Met Glu Phe Leu Gln Glu Leu Asn Ser
         80                  85                  90 gat gtc tct gga agt ttt gtg gaa gag agt cca gaa aac ctt cta gac       517
Asp Val Ser Gly Ser Phe Val Glu Glu Ser Pro Glu Asn Leu Leu Asp
 95                  100                 105 aat gat ccc tca ttt ttc tgt agg ttt act gtt gta gtt gca act cag       565
Asn Asp Pro Ser Phe Phe Cys Arg Phe Thr Val Val Val Ala Thr Gln
         110                 115                 120 ctt cct gaa agc act tca cta cgc tta gca gat gtc ctc tgg aat tcc       613
Leu Pro Glu Ser Thr Ser Leu Arg Leu Ala Asp Val Leu Trp Asn Ser
125                 130                 135                 140 cag att cct ctt ttg atc tgt agg aca tat gga cta gtt ggt tat atg       661
Gln Ile Pro Leu Leu Ile Cys Arg Thr Tyr Gly Leu Val Gly Tyr Met
                 145                 150                 155 agg atc att ata aaa gaa cat cca gta ata gaa tct cat cca gat aat       709
Arg Ile Ile Ile Lys Glu His Pro Val Ile Glu Ser His Pro Asp Asn
         160                 165                 170 gca tta gag gat cta cga cta gat aag cca ttt cct gaa ctg aga gaa       757
Ala Leu Glu Asp Leu Arg Leu Asp Lys Pro Phe Pro Glu Leu Arg Glu
 175                 180                 185 cat ttt cag tcc tat gat ttg gat cat atg gaa aaa aag gac cac agt       805
His Phe Gln Ser Tyr Asp Leu Asp His Met Glu Lys Lys Asp His Ser
         190                 195                 200 cat act cca tgg att gtg atc ata gct aaa tat tta gca cag tgg tat       853
His Thr Pro Trp Ile Val Ile Ala Lys Tyr Leu Ala Gln Trp Tyr
205                 210                 215                 220
```

```
agt gaa aca aat gga cga ata cct aaa acg tat aaa gaa aaa gag gac      901
Ser Glu Thr Asn Gly Arg Ile Pro Lys Thr Tyr Lys Glu Lys Glu Asp
                225             230             235 ttc aga gat ttg att aga caa gga att cta aaa aat gaa aat ggg gct      949
Phe Arg Asp Leu Ile Arg Gln Gly Ile Leu Lys Asn Glu Asn Gly Ala
            240             245             250 cca gaa gat gaa gag aat ttt gaa gaa gct att aaa aat gtg aac aca      997
Pro Glu Asp Glu Glu Asn Phe Glu Glu Ala Ile Lys Asn Val Asn Thr
        255             260             265 gca cta aat aca act cag atc cca agc agt att gaa gat ata ttt aat     1045
Ala Leu Asn Thr Thr Gln Ile Pro Ser Ser Ile Glu Asp Ile Phe Asn
    270             275             280 gat gat cgc tgc ata aat atc acc aaa cag act cca tca ttt tgg att     1093
Asp Asp Arg Cys Ile Asn Ile Thr Lys Gln Thr Pro Ser Phe Trp Ile
285             290             295             300 tta gct cgt gcc tta aag gaa ttt gtg gcc aaa gag ggt caa gga aat     1141
Leu Ala Arg Ala Leu Lys Glu Phe Val Ala Lys Glu Gly Gln Gly Asn
                305             310             315 tta cct gtt cga ggc aca att cct gat atg att gca gat tca ggc aaa     1189
Leu Pro Val Arg Gly Thr Ile Pro Asp Met Ile Ala Asp Ser Gly Lys
            320             325             330 tat ata aaa ctg caa aac gtt tac cgt gaa aaa gca aag aaa gat gct     1237
Tyr Ile Lys Leu Gln Asn Val Tyr Arg Glu Lys Ala Lys Lys Asp Ala
        335             340             345 gcc gct gtg ggt aat cat gtt gcc aaa ttg ctg cag tcc att ggc cag     1285
Ala Ala Val Gly Asn His Val Ala Lys Leu Leu Gln Ser Ile Gly Gln
    350             355             360 gca cca gag tcc att tca gag aaa gaa tta aaa tta ctc tgc agc aat     1333
Ala Pro Glu Ser Ile Ser Glu Lys Glu Leu Lys Leu Leu Cys Ser Asn
365             370             375             380 tct gca ttt ctt cga gtg gta aga tgt cga tcc tta gct gaa gaa tat     1381
Ser Ala Phe Leu Arg Val Val Arg Cys Arg Ser Leu Ala Glu Glu Tyr
                385             390             395 ggt ttg gat aca att aac aag gat gaa att att tct agc atg gac aat     1429
Gly Leu Asp Thr Ile Asn Lys Asp Glu Ile Ile Ser Ser Met Asp Asn
            400             405             410 cca gat aat gaa ata gtg ttg tac tta atg tta cgg gct gtt gat aga     1477
Pro Asp Asn Glu Ile Val Leu Tyr Leu Met Leu Arg Ala Val Asp Arg
        415             420             425 ttt cat aaa caa cag ggt aga tat cca gga gta tct aac tat caa gtt     1525
Phe His Lys Gln Gln Gly Arg Tyr Pro Gly Val Ser Asn Tyr Gln Val
    430             435             440 gaa gaa gat ata gga aag ttg aag tct tgt ctc act ggc ttc ctt cag     1573
Glu Glu Asp Ile Gly Lys Leu Lys Ser Cys Leu Thr Gly Phe Leu Gln
445             450             455             460 gaa tat ggt tta tct gta atg gtg aaa gat gat tat gtc cac gaa ttt     1621
Glu Tyr Gly Leu Ser Val Met Val Lys Asp Asp Tyr Val His Glu Phe
                465             470             475 tgc cga tat gga gct gct gag cca cat acc att gct gca ttc ttg ggg     1669
Cys Arg Tyr Gly Ala Ala Glu Pro His Thr Ile Ala Ala Phe Leu Gly
            480             485             490 gga gct gct gct caa gag gtc atc aaa ata atc acc aaa caa ttt gta     1717
Gly Ala Ala Ala Gln Glu Val Ile Lys Ile Ile Thr Lys Gln Phe Val
        495             500             505 att ttt aat aat act tac att tac agt ggc atg tca caa act tca gca     1765
Ile Phe Asn Asn Thr Tyr Ile Tyr Ser Gly Met Ser Gln Thr Ser Ala
    510             515             520 act ttc cag ttg tag agtaagcaag caccttaagt agtgtgttaa tgattgaaac    1820
Thr Phe Gln Leu
525
```

```
tgtaattgcc ttcgggttgt gctttagtct gtaaaattct aaaggagagc tgctaaattg    1880
ttttcttaat aaacattttt ctcatttgta aaaaaaa                             1918
```

<210> SEQ ID NO 55
<211> LENGTH: 528
<212> TYPE: PRT
<213> ORGANISM: Homo sapiens

<400> SEQUENCE: 55

```
Met Asp Ala Gln Gln Thr Lys Thr Asn Glu Ala Arg Leu Trp Gly Asp
  1               5                  10                  15

His Gly Gln Glu Ala Leu Glu Ser Ala His Val Cys Leu Ile Asn Ala
             20                  25                  30

Thr Ala Thr Gly Thr Glu Ile Leu Lys Asn Leu Val Leu Pro Gly Ile
         35                  40                  45

Gly Ser Phe Thr Ile Ile Asp Gly Asn Gln Val Ser Gly Glu Asp Ala
     50                  55                  60

Gly Asn Asn Phe Phe Leu Gln Arg Ser Ser Ile Gly Lys Asn Arg Ala
 65                  70                  75                  80

Glu Ala Ala Met Glu Phe Leu Gln Glu Leu Asn Ser Asp Val Ser Gly
                 85                  90                  95

Ser Phe Val Glu Glu Ser Pro Glu Asn Leu Leu Asp Asn Asp Pro Ser
            100                 105                 110

Phe Phe Cys Arg Phe Thr Val Val Ala Thr Gln Leu Pro Glu Ser
        115                 120                 125

Thr Ser Leu Arg Leu Ala Asp Val Leu Trp Asn Ser Gln Ile Pro Leu
    130                 135                 140

Leu Ile Cys Arg Thr Tyr Gly Leu Val Gly Tyr Met Arg Ile Ile Ile
145                 150                 155                 160

Lys Glu His Pro Val Ile Glu Ser His Pro Asp Asn Ala Leu Glu Asp
                165                 170                 175

Leu Arg Leu Asp Lys Pro Phe Pro Glu Leu Arg Glu His Phe Gln Ser
            180                 185                 190

Tyr Asp Leu Asp His Met Glu Lys Lys Asp His Ser His Thr Pro Trp
        195                 200                 205

Ile Val Ile Ala Lys Tyr Leu Ala Gln Trp Tyr Ser Glu Thr Asn
    210                 215                 220

Gly Arg Ile Pro Lys Thr Tyr Lys Glu Lys Glu Asp Phe Arg Asp Leu
225                 230                 235                 240

Ile Arg Gln Gly Ile Leu Lys Asn Glu Asn Gly Ala Pro Glu Asp Glu
                245                 250                 255

Glu Asn Phe Glu Glu Ala Ile Lys Asn Val Asn Thr Ala Leu Asn Thr
            260                 265                 270

Thr Gln Ile Pro Ser Ser Ile Glu Asp Ile Phe Asn Asp Asp Arg Cys
        275                 280                 285

Ile Asn Ile Thr Lys Gln Thr Pro Ser Phe Trp Ile Leu Ala Arg Ala
    290                 295                 300

Leu Lys Glu Phe Val Ala Lys Glu Gly Gln Gly Asn Leu Pro Val Arg
305                 310                 315                 320

Gly Thr Ile Pro Asp Met Ile Ala Asp Ser Gly Lys Tyr Ile Lys Leu
                325                 330                 335

Gln Asn Val Tyr Arg Glu Lys Ala Lys Lys Asp Ala Ala Val Gly
            340                 345                 350
```

```
Asn His Val Ala Lys Leu Leu Gln Ser Ile Gly Gln Ala Pro Glu Ser
            355                 360                 365

Ile Ser Glu Lys Glu Leu Lys Leu Leu Cys Ser Asn Ser Ala Phe Leu
    370                 375                 380

Arg Val Val Arg Cys Arg Ser Leu Ala Glu Glu Tyr Gly Leu Asp Thr
385                 390                 395                 400

Ile Asn Lys Asp Glu Ile Ile Ser Ser Met Asp Asn Pro Asp Asn Glu
                405                 410                 415

Ile Val Leu Tyr Leu Met Leu Arg Ala Val Asp Arg Phe His Lys Gln
            420                 425                 430

Gln Gly Arg Tyr Pro Gly Val Ser Asn Tyr Gln Val Glu Glu Asp Ile
        435                 440                 445

Gly Lys Leu Lys Ser Cys Leu Thr Gly Phe Leu Gln Glu Tyr Gly Leu
    450                 455                 460

Ser Val Met Val Lys Asp Asp Tyr Val His Glu Phe Cys Arg Tyr Gly
465                 470                 475                 480

Ala Ala Glu Pro His Thr Ile Ala Ala Phe Leu Gly Gly Ala Ala Ala
                485                 490                 495

Gln Glu Val Ile Lys Ile Ile Thr Lys Gln Phe Val Ile Phe Asn Asn
            500                 505                 510

Thr Tyr Ile Tyr Ser Gly Met Ser Gln Thr Ser Ala Thr Phe Gln Leu
        515                 520                 525

<210> SEQ ID NO 56
<211> LENGTH: 1808
<212> TYPE: DNA
<213> ORGANISM: Mus musculus
<220> FEATURE:
<221> NAME/KEY: CDS
<222> LOCATION: (74)...(1678)

<400> SEQUENCE: 56
agtgcgcctg cgtgaggccg agtgggtggc ggcctcctta ggcggctttg ctgttcgcgg        60
gccaggcgcg gcc atg gcg cag cca ggg aag ata ctc aag gag caa aag        109
            Met Ala Gln Pro Gly Lys Ile Leu Lys Glu Gln Lys
              1               5                  10 tac gac cgg cag ctg agg ctg tgg ggt gat cat gga caa gaa gct ttg        157
Tyr Asp Arg Gln Leu Arg Leu Trp Gly Asp His Gly Gln Glu Ala Leu
         15                  20                  25 gaa tct gct cat gtt tgc tta ata aat gca acg gct aca gga act gaa        205
Glu Ser Ala His Val Cys Leu Ile Asn Ala Thr Ala Thr Gly Thr Glu
 30                  35                  40 att ctt aaa aac ttg gtg ctg cca ggt att gga tca ttt aca att att        253
Ile Leu Lys Asn Leu Val Leu Pro Gly Ile Gly Ser Phe Thr Ile Ile
     45                  50                  55                  60 gat gga aat ctg gtc agc gga gaa gat gct gga aac aac ttt ttc ctt        301
Asp Gly Asn Leu Val Ser Gly Glu Asp Ala Gly Asn Asn Phe Phe Leu
                 65                  70                  75 caa aaa agc agt att ggc aag aac cga gct caa gct gcc atg gaa ttc        349
Gln Lys Ser Ser Ile Gly Lys Asn Arg Ala Gln Ala Ala Met Glu Phe
             80                  85                  90 tta caa gaa cta aat agc gat gtc tct gga agt ttt gtg gaa gag agt        397
Leu Gln Glu Leu Asn Ser Asp Val Ser Gly Ser Phe Val Glu Glu Ser
         95                 100                 105 cca gaa aac ctt cta gac aat gat cct tca ttt ttc tgt agg ttt act        445
Pro Glu Asn Leu Leu Asp Asn Asp Pro Ser Phe Phe Cys Arg Phe Thr
    110                 115                 120 att gtg gtt gca act cag ctt ctt gaa agt aca ttg ctg cgt tta gca        493
```

```
                                                                       -continued Ile Val Val Ala Thr Gln Leu Leu Glu Ser Thr Leu Leu Arg Leu Ala
125             130                 135                 140 gat gtt ctc tgg aat tcc cag atc cct ctt ttg atc tgt agg aca tat        541
Asp Val Leu Trp Asn Ser Gln Ile Pro Leu Leu Ile Cys Arg Thr Tyr
                145                 150                 155 gga cta gtt ggt tat atg agg att att ata aaa gaa cac cca gta ata        589
Gly Leu Val Gly Tyr Met Arg Ile Ile Ile Lys Glu His Pro Val Ile
                160                 165                 170 gaa tct cat cca gat aat gca ttg gag gat cta cga cta gat aag cca        637
Glu Ser His Pro Asp Asn Ala Leu Glu Asp Leu Arg Leu Asp Lys Pro
            175                 180                 185 ttt cct gaa ctg aga gaa cat ctt cag tct tat gac ttg gac cat atg        685
Phe Pro Glu Leu Arg Glu His Leu Gln Ser Tyr Asp Leu Asp His Met
        190                 195                 200 gaa aaa aag gac cat agc cat act cca tgg att gtg atc ata gct aaa        733
Glu Lys Lys Asp His Ser His Thr Pro Trp Ile Val Ile Ala Lys
205                 210                 215                 220 tat tta gca cag tgg tat aat gaa aca aat gga cgg att cct aaa agt        781
Tyr Leu Ala Gln Trp Tyr Asn Glu Thr Asn Gly Arg Ile Pro Lys Ser
                225                 230                 235 tat aaa gaa aaa gag gac ttc aga gat ttg ata aga caa ggg att tta        829
Tyr Lys Glu Lys Glu Asp Phe Arg Asp Leu Ile Arg Gln Gly Ile Leu
            240                 245                 250 aag aat gaa aat gga gct cca gaa gac gaa gag aat ttt gaa gaa gcc        877
Lys Asn Glu Asn Gly Ala Pro Glu Asp Glu Glu Asn Phe Glu Glu Ala
        255                 260                 265 atc aaa aat gtg aac aca gca cta aat aca act cag atc cca agc agt        925
Ile Lys Asn Val Asn Thr Ala Leu Asn Thr Thr Gln Ile Pro Ser Ser
270                 275                 280 att gaa gat ata ttt aat gat gat cga tgc ata aat atc acc aaa cag        973
Ile Glu Asp Ile Phe Asn Asp Asp Arg Cys Ile Asn Ile Thr Lys Gln
285                 290                 295                 300 aca cca act ttt tgg att cta gct cgt gcc tta aag gaa ttt gtg gcc       1021
Thr Pro Thr Phe Trp Ile Leu Ala Arg Ala Leu Lys Glu Phe Val Ala
                305                 310                 315 aag gag ggt caa gga aat tta cct gtc cga ggc aca att cct gat atg       1069
Lys Glu Gly Gln Gly Asn Leu Pro Val Arg Gly Thr Ile Pro Asp Met
            320                 325                 330 att gca gat tca aac aaa tac ata aaa ctg cag aat gtt tac cga gag       1117
Ile Ala Asp Ser Asn Lys Tyr Ile Lys Leu Gln Asn Val Tyr Arg Glu
        335                 340                 345 aaa gca aag aaa gat gct gct gct gta ggc aat cac gtt gcc aaa ttg       1165
Lys Ala Lys Lys Asp Ala Ala Ala Val Gly Asn His Val Ala Lys Leu
350                 355                 360 ctt cag tct gtt ggc cag gca cca gag tcc att tca gag aaa gaa tta       1213
Leu Gln Ser Val Gly Gln Ala Pro Glu Ser Ile Ser Glu Lys Glu Leu
365                 370                 375                 380 aaa ttg ctt tgc agc aat tct gca ttt ctt cga gtg gta aga tgt cga       1261
Lys Leu Leu Cys Ser Asn Ser Ala Phe Leu Arg Val Val Arg Cys Arg
                385                 390                 395 tct tta gct gaa gag tat ggc ttg gat aca gtc aac aaa gat gaa att       1309
Ser Leu Ala Glu Glu Tyr Gly Leu Asp Thr Val Asn Lys Asp Glu Ile
            400                 405                 410 att tct agc atg gac aat ccg gat aat gag ata gtc ctg tac ctg atg       1357
Ile Ser Ser Met Asp Asn Pro Asp Asn Glu Ile Val Leu Tyr Leu Met
        415                 420                 425 ttg cgg gct gtt gat cga ttt cat aaa cag cat ggc aga tac cca gga       1405
Leu Arg Ala Val Asp Arg Phe His Lys Gln His Gly Arg Tyr Pro Gly
430                 435                 440
```

```
gta tct aac tat caa gtt gaa gaa gat ata ggg aag ttg aag tcc tgt     1453
Val Ser Asn Tyr Gln Val Glu Glu Asp Ile Gly Lys Leu Lys Ser Cys
445                 450                 455                 460 ctt act ggc ttc ctt cag gaa tat ggg ctg tct gta atg gtg aaa gac     1501
Leu Thr Gly Phe Leu Gln Glu Tyr Gly Leu Ser Val Met Val Lys Asp
                465                 470                 475 gat tat gtc cat gaa ttt tgc cgg tac gga gct gct gag cca cac acc     1549
Asp Tyr Val His Glu Phe Cys Arg Tyr Gly Ala Ala Glu Pro His Thr
            480                 485                 490 att gct gcg ttc ctg gga gga gct gct gct caa gaa gtt atc aaa ata     1597
Ile Ala Ala Phe Leu Gly Gly Ala Ala Ala Gln Glu Val Ile Lys Ile
        495                 500                 505 atc acc aaa caa ttc gta att ttt aat aat act tat att tat agt ggt     1645
Ile Thr Lys Gln Phe Val Ile Phe Asn Asn Thr Tyr Ile Tyr Ser Gly
    510                 515                 520 atg tca caa act tct gca act ttc cag ttg tag aataagcacc atgtgtaata   1698
Met Ser Gln Thr Ser Ala Thr Phe Gln Leu
525                 530 tgttaatggt tggaactgta attgtcttca tattgtgctt tggtttgtaa aaatctgtta   1758
aaggacggaa gttaaattgt ttccttaata aagtttttc tcatttgtaa               1808

<210> SEQ ID NO 57
<211> LENGTH: 534
<212> TYPE: PRT
<213> ORGANISM: Mus musculus

<400> SEQUENCE: 57

Met Ala Gln Pro Gly Lys Ile Leu Lys Glu Gln Lys Tyr Asp Arg Gln
1               5                   10                  15

Leu Arg Leu Trp Gly Asp His Gly Gln Glu Ala Leu Glu Ser Ala His
            20                  25                  30

Val Cys Leu Ile Asn Ala Thr Ala Thr Gly Thr Glu Ile Leu Lys Asn
        35                  40                  45

Leu Val Leu Pro Gly Ile Gly Ser Phe Thr Ile Ile Asp Gly Asn Leu
    50                  55                  60

Val Ser Gly Glu Asp Ala Gly Asn Asn Phe Phe Leu Gln Lys Ser Ser
65                  70                  75                  80

Ile Gly Lys Asn Arg Ala Gln Ala Ala Met Glu Phe Leu Gln Glu Leu
                85                  90                  95

Asn Ser Asp Val Ser Gly Ser Phe Val Glu Glu Ser Pro Glu Asn Leu
            100                 105                 110

Leu Asp Asn Asp Pro Ser Phe Phe Cys Arg Phe Thr Ile Val Val Ala
        115                 120                 125

Thr Gln Leu Leu Glu Ser Thr Leu Leu Arg Leu Ala Asp Val Leu Trp
    130                 135                 140

Asn Ser Gln Ile Pro Leu Leu Ile Cys Arg Thr Tyr Gly Leu Val Gly
145                 150                 155                 160

Tyr Met Arg Ile Ile Ile Lys Glu His Pro Val Ile Glu Ser His Pro
                165                 170                 175

Asp Asn Ala Leu Glu Asp Leu Arg Leu Asp Lys Pro Phe Pro Glu Leu
            180                 185                 190

Arg Glu His Leu Gln Ser Tyr Asp Leu Asp His Met Glu Lys Lys Asp
        195                 200                 205

His Ser His Thr Pro Trp Ile Val Ile Ala Lys Tyr Leu Ala Gln
    210                 215                 220

Trp Tyr Asn Glu Thr Asn Gly Arg Ile Pro Lys Ser Tyr Lys Glu Lys
```

```
                    225                 230                 235                 240
Glu Asp Phe Arg Asp Leu Ile Arg Gln Gly Ile Leu Lys Asn Glu Asn
                        245                 250                 255

Gly Ala Pro Glu Asp Glu Asn Phe Glu Ala Ile Lys Asn Val
            260                 265                 270

Asn Thr Ala Leu Asn Thr Thr Gln Ile Pro Ser Ser Ile Glu Asp Ile
                275                 280                 285

Phe Asn Asp Asp Arg Cys Ile Asn Ile Thr Lys Gln Thr Pro Thr Phe
290                 295                 300

Trp Ile Leu Ala Arg Ala Leu Lys Glu Phe Val Ala Lys Glu Gly Gln
305                 310                 315                 320

Gly Asn Leu Pro Val Arg Gly Thr Ile Pro Asp Met Ile Ala Asp Ser
                325                 330                 335

Asn Lys Tyr Ile Lys Leu Gln Asn Val Tyr Arg Glu Lys Ala Lys Lys
                340                 345                 350

Asp Ala Ala Val Gly Asn His Val Ala Lys Leu Leu Gln Ser Val
                355                 360                 365

Gly Gln Ala Pro Glu Ser Ile Ser Glu Lys Glu Leu Lys Leu Leu Cys
370                 375                 380

Ser Asn Ser Ala Phe Leu Arg Val Val Arg Cys Arg Ser Leu Ala Glu
385                 390                 395                 400

Glu Tyr Gly Leu Asp Thr Val Asn Lys Asp Glu Ile Ile Ser Ser Met
                405                 410                 415

Asp Asn Pro Asp Asn Glu Ile Val Leu Tyr Leu Met Leu Arg Ala Val
                420                 425                 430

Asp Arg Phe His Lys Gln His Gly Arg Tyr Pro Gly Val Ser Asn Tyr
                435                 440                 445

Gln Val Glu Glu Asp Ile Gly Lys Leu Lys Ser Cys Leu Thr Gly Phe
450                 455                 460

Leu Gln Glu Tyr Gly Leu Ser Val Met Val Lys Asp Asp Tyr Val His
465                 470                 475                 480

Glu Phe Cys Arg Tyr Gly Ala Ala Glu Pro His Thr Ile Ala Ala Phe
                485                 490                 495

Leu Gly Gly Ala Ala Ala Gln Glu Val Ile Lys Ile Ile Thr Lys Gln
                500                 505                 510

Phe Val Ile Phe Asn Asn Thr Tyr Ile Tyr Ser Gly Met Ser Gln Thr
                515                 520                 525

Ser Ala Thr Phe Gln Leu
            530

<210> SEQ ID NO 58
<211> LENGTH: 2136
<212> TYPE: DNA
<213> ORGANISM: Homo sapiens
<220> FEATURE:
<221> NAME/KEY: CDS
<222> LOCATION: (21)...(1412)

<400> SEQUENCE: 58
gggaagaggc ggagaacaat atg gcg gat ggc gag gag ccg gag aag aaa aga         53
                     Met Ala Asp Gly Glu Glu Pro Glu Lys Lys Arg
                      1               5                  10 agg aga ata gag gag ctg ctg gct gag aaa atg gct gtt gat ggt ggg         101
Arg Arg Ile Glu Glu Leu Leu Ala Glu Lys Met Ala Val Asp Gly Gly
            15                  20                  25 tgt ggg gac act gga gac tgg gaa ggt cgc tgg aac cat gta aag aag         149
```

```
                Cys Gly Asp Thr Gly Asp Trp Glu Gly Arg Trp Asn His Val Lys Lys
                 30                  35                  40 ttc ctc gag cga tct gga ccc ttc aca cac cct gat ttc gaa ccg agc         197
Phe Leu Glu Arg Ser Gly Pro Phe Thr His Pro Asp Phe Glu Pro Ser
 45                  50                  55 act gaa tct ctc cag ttc ttg tta gat aca tgt aaa gtt cta gtc att         245
Thr Glu Ser Leu Gln Phe Leu Leu Asp Thr Cys Lys Val Leu Val Ile
 60                  65                  70                  75 gga gct ggc ggc tta gga tgt gag ctc ctg aaa aat ctg gcc ttg tct         293
Gly Ala Gly Gly Leu Gly Cys Glu Leu Leu Lys Asn Leu Ala Leu Ser
                 80                  85                  90 ggt ttt aga cag att cat gtt ata gat atg gac act ata gat gtt tcc         341
Gly Phe Arg Gln Ile His Val Ile Asp Met Asp Thr Ile Asp Val Ser
             95                 100                 105 aat cta aat agg cag ttt tta ttt agg cct aaa gat att gga aga cct         389
Asn Leu Asn Arg Gln Phe Leu Phe Arg Pro Lys Asp Ile Gly Arg Pro
110                 115                 120 aag gct gaa gtt gct gca gaa ttt cta aat gac aga gtt cct aat tgc         437
Lys Ala Glu Val Ala Ala Glu Phe Leu Asn Asp Arg Val Pro Asn Cys
125                 130                 135 aat gta gtt cca cat ttc aac aag att caa gat ttt aac gac act ttc         485
Asn Val Val Pro His Phe Asn Lys Ile Gln Asp Phe Asn Asp Thr Phe
140                 145                 150                 155 tat cga caa ttt cat att att gta tgt gga ctg gac tct atc atc gcc         533
Tyr Arg Gln Phe His Ile Ile Val Cys Gly Leu Asp Ser Ile Ile Ala
            160                 165                 170 aga aga tgg ata aat ggc atg ctg ata tct ctt cta aat tat gaa gat         581
Arg Arg Trp Ile Asn Gly Met Leu Ile Ser Leu Leu Asn Tyr Glu Asp
        175                 180                 185 ggt gtc tta gat cca agc tcc att gtc cct ttg ata gat ggg ggg aca         629
Gly Val Leu Asp Pro Ser Ser Ile Val Pro Leu Ile Asp Gly Gly Thr
190                 195                 200 gaa ggt ttt aaa gga aat gcc cgg gtg att ctg cct gga atg act gct         677
Glu Gly Phe Lys Gly Asn Ala Arg Val Ile Leu Pro Gly Met Thr Ala
205                 210                 215 tgt atc gaa tgc acg ctg gaa ctt tat cca cca cag gtt aat ttt ccc         725
Cys Ile Glu Cys Thr Leu Glu Leu Tyr Pro Pro Gln Val Asn Phe Pro
220                 225                 230                 235 atg tgc acc att gca tct atg ccc agg cta cca gaa cac tgt att gag         773
Met Cys Thr Ile Ala Ser Met Pro Arg Leu Pro Glu His Cys Ile Glu
                240                 245                 250 tat gta agg atg ttg cag tgg cct aag gag cag cct ttt gga gaa ggg         821
Tyr Val Arg Met Leu Gln Trp Pro Lys Glu Gln Pro Phe Gly Glu Gly
            255                 260                 265 gtt cca tta gat gga gat gat cct gaa cat ata caa tgg att ttc caa         869
Val Pro Leu Asp Gly Asp Asp Pro Glu His Ile Gln Trp Ile Phe Gln
        270                 275                 280 aaa tcc cta gag aga gca tca caa tat aat att agg ggt gtt acg tat         917
Lys Ser Leu Glu Arg Ala Ser Gln Tyr Asn Ile Arg Gly Val Thr Tyr
285                 290                 295 agg ctc act caa ggg gta gta aaa aga atc att cct gca gta gct tcc         965
Arg Leu Thr Gln Gly Val Val Lys Arg Ile Ile Pro Ala Val Ala Ser
300                 305                 310                 315 aca aat gca gtc att gca gct gtg tgt gcc act gag gtt ttt aaa ata        1013
Thr Asn Ala Val Ile Ala Ala Val Cys Ala Thr Glu Val Phe Lys Ile
                320                 325                 330 gcc aca agt gca tac att ccc ttg aat aat tac ttg gtg ttt aat gat        1061
Ala Thr Ser Ala Tyr Ile Pro Leu Asn Asn Tyr Leu Val Phe Asn Asp
            335                 340                 345
```

| | | | | | | | | | | | | | | | | |
|---|---|---|---|---|---|---|---|---|---|---|---|---|---|---|---|---|
| gta | gat | ggg | ctg | tat | aca | tac | aca | ttt | gaa | gca | gaa | aga | aag | gaa | aac | 1109 |
| Val | Asp | Gly | Leu | Tyr | Thr | Tyr | Thr | Phe | Glu | Ala | Glu | Arg | Lys | Glu | Asn | |
| | | 350 | | | | | 355 | | | | | 360 | | | | |
| tgc | cca | gct | tgt | agc | cag | ctt | cct | caa | aat | att | cag | ttt | tct | cca | tca | 1157 |
| Cys | Pro | Ala | Cys | Ser | Gln | Leu | Pro | Gln | Asn | Ile | Gln | Phe | Ser | Pro | Ser | |
| 365 | | | | | 370 | | | | | 375 | | | | | | |
| gct | aaa | cta | cag | gag | gtt | ttg | gat | tat | cta | acc | aat | agt | gct | tct | ctg | 1205 |
| Ala | Lys | Leu | Gln | Glu | Val | Leu | Asp | Tyr | Leu | Thr | Asn | Ser | Ala | Ser | Leu | |
| 380 | | | | | 385 | | | | | 390 | | | | | 395 | |
| caa | atg | aaa | tct | cca | gcc | atc | aca | gcc | acc | cta | gag | gga | aaa | aat | aga | 1253 |
| Gln | Met | Lys | Ser | Pro | Ala | Ile | Thr | Ala | Thr | Leu | Glu | Gly | Lys | Asn | Arg | |
| | | | | 400 | | | | | 405 | | | | | 410 | | |
| aca | ctt | tac | tta | cag | tcg | gta | acc | tct | att | gaa | gaa | cga | aca | agg | cca | 1301 |
| Thr | Leu | Tyr | Leu | Gln | Ser | Val | Thr | Ser | Ile | Glu | Glu | Arg | Thr | Arg | Pro | |
| | | | | 415 | | | | | 420 | | | | | 425 | | |
| aat | ctc | tcc | aaa | aca | ttg | aaa | gaa | ttg | ggg | ctt | gtt | gat | gga | caa | gaa | 1349 |
| Asn | Leu | Ser | Lys | Thr | Leu | Lys | Glu | Leu | Gly | Leu | Val | Asp | Gly | Gln | Glu | |
| | | | 430 | | | | | 435 | | | | | 440 | | | |
| ctg | gcg | gtt | gct | gat | gtc | acc | acc | cca | cag | act | gta | cta | ttc | aaa | ctt | 1397 |
| Leu | Ala | Val | Ala | Asp | Val | Thr | Thr | Pro | Gln | Thr | Val | Leu | Phe | Lys | Leu | |
| | | 445 | | | | | 450 | | | | | 455 | | | | |
| cat | ttt | act | tct | taa | ggaaaatctc | | cacataatag | | aaaactcatg | | gaaataatat | | | | | 1452 |
| His | Phe | Thr | Ser | | | | | | | | | | | | | |
| 460 | | | | | | | | | | | | | | | | | actttgtgga tgctaagaag ttgaatcgat gtcatttta gcaatagtgt tgccacgatt 1512 tgtctttttt tatataatga accactcttt tttaactttg taaccttccc ttgaagacag 1572 aattttggtg ttggtgcttg taagcatttt cattaataat atgagaaatg ataccctggag 1632 agagagatta tgagcaaatg tattgcttct tttagaggag gaagcataca acctctttttg 1692 tgtgaatttt gttattatgg tcaaagaatg cattcctaag ttttcatttg agtacccaaa 1752 tacacaaaag gtgtcccttt aaggaaaata aagaattaag ttttaaataa cattacattt 1812 tacaatctga catctggagt atattgaaca taggctattt cttgatataa cactcatta 1872 attgtggcca tccaaatgaa tattattgca gaatttatct tgttcataat gatttgtaaa 1932 tggtgttata gctgaatacc tgtgcatgaa aatgggcaat atttcatct gtttacttgt 1992 agtgccatag aggccaatat gcacaatatt aactaatgcc aagacatggc tgtttaaaaa 2052 atttaatgtt caaacagtta tcactgatgc ttttgcacta tttattaata aaatcatata 2112 ttgtgtaaaa aaaaaaaaaa aaaa 2136

<210> SEQ ID NO 59
<211> LENGTH: 463
<212> TYPE: PRT
<213> ORGANISM: Homo sapiens

<400> SEQUENCE: 59

Met Ala Asp Gly Glu Glu Pro Glu Lys Lys Arg Arg Ile Glu Glu
1               5                   10                  15

Leu Leu Ala Glu Lys Met Ala Val Asp Gly Gly Cys Gly Asp Thr Gly
                20                  25                  30

Asp Trp Glu Gly Arg Trp Asn His Val Lys Lys Phe Leu Glu Arg Ser
            35                  40                  45

Gly Pro Phe Thr His Pro Asp Phe Glu Pro Ser Thr Glu Ser Leu Gln
        50                  55                  60

Phe Leu Leu Asp Thr Cys Lys Val Leu Val Ile Gly Ala Gly Gly Leu
65                  70                  75                  80

Gly Cys Glu Leu Leu Lys Asn Leu Ala Leu Ser Gly Phe Arg Gln Ile
            85                  90                  95

His Val Ile Asp Met Asp Thr Ile Asp Val Ser Asn Leu Asn Arg Gln
            100                 105                 110

Phe Leu Phe Arg Pro Lys Asp Ile Gly Arg Pro Lys Ala Glu Val Ala
            115                 120                 125

Ala Glu Phe Leu Asn Asp Arg Val Pro Asn Cys Asn Val Val Pro His
130                 135                 140

Phe Asn Lys Ile Gln Asp Phe Asn Asp Thr Phe Tyr Arg Gln Phe His
145                 150                 155                 160

Ile Ile Val Cys Gly Leu Asp Ser Ile Ile Ala Arg Arg Trp Ile Asn
            165                 170                 175

Gly Met Leu Ile Ser Leu Leu Asn Tyr Glu Asp Gly Val Leu Asp Pro
            180                 185                 190

Ser Ser Ile Val Pro Leu Ile Asp Gly Gly Thr Glu Gly Phe Lys Gly
            195                 200                 205

Asn Ala Arg Val Ile Leu Pro Gly Met Thr Ala Cys Ile Glu Cys Thr
            210                 215                 220

Leu Glu Leu Tyr Pro Pro Gln Val Asn Phe Pro Met Cys Thr Ile Ala
225                 230                 235                 240

Ser Met Pro Arg Leu Pro Glu His Cys Ile Glu Tyr Val Arg Met Leu
            245                 250                 255

Gln Trp Pro Lys Glu Gln Pro Phe Gly Gly Val Pro Leu Asp Gly
            260                 265                 270

Asp Asp Pro Glu His Ile Gln Trp Ile Phe Gln Lys Ser Leu Glu Arg
            275                 280                 285

Ala Ser Gln Tyr Asn Ile Arg Gly Val Thr Tyr Arg Leu Thr Gln Gly
            290                 295                 300

Val Val Lys Arg Ile Ile Pro Ala Val Ala Ser Thr Asn Ala Val Ile
305                 310                 315                 320

Ala Ala Val Cys Ala Thr Glu Val Phe Lys Ile Ala Thr Ser Ala Tyr
            325                 330                 335

Ile Pro Leu Asn Asn Tyr Leu Val Phe Asn Asp Val Asp Gly Leu Tyr
            340                 345                 350

Thr Tyr Thr Phe Glu Ala Glu Arg Lys Glu Asn Cys Pro Ala Cys Ser
            355                 360                 365

Gln Leu Pro Gln Asn Ile Gln Phe Ser Pro Ser Ala Lys Leu Gln Glu
            370                 375                 380

Val Leu Asp Tyr Leu Thr Asn Ser Ala Ser Leu Gln Met Lys Ser Pro
385                 390                 395                 400

Ala Ile Thr Ala Thr Leu Glu Gly Lys Asn Arg Thr Leu Tyr Leu Gln
            405                 410                 415

Ser Val Thr Ser Ile Glu Glu Arg Thr Arg Pro Asn Leu Ser Lys Thr
            420                 425                 430

Leu Lys Glu Leu Gly Leu Val Asp Gly Gln Gly Leu Ala Val Ala Asp
            435                 440                 445

Val Thr Thr Pro Gln Thr Val Leu Phe Lys Leu His Phe Thr Ser
450                 455                 460

<210> SEQ ID NO 60
<211> LENGTH: 2443
<212> TYPE: DNA
<213> ORGANISM: Mus musculus
<220> FEATURE:
<221> NAME/KEY: CDS -continued

<222> LOCATION: (91)...(1479)

<400> SEQUENCE: 60

```
ggctctccct ccttccattc acctgcagtc ccgcccctcc cgggcggacc cgctcggcgc        60
gagggcctct gggaagaggc ggggaacaat atg gcg gat ggc gag gag ccg gag        114
                                Met Ala Asp Gly Glu Glu Pro Glu
                                  1               5 aag aaa aga agg aga ata gag gag ctg ctg gct gag aaa atg gct gtt        162
Lys Lys Arg Arg Arg Ile Glu Glu Leu Leu Ala Glu Lys Met Ala Val
         10                  15                  20 gat ggt ggg tgt ggg gac act gga gac tgg gaa ggt cgc tgg aac cat        210
Asp Gly Gly Cys Gly Asp Thr Gly Asp Trp Glu Gly Arg Trp Asn His
 25                  30                  35                  40 gta aag aag ttc ctc gag cgg tct gga ccc ttc aca cac ccc gat ttc        258
Val Lys Lys Phe Leu Glu Arg Ser Gly Pro Phe Thr His Pro Asp Phe
                 45                  50                  55 gaa cca agc act gaa tca ctc cag ttc ttg tta gat aca tgt aaa gtt        306
Glu Pro Ser Thr Glu Ser Leu Gln Phe Leu Leu Asp Thr Cys Lys Val
             60                  65                  70 cta gtc att gga gct ggt ggc tta gga tgt gag ctt ctg aaa aat ctg        354
Leu Val Ile Gly Ala Gly Gly Leu Gly Cys Glu Leu Leu Lys Asn Leu
         75                  80                  85 gca tta tct ggt ttt aga cag att cat gtt ata gac atg gac act ata        402
Ala Leu Ser Gly Phe Arg Gln Ile His Val Ile Asp Met Asp Thr Ile
 90                  95                 100 gat gtt tcc aat tta aat aga cag ttt tta ttt agg cct aaa gat gtc        450
Asp Val Ser Asn Leu Asn Arg Gln Phe Leu Phe Arg Pro Lys Asp Val
105                 110                 115                 120 gga aga ccc aag gct gaa gtt gct gca gaa ttc cta aat gac aga gtt        498
Gly Arg Pro Lys Ala Glu Val Ala Ala Glu Phe Leu Asn Asp Arg Val
                125                 130                 135 cct aac tgc aac gtg gta cca cat ttc aac aag ata caa gat ttt aac        546
Pro Asn Cys Asn Val Val Pro His Phe Asn Lys Ile Gln Asp Phe Asn
            140                 145                 150 gac act ttc tac cga caa ttt cat atc att gta tgt ggc ctg gac tct        594
Asp Thr Phe Tyr Arg Gln Phe His Ile Ile Val Cys Gly Leu Asp Ser
        155                 160                 165 atc ata gcg aga aga tgg atc aat gga atg ctg ata tct ctt cta aat        642
Ile Ile Ala Arg Arg Trp Ile Asn Gly Met Leu Ile Ser Leu Leu Asn
170                 175                 180 tat gaa gat ggt gtg ttg gat cca agc tcc att gta cct ttg ata gat        690
Tyr Glu Asp Gly Val Leu Asp Pro Ser Ser Ile Val Pro Leu Ile Asp
185                 190                 195                 200 ggg ggg aca gaa ggc ttt aaa ggg aat gcc cga gtg att ttg cct gga        738
Gly Gly Thr Glu Gly Phe Lys Gly Asn Ala Arg Val Ile Leu Pro Gly
                205                 210                 215 atg acc gct tgt att gag tgc act ctg gaa ctt tac cca cca cag gtc        786
Met Thr Ala Cys Ile Glu Cys Thr Leu Glu Leu Tyr Pro Pro Gln Val
            220                 225                 230 aat ttc ccc atg tgt acc att gca tct atg ccc agg ctc cca gaa cac        834
Asn Phe Pro Met Cys Thr Ile Ala Ser Met Pro Arg Leu Pro Glu His
        235                 240                 245 tgt atc gag tat gtg agg atg ttg caa tgg cct aaa gag cag cct ttt        882
Cys Ile Glu Tyr Val Arg Met Leu Gln Trp Pro Lys Glu Gln Pro Phe
250                 255                 260 gga gat ggg gtt cca tta gat gga gat gac cct gaa cat att cag tgg        930
Gly Asp Gly Val Pro Leu Asp Gly Asp Asp Pro Glu His Ile Gln Trp
265                 270                 275                 280 att ttc caa aag tcc ata gag aga gca tca caa tat aat att aga ggc        978
```

```
Ile Phe Gln Lys Ser Ile Glu Arg Ala Ser Gln Tyr Asn Ile Arg Gly
                285                 290                 295 gtt acc tac aga ctc act caa ggg gtg gta aaa cga atc att cct gca      1026
Val Thr Tyr Arg Leu Thr Gln Gly Val Val Lys Arg Ile Ile Pro Ala
            300                 305                 310 gta gct tct aca aat gca gtc att gca gct gtg tgt gcc act gag gtt      1074
Val Ala Ser Thr Asn Ala Val Ile Ala Ala Val Cys Ala Thr Glu Val
                315                 320                 325 ttc aag ata gct aca agt gcg tac att ccc ctt aat aac tac ctg gta      1122
Phe Lys Ile Ala Thr Ser Ala Tyr Ile Pro Leu Asn Asn Tyr Leu Val
            330                 335                 340 ttc aat gat gta gat ggg ctg tac act tac acg ttt gaa gca gag aga      1170
Phe Asn Asp Val Asp Gly Leu Tyr Thr Tyr Thr Phe Glu Ala Glu Arg
345                 350                 355                 360 aag gaa aac tgt cca gca tgt agc caa ctt cct caa aac att cag ttt      1218
Lys Glu Asn Cys Pro Ala Cys Ser Gln Leu Pro Gln Asn Ile Gln Phe
                365                 370                 375 tcc cca tca gct aaa cta cag gag gtc tta gac tac cta acc aac agt      1266
Ser Pro Ser Ala Lys Leu Gln Glu Val Leu Asp Tyr Leu Thr Asn Ser
            380                 385                 390 gct tct ctg caa atg aag tct ccg gct atc aca gcc aca tta gag ggg      1314
Ala Ser Leu Gln Met Lys Ser Pro Ala Ile Thr Ala Thr Leu Glu Gly
                395                 400                 405 aag aac agg aca ctt tac tta cag tca gta acg tct att gaa gaa cga      1362
Lys Asn Arg Thr Leu Tyr Leu Gln Ser Val Thr Ser Ile Glu Glu Arg
            410                 415                 420 acc agg ccc aat ctt tcc aaa aca tta aaa gaa ctg gga cta gtt gat      1410
Thr Arg Pro Asn Leu Ser Lys Thr Leu Lys Glu Leu Gly Leu Val Asp
425                 430                 435                 440 gga caa gaa ctg gct gtt gct gat gtc act aca cca cag act gta cta      1458
Gly Gln Glu Leu Ala Val Ala Asp Val Thr Thr Pro Gln Thr Val Leu
                445                 450                 455 ttc aaa ctt cat ttt act taa ggaaaataaa tctgcacata atagaaaatt         1509
Phe Lys Leu His Phe Thr
            460 catagaaata atatacttta taaatgatat gaaattgaag agcctggaag atgaggcaga    1569 ggggaacatc caagaaagga aatttaattg gtgtcatttt tagcattagt gtggctagaa    1629 tttgactttt atatatatac atatatataa aaaaggactg actctttttt aactttataa    1689 gtttctcttg aagactgaac tttggggttg ggctagcaag catttcatt ttattactat     1749 ggaaagctat gccttcagga gagattatga acaagtgtgt tgcttcttta aagcaggaca    1809 aacactgtct tgtgtgtgag tttgttgtgg tcaaagagca tattcctcag cgtgtatctg    1869 aaatccacat gtgtagaaat gtctcctggg atggaaatga ggagctatgt ctgaagaata    1929 gtaaatattc acagcctgac atctagagta tatcaaacat aggcagtgtc ttcattgcta    1989 ctcatataat tgtgactatc catgtgtgta ttaattattg cagaatttaa cttgtccatg    2049 ataatttgta aacagtatta tagattcata cctgtgcatg aaaatacaaa atattttcat    2109 gtatttgttt gcaatgccac agagaccagt atgcacaaat ttaaaccaag acatggctgt    2169 tcaaagaaaa ttaatgttta aacagttatc attgatgctt ttgcactatt tattaataaa    2229 attgtacatt gtctttttat tggaaaactt aagtatatc aataatagta aataacttta     2289 tagtgatgta gaaataattt ttaaatgttt accagttatt atttccagac ttttattgcg    2349 cctgagttaa attttaaaa ttttattata gtgattccca tagtacagac taggttcact     2409 cattctaact agtaaatgaa atggaatgac ttaa                                2443
```

```
<210> SEQ ID NO 61
<211> LENGTH: 462
<212> TYPE: PRT
<213> ORGANISM: Mus musculus

<400> SEQUENCE: 61
```

| | | | | | | | | | | | | | | | |
|---|---|---|---|---|---|---|---|---|---|---|---|---|---|---|---|
| Met | Ala | Asp | Gly | Glu | Pro | Glu | Lys | Lys | Arg | Arg | Arg | Ile | Glu | Glu | |
| 1 | | | | 5 | | | | | 10 | | | | | 15 | |
| Leu | Leu | Ala | Glu | Lys | Met | Ala | Val | Asp | Gly | Cys | Gly | Asp | Thr | Gly | |
| | | | 20 | | | | | 25 | | | | | 30 | | |
| Asp | Trp | Glu | Gly | Arg | Trp | Asn | His | Val | Lys | Lys | Phe | Leu | Glu | Arg | Ser |
| | | 35 | | | | | 40 | | | | | 45 | | | |
| Gly | Pro | Phe | Thr | His | Pro | Asp | Phe | Glu | Pro | Ser | Thr | Glu | Ser | Leu | Gln |
| | 50 | | | | | 55 | | | | | 60 | | | | |
| Phe | Leu | Leu | Asp | Thr | Cys | Lys | Val | Leu | Val | Ile | Gly | Ala | Gly | Gly | Leu |
| 65 | | | | | 70 | | | | | 75 | | | | | 80 |
| Gly | Cys | Glu | Leu | Leu | Lys | Asn | Leu | Ala | Leu | Ser | Gly | Phe | Arg | Gln | Ile |
| | | | | 85 | | | | | 90 | | | | | 95 | |
| His | Val | Ile | Asp | Met | Asp | Thr | Ile | Asp | Val | Ser | Asn | Leu | Asn | Arg | Gln |
| | | | | 100 | | | | | 105 | | | | | 110 | |
| Phe | Leu | Phe | Arg | Pro | Lys | Asp | Val | Gly | Arg | Pro | Lys | Ala | Glu | Val | Ala |
| | | | 115 | | | | | 120 | | | | | 125 | | |
| Ala | Glu | Phe | Leu | Asn | Asp | Arg | Val | Pro | Asn | Cys | Asn | Val | Val | Pro | His |
| | 130 | | | | | 135 | | | | | 140 | | | | |
| Phe | Asn | Lys | Ile | Gln | Asp | Phe | Asn | Asp | Thr | Phe | Tyr | Arg | Gln | Phe | His |
| 145 | | | | | 150 | | | | | 155 | | | | | 160 |
| Ile | Ile | Val | Cys | Gly | Leu | Asp | Ser | Ile | Ile | Ala | Arg | Arg | Trp | Ile | Asn |
| | | | | 165 | | | | | 170 | | | | | 175 | |
| Gly | Met | Leu | Ile | Ser | Leu | Leu | Asn | Tyr | Glu | Asp | Gly | Val | Leu | Asp | Pro |
| | | | 180 | | | | | 185 | | | | | 190 | | |
| Ser | Ser | Ile | Val | Pro | Leu | Ile | Asp | Gly | Gly | Thr | Glu | Gly | Phe | Lys | Gly |
| | | 195 | | | | | 200 | | | | | 205 | | | |
| Asn | Ala | Arg | Val | Ile | Leu | Pro | Gly | Met | Thr | Ala | Cys | Ile | Glu | Cys | Thr |
| | 210 | | | | | 215 | | | | | 220 | | | | |
| Leu | Glu | Leu | Tyr | Pro | Pro | Gln | Val | Asn | Phe | Pro | Met | Cys | Thr | Ile | Ala |
| 225 | | | | | 230 | | | | | 235 | | | | | 240 |
| Ser | Met | Pro | Arg | Leu | Pro | Glu | His | Cys | Ile | Glu | Tyr | Val | Arg | Met | Leu |
| | | | | 245 | | | | | 250 | | | | | 255 | |
| Gln | Trp | Pro | Lys | Glu | Gln | Pro | Phe | Gly | Asp | Gly | Val | Pro | Leu | Asp | Gly |
| | | | 260 | | | | | 265 | | | | | 270 | | |
| Asp | Asp | Pro | Glu | His | Ile | Gln | Trp | Ile | Phe | Gln | Lys | Ser | Ile | Glu | Arg |
| | | 275 | | | | | 280 | | | | | 285 | | | |
| Ala | Ser | Gln | Tyr | Asn | Ile | Arg | Gly | Val | Thr | Tyr | Arg | Leu | Thr | Gln | Gly |
| | 290 | | | | | 295 | | | | | 300 | | | | |
| Val | Val | Lys | Arg | Ile | Ile | Pro | Ala | Val | Ala | Ser | Thr | Asn | Ala | Val | Ile |
| 305 | | | | | 310 | | | | | 315 | | | | | 320 |
| Ala | Ala | Val | Cys | Ala | Thr | Glu | Val | Phe | Lys | Ile | Ala | Thr | Ser | Ala | Tyr |
| | | | | 325 | | | | | 330 | | | | | 335 | |
| Ile | Pro | Leu | Asn | Asn | Tyr | Leu | Val | Phe | Asn | Asp | Val | Asp | Gly | Leu | Tyr |
| | | | 340 | | | | | 345 | | | | | 350 | | |
| Thr | Tyr | Thr | Phe | Glu | Ala | Glu | Arg | Lys | Glu | Asn | Cys | Pro | Ala | Cys | Ser |
| | | 355 | | | | | 360 | | | | | 365 | | | |
| Gln | Leu | Pro | Gln | Asn | Ile | Gln | Phe | Ser | Pro | Ser | Ala | Lys | Leu | Gln | Glu |
| | 370 | | | | | 375 | | | | | 380 | | | | |

```
Val Leu Asp Tyr Leu Thr Asn Ser Ala Ser Leu Gln Met Lys Ser Pro
385                 390                 395                 400

Ala Ile Thr Ala Thr Leu Glu Gly Lys Asn Arg Thr Leu Tyr Leu Gln
            405                 410                 415

Ser Val Thr Ser Ile Glu Glu Arg Thr Arg Pro Asn Leu Ser Lys Thr
        420                 425                 430

Leu Lys Glu Leu Gly Leu Val Asp Gly Gln Glu Leu Ala Val Ala Asp
            435                 440                 445

Val Thr Thr Pro Gln Thr Val Leu Phe Lys Leu His Phe Thr
        450                 455                 460

<210> SEQ ID NO 62
<211> LENGTH: 1192
<212> TYPE: DNA
<213> ORGANISM: Mus musculus
<220> FEATURE:
<221> NAME/KEY: CDS
<222> LOCATION: (248)...(799)

<400> SEQUENCE: 62
ccgaggatcg ccgagtcctc ccgagcacct ccgaacacac ccgaggtgct tagccaggcc      60
agagccggac tacgggagcc gaggcgggcc gtgcggtggg cgcggagcag cgcggcaggc     120
cgggcgagcg gcagcggagg aggccgcggt agcgggtccg aggagcggaa gcggcgcagg     180
cggcggcggg gggccgggtg gccggggtcc cgggccccgc ggcggcggct gcggcggcgg     240
```

```
cggcagg atg atc aag ctg ttc tcg ctg aag cag cag aag aag gag gag      289
        Met Ile Lys Leu Phe Ser Leu Lys Gln Gln Lys Lys Glu Glu
          1               5                  10 gag tcg gcc ggc ggc acc aag ggc agc agc aag aag gcg tcg gcg gcg      337
Glu Ser Ala Gly Gly Thr Lys Gly Ser Ser Lys Lys Ala Ser Ala Ala
 15              20                  25                  30 cag ctc cgg att cag aag gac att aac gag ctg aac ctg ccc aag acg      385
Gln Leu Arg Ile Gln Lys Asp Ile Asn Glu Leu Asn Leu Pro Lys Thr
             35                  40                  45 tgt gac atc agc ttc tca gac cca gac gac ctc ctc aac ttc aag ctg      433
Cys Asp Ile Ser Phe Ser Asp Pro Asp Asp Leu Leu Asn Phe Lys Leu
         50                  55                  60 gtg atc tgt cct gat gaa ggc ttc tac aaa agt ggc aag ttt gta ttc      481
Val Ile Cys Pro Asp Glu Gly Phe Tyr Lys Ser Gly Lys Phe Val Phe
     65                  70                  75 agc ttt aag gtg gga cag ggt tac cca cat gac cct ccc aag gtg aag      529
Ser Phe Lys Val Gly Gln Gly Tyr Pro His Asp Pro Pro Lys Val Lys
 80                  85                  90 tgt gaa aca atg gtt tat cat ccc aac att gac ctc gag ggc aac gtc      577
Cys Glu Thr Met Val Tyr His Pro Asn Ile Asp Leu Glu Gly Asn Val
 95                 100                 105                 110 tgc ctc aac atc ctc aga gag gac tgg aag cca gtg ctt acg ata aac      625
Cys Leu Asn Ile Leu Arg Glu Asp Trp Lys Pro Val Leu Thr Ile Asn
             115                 120                 125 tcc ata att tat ggc ctg cag tat ctc ttc ttg gag ccg aac cct gag      673
Ser Ile Ile Tyr Gly Leu Gln Tyr Leu Phe Leu Glu Pro Asn Pro Glu
         130                 135                 140 gac cca ctg aac aag gag gct gct gag gtc ctg cag aac aac cgg cgg      721
Asp Pro Leu Asn Lys Glu Ala Ala Glu Val Leu Gln Asn Asn Arg Arg
     145                 150                 155 ctg ttt gaa caa aat gtg cag cgc tcc atg aga ggt ggt tac atc ggg      769
Leu Phe Glu Gln Asn Val Gln Arg Ser Met Arg Gly Gly Tyr Ile Gly
160                 165                 170
```

-continued

```
tcc acc tac ttc gag cgc tgc ctg aaa tag ggttagcaat tacccatccc        819
Ser Thr Tyr Phe Glu Arg Cys Leu Lys
175                 180 tgccagggtt accggcccag gcatccctg caaatattta ttgggggccc gggtaaggtg      879
tgtggggtag ccttggcccc tgccttggcc ttgcctctct tccctgtcac ctgcccctag    939 ttatttttt tttgaccacc acgtgattat ggtcggtgct gcctcccccc cgacctgctc    999
agcgatggga aatgaattgg cttgtttagc gcccccccc tcccgctggg tgctgtccaa   1059
ctccccactc ttgactgtgg ggtaagtggg caatgggcct gggtcgctag gcccaagcaa   1119
cccaccccac caccactgga ggtcccacca ggctattaaa ggggaatgtt actgcaaaaa   1179
aaaaaaaaaa aaa                                                     1192
```

<210> SEQ ID NO 63
<211> LENGTH: 183
<212> TYPE: PRT
<213> ORGANISM: Mus musculus

<400> SEQUENCE: 63

```
Met Ile Lys Leu Phe Ser Leu Lys Gln Gln Lys Lys Glu Glu Glu Ser
1               5                   10                  15

Ala Gly Gly Thr Lys Gly Ser Ser Lys Lys Ala Ser Ala Ala Gln Leu
            20                  25                  30

Arg Ile Gln Lys Asp Ile Asn Glu Leu Asn Leu Pro Lys Thr Cys Asp
        35                  40                  45

Ile Ser Phe Ser Asp Pro Asp Asp Leu Leu Asn Phe Lys Leu Val Ile
    50                  55                  60

Cys Pro Asp Glu Gly Phe Tyr Lys Ser Gly Lys Phe Val Phe Ser Phe
65                  70                  75                  80

Lys Val Gly Gln Gly Tyr Pro His Asp Pro Lys Val Lys Cys Glu
                85                  90                  95

Thr Met Val Tyr His Pro Asn Ile Asp Leu Glu Gly Asn Val Cys Leu
            100                 105                 110

Asn Ile Leu Arg Glu Asp Trp Lys Pro Val Leu Thr Ile Asn Ser Ile
        115                 120                 125

Ile Tyr Gly Leu Gln Tyr Leu Phe Leu Glu Pro Asn Pro Glu Asp Pro
    130                 135                 140

Leu Asn Lys Glu Ala Ala Glu Val Leu Gln Asn Asn Arg Arg Leu Phe
145                 150                 155                 160

Glu Gln Asn Val Gln Arg Ser Met Arg Gly Gly Tyr Ile Gly Ser Thr
                165                 170                 175

Tyr Phe Glu Arg Cys Leu Lys
            180
```

<210> SEQ ID NO 64
<211> LENGTH: 1363
<212> TYPE: DNA
<213> ORGANISM: Mus musculus
<220> FEATURE:
<221> NAME/KEY: CDS
<222> LOCATION: (136)...(693)

<400> SEQUENCE: 64

```
acttccggtc tcgccgccgg gagccggtgc ggctgtgaag gccagcgcga ctcagtgccg    60
ctgctccgcc gggcatggtt ttgggtgccg gctcgcctcg cctgactcgc ggtgctcaga   120
agaaaggtgg cagga atg cta acg ctg gca agc aag ttg aag cgg gat gat    171
              Met Leu Thr Leu Ala Ser Lys Leu Lys Arg Asp Asp
```

```
             1               5                      10
ggt ctc aaa gga tcc cgg aca tca gcc tcc aca tct gac tct acc cgg        219
Gly Leu Lys Gly Ser Arg Thr Ser Ala Ser Thr Ser Asp Ser Thr Arg
         15                  20                  25 agg gtt tct gtg aga gac aag ttg ctt gtt aaa gag gtt gca gaa ctt        267
Arg Val Ser Val Arg Asp Lys Leu Leu Val Lys Glu Val Ala Glu Leu
 30                  35                  40 gaa gct aat tta cct tgt aca tgt aaa gta cat ttt cct gat cca aac        315
Glu Ala Asn Leu Pro Cys Thr Cys Lys Val His Phe Pro Asp Pro Asn
     45                  50                  55                  60 aag ctt cat tgc ttt cag ctg act gta agc cca gat gag ggt tac tac        363
Lys Leu His Cys Phe Gln Leu Thr Val Ser Pro Asp Glu Gly Tyr Tyr
                 65                  70                  75 cag ggt gga aaa ttt cag ttt gaa act gaa gtt ccc gat gcc tac aac        411
Gln Gly Gly Lys Phe Gln Phe Glu Thr Glu Val Pro Asp Ala Tyr Asn
             80                  85                  90 atg gtg cct ccc aag gtg aaa tgc ttg act aaa atc tgg cac ccc aac        459
Met Val Pro Pro Lys Val Lys Cys Leu Thr Lys Ile Trp His Pro Asn
                 95                  100                 105 atc aca gaa acg ggg gaa ata tgt cta agt tta cta aga gaa cat tca        507
Ile Thr Glu Thr Gly Glu Ile Cys Leu Ser Leu Leu Arg Glu His Ser
         110                 115                 120 att gat ggc act ggc tgg gct ccc act aga aca tta aag gat gtt gtt        555
Ile Asp Gly Thr Gly Trp Ala Pro Thr Arg Thr Leu Lys Asp Val Val
125                 130                 135                 140 tgg gga tta aac tct tta ttt acc gat ctc ttg aat ttt gat gat cca        603
Trp Gly Leu Asn Ser Leu Phe Thr Asp Leu Leu Asn Phe Asp Asp Pro
                     145                 150                 155 ctg aat att gaa gct gca gaa cat cat ttg cgg gac aag gag gat ttt        651
Leu Asn Ile Glu Ala Ala Glu His His Leu Arg Asp Lys Glu Asp Phe
             160                 165                 170 cgg gac aaa gtg gat gaa tac atc aaa cgc tat gcc aga tga              693
Arg Asp Lys Val Asp Glu Tyr Ile Lys Arg Tyr Ala Arg
        175                 180                 185 taagaggaga gatcgcaggt ctgaggactt tgtcacagtt gtctctgatg tgaaacagct      753
cgaggtagcc ctcctcccca tcctcatact ccctgtcagc cccttgggat tgtcccagtc      813
ctgcgaccat gctgtcctga agaagaccct cctgactgcc cactataggt ggcgaacaac      873
ataatacagc aagaaagtgt gtctgggcct caagagagtt gtctgcttcc cttaacatgt      933
ttactgaaac tactgtctag ctgtctggt ggaatccctc tgaagttgta atgaactcac       993
cactgaggat atagcgcttg cttcctttcc cccaacaatc ggtgtcctgc acaagtggtg     1053
taatgacatg ttccatgtga ctggcagatt ggcaataaga aacccgctat aaactgtgat     1113
tggatgcaca ctctcttagc ttcttccacg aatgttgacc ctaccatagt gtgaagcttc     1173
ccagaatgca tagtcattca ctgtagatct tactgaaatg cgtattttat ttaatgtaag     1233
tatattttgg aacagatttg taatttgtac aatttgatgc tttaattatt ttttctattc     1293
ttatttactt tgtattcatt gtatagagca aacacaaaga cattgagtca agaaactact     1353
gaagagaaat                                                            1363
```

<210> SEQ ID NO 65
<211> LENGTH: 185
<212> TYPE: PRT
<213> ORGANISM: Mus musculus

<400> SEQUENCE: 65

Met Leu Thr Leu Ala Ser Lys Leu Lys Arg Asp Asp Gly Leu Lys Gly

```
              1               5                  10                 15
           Ser Arg Thr Ser Ala Ser Thr Ser Asp Ser Thr Arg Arg Val Ser Val
                           20                  25                 30

Arg Asp Lys Leu Leu Val Lys Glu Val Ala Glu Leu Glu Ala Asn Leu
                           35                  40                 45

Pro Cys Thr Cys Lys Val His Phe Pro Asp Pro Asn Lys Leu His Cys
                           50                  55                 60

Phe Gln Leu Thr Val Ser Pro Asp Glu Gly Tyr Tyr Gln Gly Gly Lys
           65                          70                  75                 80

Phe Gln Phe Glu Thr Glu Val Pro Asp Ala Tyr Asn Met Val Pro Pro
                           85                  90                 95

Lys Val Lys Cys Leu Thr Lys Ile Trp His Pro Asn Ile Thr Glu Thr
                           100                 105                110

Gly Glu Ile Cys Leu Ser Leu Leu Arg Glu His Ser Ile Asp Gly Thr
                           115                 120                125

Gly Trp Ala Pro Thr Arg Thr Leu Lys Asp Val Trp Gly Leu Asn
                           130                 135                140

Ser Leu Phe Thr Asp Leu Leu Asn Phe Asp Asp Pro Leu Asn Ile Glu
           145                         150                 155                160

Ala Ala Glu His His Leu Arg Asp Lys Glu Asp Phe Arg Asp Lys Val
                           165                 170                175

Asp Glu Tyr Ile Lys Arg Tyr Ala Arg
                           180                 185

<210> SEQ ID NO 66
<211> LENGTH: 906
<212> TYPE: DNA
<213> ORGANISM: Homo sapiens
<220> FEATURE:
<221> NAME/KEY: CDS
<222> LOCATION: (53)...(379)

<400> SEQUENCE: 66
gtgcgctgct gcgcaggcgc ggtggtcgga cgacagaccg tgtgtttcca aa atg gcg      58
                                                           Met Ala
                                                             1 gca gcg atg gat gtg gat acc ccg agc ggc acc aac agc ggc gcg ggc      106
Ala Ala Met Asp Val Asp Thr Pro Ser Gly Thr Asn Ser Gly Ala Gly
          5                   10                  15 aag aag cgc ttt gaa gtg aaa aag tgg aat gca gta gcc ctc tgg gcc      154
Lys Lys Arg Phe Glu Val Lys Lys Trp Asn Ala Val Ala Leu Trp Ala
         20                  25                  30 tgg gat att gtg gtt gat aac tgt gcc atc tgc agg aac cac att atg      202
Trp Asp Ile Val Val Asp Asn Cys Ala Ile Cys Arg Asn His Ile Met
 35                  40                  45                  50 gat ctt tgc ata gaa tgt caa gct aac cag gcg tcc gct act tca gaa      250
Asp Leu Cys Ile Glu Cys Gln Ala Asn Gln Ala Ser Ala Thr Ser Glu
                 55                  60                  65 gag tgt act gtc gca tgg gga gtc tgt aac cat gct ttt cac ttc cac      298
Glu Cys Thr Val Ala Trp Gly Val Cys Asn His Ala Phe His Phe His
             70                  75                  80 tgc atc tct cgc tgg ctc aaa aca cga cag gtg tgt cca ttg gac aac      346
Cys Ile Ser Arg Trp Leu Lys Thr Arg Gln Val Cys Pro Leu Asp Asn
         85                  90                  95 aga gag tgg gaa ttc caa aag tat ggg cac tag gaaaagactt cttccatcaa    399
Arg Glu Trp Glu Phe Gln Lys Tyr Gly His
        100                 105 gcttaattgt tttgttattc atttaatgac tttccctgct gttacctaat tacaaattgg   459
```

```
atggaactgt gttttttct gctttgtttt ttcagtttgc tgtttctgta gccatattgt    519
attctgtgtc aaataaagtc cagttggatt ctggaacgga tgctctctct tgtgtatgtg    579
aacaaagtga acataaatga agagtctccc cttccaaggc tgaaaactca gcttttgaaa    639
gtgaaatgtt tgttcatcgg ggccagagca gggttgtcct ctgagcgcat cacttagtga    699
cgaggaatcc aacagctcaa ggcagagtgt ggatcaccgg ctcccgaaaa cagcagtcag    759
cccttctttc tcctgtgtga cagcagtggg cagctgaaag agggaagaat gtgggattca    819
gtcatcaaac ccagttctga gtcctggttc cacagcttgg gtactgatgg caatcttggc    879
caagttgtct ctctactctg aactttc                                         906
```

<210> SEQ ID NO 67
<211> LENGTH: 108
<212> TYPE: PRT
<213> ORGANISM: Homo sapiens

<400> SEQUENCE: 67

```
Met Ala Ala Ala Met Asp Val Asp Thr Pro Ser Gly Thr Asn Ser Gly
 1               5                  10                  15

Ala Gly Lys Lys Arg Phe Glu Val Lys Lys Trp Asn Ala Val Ala Leu
             20                  25                  30

Trp Ala Trp Asp Ile Val Val Asp Asn Cys Ala Ile Cys Arg Asn His
         35                  40                  45

Ile Met Asp Leu Cys Ile Glu Cys Gln Ala Asn Gln Ala Ser Ala Thr
     50                  55                  60

Ser Glu Glu Cys Thr Val Ala Trp Gly Val Cys Asn His Ala Phe His
 65                  70                  75                  80

Phe His Cys Ile Ser Arg Trp Leu Lys Thr Arg Gln Val Cys Pro Leu
                 85                  90                  95

Asp Asn Arg Glu Trp Glu Phe Gln Lys Tyr Gly His
            100                 105
```

<210> SEQ ID NO 68
<211> LENGTH: 1655
<212> TYPE: DNA
<213> ORGANISM: Mus musculus
<220> FEATURE:
<221> NAME/KEY: CDS
<222> LOCATION: (58)...(384)

<400> SEQUENCE: 68

```
ggaaagtgag ccggtgcgca ggcgcagtgg tcacacgaca gactgtgtgt ttccaaa atg    60
                                                                Met
                                                                 1 gcg gcg gcg atg gat gtg gat acc ccc agc ggc acc aac agc ggc gcg      108
Ala Ala Ala Met Asp Val Asp Thr Pro Ser Gly Thr Asn Ser Gly Ala
         5                  10                  15 ggc aag aag cgc ttt gaa gtt aaa aag tgg aat gca gtg gcc ctc tgg      156
Gly Lys Lys Arg Phe Glu Val Lys Lys Trp Asn Ala Val Ala Leu Trp
     20                  25                  30 gcc tgg gac att gtg gtt gat aac tgt gcc atc tgc agg aac cac att      204
Ala Trp Asp Ile Val Val Asp Asn Cys Ala Ile Cys Arg Asn His Ile
 35                  40                  45 atg gat ctt tgt atc gaa tgt cag gcc aac cag gcg tca gct act tcc      252
Met Asp Leu Cys Ile Glu Cys Gln Ala Asn Gln Ala Ser Ala Thr Ser
         50                  55                  60                  65 gaa gag tgt acg gtt gca tgg gga gtc tgc aac cat gct ttt cat ttc      300
Glu Glu Cys Thr Val Ala Trp Gly Val Cys Asn His Ala Phe His Phe
                 70                  75                  80
```

```
                            70                  75                  80
cac tgc atc tct cga tgg ctc aaa acg agg cag gtg tgt ccg ttg gac      348
His Cys Ile Ser Arg Trp Leu Lys Thr Arg Gln Val Cys Pro Leu Asp
             85                  90                  95 aac aga gag tgg gag ttc cag aag tat ggg cat tag gaaagacttt           394
Asn Arg Glu Trp Glu Phe Gln Lys Tyr Gly His
            100                 105 cccgcaaggc gtaccatct gttactcgtc tagtgacttc ctgttaatta tacattagat     454
agaaccatgg tccttttcg ttcctttgtt tttggagttt ggtgttcccg cagccatatt     514
gtatttgtg tcaaataaag cctttaagtt ggaggtggtt gctgtttcat gtatgtggag     574
agtgatctga gaaggagcca gaaagccaga aaggcagcct caagaagtgc tctgttctta    634
aggagaacac acttggccca tgggttcatc ttcacaaggt cacgaggaac ctgtcagagt    694
cgggagtgcg ggtaactggc acctggaaac ccctccagct ctgtcttcct tctgagatag   754
caccaggcag gaatgaggaa gaacatggca gccttggacc agccaggtct gctctgagtt    814
ttcatctcat gatggagtct aagaacgagt gactggcatc aagtgggcac aggaaggctt    874
tgtaaactct aaacactaca gggttagcag tgactgtgaa tgacatgcag caatctctag    934
aacaaaagtt gacccaaaaa atcgtactgt gtaatcttgg ctggcaataa agtcatcata    994
aagttcacct gaaactgat gtttggacag tttgcatata tgcctgtaat cccaggtact    1054
tggaaattag gtaaagatcc tttgagtcca ggagaccttg tttctaaaac agaaattcta   1114
gtttggggtc taggggcgc tgtagctcag ctgtaaggcc ccgtgttcaa ttgctggcat    1174
aaatttcaaa aaagaaaaa ggtagaaatt gaattagcaa gagcttaagt tttctttaaa    1234
catgctggcc agggccaggc agtggtggtg catgcctta atcccaacac ttgggagcca    1294
gaggcaggca gatttctgag tttgaggcca gcctacagag tgagtttcag gacaaccagg   1354
gctatataaa gaaaccctgt tgccaaaaaa acaaaaacat gccggccagg gaaggagcgg   1414
ccatcctgat gctggttcag tggctgtatt ctaccgagac accgtttctg ttgctgtggt   1474
tttcatgtag ttaacagatc ctacaaaggt cttgaaatcc ttcaggggag ttttcctttc   1534
tccggtgcca ctacttcaac tgtcttctgt tgtcaagcag aaaagattg caaaaatgtg    1594
aaacaatgct gtcattcttg ttttcaaagt taatttaat aaaaatattt atgttaatgg   1654
c                                                                  1655

<210> SEQ ID NO 69
<211> LENGTH: 108
<212> TYPE: PRT
<213> ORGANISM: Mus musculus

<400> SEQUENCE: 69

Met Ala Ala Ala Met Asp Val Asp Thr Pro Ser Gly Thr Asn Ser Gly
  1               5                  10                  15

Ala Gly Lys Lys Arg Phe Glu Val Lys Lys Trp Asn Ala Val Ala Leu
             20                  25                  30

Trp Ala Trp Asp Ile Val Val Asp Asn Cys Ala Ile Cys Arg Asn His
         35                  40                  45

Ile Met Asp Leu Cys Ile Glu Cys Gln Ala Asn Gln Ala Ser Ala Thr
     50                  55                  60

Ser Glu Glu Cys Thr Val Ala Trp Gly Val Cys Asn His Ala Phe His
 65                  70                  75                  80

Phe His Cys Ile Ser Arg Trp Leu Lys Thr Arg Gln Val Cys Pro Leu
                 85                  90                  95
```

```
Asp Asn Arg Glu Trp Glu Phe Gln Lys Tyr Gly His
            100                 105

<210> SEQ ID NO 70
<211> LENGTH: 4474
<212> TYPE: DNA
<213> ORGANISM: Mus musculus
<220> FEATURE:
<221> NAME/KEY: CDS
<222> LOCATION: (180)...(959)

<400> SEQUENCE: 70
ggccaggccg cccaccccgg ggcccgcgcc ctccgcctcc cgcggcccgg ccgctccgcg      60
ggccgccgca ctgcgcatga gcgggagccc ggcgagcccg tgagaggcgc cgccgccgcc     120
gccgccgtcc attcgctgcg gagccggagg aggaggggag aggtccggag gacaccaac     179 atg aac aag ttg aaa tca tcg cag aag gat aaa gtt cgt cag ttt atg      227
Met Asn Lys Leu Lys Ser Ser Gln Lys Asp Lys Val Arg Gln Phe Met
  1               5                  10                  15 atc ttc aca caa tct agt gag aaa act gca gta agt tgt ctt tct caa      275
Ile Phe Thr Gln Ser Ser Glu Lys Thr Ala Val Ser Cys Leu Ser Gln
                 20                  25                  30 aat gac tgg aag tta gat gtt gca aca gat aat ttt ttt caa aat cca      323
Asn Asp Trp Lys Leu Asp Val Ala Thr Asp Asn Phe Phe Gln Asn Pro
             35                  40                  45 gaa ctt tat ata cgg gag agt gta aaa gga tcg ttg gac agg aag aag      371
Glu Leu Tyr Ile Arg Glu Ser Val Lys Gly Ser Leu Asp Arg Lys Lys
         50                  55                  60 tta gag caa ctg tac act aga tac aaa gac cct cag gat gaa aat aaa      419
Leu Glu Gln Leu Tyr Thr Arg Tyr Lys Asp Pro Gln Asp Glu Asn Lys
 65                  70                  75                  80 att gga ata gat ggt ata cag cag ttc tgt gat gat ctg gcc ctc gat      467
Ile Gly Ile Asp Gly Ile Gln Gln Phe Cys Asp Asp Leu Ala Leu Asp
                 85                  90                  95 cca gcc agc atc agt gtg ttg atc att gca tgg aag ttc agg gcg gcc      515
Pro Ala Ser Ile Ser Val Leu Ile Ile Ala Trp Lys Phe Arg Ala Ala
                100                 105                 110 aca cag tgc gag ttc tcc aaa cag gag ttc atg gat ggc atg aca gag      563
Thr Gln Cys Glu Phe Ser Lys Gln Glu Phe Met Asp Gly Met Thr Glu
            115                 120                 125 tta gga tgt gac agc ata gaa aaa cta aag gcc caa ata ccc aag atg      611
Leu Gly Cys Asp Ser Ile Glu Lys Leu Lys Ala Gln Ile Pro Lys Met
        130                 135                 140 gaa caa gaa ttg aaa gaa cca gga cga ttt aag gat ttt tac cag ttt      659
Glu Gln Glu Leu Lys Glu Pro Gly Arg Phe Lys Asp Phe Tyr Gln Phe
145                 150                 155                 160 act ttt aat ttt gca aag aat cca gga caa aaa gga tta gat cta gaa      707
Thr Phe Asn Phe Ala Lys Asn Pro Gly Gln Lys Gly Leu Asp Leu Glu
                165                 170                 175 atg gcc att gct tac tgg aac tta gtg ctt aat gga aga ttt aaa ttc      755
Met Ala Ile Ala Tyr Trp Asn Leu Val Leu Asn Gly Arg Phe Lys Phe
                180                 185                 190 tta gac tta tgg aat aaa ttt ttg ttg gag cat cat aaa cga tca ata      803
Leu Asp Leu Trp Asn Lys Phe Leu Leu Glu His His Lys Arg Ser Ile
        195                 200                 205 cca aaa gac acg tgg aat ctt ctg tta gac ttc agt tca atg att gca      851
Pro Lys Asp Thr Trp Asn Leu Leu Leu Asp Phe Ser Ser Met Ile Ala
    210                 215                 220 gat gac atg tcc aat tat gat gaa gaa gga gca tgg cct gtc ctt att      899
Asp Asp Met Ser Asn Tyr Asp Glu Glu Gly Ala Trp Pro Val Leu Ile
```

```
                 225                 230                 235                 240
gat gac ttt gtg gaa ttt gca cgc cct caa att gct ggg aca aaa agt            947
Asp Asp Phe Val Glu Phe Ala Arg Pro Gln Ile Ala Gly Thr Lys Ser
                 245                 250                 255 aca aca gtg tag cactaaagga accttctaga atgtacatag tctgtacaat                999
Thr Thr Val aaatacaacg gaaaatgcac agtcaatttc tgctggctgg actgaagatc aatcctcata         1059
attcaaactg agggttgaga caaaacttTT aaggatacat cttggaccat atcgtactcc         1119
attcttctac tggtggtttg ggcttgtctt ctagtctggg ccactctaag catttataat         1179
tccgacattg tggatttcat cttacacctg tggaccatct tagtctgtct tcccataagt         1239
catagaagct tgatggtgat tattttgagg tttccattct tgcataaagc acaatgctgt         1299
cttcatcaga aaacagtttg gcataagaat taaacataat aatgaacacc acaacaattt         1359
ataaaaactt cttaagtata tgctttgggc tagttgcaaa gactgtgctg gcagcacttc         1419
aaatgagagt gatttatctg agtgtaccgc atctgaaatg gtgtttggtt gggggaattt         1479
aattttcctg gcaaactaca tgtactgctg gtgtgagtag aatacctgat ataagaaata         1539
tcaaaataac caacacatga aaaaaaaaaa ggataatctg gggactccct gaaatatgtc         1599
ttgtgtttca gacgctcaga aaggttctac agaacaggtc tgtggttatc ttacccatgt         1659
ttatacagtg tcctgcagtg aacttttatt taaaaaaata ttgtaatgag atcagatgtt         1719
agactccaca ctcgtgcatc acacaccaca taatcggatt tcattgtgct ctgaaatact         1779
tctatgcctt ctgaataagt taaactattt catttgtttt gaatgttttg gattgctata         1839
caatataata ttctaaattt aggcatgagg gtattaggtt tgtttgtttt ttttttttaat         1899 ttttgtcat cgcactatgg aacacaatgc aattcactta atttataaga agatagtaag          1959
atttagattt tgaaaatggt tgtgatgagc cgtgaagttc aacctttctc ccatggcact         2019
gctctttgag gcgtggtcca gccatgttgg ctgctgactg ttgagatggc ttactgctaa         2079
atcactgtgg ttgccaagtc tactccagaa gcagagattg tcagacaggc gagcactggt         2139
gcagatacca atggcttctg ttctataaat tatttgactt ttgactgttt ttgtctcact         2199
tgcatttgct atttccacat cacagcagaa tgcagtcttg attggttttg ttttttgttt         2259
ttccatgaca ggactcatgc cttgctctcc tgctgaaaat gcttgtttct ctgataacat         2319
actgacatgt gaaggggtg tattcataca tatttccatg aggaagttaa aatgatgaac          2379
taaatgttgg gtgactggtc ttcaatagga acagattttg cttcatgtat ccaggtcctc         2439
tgcagggtac caaggaatgt tcttcaggat agcggaacaa tttatgcaga tatggaaatg         2499
attaaaactg cttttTagtc acatgatttg gaaaatgcat tgaaagctta ccttacagat         2559
atatcattaa tccaatcata actttaattt aggaatgcat ttctaccaaa agaagcttag         2619
agtaaatttc tattcacgtt acagggattg gtcattaaaa ggaaaagaat cttgctgttt         2679
tcagtatttc ttgatttcat tttttgtaaa tataaagaac ttcaattatg aaaaaaatta         2739
aagatatatg tatatatatc tttaaaagtt ttacagacct atattgttta ttccctacat         2799
ggaacatttt gagttttggt attgttttca gattgattga ttcagatatg atttgttttc         2859
aaatgagact ccattagctt ctttccctgc ctcataaatt ttttttcata aaatcttga          2919 tatttgtgtg tggcctaatg ctttgggttt tacagatttt atttttaaat gcaagctttt        2979
ttaacaaaat agtgtttgtc atcagtttgg tactaaacat ttacaattac tgtgtaatta        3039
taaacaaaaa tatataaagc ttttattatg tagcaaaaag agttaaggtt gttcaccatg        3099
```

| | |
|---|---|
| atggcatctt agaattaaac aagacttgct agggctccaa gagaaaattg atttaatgtg | 3159 |
| tttattctga gggtgactgt ctggttctag gaaatgtttt gtaatacaaa tgcttaccct | 3219 |
| attggggggcg gggcgtcggg gagtcttcca gaggaagggc acactcactc acacacagcc | 3279 |
| agctattgcc ggcagaggat catggggttc agtcttcgtg tgggtcaggt ctccaagctg | 3339 |
| attcttttct ttccagacag aaccataggg agagtttact ttttgccaaa tgtcagaaca | 3399 |
| ggtacacatt tttaaatgta atgcttttta aatagtaaac tgtataaaat gagaagtacc | 3459 |
| cacatataaa aatacttgag gtcaaggttc tcttgagtga ctatcatctg catatctctg | 3519 |
| taagttcaag tgtgtcgttt ccaatccctg tcatattacc cacagaggca ataaaagctt | 3579 |
| cagtaaattt gccatgacta aatcttctcc catattattt cagtgtttta gtgtttcaca | 3639 |
| taactagact agacttgaag acttttcatg gccgagcgct gtaatggcac atctggggga | 3699 |
| agagaagcta cgccacgtgt tgctccgta atgtttacaa tgtgctcagc tgtgttgttt | 3759 |
| atttaactgc gttagttgta tactgcggca ctgtgagtgc acccctcatc gaactttta a | 3819 |
| aaagttttag tgttggtaaa ttcgctcact gaaaccatcg ggagcctttt atgtaatctc | 3879 |
| tttcctgaat aattcttaaa caaggttgac atttttttccc ccctcaagga tctgagtgca | 3939 |
| gagttctttt tttattttt tctttgatga taagttttttg agccattcca tgcccaccct | 3999 |
| gcttgtgtgt ttacgtgtgt tgctgttaag gactgtttgg aaacctgtca ttttggcata | 4059 |
| caaataggag caagttgacc taagagaata atttggggat gaaaaatgga aaatggtgtt | 4119 |
| gggaaaagtt atacttgttt acaaagtatg cccttgtaac atgaatgacc gttcagtgag | 4179 |
| cgtttatgtg gctctgaatg ttaaattgtg tctttaatag gaaatattta cctgacacct | 4239 |
| ctgggctttt tgttgttgtt gttaccttaa acttttaata atatggttta tattgaatgc | 4299 |
| tgagatgttt tgataagagt ttaccaaatt tgataatgta atgataaatg ttttaaaatg | 4359 |
| tgaactattt atcatatatc ttaataattg aactgtggct tttatatgac agatgatgaa | 4419 |
| tagggtcaaa ttatggctca ccctttaatt gattataaac ttgagtgtat ttctg | 4474 |

<210> SEQ ID NO 71
<211> LENGTH: 259
<212> TYPE: PRT
<213> ORGANISM: Mus musculus

<400> SEQUENCE: 71

Met Asn Lys Leu Lys Ser Ser Gln Lys Asp Lys Val Arg Gln Phe Met
1               5                   10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asp Asn Phe Phe Gln Asn Pro
        35                  40                  45

Glu Leu Tyr Ile Arg Glu Ser Val Lys Gly Ser Leu Asp Arg Lys Lys
    50                  55                  60

Leu Glu Gln Leu Tyr Thr Arg Tyr Lys Asp Pro Gln Asp Glu Asn Lys
65                  70                  75                  80

Ile Gly Ile Asp Gly Ile Gln Gln Phe Cys Asp Asp Leu Ala Leu Asp
                85                  90                  95

Pro Ala Ser Ile Ser Val Leu Ile Ile Ala Trp Lys Phe Arg Ala Ala
            100                 105                 110

Thr Gln Cys Glu Phe Ser Lys Gln Glu Phe Met Asp Gly Met Thr Glu
        115                 120                 125

Leu Gly Cys Asp Ser Ile Glu Lys Leu Lys Ala Gln Ile Pro Lys Met

```
Glu Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Lys Phe
            180                 185                 190

Leu Asp Leu Trp Asn Lys Phe Leu Leu Glu His His Lys Arg Ser Ile
        195                 200                 205

Pro Lys Asp Thr Trp Asn Leu Leu Leu Asp Phe Ser Ser Met Ile Ala
    210                 215                 220

Asp Asp Met Ser Asn Tyr Asp Glu Glu Gly Ala Trp Pro Val Leu Ile
225                 230                 235                 240

Asp Asp Phe Val Glu Phe Ala Arg Pro Gln Ile Ala Gly Thr Lys Ser
                245                 250                 255

Thr Thr Val

<210> SEQ ID NO 72
<211> LENGTH: 307
<212> TYPE: DNA
<213> ORGANISM: Saccharomyces cerevisiae

<400> SEQUENCE: 72
atgattgtta aagtgaagac actgactggg aaggagatct ctgttgagct gaaggaatca      60
gatctcgtat atcacatcaa ggaacttttg gaggaaaaag aagggattcc accatctcaa     120
caaagactta tattccaggg aaaacaaatg tatgttcatt cagtggttaa ttatctttta     180
agtttattta cgttttttgag accttactaa cgaccaggat agtgatgata aattaacagt     240
aacggatgca catctagtag agggaatgca actccacttg gtattaacac taagaggtgg     300
taactag                                                                307

<210> SEQ ID NO 73
<211> LENGTH: 77
<212> TYPE: PRT
<213> ORGANISM: Saccharomyces cerevisiae

<400> SEQUENCE: 73

Met Ile Val Lys Val Lys Thr Leu Thr Gly Lys Glu Ile Ser Val Glu
1               5                   10                  15

Leu Lys Glu Ser Asp Leu Val Tyr His Ile Lys Glu Leu Leu Glu Glu
            20                  25                  30

Lys Glu Gly Ile Pro Pro Ser Gln Gln Arg Leu Ile Phe Gln Gly Lys
        35                  40                  45

Gln Ile Asp Asp Lys Leu Thr Val Thr Asp Ala His Leu Val Glu Gly
    50                  55                  60

Met Gln Leu His Leu Val Leu Thr Leu Arg Gly Gly Asn
65                  70                  75

<210> SEQ ID NO 74
<211> LENGTH: 462
<212> TYPE: PRT
<213> ORGANISM: Rattus norvegicus

<400> SEQUENCE: 74

Met Ala Asp Gly Glu Glu Pro Glu Lys Lys Arg Arg Arg Ile Glu Glu
1               5                   10                  15
```

Leu Leu Ala Glu Lys Met Ala Val Asp Gly Gly Cys Gly Asp Thr Gly
            20                  25                  30

Asp Trp Glu Gly Arg Trp Asn His Val Lys Lys Phe Leu Glu Arg Ser
        35                  40                  45

Gly Pro Phe Thr His Pro Asp Phe Glu Pro Ser Thr Glu Ser Leu Gln
    50                  55                  60

Phe Leu Leu Asp Thr Cys Lys Val Leu Val Ile Gly Ala Gly Gly Leu
65                  70                  75                  80

Gly Cys Glu Leu Leu Lys Asn Leu Ala Leu Ser Gly Phe Arg Gln Ile
                85                  90                  95

His Val Ile Asp Met Asp Thr Ile Asp Val Ser Asn Leu Asn Arg Gln
                100                 105                 110

Phe Leu Phe Arg Pro Lys Asp Val Gly Arg Pro Lys Ala Glu Val Ala
            115                 120                 125

Ala Glu Phe Leu Asn Asp Arg Val Pro Asn Cys Asn Val Val Pro His
        130                 135                 140

Phe Asn Lys Ile Gln Asp Phe Asn Asp Thr Phe Tyr Arg Gln Phe His
145                 150                 155                 160

Ile Ile Val Cys Gly Leu Asp Ser Ile Ile Ala Arg Arg Trp Ile Asn
                165                 170                 175

Gly Met Leu Ile Ser Leu Leu Asn Tyr Glu Asp Gly Val Leu Asp Pro
                180                 185                 190

Ser Ser Ile Val Pro Leu Ile Asp Gly Gly Thr Glu Gly Phe Lys Gly
            195                 200                 205

Asn Ala Arg Val Ile Leu Pro Gly Met Thr Ala Cys Ile Glu Cys Thr
210                 215                 220

Leu Glu Leu Tyr Pro Pro Gln Val Asn Phe Pro Met Cys Thr Ile Ala
225                 230                 235                 240

Ser Met Pro Arg Leu Pro Glu His Cys Ile Glu Tyr Val Arg Met Leu
            245                 250                 255

Gln Trp Pro Lys Glu Gln Pro Phe Gly Asp Gly Val Pro Leu Asp Gly
        260                 265                 270

Asp Asp Pro Glu His Ile Gln Trp Ile Phe Gln Lys Ser Val Glu Arg
    275                 280                 285

Ala Ser Gln Tyr Asn Ile Arg Gly Val Thr Tyr Arg Leu Thr Gln Gly
290                 295                 300

Val Val Lys Arg Ile Ile Pro Ala Val Ala Ser Thr Asn Ala Val Ile
305                 310                 315                 320

Ala Ala Val Cys Ala Thr Glu Val Phe Lys Ile Ala Thr Ser Ala Tyr
                325                 330                 335

Ile Pro Leu Asn Asn Tyr Leu Val Phe Asn Asp Val Asp Gly Leu Tyr
                340                 345                 350

Thr Tyr Thr Phe Glu Ala Glu Arg Lys Glu Asn Cys Pro Ala Cys Ser
            355                 360                 365

Gln Leu Pro Gln Asn Ile Gln Phe Ser Pro Ser Ala Lys Leu Gln Glu
        370                 375                 380

Val Leu Asp Tyr Leu Thr Asn Ser Ala Ser Leu Gln Met Lys Ser Pro
385                 390                 395                 400

Ala Ile Thr Ala Thr Leu Glu Gly Lys Asn Arg Thr Leu Tyr Leu Gln
                405                 410                 415

Ser Val Thr Ser Ile Glu Glu Arg Thr Arg Pro Asn Leu Ser Lys Thr
            420                 425                 430

Leu Lys Glu Leu Gly Leu Val Asp Gly Gln Glu Leu Ala Val Ala Asp

```
                     435                 440                 445
Val Thr Thr Pro Gln Thr Val Leu Phe Lys Leu His Phe Thr
        450                 455                 460

<210> SEQ ID NO 75
<211> LENGTH: 449
<212> TYPE: PRT
<213> ORGANISM: Xenopus tropicalis

<400> SEQUENCE: 75

Met Ala Asp Ala Glu Glu Pro Met Ala Val Asp Gly Gly Cys Gly Asp
  1               5                  10                  15

Thr Gly Asp Trp Glu Gly Arg Trp Asn His Val Lys Lys Phe Leu Glu
                 20                  25                  30

Arg Ser Gly Pro Phe Thr His Pro Glu Phe Glu Pro Ser Asn Glu Ser
             35                  40                  45

Leu Gln Phe Leu Leu Glu Thr Cys Lys Ile Leu Val Val Gly Ala Gly
         50                  55                  60

Gly Leu Gly Cys Glu Leu Leu Lys Asn Leu Ala Leu Ser Gly Phe Arg
 65                  70                  75                  80

Gln Ile His Val Ile Asp Met Asp Thr Ile Asp Val Ser Asn Leu Asn
                 85                  90                  95

Arg Gln Phe Leu Phe Arg Pro Lys Asp Val Gly Arg Pro Lys Ala Glu
            100                 105                 110

Val Ala Ala Glu Phe Ile Asn Thr Arg Ile Pro Asp Cys Cys Val Thr
        115                 120                 125

Pro His Phe Thr Lys Ile Gln Asp Phe Asp Glu Thr Phe Tyr Arg Glu
130                 135                 140

Phe His Ile Ile Val Cys Gly Leu Asp Ser Ile Ile Ala Arg Arg Trp
145                 150                 155                 160

Leu Asn Gly Met Leu Met Ser Leu Leu Asn Tyr Glu Asp Gly Val Leu
                165                 170                 175

Gln Gln Ser Thr Val Ile Pro Leu Ile Asp Gly Gly Thr Glu Gly Phe
            180                 185                 190

Lys Gly Asn Ser Arg Val Ile Leu Pro Gly Met Thr Ala Cys Val Glu
        195                 200                 205

Cys Thr Leu Glu Leu Tyr Pro Pro Gln Ile Asn Phe Pro Met Cys Thr
210                 215                 220

Ile Ala Ser Met Pro Arg Leu Pro Glu His Cys Ile Glu Tyr Val Arg
225                 230                 235                 240

Ile Leu Gln Trp Pro Lys Glu Gln Pro Phe Gly Glu Gly Val Gln Leu
                245                 250                 255

Asp Gly Asp Asp Pro Glu His Ile Gln Trp Ile Phe Met Asn Ser Leu
            260                 265                 270

Glu Arg Ala Lys Gln Phe Asn Ile Arg Gly Val Thr Tyr Arg Leu Thr
        275                 280                 285

Gln Gly Val Val Lys Arg Ile Ile Pro Ala Val Ala Ser Thr Asn Ala
290                 295                 300

Val Ile Ala Ala Ala Cys Ala Thr Glu Val Phe Lys Ile Ala Thr Ser
305                 310                 315                 320

Ala Tyr Ile Pro Leu Asn Asn Tyr Leu Val Phe Asn Asp Val Asp Gly
                325                 330                 335

Leu Tyr Tyr Thr Phe Glu Ala Glu Lys Lys Glu Asn Cys Pro Ala
            340                 345                 350
```

```
Cys Ser Gln Leu Pro Gln Asn Ile Gln Phe Pro Ser Ser Ala Lys Leu
        355                 360                 365

Gln Glu Val Leu Asp Tyr Leu Thr Asn Asp Thr Ser Leu Gln Met Lys
    370                 375                 380

Ser Pro Ala Ile Thr Ala Thr Leu Asp Gly Lys Asn Lys Thr Leu Tyr
385                 390                 395                 400

Leu Gln Thr Val Ala Ser Ile Glu Glu Arg Thr Arg Pro Asn Leu Cys
                405                 410                 415

Lys Thr Leu Lys Glu Leu Gly Leu Val Asp Gly Gln Glu Leu Ala Val
            420                 425                 430

Ala Asp Val Thr Thr Pro Gln Thr Val Leu Phe Lys Leu His Phe Thr
                435                 440                 445

Thr

<210> SEQ ID NO 76
<211> LENGTH: 462
<212> TYPE: PRT
<213> ORGANISM: Danio rerio

<400> SEQUENCE: 76

Met Ala Glu Gly Glu Pro Glu Lys Lys Arg Arg Arg Ile Glu Glu
1               5                   10                  15

Leu Asn Glu Lys Met Val Val Asp Gly Gly Ser Gly Asp Arg Ser Glu
            20                  25                  30

Trp Gln Gly Arg Trp Asp His Val Arg Lys Phe Leu Glu Arg Thr Gly
        35                  40                  45

Pro Phe Thr His Pro Asp Phe Glu Ala Ser Thr Glu Ser Leu Gln Phe
    50                  55                  60

Leu Leu Asp Thr Cys Lys Ile Leu Val Ile Gly Ala Gly Gly Leu Gly
65                  70                  75                  80

Cys Glu Leu Leu Lys Asp Leu Ala Leu Ser Gly Phe Arg His Ile His
                85                  90                  95

Val Val Asp Met Asp Thr Ile Asp Val Ser Asn Leu Asn Arg Gln Phe
                100                 105                 110

Leu Phe Arg Pro Lys Asp Val Gly Arg Pro Lys Ala Glu Val Ala Ala
            115                 120                 125

Asp Phe Val Asn Asp Arg Val Pro Gly Cys Ser Val Val Pro His Phe
    130                 135                 140

Lys Lys Ile Gln Asp Leu Asp Glu Thr Phe Tyr Arg Gln Phe His Ile
145                 150                 155                 160

Val Val Cys Gly Leu Asp Ser Val Ile Ala Arg Arg Trp Met Asn Gly
                165                 170                 175

Met Leu Leu Ser Leu Leu Ile Tyr Glu Asp Gly Val Leu Asp Pro Ser
            180                 185                 190

Ser Ile Ile Pro Leu Ile Asp Gly Gly Thr Glu Gly Phe Lys Gly Asn
        195                 200                 205

Ala Arg Val Ile Leu Pro Gly Met Thr Ala Cys Ile Asp Cys Thr Leu
    210                 215                 220

Glu Leu Tyr Pro Pro Gln Ile Asn Phe Pro Met Cys Thr Ile Ala Ser
225                 230                 235                 240

Met Pro Arg Leu Pro Glu His Cys Val Glu Tyr Val Arg Met Leu Leu
                245                 250                 255

Trp Pro Lys Glu Lys Pro Phe Gly Asp Gly Val Val Leu Asp Gly Asp
            260                 265                 270
```

Asp Pro Lys His Ile Gln Trp Val Tyr Gln Lys Ser Leu Glu Arg Ala
        275                 280                 285

Ala Glu Phe Asn Ile Thr Gly Val Thr Tyr Arg Leu Thr Gln Gly Val
    290                 295                 300

Val Lys Arg Ile Ile Pro Ala Val Ala Ser Thr Asn Ala Val Ile Ala
305                 310                 315                 320

Ala Ala Cys Ala Thr Glu Val Phe Lys Ile Ala Thr Ser Ala Tyr Val
                325                 330                 335

Pro Leu Asn Asn Tyr Leu Val Phe Asn Asp Val Asp Gly Leu Tyr Thr
            340                 345                 350

Tyr Thr Phe Glu Ala Glu Arg Lys Glu Asn Cys Ser Ala Cys Ser Gln
        355                 360                 365

Val Pro Gln Asp Met Gln Phe Thr Pro Ser Ala Lys Leu Gln Glu Val
    370                 375                 380

Leu Asp Tyr Leu Thr Glu Asn Ala Ser Leu Gln Met Lys Ser Pro Ala
385                 390                 395                 400

Ile Thr Thr Thr Leu Asp Gly Lys Asn Lys Thr Leu Tyr Leu Gln Thr
                405                 410                 415

Val Ala Ser Ile Glu Glu Arg Thr Arg Pro Asn Leu Ser Lys Thr Leu
            420                 425                 430

Lys Glu Leu Gly Leu Val Asp Gly Gln Glu Leu Ala Val Ala Asp Val
        435                 440                 445

Thr Thr Pro Gln Thr Val Leu Phe Lys Leu Lys Phe Ile Ser
    450                 455                 460

<210> SEQ ID NO 77
<211> LENGTH: 444
<212> TYPE: PRT
<213> ORGANISM: Schizosaccharomyces pombe

<400> SEQUENCE: 77

Met Pro Ser Ser Asp Val Cys Lys Ala Gly Ser His Arg His Ser Gly
1               5                   10                  15

Trp Ile Gln Ser Leu Lys Lys Pro Gly Pro Phe Asn Leu Asp Ala Pro
            20                  25                  30

Glu Asn Pro Glu Glu Thr Leu Lys Ser Ala Phe Ser Ser Lys Ile Leu
        35                  40                  45

Ile Ile Gly Ala Gly Gly Leu Gly Cys Glu Ile Leu Lys Asp Leu Ala
    50                  55                  60

Leu Ser Gly Phe Arg Asp Leu Ser Val Ile Asp Met Asp Thr Ile Asp
65                  70                  75                  80

Ile Thr Asn Leu Asn Arg Gln Phe Leu Phe Asn Glu Ser Asn Ile Asp
                85                  90                  95

Glu Pro Lys Ala Asn Val Ala Ala Ser Met Ile Met Lys Arg Ile Pro
            100                 105                 110

Ser Thr Val Val Thr Pro Phe Tyr Gly Lys Ile Gln Asp Lys Thr Ile
        115                 120                 125

Glu Phe Tyr Lys Glu Phe Lys Leu Ile Ile Cys Gly Leu Asp Ser Val
    130                 135                 140

Glu Ala Arg Arg Trp Ile Asn Ser Thr Leu Val Ala Ile Ala Lys Thr
145                 150                 155                 160

Gly Asp Leu Ile Pro Leu Val Asp Gly Gly Ser Glu Gly Leu Lys Gly
                165                 170                 175

Gln Ala Arg Val Ile Ile Pro Thr Ile Thr Ser Cys Tyr Glu Cys Ser
            180                 185                 190

```
Leu Asp Met Leu Thr Pro Lys Ile Ser Tyr Pro Ile Cys Thr Leu Ala
        195                 200                 205

Asn Thr Pro Arg Leu Pro Glu His Cys Val Glu Trp Ala Tyr Leu Leu
        210                 215                 220

Glu Trp Pro Arg Val Phe Leu Asn Ala Ser Val Asp Ser Phe Ser Lys
225                 230                 235                 240

Gln Glu Val Phe Glu Pro Leu Asp Gly Lys Asn Ser Asn Phe Glu Pro
                245                 250                 255

Asp Asn Ile Arg His Ile Asp Trp Leu Val Lys Arg Ser Ile Glu Arg
                260                 265                 270

Ala Asn Lys Phe Gln Ile Pro Ser Ser Ile Asn Arg Phe Val
        275                 280                 285

Gln Gly Ile Val Lys Arg Ile Ile Pro Ala Val Ala Ser Thr Asn Ala
        290                 295                 300

Ile Ile Ala Ala Ser Cys Cys Asn Glu Ala Leu Lys Ile Leu Thr Glu
305                 310                 315                 320

Ser Asn Pro Phe Leu Asp Asn Tyr Met Met Tyr Val Gly Glu Asp Gly
                325                 330                 335

Ala Tyr Thr Tyr Thr Phe Asn Leu Glu Lys Arg Ser Asp Cys Pro Val
        340                 345                 350

Cys Gly Val Leu Ser Glu Val Tyr Asp Ile Ser Ala Ser Ser Thr Val
        355                 360                 365

Thr Leu Lys Asp Ile Leu Asn His Tyr Ser Lys Ser Tyr Asn Leu Gln
        370                 375                 380

Asn Pro Ser Val Ser Thr Ala Ala Gly Thr Pro Leu Tyr Leu Ala Ser
385                 390                 395                 400

Pro Pro Ala Leu Gln Val Ala Thr Ser Lys Asn Leu Ser Gln Pro Ile
                405                 410                 415

Leu Ser Ile Thr Ser Val Asp Val Asn Leu Val Ile Thr Asp Lys Asn
                420                 425                 430

Leu Ser Thr Ser Leu Ser Val Gln Leu Arg Glu Cys
        435                 440
```

<210> SEQ ID NO 78
<211> LENGTH: 299
<212> TYPE: PRT
<213> ORGANISM: Saccharomyces cerevisiae

<400> SEQUENCE: 78

```
Met Asp Cys Lys Ile Leu Val Leu Gly Ala Gly Gly Leu Gly Cys Glu
  1               5                  10                  15

Ile Leu Lys Asn Leu Thr Met Leu Ser Phe Val Lys Gln Val His Ile
            20                  25                  30

Val Asp Ile Asp Thr Ile Glu Leu Thr Asn Leu Asn Arg Gln Phe Leu
        35                  40                  45

Phe Cys Asp Lys Asp Ile Gly Lys Pro Lys Ala Gln Val Ala Ala Gln
    50                  55                  60

Tyr Val Asn Thr Arg Phe Pro Gln Leu Glu Val Val Ala His Val Gln
65                  70                  75                  80

Asp Leu Thr Thr Leu Pro Pro Ser Phe Tyr Lys Asp Phe Gln Phe Ile
                85                  90                  95

Ile Ser Gly Leu Asp Ala Ile Glu Pro Arg Arg Phe Ile Asn Glu Thr
            100                 105                 110

Leu Val Lys Leu Thr Leu Glu Ser Asn Tyr Glu Ile Cys Ile Pro Phe
```

```
                115                 120                 125
Ile Asp Gly Gly Thr Glu Gly Leu Lys Gly His Val Lys Thr Ile Ile
130                 135                 140

Pro Gly Ile Thr Ala Cys Trp Glu Cys Ser Ile Asp Thr Leu Pro Ser
145                 150                 155                 160

Gln Gln Asp Thr Val Pro Met Cys Thr Ile Ala Asn Asn Pro Arg Cys
                165                 170                 175

Ile Glu His Val Val Glu Tyr Val Ser Thr Ile Gln Tyr Pro Asp Leu
                180                 185                 190

Asn Ile Glu Ser Thr Ala Asp Met Glu Phe Leu Leu Glu Lys Cys Cys
                195                 200                 205

Glu Arg Ala Ala Gln Phe Ser Ile Ser Thr Glu Lys Leu Ser Thr Ser
210                 215                 220

Phe Ile Leu Gly Ile Ile Lys Ser Ile Ile Pro Ser Val Ser Thr Thr
225                 230                 235                 240

Asn Ala Met Val Ala Thr Cys Cys Thr Gln Met Val Lys Ile Tyr
                245                 250                 255

Asn Asp Leu Ile Asp Leu Glu Asn Gly Asn Asn Phe Thr Leu Ile Asn
                260                 265                 270

Cys Ser Glu Gly Cys Phe Met Tyr Ser Phe Lys Phe Glu Arg Leu Pro
                275                 280                 285

Asp Cys Thr Val Cys Ser Asn Ser Asn Ser Asn
                290                 295

<210> SEQ ID NO 79
<211> LENGTH: 776
<212> TYPE: PRT
<213> ORGANISM: Homo sapiens

<400> SEQUENCE: 79

Met Ser Ser Thr Arg Ser Gln Asn Pro His Gly Leu Lys Gln Ile Gly
1               5                   10                  15

Leu Asp Gln Ile Trp Asp Asp Leu Arg Ala Gly Ile Gln Gln Val Tyr
                20                  25                  30

Thr Arg Gln Ser Met Ala Lys Ser Arg Tyr Met Glu Leu Tyr Thr His
                35                  40                  45

Val Tyr Asn Tyr Cys Thr Ser Val His Gln Ser Asn Gln Ala Arg Gly
50                  55                  60

Ala Gly Val Pro Pro Ser Lys Ser Lys Lys Gly Gln Thr Pro Gly Gly
65                  70                  75                  80

Ala Gln Phe Val Gly Leu Glu Leu Tyr Lys Arg Leu Lys Glu Phe Leu
                85                  90                  95

Lys Asn Tyr Leu Thr Asn Leu Leu Lys Asp Gly Glu Asp Leu Met Asp
                100                 105                 110

Glu Ser Val Leu Lys Phe Tyr Thr Gln Gln Trp Glu Asp Tyr Arg Phe
                115                 120                 125

Ser Ser Lys Val Leu Asn Gly Ile Cys Ala Tyr Leu Asn Arg His Trp
                130                 135                 140

Val Arg Arg Glu Cys Asp Glu Gly Arg Lys Gly Ile Tyr Glu Ile Tyr
145                 150                 155                 160

Ser Leu Ala Leu Val Thr Trp Arg Asp Cys Leu Phe Arg Pro Leu Asn
                165                 170                 175

Lys Gln Val Thr Asn Ala Val Leu Lys Leu Ile Glu Lys Glu Arg Asn
                180                 185                 190
```

-continued

```
Gly Glu Thr Ile Asn Thr Arg Leu Ile Ser Gly Val Gln Ser Tyr
            195                 200                 205
Val Glu Leu Gly Leu Asn Glu Asp Asp Ala Phe Ala Lys Gly Pro Thr
210                 215                 220
Leu Thr Val Tyr Lys Glu Ser Phe Glu Ser Gln Phe Leu Ala Asp Thr
225                 230                 235                 240
Glu Arg Phe Tyr Thr Arg Glu Ser Thr Glu Phe Leu Gln Gln Asn Pro
                245                 250                 255
Val Thr Glu Tyr Met Lys Lys Ala Glu Ala Arg Leu Leu Glu Gln
            260                 265                 270
Arg Arg Val Gln Val Tyr Leu His Glu Ser Thr Gln Asp Glu Leu Ala
            275                 280                 285
Arg Lys Cys Glu Gln Val Leu Ile Glu Lys His Leu Glu Ile Phe His
            290                 295                 300
Thr Glu Phe Gln Asn Leu Leu Asp Ala Asp Lys Asn Glu Asp Leu Gly
305                 310                 315                 320
Arg Met Tyr Asn Leu Val Ser Arg Ile Gln Asp Gly Leu Gly Glu Leu
                325                 330                 335
Lys Lys Leu Leu Glu Thr His Ile His Asn Gln Gly Leu Ala Ala Ile
            340                 345                 350
Glu Lys Cys Gly Glu Ala Ala Leu Asn Asp Pro Lys Met Tyr Val Gln
            355                 360                 365
Thr Val Leu Asp Val His Lys Lys Tyr Asn Ala Leu Val Met Ser Ala
            370                 375                 380
Phe Asn Asn Asp Ala Gly Phe Val Ala Ala Leu Asp Lys Ala Cys Gly
385                 390                 395                 400
Arg Phe Ile Asn Asn Ala Val Thr Lys Met Ala Gln Ser Ser Ser
                405                 410                 415
Lys Ser Pro Glu Leu Leu Ala Arg Tyr Cys Asp Ser Leu Leu Lys Lys
            420                 425                 430
Ser Ser Lys Asn Pro Glu Glu Ala Glu Leu Asp Thr Leu Asn Gln
            435                 440                 445
Val Met Val Val Phe Lys Tyr Ile Glu Asp Lys Asp Val Phe Gln Lys
450                 455                 460
Phe Tyr Ala Lys Met Leu Ala Lys Arg Leu Val His Gln Asn Ser Ala
465                 470                 475                 480
Ser Asp Asp Ala Glu Ala Ser Met Ile Ser Lys Leu Lys Gln Ala Cys
                485                 490                 495
Gly Phe Glu Tyr Thr Ser Lys Leu Gln Arg Met Phe Gln Asp Ile Gly
            500                 505                 510
Val Ser Lys Asp Leu Asn Glu Gln Phe Lys Lys His Leu Thr Asn Ser
            515                 520                 525
Glu Pro Leu Asp Leu Asp Phe Ser Ile Gln Val Leu Ser Ser Gly Ser
            530                 535                 540
Trp Pro Phe Gln Gln Ser Cys Thr Phe Ala Leu Pro Ser Glu Leu Glu
545                 550                 555                 560
Arg Ser Tyr Gln Arg Phe Thr Ala Phe Tyr Ala Ser Arg His Ser Gly
                565                 570                 575
Arg Lys Leu Thr Trp Leu Tyr Gln Leu Ser Lys Gly Glu Leu Val Thr
            580                 585                 590
Asn Cys Phe Lys Asn Arg Tyr Thr Leu Gln Ala Ser Thr Phe Gln Met
            595                 600                 605
Ala Ile Leu Leu Gln Tyr Asn Thr Glu Asp Ala Tyr Thr Val Gln Gln
```

```
                  610               615               620
Leu Thr Asp Ser Thr Gln Ile Lys Met Asp Ile Leu Ala Gln Val Leu
625                 630                 635                 640

Gln Ile Leu Leu Lys Ser Lys Leu Leu Val Leu Glu Asp Glu Asn Ala
                    645                 650                 655

Asn Val Asp Glu Val Glu Leu Lys Pro Asp Thr Leu Ile Lys Leu Tyr
                660                 665                 670

Leu Gly Tyr Lys Asn Lys Lys Leu Arg Val Asn Ile Asn Val Pro Met
            675                 680                 685

Lys Thr Glu Gln Lys Gln Glu Gln Thr Thr His Lys Asn Ile Glu
        690                 695                 700

Glu Asp Arg Lys Leu Leu Ile Gln Ala Ala Ile Val Arg Ile Met Lys
705                 710                 715                 720

Met Arg Lys Val Leu Lys His Gln Leu Leu Gly Glu Val Leu Thr
                    725                 730                 735

Gln Leu Ser Ser Arg Phe Lys Pro Arg Val Pro Val Ile Lys Lys Cys
                740                 745                 750

Ile Asp Ile Leu Ile Glu Lys Glu Tyr Leu Glu Arg Val Asp Gly Glu
            755                 760                 765

Lys Asp Thr Tyr Ser Tyr Leu Ala
        770                 775

<210> SEQ ID NO 80
<211> LENGTH: 745
<212> TYPE: PRT
<213> ORGANISM: Homo sapiens

<400> SEQUENCE: 80

Met Ser Leu Lys Pro Arg Val Val Asp Phe Asp Glu Thr Trp Asn Lys
1               5                   10                  15

Leu Leu Thr Thr Ile Lys Ala Val Val Met Leu Glu Tyr Val Glu Arg
                20                  25                  30

Ala Thr Trp Asn Asp Arg Phe Ser Asp Ile Tyr Ala Leu Cys Val Ala
            35                  40                  45

Tyr Pro Glu Pro Leu Gly Glu Arg Leu Tyr Thr Glu Thr Lys Ile Phe
        50                  55                  60

Leu Glu Asn His Val Arg His Leu His Lys Arg Val Leu Glu Ser Glu
65                  70                  75                  80

Glu Gln Val Leu Val Met Tyr His Arg Tyr Trp Glu Tyr Ser Lys
                85                  90                  95

Gly Ala Asp Tyr Met Asp Cys Leu Tyr Arg Tyr Leu Asn Thr Gln Phe
            100                 105                 110

Ile Lys Lys Asn Lys Leu Thr Glu Ala Asp Leu Gln Tyr Gly Tyr Gly
        115                 120                 125

Gly Val Asp Met Asn Glu Pro Leu Met Glu Ile Gly Glu Leu Ala Leu
    130                 135                 140

Asp Met Trp Arg Lys Leu Met Val Glu Pro Leu Gln Ala Ile Leu Ile
145                 150                 155                 160

Arg Met Leu Leu Arg Glu Ile Lys Asn Asp Arg Gly Gly Glu Asp Pro
                165                 170                 175

Asn Gln Lys Val Ile His Gly Val Ile Asn Ser Phe Val His Val Glu
            180                 185                 190

Gln Tyr Lys Lys Lys Phe Pro Leu Lys Phe Tyr Gln Glu Ile Phe Glu
        195                 200                 205
```

```
Ser Pro Phe Leu Thr Glu Thr Gly Glu Tyr Tyr Lys Gln Glu Ala Ser
    210                 215                 220

Asn Leu Leu Gln Glu Ser Asn Cys Ser Gln Tyr Met Glu Lys Val Leu
225                 230                 235                 240

Gly Arg Leu Lys Asp Glu Glu Ile Arg Cys Arg Lys Tyr Leu His Pro
                245                 250                 255

Ser Ser Tyr Thr Lys Val Ile His Glu Cys Gln Gln Arg Met Val Ala
            260                 265                 270

Asp His Leu Gln Phe Leu His Ala Glu Cys His Asn Ile Ile Arg Gln
        275                 280                 285

Glu Lys Lys Asn Asp Met Ala Asn Met Tyr Val Leu Leu Arg Ala Val
290                 295                 300

Ser Thr Gly Leu Pro His Met Ile Gln Glu Leu Gln Asn His Ile His
305                 310                 315                 320

Asp Glu Gly Leu Arg Ala Thr Ser Asn Leu Thr Gln Glu Asn Met Pro
                325                 330                 335

Thr Leu Phe Val Glu Ser Val Leu Glu Val His Gly Lys Phe Val Gln
            340                 345                 350

Leu Ile Asn Thr Val Leu Asn Gly Asp Gln His Phe Met Ser Ala Leu
        355                 360                 365

Asp Lys Ala Leu Thr Ser Val Val Asn Tyr Arg Glu Pro Lys Ser Val
370                 375                 380

Cys Lys Ala Pro Glu Leu Leu Ala Lys Tyr Cys Asp Asn Leu Leu Lys
385                 390                 395                 400

Lys Ser Ala Lys Gly Met Thr Glu Asn Glu Val Glu Asp Arg Leu Thr
                405                 410                 415

Ser Phe Ile Thr Val Phe Lys Tyr Ile Asp Asp Lys Asp Val Phe Gln
            420                 425                 430

Lys Phe Tyr Ala Arg Met Leu Ala Lys Arg Leu Ile His Gly Leu Ser
        435                 440                 445

Met Ser Met Asp Ser Glu Glu Ala Met Ile Asn Lys Leu Lys Gln Ala
450                 455                 460

Cys Gly Tyr Glu Phe Thr Ser Lys Leu His Arg Met Tyr Thr Asp Met
465                 470                 475                 480

Ser Val Ser Ala Asp Leu Asn Asn Lys Phe Asn Asn Phe Ile Lys Asn
                485                 490                 495

Gln Asp Thr Val Ile Asp Leu Gly Ile Ser Phe Gln Ile Tyr Val Leu
            500                 505                 510

Gln Ala Gly Ala Trp Pro Leu Thr Gln Ala Pro Ser Ser Thr Phe Ala
        515                 520                 525

Ile Pro Gln Glu Leu Glu Lys Ser Val Gln Met Phe Glu Leu Phe Tyr
530                 535                 540

Ser Gln His Phe Ser Gly Arg Lys Leu Thr Trp Leu His Tyr Leu Cys
545                 550                 555                 560

Thr Gly Glu Val Lys Met Asn Tyr Leu Gly Lys Pro Tyr Val Ala Met
                565                 570                 575

Val Thr Thr Tyr Gln Met Ala Val Leu Leu Ala Phe Asn Asn Ser Glu
            580                 585                 590

Thr Val Ser Tyr Lys Glu Leu Gln Asp Ser Thr Gln Met Asn Glu Lys
        595                 600                 605

Glu Leu Thr Lys Thr Ile Lys Ser Leu Leu Asp Val Lys Met Ile Asn
610                 615                 620

His Asp Ser Glu Lys Glu Asp Ile Asp Ala Glu Ser Ser Phe Ser Leu
```

```
                625                 630                 635                 640
Asn Met Asn Phe Ser Ser Lys Arg Thr Lys Phe Lys Ile Thr Thr Ser
                    645                 650                 655
Met Gln Lys Asp Thr Pro Gln Glu Met Glu Gln Thr Arg Ser Ala Val
                660                 665                 670
Asp Glu Asp Arg Lys Met Tyr Leu Gln Ala Ala Ile Val Arg Ile Met
            675                 680                 685
Lys Ala Arg Lys Val Leu Arg His Asn Ala Leu Ile Gln Glu Val Ile
        690                 695                 700
Ser Gln Ser Arg Ala Arg Phe Asn Pro Ser Ile Ser Met Ile Lys Lys
705                 710                 715                 720
Cys Ile Glu Val Leu Ile Asp Lys Gln Tyr Ile Glu Arg Ser Gln Ala
                    725                 730                 735
Ser Ala Asp Glu Tyr Ser Tyr Val Ala
                740                 745
```

<210> SEQ ID NO 81
<211> LENGTH: 768
<212> TYPE: PRT
<213> ORGANISM: Homo sapiens

<400> SEQUENCE: 81

```
Met Ser Asn Leu Ser Lys Gly Thr Gly Ser Arg Lys Asp Thr Lys Met
1               5                   10                  15
Arg Ile Arg Ala Phe Pro Met Thr Met Asp Glu Lys Tyr Val Asn Ser
            20                  25                  30
Ile Trp Asp Leu Leu Lys Asn Ala Ile Gln Glu Ile Gln Arg Lys Asn
        35                  40                  45
Asn Ser Gly Leu Ser Phe Glu Glu Leu Tyr Arg Asn Ala Tyr Thr Met
    50                  55                  60
Val Leu His Lys His Gly Glu Lys Leu Tyr Thr Gly Leu Arg Glu Val
65                  70                  75                  80
Val Thr Glu His Leu Ile Asn Lys Val Arg Glu Asp Val Leu Asn Ser
                85                  90                  95
Leu Asn Asn Asn Phe Leu Gln Thr Leu Asn Gln Ala Trp Asn Asp His
            100                 105                 110
Gln Thr Ala Met Val Met Ile Arg Asp Ile Leu Met Tyr Met Asp Arg
        115                 120                 125
Val Tyr Val Gln Gln Asn Asn Val Glu Asn Val Tyr Asn Leu Gly Leu
    130                 135                 140
Ile Ile Phe Arg Asp Gln Val Val Arg Tyr Gly Cys Ile Arg Asp His
145                 150                 155                 160
Leu Arg Gln Thr Leu Leu Asp Met Ile Ala Arg Glu Arg Lys Gly Glu
                165                 170                 175
Val Val Asp Arg Gly Ala Ile Arg Asn Ala Cys Gln Met Leu Met Ile
            180                 185                 190
Leu Gly Leu Glu Gly Arg Ser Val Tyr Glu Glu Asp Phe Glu Ala Pro
        195                 200                 205
Phe Leu Glu Met Ser Ala Glu Phe Phe Gln Met Glu Ser Gln Lys Phe
    210                 215                 220
Leu Ala Glu Asn Ser Ala Ser Val Tyr Ile Lys Lys Val Glu Ala Arg
225                 230                 235                 240
Ile Asn Glu Glu Ile Glu Arg Val Met His Cys Leu Asp Lys Ser Thr
                245                 250                 255
```

-continued

Glu Glu Pro Ile Val Lys Val Val Glu Arg Glu Leu Ile Ser Lys His
            260                 265                 270

Met Lys Thr Ile Val Glu Met Glu Asn Ser Gly Leu Val His Met Leu
        275                 280                 285

Lys Asn Gly Lys Thr Glu Asp Leu Gly Cys Met Tyr Lys Leu Phe Ser
    290                 295                 300

Arg Val Pro Asn Gly Leu Lys Thr Met Cys Glu Cys Met Ser Ser Tyr
305                 310                 315                 320

Leu Arg Glu Gln Gly Lys Ala Leu Val Ser Glu Gly Glu Gly Lys
                325                 330                 335

Asn Pro Val Asp Tyr Ile Gln Gly Leu Leu Asp Leu Lys Ser Arg Phe
            340                 345                 350

Asp Arg Phe Leu Leu Glu Ser Phe Asn Asn Asp Arg Leu Phe Lys Gln
            355                 360                 365

Thr Ile Ala Gly Asp Phe Glu Tyr Phe Leu Asn Leu Asn Ser Arg Ser
        370                 375                 380

Pro Glu Tyr Leu Ser Leu Phe Ile Asp Asp Lys Leu Lys Lys Gly Val
385                 390                 395                 400

Lys Gly Leu Thr Glu Gln Glu Val Glu Thr Ile Leu Asp Lys Ala Met
            405                 410                 415

Val Leu Phe Arg Phe Met Gln Glu Lys Asp Val Phe Glu Arg Tyr Tyr
            420                 425                 430

Lys Gln His Leu Ala Arg Arg Leu Leu Thr Asn Lys Ser Val Ser Asp
            435                 440                 445

Asp Ser Glu Lys Asn Met Ile Ser Lys Leu Lys Thr Glu Cys Gly Cys
450                 455                 460

Gln Phe Thr Ser Lys Leu Glu Gly Met Phe Arg Asp Met Ser Ile Ser
465                 470                 475                 480

Asn Thr Thr Met Asp Glu Phe Arg Gln His Leu Gln Ala Thr Gly Val
            485                 490                 495

Ser Leu Gly Gly Val Asp Leu Thr Val Arg Val Leu Thr Thr Gly Tyr
            500                 505                 510

Trp Pro Thr Gln Ser Ala Thr Pro Lys Cys Asn Ile Pro Pro Ala Pro
        515                 520                 525

Arg His Ala Phe Glu Ile Phe Arg Arg Phe Tyr Leu Ala Lys His Ser
            530                 535                 540

Gly Arg Gln Leu Thr Leu Gln His His Met Gly Ser Ala Asp Leu Asn
545                 550                 555                 560

Ala Thr Phe Tyr Gly Pro Val Lys Lys Glu Asp Gly Ser Glu Val Gly
            565                 570                 575

Val Gly Gly Ala Gln Val Thr Gly Ser Asn Thr Arg Lys His Ile Leu
        580                 585                 590

Gln Val Ser Thr Phe Gln Met Thr Ile Leu Met Leu Phe Asn Asn Arg
    595                 600                 605

Glu Lys Tyr Thr Phe Glu Glu Ile Gln Gln Glu Thr Asp Ile Pro Glu
    610                 615                 620

Arg Glu Leu Val Arg Ala Leu Gln Ser Leu Ala Cys Gly Lys Pro Thr
625                 630                 635                 640

Gln Arg Val Leu Thr Lys Glu Pro Lys Ser Lys Glu Ile Glu Asn Gly
            645                 650                 655

His Ile Phe Thr Val Asn Asp Gln Phe Thr Ser Lys Leu His Arg Val
            660                 665                 670

Lys Ile Gln Thr Val Ala Ala Lys Gln Gly Glu Ser Asp Pro Glu Arg

```
            675                 680                 685
Lys Glu Thr Arg Gln Lys Val Asp Asp Arg Lys His Glu Ile Glu
        690                 695                 700

Ala Ala Ile Val Arg Ile Met Lys Ser Arg Lys Lys Met Gln His Asn
705                 710                 715                 720

Val Leu Val Ala Glu Val Thr Gln Gln Leu Lys Ala Arg Phe Leu Pro
                725                 730                 735

Ser Pro Val Val Ile Lys Lys Arg Ile Glu Gly Leu Ile Glu Arg Glu
            740                 745                 750

Tyr Leu Ala Arg Thr Pro Glu Asp Arg Lys Val Tyr Thr Tyr Val Ala
            755                 760                 765

<210> SEQ ID NO 82
<211> LENGTH: 759
<212> TYPE: PRT
<213> ORGANISM: Homo sapiens

<400> SEQUENCE: 82

Met Ala Asp Glu Ala Pro Arg Lys Gly Ser Phe Ser Ala Leu Val Gly
 1               5                  10                  15

Arg Thr Asn Gly Leu Thr Lys Pro Ala Ala Leu Ala Ala Ala Pro Ala
            20                  25                  30

Lys Pro Gly Gly Ala Gly Gly Ser Lys Lys Leu Val Ile Lys Asn Phe
        35                  40                  45

Arg Asp Arg Pro Arg Leu Pro Asp Asn Tyr Thr Gln Asp Thr Trp Arg
    50                  55                  60

Lys Leu His Glu Ala Val Arg Ala Val Gln Ser Ser Thr Ser Ile Arg
65                  70                  75                  80

Tyr Asn Leu Glu Glu Leu Tyr Gln Ala Val Glu Asn Leu Cys Ser His
                85                  90                  95

Lys Val Ser Pro Met Leu Tyr Lys Gln Leu Arg Gln Ala Cys Glu Asp
            100                 105                 110

His Val Gln Ala Gln Ile Leu Pro Phe Arg Glu Asp Ser Leu Asp Ser
        115                 120                 125

Val Leu Phe Leu Lys Lys Ile Asn Thr Cys Trp Gln Asp His Cys Arg
    130                 135                 140

Gln Met Ile Met Ile Arg Ser Ile Phe Leu Phe Leu Asp Arg Thr Tyr
145                 150                 155                 160

Val Leu Gln Asn Ser Thr Leu Pro Ser Ile Trp Asp Met Gly Leu Glu
                165                 170                 175

Leu Phe Arg Thr His Ile Ile Ser Asp Lys Met Val Gln Ser Lys Thr
            180                 185                 190

Ile Asp Gly Ile Leu Leu Ile Glu Arg Glu Arg Ser Gly Glu Ala
        195                 200                 205

Val Asp Arg Ser Leu Leu Arg Ser Leu Leu Gly Met Leu Ser Asp Leu
    210                 215                 220

Gln Val Tyr Lys Asp Ser Phe Glu Leu Lys Phe Leu Glu Glu Thr Asn
225                 230                 235                 240

Cys Leu Tyr Ala Ala Glu Gly Gln Arg Leu Met Gln Glu Arg Glu Val
                245                 250                 255

Pro Glu Tyr Leu Asn His Val Ser Lys Arg Leu Glu Glu Glu Gly Asp
            260                 265                 270

Arg Val Ile Thr Tyr Leu Asp His Ser Thr Gln Lys Pro Leu Ile Ala
        275                 280                 285
```

```
Cys Val Glu Lys Gln Leu Leu Gly Glu His Leu Thr Ala Ile Leu Gln
    290                 295                 300
Lys Gly Leu Asp His Leu Leu Asp Glu Asn Arg Val Pro Asp Leu Ala
305                 310                 315                 320
Gln Met Tyr Gln Leu Phe Ser Arg Val Arg Gly Gln Gln Ala Leu
                325                 330                 335
Leu Gln His Trp Ser Glu Tyr Ile Lys Thr Phe Gly Thr Ala Ile Val
            340                 345                 350
Ile Asn Pro Glu Lys Asp Lys Asp Met Val Gln Asp Leu Leu Asp Phe
        355                 360                 365
Lys Asp Lys Val Asp His Val Ile Glu Val Cys Phe Gln Lys Asn Glu
370                 375                 380
Arg Phe Val Asn Leu Met Lys Glu Ser Phe Glu Thr Phe Ile Asn Lys
385                 390                 395                 400
Arg Pro Asn Lys Pro Ala Glu Leu Ile Ala Lys His Val Asp Ser Lys
                405                 410                 415
Leu Arg Ala Gly Asn Lys Glu Ala Thr Asp Glu Glu Leu Glu Arg Thr
            420                 425                 430
Leu Asp Lys Ile Met Ile Leu Phe Arg Phe Ile His Gly Lys Asp Val
        435                 440                 445
Phe Glu Ala Phe Tyr Lys Lys Asp Leu Ala Lys Arg Leu Leu Val Gly
450                 455                 460
Lys Ser Ala Ser Val Asp Ala Glu Lys Ser Met Leu Ser Lys Leu Lys
465                 470                 475                 480
His Glu Cys Gly Ala Ala Phe Thr Ser Lys Leu Glu Gly Met Phe Lys
                485                 490                 495
Asp Met Glu Leu Ser Lys Asp Ile Met Val His Phe Lys Gln His Met
            500                 505                 510
Gln Asn Gln Ser Asp Ser Gly Pro Ile Asp Leu Thr Val Asn Ile Leu
        515                 520                 525
Thr Met Gly Tyr Trp Pro Thr Tyr Thr Pro Met Glu Val His Leu Thr
530                 535                 540
Pro Glu Met Ile Lys Leu Gln Glu Val Phe Lys Ala Phe Tyr Leu Gly
545                 550                 555                 560
Lys His Ser Gly Arg Lys Leu Gln Trp Gln Thr Thr Leu Gly His Ala
                565                 570                 575
Val Leu Lys Ala Glu Phe Lys Glu Gly Lys Lys Glu Phe Gln Val Ser
            580                 585                 590
Leu Phe Gln Thr Leu Val Leu Leu Met Phe Asn Glu Gly Asp Gly Phe
        595                 600                 605
Ser Phe Glu Glu Ile Lys Met Ala Thr Gly Ile Glu Asp Ser Glu Leu
610                 615                 620
Arg Arg Thr Leu Gln Ser Leu Ala Cys Gly Lys Ala Arg Val Leu Ile
625                 630                 635                 640
Lys Ser Pro Lys Gly Lys Glu Val Glu Asp Gly Asp Lys Phe Ile Phe
                645                 650                 655
Asn Gly Glu Phe Lys His Lys Leu Phe Arg Ile Lys Ile Asn Gln Ile
            660                 665                 670
Gln Met Lys Glu Thr Val Glu Glu Val Ser Thr Thr Glu Arg Val
        675                 680                 685
Phe Gln Asp Arg Gln Tyr Gln Ile Asp Ala Ala Ile Val Arg Ile Met
690                 695                 700
Lys Met Arg Lys Thr Leu Gly His Asn Leu Leu Val Ser Glu Leu Tyr
```

-continued

```
            705                 710                 715                 720
Asn Gln Leu Lys Phe Pro Val Lys Pro Gly Asp Leu Lys Lys Arg Ile
                    725                 730                 735

Glu Ser Leu Ile Asp Arg Asp Tyr Met Glu Arg Asp Lys Asp Asn Pro
            740                 745                 750

Asn Gln Tyr His Tyr Val Ala
            755

<210> SEQ ID NO 83
<211> LENGTH: 913
<212> TYPE: PRT
<213> ORGANISM: Homo sapiens

<400> SEQUENCE: 83

Met Met Ser Gln Ser Ser Gly Ser Gly Asp Gly Asn Asp Asp Glu Ala
 1               5                  10                  15

Thr Thr Ser Lys Asp Gly Gly Phe Ser Ser Pro Ser Pro Ser Ala Ala
                20                  25                  30

Ala Ala Ala Gln Glu Val Arg Ser Ala Thr Asp Gly Asn Thr Ser Thr
            35                  40                  45

Thr Pro Pro Thr Ser Ala Lys Lys Arg Lys Leu Asn Ser Ser Ser Ser
         50                  55                  60

Ser Ser Ser Asn Ser Ser Asn Glu Arg Glu Asp Phe Asp Ser Thr Ser
 65                  70                  75                  80

Ser Ser Ser Ser Thr Pro Pro Leu Gln Pro Arg Asp Ser Ala Ser Pro
                 85                  90                  95

Ser Thr Ser Ser Phe Cys Leu Gly Val Ser Val Ala Ala Ser Ser His
                100                 105                 110

Val Pro Ile Gln Lys Lys Leu Arg Phe Glu Asp Thr Leu Glu Phe Val
            115                 120                 125

Gly Phe Asp Ala Lys Met Ala Glu Glu Ser Ser Ser Ser Ser Ser Ser
        130                 135                 140

Ser Ser Pro Thr Ala Ala Thr Ser Gln Gln Gln Gln Leu Lys Asn Lys
145                 150                 155                 160

Ser Ile Leu Ile Ser Ser Val Ala Ser Val His His Ala Asn Gly Leu
                165                 170                 175

Ala Lys Ser Ser Thr Thr Val Ser Ser Phe Ala Asn Ser Lys Pro Gly
            180                 185                 190

Ser Ala Lys Lys Leu Val Ile Lys Asn Phe Lys Asp Lys Pro Lys Leu
        195                 200                 205

Pro Glu Asn Tyr Thr Asp Glu Thr Trp Gln Lys Leu Lys Glu Ala Val
    210                 215                 220

Glu Ala Ile Gln Asn Ser Thr Ser Ile Lys Tyr Asn Leu Glu Glu Leu
225                 230                 235                 240

Tyr Gln Ala Val Glu Asn Leu Cys Ser Tyr Lys Ile Ser Ala Asn Leu
                245                 250                 255

Tyr Lys Gln Leu Arg Gln Ile Cys Glu Asp His Ile Lys Ala Gln Ile
            260                 265                 270

His Gln Phe Arg Glu Asp Ser Leu Asp Ser Val Leu Phe Leu Lys Lys
        275                 280                 285

Ile Asp Arg Cys Trp Gln Asn His Cys Arg Gln Met Ile Met Ile Arg
    290                 295                 300

Ser Ile Phe Leu Phe Leu Asp Arg Thr Tyr Val Leu Gln Asn Ser Met
305                 310                 315                 320
```

```
Leu Pro Ser Ile Trp Asp Met Gly Leu Glu Leu Phe Arg Ala His Ile
            325                 330                 335

Ile Ser Asp Gln Lys Val Gln Asn Lys Thr Ile Asp Gly Ile Leu Leu
            340                 345                 350

Leu Ile Glu Arg Glu Arg Asn Gly Glu Ala Ile Asp Arg Ser Leu Leu
            355                 360                 365

Arg Ser Leu Leu Ser Met Leu Ser Asp Leu Gln Ile Tyr Gln Asp Ser
            370                 375                 380

Phe Glu Gln Arg Phe Leu Glu Glu Thr Asn Arg Leu Tyr Ala Ala Glu
385                 390                 395                 400

Gly Gln Lys Leu Met Gln Glu Arg Glu Val Pro Glu Tyr Leu His His
            405                 410                 415

Val Asn Lys Arg Leu Glu Glu Ala Asp Arg Leu Ile Thr Tyr Leu
            420                 425                 430

Asp Gln Thr Thr Gln Lys Ser Leu Ile Ala Thr Val Glu Lys Gln Leu
            435                 440                 445

Leu Gly Glu His Leu Thr Ala Ile Leu Gln Lys Gly Leu Asn Asn Leu
            450                 455                 460

Leu Asp Glu Asn Arg Ile Gln Asp Leu Ser Leu Leu Tyr Gln Leu Phe
465                 470                 475                 480

Ser Arg Val Arg Gly Val Gln Val Leu Leu Gln Gln Trp Ile Glu
            485                 490                 495

Tyr Ile Lys Ala Phe Gly Ser Thr Ile Val Ile Asn Pro Glu Lys Asp
            500                 505                 510

Lys Thr Met Val Gln Glu Leu Leu Asp Phe Lys Asp Lys Val Asp His
            515                 520                 525

Ile Ile Asp Ile Cys Phe Leu Lys Asn Glu Lys Phe Ile Asn Ala Met
            530                 535                 540

Lys Glu Ala Phe Glu Thr Phe Ile Asn Lys Arg Pro Asn Lys Pro Ala
545                 550                 555                 560

Glu Leu Ile Ala Lys Tyr Val Asp Ser Lys Leu Arg Ala Gly Asn Lys
            565                 570                 575

Glu Ala Thr Asp Glu Glu Leu Glu Lys Met Leu Asp Lys Ile Met Ile
            580                 585                 590

Ile Phe Arg Phe Ile Tyr Gly Lys Asp Val Phe Glu Ala Phe Tyr Lys
            595                 600                 605

Lys Asp Leu Ala Lys Arg Leu Leu Val Gly Lys Ser Ala Ser Val Asp
            610                 615                 620

Ala Glu Lys Ser Met Leu Ser Lys Leu Lys His Glu Cys Gly Ala Ala
625                 630                 635                 640

Phe Thr Ser Lys Leu Glu Gly Met Phe Lys Asp Met Glu Leu Ser Lys
            645                 650                 655

Asp Ile Met Ile Gln Phe Lys Gln Tyr Met Gln Asn Gln Asn Val Pro
            660                 665                 670

Gly Asn Ile Glu Leu Thr Val Asn Ile Leu Thr Met Gly Tyr Trp Pro
            675                 680                 685

Thr Tyr Val Pro Met Glu Val His Leu Pro Pro Glu Met Val Lys Leu
            690                 695                 700

Gln Glu Ile Phe Lys Thr Phe Tyr Leu Gly Lys His Ser Gly Arg Lys
705                 710                 715                 720

Leu Gln Trp Gln Ser Thr Leu Gly His Cys Val Leu Lys Ala Glu Phe
            725                 730                 735

Lys Glu Gly Lys Lys Glu Leu Gln Val Ser Leu Phe Gln Thr Leu Val
```

```
                    740                 745                 750
Leu Leu Met Phe Asn Glu Gly Glu Glu Phe Ser Leu Glu Glu Ile Lys
                755                 760                 765
Gln Ala Thr Gly Ile Glu Asp Gly Glu Leu Arg Arg Thr Leu Gln Ser
        770                 775                 780
Leu Ala Cys Gly Lys Ala Arg Val Leu Ala Lys Asn Pro Lys Gly Lys
785                 790                 795                 800
Asp Ile Glu Asp Gly Asp Lys Phe Ile Cys Asn Asp Asp Phe Lys His
                805                 810                 815
Lys Leu Phe Arg Ile Lys Ile Asn Gln Ile Gln Met Lys Glu Thr Val
                820                 825                 830
Glu Glu Gln Ala Ser Thr Thr Glu Arg Val Phe Gln Asp Arg Gln Tyr
                835                 840                 845
Gln Ile Asp Ala Ala Ile Val Arg Ile Met Lys Met Arg Lys Thr Leu
        850                 855                 860
Ser His Asn Leu Leu Val Ser Glu Val Tyr Asn Gln Leu Lys Phe Pro
865                 870                 875                 880
Val Lys Pro Ala Asp Leu Lys Lys Arg Ile Glu Ser Leu Ile Asp Arg
                885                 890                 895
Asp Tyr Met Glu Arg Asp Lys Glu Asn Pro Asn Gln Tyr Asn Tyr Ile
                900                 905                 910
Ala
```

<210> SEQ ID NO 84
<211> LENGTH: 780
<212> TYPE: PRT
<213> ORGANISM: Homo sapiens

<400> SEQUENCE: 84

```
Met Ala Thr Ser Asn Leu Leu Lys Asn Lys Gly Ser Leu Gln Phe Glu
1               5                   10                  15
Asp Lys Trp Asp Phe Met Arg Pro Ile Val Leu Lys Leu Leu Arg Gln
                20                  25                  30
Glu Ser Val Thr Lys Gln Gln Trp Phe Asp Leu Phe Ser Asp Val His
        35                  40                  45
Ala Val Cys Leu Trp Asp Asp Lys Gly Pro Ala Lys Ile His Gln Ala
    50                  55                  60
Leu Lys Glu Asp Ile Leu Glu Phe Ile Lys Gln Ala Gln Ala Arg Val
65                  70                  75                  80
Leu Ser His Gln Asp Asp Thr Ala Leu Leu Lys Ala Tyr Ile Val Glu
                85                  90                  95
Trp Arg Lys Phe Phe Thr Gln Cys Asp Ile Leu Pro Lys Pro Phe Cys
                100                 105                 110
Gln Leu Glu Ile Thr Leu Met Gly Lys Gln Gly Ser Asn Lys Lys Ser
        115                 120                 125
Asn Val Glu Asp Ser Ile Val Arg Lys Leu Met Leu Asp Thr Trp Asn
    130                 135                 140
Glu Ser Ile Phe Ser Asn Ile Lys Asn Arg Leu Gln Asp Ser Ala Met
145                 150                 155                 160
Lys Leu Val His Ala Glu Arg Leu Gly Glu Ala Phe Asp Ser Gln Leu
                165                 170                 175
Val Ile Gly Val Arg Glu Ser Tyr Val Asn Leu Cys Ser Asn Pro Glu
                180                 185                 190
Asp Lys Leu Gln Ile Tyr Arg Asp Asn Phe Glu Lys Ala Tyr Leu Asp
```

```
            195                 200                 205
Ser Thr Glu Arg Phe Tyr Arg Thr Gln Ala Pro Ser Tyr Leu Gln Gln
210                 215                 220

Asn Gly Val Gln Asn Tyr Met Lys Tyr Ala Asp Ala Lys Leu Lys Glu
225                 230                 235                 240

Glu Glu Lys Arg Ala Leu Arg Tyr Leu Glu Thr Arg Arg Glu Cys Asn
                245                 250                 255

Ser Val Glu Ala Leu Met Glu Cys Cys Val Asn Ala Leu Val Thr Ser
                260                 265                 270

Phe Lys Glu Thr Ile Leu Ala Glu Cys Gln Gly Met Ile Lys Arg Asn
            275                 280                 285

Glu Thr Glu Lys Leu His Leu Met Phe Ser Leu Met Asp Lys Val Pro
290                 295                 300

Asn Gly Ile Glu Pro Met Leu Lys Asp Leu Glu His Ile Ile Ser
305                 310                 315                 320

Ala Gly Leu Ala Asp Met Val Ala Ala Glu Thr Ile Thr Thr Asp
                325                 330                 335

Ser Glu Lys Tyr Val Glu Gln Leu Leu Thr Leu Phe Asn Arg Phe Ser
                340                 345                 350

Lys Leu Val Lys Glu Ala Phe Gln Asp Asp Pro Arg Phe Leu Thr Ala
            355                 360                 365

Arg Asp Lys Ala Tyr Lys Ala Val Val Asn Asp Ala Thr Ile Phe Lys
370                 375                 380

Leu Glu Leu Pro Leu Lys Gln Lys Gly Val Gly Leu Lys Thr Gln Pro
385                 390                 395                 400

Glu Ser Lys Cys Pro Glu Leu Leu Ala Asn Tyr Cys Asp Met Leu Leu
                405                 410                 415

Arg Lys Thr Pro Leu Ser Lys Lys Leu Thr Ser Glu Ile Glu Ala
                420                 425                 430

Lys Leu Lys Glu Val Leu Leu Val Leu Lys Tyr Val Gln Asn Lys Asp
            435                 440                 445

Val Phe Met Arg Tyr His Lys Ala His Leu Thr Arg Arg Leu Ile Leu
450                 455                 460

Asp Ile Ser Ala Asp Ser Glu Ile Glu Glu Asn Met Val Glu Trp Leu
465                 470                 475                 480

Arg Glu Val Gly Met Pro Ala Asp Tyr Val Asn Lys Leu Ala Arg Met
                485                 490                 495

Phe Gln Asp Ile Lys Val Ser Glu Asp Leu Asn Gln Ala Phe Lys Glu
                500                 505                 510

Met His Lys Asn Asn Lys Leu Ala Leu Pro Ala Asp Ser Val Asn Ile
            515                 520                 525

Lys Ile Leu Asn Ala Gly Ala Trp Ser Arg Ser Ser Glu Lys Val Phe
530                 535                 540

Val Ser Leu Pro Thr Glu Leu Glu Asp Leu Ile Pro Glu Val Glu Glu
545                 550                 555                 560

Phe Tyr Lys Lys Asn His Ser Gly Arg Lys Leu His Trp His His Leu
                565                 570                 575

Met Ser Asn Gly Ile Ile Thr Phe Lys Asn Glu Val Gly Gln Tyr Asp
                580                 585                 590

Leu Glu Val Thr Thr Phe Gln Leu Ala Val Leu Phe Ala Trp Asn Gln
            595                 600                 605

Arg Pro Arg Glu Lys Ile Ser Phe Glu Asn Leu Lys Leu Ala Thr Glu
610                 615                 620
```

```
Leu Pro Asp Ala Glu Leu Arg Arg Thr Leu Trp Ser Leu Val Ala Phe
625                 630                 635                 640

Pro Lys Leu Lys Arg Gln Val Leu Leu Tyr Glu Pro Gln Val Asn Ser
            645                 650                 655

Pro Lys Asp Phe Thr Glu Gly Thr Leu Phe Ser Val Asn Gln Glu Phe
            660                 665                 670

Ser Leu Ile Lys Asn Ala Lys Val Gln Lys Arg Gly Lys Ile Asn Leu
            675                 680                 685

Ile Gly Arg Leu Gln Leu Thr Thr Glu Arg Met Arg Glu Glu Glu Asn
    690                 695                 700

Glu Gly Ile Val Gln Leu Arg Ile Leu Arg Thr Gln Glu Ala Ile Ile
705                 710                 715                 720

Gln Ile Met Lys Met Arg Lys Lys Ile Ser Asn Ala Gln Leu Gln Thr
                725                 730                 735

Glu Leu Val Glu Ile Leu Lys Asn Met Phe Leu Pro Gln Lys Lys Met
            740                 745                 750

Ile Lys Glu Gln Ile Glu Trp Leu Ile Glu His Lys Tyr Ile Arg Arg
            755                 760                 765

Asp Glu Ser Asp Ile Asn Thr Phe Ile Tyr Met Ala
            770                 775                 780

<210> SEQ ID NO 85
<211> LENGTH: 1698
<212> TYPE: PRT
<213> ORGANISM: Homo sapiens

<400> SEQUENCE: 85

Met Val Gly Glu Leu Arg Tyr Arg Glu Phe Arg Val Pro Leu Gly Pro
1               5                   10                  15

Gly Leu His Ala Tyr Pro Asp Glu Leu Ile Arg Gln Arg Val Gly His
            20                  25                  30

Asp Gly His Pro Glu Tyr Gln Ile Arg Trp Leu Ile Leu Arg Arg Gly
        35                  40                  45

Asp Glu Gly Asp Gly Gly Ser Gly Gln Val Asp Cys Lys Ala Glu His
    50                  55                  60

Ile Leu Leu Trp Met Ser Lys Asp Glu Ile Tyr Ala Asn Cys His Lys
65                  70                  75                  80

Met Leu Gly Glu Asp Gly Gln Val Ile Gly Pro Ser Gln Glu Ser Ala
                85                  90                  95

Gly Glu Val Gly Ala Leu Asp Lys Ser Val Leu Glu Glu Met Glu Thr
            100                 105                 110

Asp Val Lys Ser Leu Ile Gln Arg Ala Leu Arg Gln Leu Glu Glu Cys
        115                 120                 125

Val Gly Thr Ile Pro Pro Ala Pro Leu Leu His Thr Val His Val Leu
    130                 135                 140

Ser Ala Tyr Ala Ser Ile Glu Pro Leu Thr Gly Val Phe Lys Asp Pro
145                 150                 155                 160

Arg Val Leu Asp Leu Leu Met His Met Leu Ser Ser Pro Asp Tyr Gln
                165                 170                 175

Ile Arg Trp Ser Ala Gly Arg Met Ile Gln Ala Leu Ser Ser His Asp
            180                 185                 190

Ala Gly Thr Arg Thr Gln Ile Leu Leu Ser Leu Ser Gln Gln Glu Ala
        195                 200                 205

Ile Glu Lys His Leu Asp Phe Asp Ser Arg Cys Ala Leu Leu Ala Leu
```

```
                210                 215                 220

Phe Ala Gln Ala Thr Leu Ser Glu His Pro Met Ser Phe Glu Gly Ile
225                 230                 235                 240

Gln Leu Pro Gln Val Pro Gly Arg Val Leu Phe Ser Leu Val Lys Arg
            245                 250                 255

Tyr Leu His Val Thr Ser Leu Leu Asp Gln Leu Asn Asp Ser Ala Ala
                260                 265                 270

Glu Pro Gly Ala Gln Asn Thr Ser Ala Pro Glu Glu Leu Ser Gly Glu
            275                 280                 285

Arg Gly Gln Leu Glu Leu Glu Phe Ser Met Ala Met Gly Thr Leu Ile
        290                 295                 300

Ser Glu Leu Val Gln Ala Met Arg Trp Asp Gln Ala Ser Asp Arg Pro
305                 310                 315                 320

Arg Ser Ser Ala Arg Ser Pro Gly Ser Ile Phe Gln Pro Gln Leu Ala
                325                 330                 335

Asp Val Ser Pro Gly Leu Pro Ala Ala Gln Ala Gln Pro Ser Phe Arg
            340                 345                 350

Arg Ser Arg Arg Phe Arg Pro Arg Ser Glu Phe Ala Ser Gly Asn Thr
        355                 360                 365

Tyr Ala Leu Tyr Val Arg Asp Thr Leu Gln Pro Gly Met Arg Val Arg
370                 375                 380

Met Leu Asp Asp Tyr Glu Glu Ile Ser Ala Gly Asp Glu Gly Glu Phe
385                 390                 395                 400

Arg Gln Ser Asn Asn Gly Val Pro Pro Val Gln Val Phe Trp Glu Ser
                405                 410                 415

Thr Gly Arg Thr Tyr Trp Val His Trp His Met Leu Glu Ile Leu Gly
            420                 425                 430

Phe Glu Glu Asp Ile Glu Asp Met Val Glu Ala Asp Tyr Gln Gly
        435                 440                 445

Ala Val Ala Ser Arg Val Leu Gly Arg Ala Leu Pro Ala Trp Arg Trp
450                 455                 460

Arg Pro Met Thr Glu Leu Tyr Ala Val Pro Tyr Val Leu Pro Glu Asp
465                 470                 475                 480

Glu Asp Thr Glu Glu Cys Glu His Leu Thr Leu Ala Glu Trp Trp Glu
                485                 490                 495

Leu Leu Phe Phe Ile Lys Lys Leu Asp Gly Pro Asp His Gln Glu Val
            500                 505                 510

Leu Gln Ile Leu Gln Glu Asn Leu Asp Gly Glu Ile Leu Asp Asp Glu
        515                 520                 525

Ile Leu Ala Glu Leu Ala Val Pro Ile Glu Leu Ala Gln Asp Leu Leu
530                 535                 540

Leu Thr Leu Pro Gln Arg Leu Asn Asp Ser Ala Leu Arg Asp Leu Ile
545                 550                 555                 560

Asn Cys His Val Tyr Lys Lys Tyr Gly Pro Glu Ala Leu Ala Gly Asn
                565                 570                 575

Gln Ala Tyr Pro Ser Leu Leu Glu Ala Gln Glu Asp Val Leu Leu Leu
            580                 585                 590

Asp Ala Gln Ala Gln Ala Lys Asp Ser Glu Asp Ala Ala Lys Val Glu
        595                 600                 605

Ala Lys Glu Pro Pro Ser Gln Ser Pro Asn Thr Pro Leu Gln Arg Leu
610                 615                 620

Val Glu Gly Tyr Gly Pro Ala Gly Lys Ile Leu Leu Asp Leu Glu Gln
625                 630                 635                 640
```

-continued

```
Ala Leu Ser Ser Glu Gly Thr Gln Glu Asn Lys Val Lys Pro Leu Leu
            645                 650                 655
Leu Gln Leu Gln Arg Gln Pro Gln Pro Phe Leu Ala Leu Met Gln Ser
            660                 665                 670
Leu Asp Thr Pro Glu Thr Asn Arg Thr Leu His Leu Thr Val Leu Arg
            675                 680                 685
Ile Leu Lys Gln Leu Val Asp Phe Pro Glu Ala Leu Leu Leu Pro Trp
690                 695                 700
His Glu Ala Val Asp Ala Cys Met Ala Cys Leu Arg Ser Pro Asn Thr
705                 710                 715                 720
Asp Arg Glu Val Leu Gln Glu Leu Ile Phe Phe Leu His Arg Leu Thr
            725                 730                 735
Ser Val Ser Arg Asp Tyr Ala Val Val Leu Asn Gln Leu Gly Ala Arg
            740                 745                 750
Asp Ala Ile Ser Lys Ala Leu Glu Lys His Leu Gly Lys Leu Glu Leu
            755                 760                 765
Ala Gln Glu Leu Arg Asp Met Val Phe Lys Cys Glu Lys His Ala His
            770                 775                 780
Leu Tyr Arg Lys Leu Ile Thr Asn Ile Leu Gly Gly Cys Ile Gln Met
785                 790                 795                 800
Val Leu Gly Gln Ile Glu Asp His Arg Arg Thr His Gln Pro Ile Asn
            805                 810                 815
Ile Pro Phe Phe Asp Val Phe Leu Arg Tyr Leu Cys Gln Gly Ser Ser
            820                 825                 830
Val Glu Val Lys Glu Asp Lys Cys Trp Glu Lys Val Glu Val Ser Ser
            835                 840                 845
Asn Pro His Arg Ala Ser Lys Leu Thr Asp His Asn Pro Lys Thr Tyr
850                 855                 860
Trp Glu Ser Asn Gly Ser Ala Gly Ser His Tyr Ile Thr Leu His Met
865                 870                 875                 880
Arg Arg Gly Ile Leu Ile Arg Gln Leu Thr Leu Leu Val Ala Ser Glu
            885                 890                 895
Asp Ser Ser Tyr Met Pro Ala Arg Val Val Cys Gly Gly Asp Ser
            900                 905                 910
Thr Ser Ser Leu His Thr Glu Leu Asn Ser Val Asn Val Met Pro Ser
            915                 920                 925
Ala Ser Arg Val Ile Leu Leu Glu Asn Leu Thr Arg Phe Trp Pro Ile
930                 935                 940
Ile Gln Ile Arg Ile Lys Arg Cys Gln Gln Gly Gly Ile Asp Thr Arg
945                 950                 955                 960
Ile Arg Gly Leu Glu Ile Leu Gly Pro Lys Pro Thr Phe Trp Pro Val
            965                 970                 975
Phe Arg Glu Gln Leu Cys Arg His Thr Arg Leu Phe Tyr Met Val Arg
            980                 985                 990
Ala Gln Ala Trp Ser Gln Asp Met Ala Glu Asp Arg Ser Leu Leu
            995                 1000                1005
His Leu Ser Ser Arg Leu Asn Gly Ala Leu Arg Gln Glu Gln Asn Phe
            1010                1015                1020
Ala Asp Arg Phe Leu Pro Asp Glu Ala Gln Ala Leu Gly Lys
1025                1030                1035                1040
Thr Cys Trp Glu Ala Leu Val Ser Pro Val Val Gln Asn Ile Thr Ser
            1045                1050                1055
```

```
Pro Asp Glu Asp Gly Ile Ser Pro Leu Gly Trp Leu Leu Asp Gln Tyr
            1060                1065                1070

Leu Glu Cys Gln Glu Ala Val Phe Asn Pro Gln Ser Arg Gly Pro Ala
        1075                1080                1085

Phe Phe Ser Arg Val Arg Arg Leu Thr His Leu Leu His Val Glu
        1090                1095                1100

Pro Cys Glu Ala Pro Pro Val Val Ala Thr Pro Arg Pro Lys Gly
1105            1110                1115                1120

Arg Asn Arg Ser His Asp Trp Ser Ser Leu Ala Thr Gly Leu Pro
                1125                1130                1135

Ser Ser Ile Met Arg Asn Leu Thr Arg Cys Trp Arg Ala Val Val Glu
            1140                1145                1150

Lys Gln Val Asn Asn Phe Leu Thr Ser Ser Trp Arg Asp Asp Asp Phe
        1155                1160                1165

Val Pro Arg Tyr Cys Glu His Phe Asn Ile Leu Gln Asn Ser Ser Ser
        1170                1175                1180

Glu Leu Phe Gly Pro Arg Ala Ala Phe Leu Leu Ala Leu Gln Asn Gly
1185                1190                1195                1200

Cys Ala Gly Ala Leu Leu Lys Leu Pro Phe Leu Lys Ala Ala His Val
                1205                1210                1215

Ser Glu Gln Phe Ala Arg His Ile Asp Gln Gln Ile Gln Gly Ser Arg
            1220                1225                1230

Ile Gly Gly Ala Gln Glu Met Glu Arg Leu Ala Gln Leu Gln Gln Cys
        1235                1240                1245

Leu Gln Ala Val Leu Ile Phe Ser Gly Leu Glu Ile Ala Thr Thr Phe
    1250                1255                1260

Glu His Tyr Tyr Gln His Tyr Met Ala Asp Arg Leu Leu Gly Val Val
1265                1270                1275                1280

Ser Ser Trp Leu Glu Gly Ala Val Leu Glu Gln Ile Gly Pro Cys Phe
            1285                1290                1295

Pro Asn Arg Leu Pro Gln Gln Met Leu Gln Ser Leu Ser Thr Ser Lys
        1300                1305                1310

Glu Leu Gln Arg Gln Phe His Val Tyr Gln Leu Gln Gln Leu Asp Gln
        1315                1320                1325

Glu Leu Leu Lys Leu Glu Asp Thr Glu Lys Lys Ile Gln Val Gly Leu
    1330                1335                1340

Gly Ala Ser Gly Lys Glu His Lys Ser Glu Lys Glu Glu Glu Ala Gly
1345                1350                1355                1360

Ala Ala Ala Val Val Asp Val Ala Glu Gly Glu Glu Glu Glu Glu
                1365                1370                1375

Asn Glu Asp Leu Tyr Tyr Glu Gly Ala Met Pro Glu Val Ser Val Leu
            1380                1385                1390

Val Leu Ser Arg His Ser Trp Pro Val Ala Ser Ile Cys His Thr Leu
        1395                1400                1405

Asn Pro Arg Thr Cys Leu Pro Ser Tyr Leu Arg Gly Thr Leu Asn Arg
    1410                1415                1420

Tyr Ser Asn Phe Tyr Asn Lys Ser Gln Ser His Pro Ala Leu Glu Arg
1425                1430                1435                1440

Gly Ser Gln Arg Arg Leu Gln Trp Thr Trp Leu Gly Trp Ala Glu Leu
            1445                1450                1455

Gln Phe Gly Asn Gln Thr Leu His Val Ser Thr Val Gln Met Trp Leu
        1460                1465                1470
```

```
Leu Leu Tyr Leu Asn Asp Leu Lys Ala Val Ser Val Glu Ser Leu Leu
        1475                1480                1485

Ala Phe Ser Gly Leu Ser Ala Asp Met Leu Asn Gln Ala Ile Gly Pro
    1490                1495                1500

Leu Thr Ser Ser Arg Gly Pro Leu Asp Leu His Glu Gln Lys Asp Ile
1505                1510                1515                1520

Pro Gly Gly Val Leu Lys Ile Arg Asp Gly Ser Lys Glu Pro Arg Ser
                1525                1530                1535

Arg Trp Asp Ile Val Arg Leu Ile Pro Pro Gln Thr Tyr Leu Gln Ala
            1540                1545                1550

Glu Gly Glu Asp Gly Gln Asn Leu Glu Lys Arg Arg Asn Leu Leu Asn
        1555                1560                1565

Cys Leu Ile Val Arg Ile Leu Lys Ala His Gly Asp Glu Gly Leu His
    1570                1575                1580

Ile Asp Gln Leu Val Cys Leu Val Leu Glu Ala Trp Gln Lys Gly Pro
1585                1590                1595                1600

Cys Pro Pro Arg Gly Leu Val Ser Ser Leu Gly Lys Gly Ser Ala Cys
                1605                1610                1615

Ser Ser Thr Asp Val Leu Ser Cys Ile Leu His Leu Gly Lys Gly
            1620                1625                1630

Thr Leu Arg Arg His Asp Asp Arg Pro Gln Val Leu Ser Tyr Ala Val
        1635                1640                1645

Pro Val Thr Val Met Glu Pro His Thr Glu Ser Leu Asn Pro Gly Ser
    1650                1655                1660

Ser Gly Pro Asn Pro Pro Leu Thr Phe His Thr Leu Gln Ile Arg Ser
1665                1670                1675                1680

Arg Gly Val Pro Tyr Ala Ser Cys Thr Ala Thr Gln Ser Phe Ser Thr
                1685                1690                1695

Phe Arg

<210> SEQ ID NO 86
<211> LENGTH: 121
<212> TYPE: PRT
<213> ORGANISM: Saccharomyces cerevisiae

<400> SEQUENCE: 86

Met Ser Asn Glu Val Asp Arg Met Asp Val Asp Glu Asp Glu Ser Gln
1               5                   10                  15

Asn Ile Ala Gln Ser Ser Asn Gln Ser Ala Pro Val Glu Thr Lys Lys
            20                  25                  30

Lys Arg Phe Glu Ile Lys Lys Trp Thr Ala Val Ala Phe Trp Ser Trp
        35                  40                  45

Asp Ile Ala Val Asp Asn Cys Ala Ile Cys Arg Asn His Ile Met Glu
    50                  55                  60

Pro Cys Ile Glu Cys Gln Pro Lys Ala Met Thr Asp Thr Asp Asn Glu
65                  70                  75                  80

Cys Val Ala Ala Trp Gly Val Cys Asn His Ala Phe His Leu His Cys
                85                  90                  95

Ile Asn Lys Trp Ile Lys Thr Arg Asp Ala Cys Pro Leu Asp Asn Gln
            100                 105                 110

Pro Trp Gln Leu Ala Arg Cys Gly Arg
        115                 120
```

```
<210> SEQ ID NO 87
<211> LENGTH: 24
<212> TYPE: PRT
<213> ORGANISM: Artificial Sequence
<220> FEATURE:
<223> OTHER INFORMATION: Fragment of N-terminally acetylated
      Saccharomyces cerevisiae Ubc12 (residues 1-24)
<220> FEATURE:
<221> NAME/KEY: ACETYLATION
<222> LOCATION: (1)...(1)
<223> OTHER INFORMATION: The acetyl group is covalently bound to the
      backbone nitrogen of methionine

<400> SEQUENCE: 87

Met Leu Lys Leu Arg Gln Leu Gln Lys Lys Gln Lys Glu Asn Glu
1               5                   10                  15

Asn Ser Ser Ser Ile Gln Pro Asn
            20

<210> SEQ ID NO 88
<211> LENGTH: 25
<212> TYPE: PRT
<213> ORGANISM: Artificial Sequence
<220> FEATURE:
<223> OTHER INFORMATION: Fragment of N-terminally acetylated Homo
      sapiens Ube2F (residues 1-25)
<220> FEATURE:
<221> NAME/KEY: ACETYLATION
<222> LOCATION: (1)...(1)
<223> OTHER INFORMATION: The acetyl group is covalently bound to the
      backbone nitrogen of methionine

<400> SEQUENCE: 88

Met Leu Thr Leu Ala Ser Lys Leu Lys Arg Asp Asp Gly Leu Lys Gly
1               5                   10                  15

Ser Arg Thr Ala Ala Thr Ala Ser Asp
            20                  25

<210> SEQ ID NO 89
<211> LENGTH: 23
<212> TYPE: PRT
<213> ORGANISM: Artificial Sequence
<220> FEATURE:
<223> OTHER INFORMATION: Fragment of N-terminally acetylated
      Saccharomyces cerevisiae Ubc12 (residues 2-24)
<220> FEATURE:
<221> NAME/KEY: ACETYLATION
<222> LOCATION: (1)...(1)
<223> OTHER INFORMATION: The acetyl group is covalently bound to the
      backbone nitrogen of leucine

<400> SEQUENCE: 89

Leu Lys Leu Arg Gln Leu Gln Lys Lys Gln Lys Glu Asn Glu Asn
1               5                   10                  15

Ser Ser Ser Ile Gln Pro Asn
            20

<210> SEQ ID NO 90
<211> LENGTH: 12
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-12)
<220> FEATURE:
<221> NAME/KEY: ACETYLATION
<222> LOCATION: (1)...(1)
<223> OTHER INFORMATION: The acetyl group is covalently bound to the
      backbone nitrogen of methionine
```

```
<400> SEQUENCE: 90

Met Ile Lys Leu Phe Ser Leu Lys Gln Gln Lys Lys
1               5                   10

<210> SEQ ID NO 91
<211> LENGTH: 24
<212> TYPE: PRT
<213> ORGANISM: Artificial Sequence
<220> FEATURE:
<223> OTHER INFORMATION: Fragment of N-terminally formylated
      Saccharomyces cerevisiae Ubc12 (residues 1-24)
<220> FEATURE:
<221> NAME/KEY: FORMYLATION
<222> LOCATION: (1)...(1)
<223> OTHER INFORMATION: The formyl group is covalently bound to the
      backbone nitrogen of methionine

<400> SEQUENCE: 91

Met Leu Lys Leu Arg Gln Leu Gln Lys Lys Gln Lys Glu Asn Glu
1               5                   10                  15

Asn Ser Ser Ser Ile Gln Pro Asn
            20

<210> SEQ ID NO 92
<211> LENGTH: 15
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-15)
<220> FEATURE:
<221> NAME/KEY: ACETYLATION
<222> LOCATION: (1)...(1)
<223> OTHER INFORMATION: The acetyl group is covalently bound to the
      backbone nitrogen of methionine

<400> SEQUENCE: 92

Met Ile Lys Leu Phe Ser Leu Lys Gln Gln Lys Lys Glu Glu Glu
1               5                   10                  15

<210> SEQ ID NO 93
<211> LENGTH: 12
<212> TYPE: PRT
<213> ORGANISM: Artificial Sequence
<220> FEATURE:
<223> OTHER INFORMATION: Fragment of N-terminally acetylated Homo
      sapiens Ubc12 (residues 1-12) with N-acetylnorleucine at
      position 1
<220> FEATURE:
<221> NAME/KEY: VARIANT
<222> LOCATION: (1)...(1)
<223> OTHER INFORMATION: Xaa= N-acetylnorleucine

<400> SEQUENCE: 93

Xaa Ile Lys Leu Phe Ser Leu Lys Gln Gln Lys Lys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Fragment of N-terminally acetylated human Ubc12
      (residues 1-12) with lysine at position 6 and
      glutamic acid at position 10
```

```
<400> SEQUENCE: 94

Met Ile Lys Leu Phe Lys Leu Lys Gln Glu Lys Lys
1               5                   10
```